United States Patent
Wu

(10) Patent No.: US 10,287,253 B2
(45) Date of Patent: May 14, 2019

(54) SUBSTITUTED PYRIMIDINES CONTAINING ACIDIC GROUPS AS TLR7 MODULATORS

(71) Applicant: Apros Therapeutics, Inc., San Diego, CA (US)

(72) Inventor: Tom Yao-Hsiang Wu, San Diego, CA (US)

(73) Assignee: APROS THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 15/831,131

(22) Filed: Dec. 4, 2017

(65) Prior Publication Data

US 2018/0155298 A1    Jun. 7, 2018

Related U.S. Application Data

(60) Provisional application No. 62/430,183, filed on Dec. 5, 2016, provisional application No. 62/532,230, filed on Jul. 13, 2017.

(51) Int. Cl.

| | | |
|---|---|---|
| *A61K 31/505* | (2006.01) | |
| *C07D 239/48* | (2006.01) | |
| *C07D 239/49* | (2006.01) | |
| *C07D 403/12* | (2006.01) | |
| *A61P 31/20* | (2006.01) | |
| *A61P 35/00* | (2006.01) | |
| *A61K 31/7052* | (2006.01) | |
| *A61K 39/395* | (2006.01) | |
| *C07K 16/28* | (2006.01) | |
| *C07K 16/30* | (2006.01) | |
| *C07D 403/10* | (2006.01) | |
| *A61K 31/506* | (2006.01) | |
| *C07F 9/6512* | (2006.01) | |
| *A61K 31/675* | (2006.01) | |
| *C07F 5/02* | (2006.01) | |
| *A61K 31/69* | (2006.01) | |

(52) U.S. Cl.
CPC .......... *C07D 239/49* (2013.01); *A61K 31/505* (2013.01); *A61K 31/506* (2013.01); *A61K 31/675* (2013.01); *A61K 31/69* (2013.01); *A61K 31/7052* (2013.01); *A61K 39/3955* (2013.01); *A61P 31/20* (2018.01); *A61P 35/00* (2018.01); *C07D 239/48* (2013.01); *C07D 403/10* (2013.01); *C07D 403/12* (2013.01); *C07F 5/025* (2013.01); *C07F 9/6512* (2013.01); *C07K 16/2818* (2013.01); *C07K 16/2827* (2013.01); *C07K 16/30* (2013.01)

(58) Field of Classification Search
CPC .............. A61K 31/505; C07D 239/48
USPC .......................... 514/275; 544/323
See application file for complete search history.

(56) References Cited

U.S. PATENT DOCUMENTS 4,689,338 A    8/1987   Gerster

FOREIGN PATENT DOCUMENTS

| WO | WO-97/22596 | 6/1997 |
|---|---|---|
| WO | WO-97/30035 | 8/1997 |
| WO | WO-97/32856 | 9/1997 |
| WO | WO-98/01448 | 1/1998 |
| WO | WO-98/13354 | 4/1998 |
| WO | WO-98/35985 | 8/1998 |
| WO | WO 99/02166 | 1/1999 |
| WO | WO-99/28321 | 6/1999 |
| WO | WO-00/40529 | 7/2000 |
| WO | WO-00/41669 | 7/2000 |
| WO | WO-00/47212 | 8/2000 |
| WO | WO-01/32651 A1 | 5/2001 |
| WO | WO-01/60814 A2 | 8/2001 |
| WO | WO-01/92224 A1 | 12/2001 |
| WO | WO-01/94341 A1 | 12/2001 |
| WO | WO-02/04434 A1 | 1/2002 |
| WO | WO-02/08213 A1 | 1/2002 |
| WO | WO-2009/067081 A1 | 5/2009 |
| WO | WO-2010/133885 A1 | 11/2010 |
| WO | WO-2012/031140 A1 | 3/2012 |
| WO | WO-2012/066336 A1 | 5/2012 |
| WO | WO-2013/172479 A1 | 11/2013 |
| WO | WO-2014/128189 A1 | 8/2014 |

OTHER PUBLICATIONS

International Search Report and Written Opinion issue by the International Searching Authority for Application No. PCT/US2017/064541, dated Mar. 5, 2018, 17 pages.
Santarpia et al., "Programmed cell death protein-1/programmed cell death ligand-1 pathway inhibition and predictive biomarkers: understanding transforming growth factor-beta role," Transl. Lung Cancer Res 2015; 4(6): 728-742.
Flyleaf of "Introduction to Organic Chemistry", Clayton Heathcock and Andrew Streitweiser, MacMillan Publishing Co., Inc., 1976.
(Continued)

*Primary Examiner* — Douglas M Willis
(74) *Attorney, Agent, or Firm* — Cooley LLP

(57) ABSTRACT

The present disclosure relates to a class of pyrimidine derivatives having immunomodulating properties that act via TLR7 which are useful in the treatment of viral infections and cancers. One aspect of the present disclosure relates to a compound represented by Formula 1:

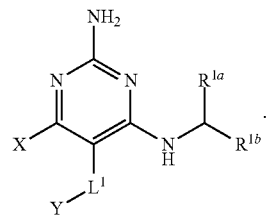

(1)

39 Claims, No Drawings

(56) References Cited

OTHER PUBLICATIONS

Lombardo et al., "Discovery of N-(2-chloro-6-methyl-phenyl)-2-(6-(4-(2-hydroxyethyl)-piperazin-1-yl)-2-methylpyrimidin-4-ylamino)thiazole-5-carboxamide (BMS-354825), a dual Src/Abl kinase inhibitor with potent antitumor activity in preclinical assays," J. Med. Chem. 47(27): 6658-6661 (2004).

McGowan et al., "Novel Pyrimidine Toll-like Receptor 7 and 8 Dual Agonists to Treat Hepatitis B Virus," J. Med. Chem. 59(17):7936-7949.

Oballa et al., "Development of a liver-targeted stearoyl-CoA desaturase (SCD) inhibitor (MK-8245) to establish a therapeutic window for the treatment of diabetes and dyslipidemia," J. Med. Chem. 54(14):5082-5096 (2011).

Pfefferkorn et al., Discovery of (S)-6-(3-cyclopentyl-2-(4-(trifluoromethyl)-1H-imidazol-1-yl)propanamido)nicotinic acid as a hepatoselective glucokinase activator clinical candidate for treating type 2 diabetes mellitus, J. Med. Chem., 2012, 55(3):1318-1333 (2012).

Stern et al., "Overview of monoclonal antibodies in cancer therapy: present and promise," Crit Rev Oncol Hematol. 54(1):11-29 (2005).

Tu et al., "Medicinal Chemistry Design Principles for Liver Targeting Through OATP Transporters," Current Topics in Medicinal Chemistry 13(7): 857-866 (2013).

SUBSTITUTED PYRIMIDINES CONTAINING ACIDIC GROUPS AS TLR7 MODULATORS

CROSS REFERENCE TO RELATED APPLICATIONS

This application claims the benefit of U.S. Provisional Application No. 62/430,183, filed Dec. 5, 2016, and U.S. Provisional Application No. 62/532,230, filed Jul. 13, 2017, the contents of which are incorporated herein by reference in their entireties.

FIELD OF THE INVENTION

The present disclosure relates to a class of pyrimidine derivatives having immunomodulating properties that act via TLR7 which are useful in the treatment of viral or allergic diseases and cancers.

BACKGROUND OF THE INVENTION

The present disclosure relates to pyrimidine derivatives, processes for their preparation, pharmaceutical compositions containing them and their use in therapy.

The immune system is comprised of innate and acquired immunity, both of which work cooperatively to protect the host from microbial infections. It has been shown that innate immunity can recognize conserved pathogen-associated molecular patterns through toll-like receptors (TLRs) expressed on the cell surface of immune cells. Recognition of invading pathogens then triggers cytokine production (including interferon alpha (IFNα)) and upregulation of co-stimulatory molecules on phagocytes, leading to modulation of T cell function. Thus, innate immunity is closely linked to acquired immunity and can influence the development and regulation of an acquired response.

TLRs are a family of type I transmembrane receptors characterized by an $NH_2$-terminal extracellular leucine-rich repeat domain (LRR) and a COOH-terminal intracellular tail containing a conserved region called the Toll/IL-1 receptor (TIR) homology domain. The extracellular domain contains a varying number of LRR, which are thought to be involved in ligand binding. Eleven TLRs have been described to date in humans and mice. They differ from each other in ligand specificities, expression patterns, and in the target genes they can induce.

Ligands which act via TLRs (also known as immune response modifiers (IRMS)) have been developed, for example, the imidazoquinoline derivatives described in U.S. Pat. No. 4,689,338 which include the product Imiquimod for treating genital warts, and the adenine derivatives described in WO 98/01448 and WO 99/28321.

Compounds with liver targeting property are desirable. Certain moieties that aid in liver targeting that have been disclosed in references include acidic moieties. (Tu et al., Current Topics in Medicinal Chemistry, 2013, 13, 857-866; Oballa et al., J. Med. Chem., 2011, 54, 5082-5096; Pfefferkorn et al., J. Med. Chem., 2012, 55, 1318-1333, the contents of which are incorporated herein by reference in their entireties)

SUMMARY OF THE INVENTION

The present disclosure provides a compound having the structure of Formula (1), and pharmaceutically acceptable salts thereof,

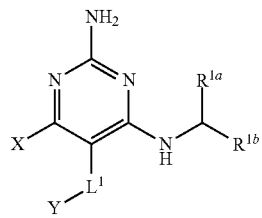

wherein $R^{1a}$ is selected from the group consisting of H, $C_1$-$C_4$ alkyl, —$NH_2$, —NHAc, —COOH, —$SO_2CH_3$, —$SCH_3$, —$OCH_3$,

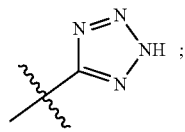 [SMILES: *c1nn[nH]n1]

and A,
  wherein the alkyl is optionally substituted with —OH, —$NH_2$, —NHAc, —COOH, —$SO_2CH_3$, —$SCH_3$, —$OCH_3$,

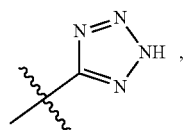 [SMILES: *c1nn[nH]n1]

or A;

$R^{1b}$ is $C_2$-$C_5$ alkyl;

X is selected from the group consisting of H and $C_1$-$C_4$ alkyl, wherein the alkyl is optionally substituted with A, —OH, or —$C(CH_3)_2OH$;

$L^1$ is selected from the group consisting of a bond, —$CH_2$—, —$CF_2$—,

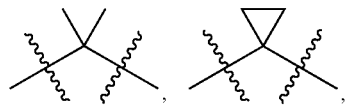

—O—, —S—, —$SO_2$—, —NH—, and —$CH_2CH_2$—;

Y is selected from the group consisting of $C_1$-$C_3$ alkyl, aryl, and heteroaryl, wherein the alkyl, aryl, and heteroaryl are optionally substituted with 1-5 substituents that are independently selected from A, $C_1$-$C_3$ alkyl, and $C_1$-$C_3$ alkoxy;

A is selected from the group consisting of

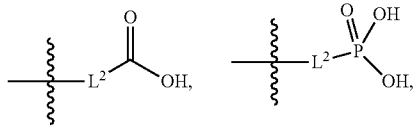

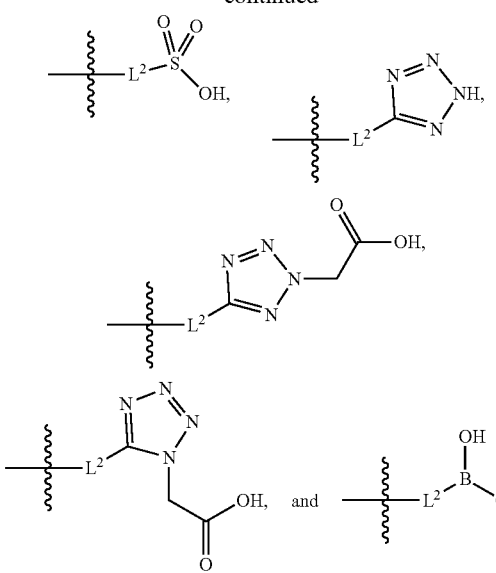

$L^2$ is selected from the group consisting of a bond, —(CH$_2$)$_n$—, —C(O)NH(CH$_2$)$_n$—,

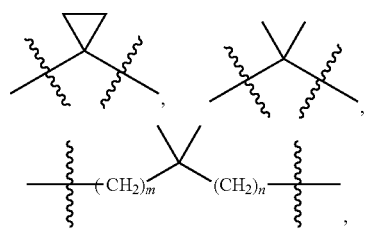

—[O(CH$_2$CH$_2$)]$_n$—, —[O(C$_1$-C$_4$ alkylene)]-, —[O(CH$_2$CH$_2$)]$_n$—OCH$_2$CH$_2$CF$_2$—; —C(O)NHCH$_2$CH$_2$—[O(CH$_2$CH$_2$)]$_m$—; and —C(O)NHCH$_2$CH$_2$—[O(CH$_2$CH$_2$)]$_m$—OCH$_2$CH$_2$CF$_2$—;

m is an integer from zero to four; and n is an integer from one to four; and wherein the compound is substituted with at least one A.

The present disclosure provides a compound having the structure of Formula (1), and pharmaceutically acceptable salts thereof,

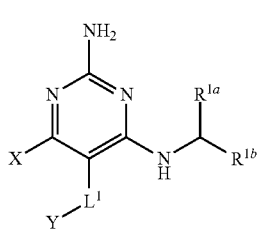

(1)

wherein

R$^{1a}$ is selected from the group consisting of H, C$_1$-C$_4$ alkyl, —NH$_2$, —NHAc, —COOH, —SO$_2$CH$_3$, —SCH$_3$, —OCH$_3$, and

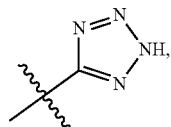 [SMILES: *c1nn[nH]n1]

wherein the alkyl is optionally substituted with —OH, —NH$_2$, —NHAc, —COOH, —SO$_2$CH$_3$, —SCH$_3$, —OCH$_3$, or

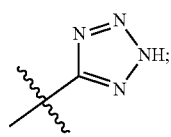 [SMILES: *c1nn[nH]n1]

R$^{1b}$ is C$_2$-C$_5$ alkyl;

X is selected from the group consisting of H and C$_1$-C$_4$ alkyl, wherein the alkyl is optionally substituted with A, —OH, or —C(CH$_3$)$_2$OH;

L$^1$ is selected from the group consisting of a bond, —CH$_2$—, —CF$_2$—,

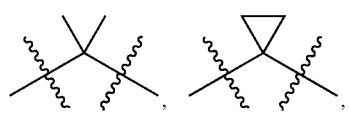

—O—, —S—, —SO$_2$—, —NH—, and —CH$_2$CH$_2$—;

Y is selected from the group consisting of C$_1$-C$_3$ alkyl, aryl, and heteroaryl, wherein the alkyl, aryl, and heteroaryl are optionally substituted with 1-5 substituents that are independently selected from A, C$_1$-C$_3$ alkyl, and C$_1$-C$_3$ alkoxy;

A is selected from the group consisting of

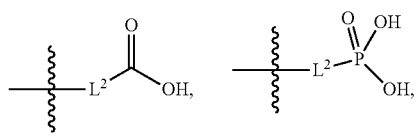

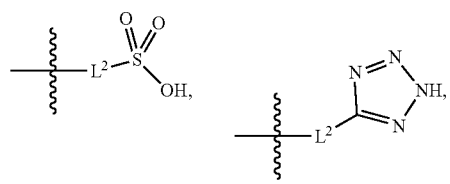

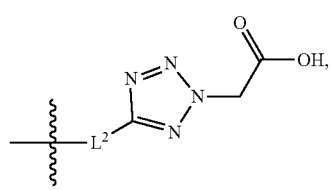

-continued

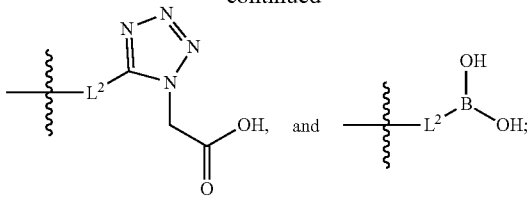

L² is selected from the group consisting of a bond, —(CH₂)ₙ—, —C(O)NH(CH₂)ₙ—,

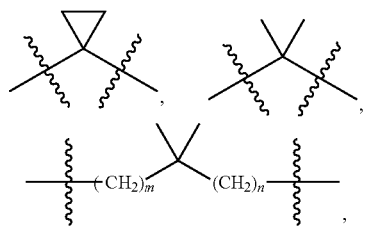

—[O(CH₂CH₂)]ₙ—, —[O(C₁-C₄ alkylene)]-, —[O(CH₂CH₂)]ₙ—OCH₂CH₂CF₂—; —C(O)NHCH₂CH₂—[O(CH₂CH₂)]ₘ—; and —C(O)NHCH₂CH₂—[O(CH₂CH₂)]ₘ—OCH₂CH₂CF₂—;

m is an integer from zero to four; and
n is an integer from one to four; and
wherein the compound is substituted with at least one A.

The present disclosure provides a compound having the structure of Formula (1), and pharmaceutically acceptable salts thereof,

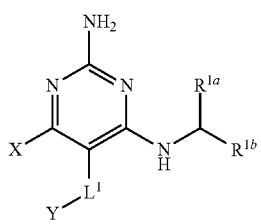

(1)

wherein
R^{1a} is selected from the group consisting of H, C₁-C₄ alkyl, —NH₂, —COOH, and —SO₂CH₃, wherein the alkyl is optionally substituted with —OH, —NH₂, —COOH, or —SO₂CH₃;
R^{1b} is C₂-C₅ alkyl;
X is selected from the group consisting of H and C₁-C₄ alkyl, wherein the alkyl is optionally substituted with A;
L¹ is selected from the group consisting of a bond, —CH₂—, —CF₂—,

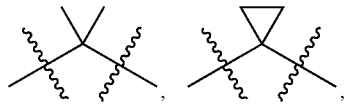

—O—, —S—, —SO₂—, —NH—, and —CH₂CH₂—;
Y is selected from the group consisting of C₁-C₃ alkyl, aryl, and heteroaryl, wherein the alkyl, aryl, and heteroaryl are optionally substituted with 1-5 substituents that are independently selected from A, C₁-C₃ alkyl, and C₁-C₃ alkoxy;
A is selected from the group consisting of

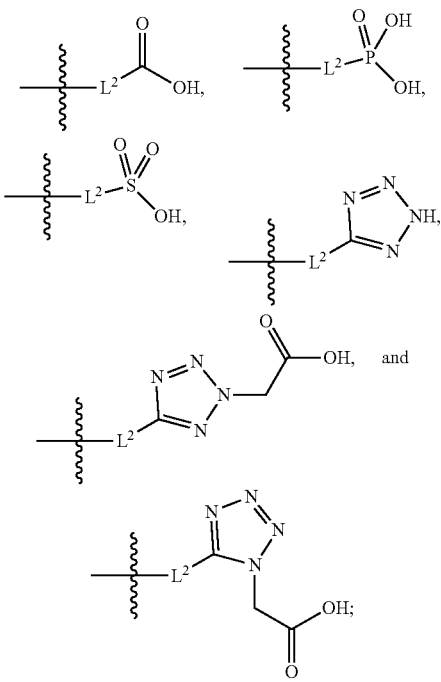

L² is selected from the group consisting of a bond, —(CH₂)ₙ—, —C(O)NH(CH₂)ₙ—,

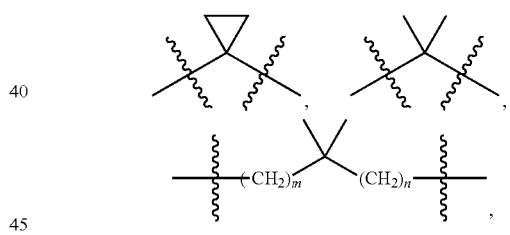

—[O(CH₂CH₂)]ₙ—, —[O(C₁-C₄ alkylene)]-, and —[O(CH₂CH₂)]ₙ—OCH₂CH₂CF₂—;
m is an integer from zero to four; and
n is an integer from one to four; and
wherein the compound is substituted with at least one A.

In certain embodiments, the compound having the structure of Formula (1) can have any one or more of the following features, (a) when X is —CH₃; L¹ is —CH₂—; Y is aryl substituted with A; and L² is —CH₂—; then A is not -L²-COOH;
(b) when X is —CH₃; L¹ is —CH₂—; Y is aryl substituted with A; and L² is —CH₂—; then A is not -L²-COOH, except when R^{1a} comprises —COOH;
(c) when L¹ is —CH₂—; Y is aryl substituted with A; and A is -L²-COOH; and L² is —CH₂—; then X is not —CH₃;
(d) when L¹ is —CH₂—; Y is aryl substituted with A; and A is -L²-COOH; and L² is —CH₂—; then X is not —CH₃, except when R^{1a} comprises —COOH;
(e) when X is —CH₃; L¹ is —CH₂—; Y is aryl substituted with A; and A is -L²-COOH; then L² is not —CH₂—;

(f) when X is —CH$_3$; L$^1$ is —CH$_2$—; Y is aryl substituted with A; and A is -L$^2$-COOH; then L$^2$ is not —CH$_2$—, except when R$^{1a}$ comprises —COOH;

(g) when X is —CH$_3$; Y is aryl substituted with A; and A is -L$^2$-COOH; and L$^2$ is —CH$_2$—; then L$^1$ is not —CH$_2$—;

(h) when X is —CH$_3$; Y is aryl substituted with A; and A is -L$^2$-COOH; and L$^2$ is —CH$_2$—; then L$^1$ is not —CH$_2$—, except when R$^{1a}$ comprises —COOH;

(i) when X is —CH$_3$; L$^1$ is —CH$_2$—; Y is aryl substituted with A; and A is -L$^2$-COOH; and L$^2$ is —CH$_2$—; then R$^{1a}$ comprises COOH;

(j) when X is —CH$_3$; L$^1$ is —CH$_2$—; Y is aryl substituted A and —OCH$_3$; and L$^2$ is —CH$_2$—; then A is not -L$^2$-COOH;

(k) when X is —CH$_3$; L$^1$ is —CH$_2$—; Y is aryl substituted A and —OCH$_3$; and L$^2$ is —CH$_2$—; then A is not -L$^2$-COOH, except when R$^{1a}$ comprises —COOH;

(l) when X is —CH$_3$; L$^1$ is —CH$_2$—; Y is aryl substituted A and —OCH$_3$; and L$^2$ is —CH$_2$—; and R$^{1a}$ does not comprise COOH; then A is not -L$^2$-COOH.

In certain embodiments, the compound having the structure of Formula (1) can have any one or more of the following features, (m) when X is —CH$_3$; L$^1$ is —CH$_2$—; Y is aryl substituted with A; and L$^2$ is —CH$_2$—; then A is not -L$^2$-COOH;

(n) when X is —CH$_3$; L$^1$ is —CH$_2$—; Y is aryl substituted with A; and L$^2$ is —CH$_2$—; then A is not -L$^2$-COOH, except when R$^{1a}$ comprises —COOH or —SO$_2$CH$_3$;

(o) when L$^1$ is —CH$_2$—; Y is aryl substituted with A; and A is -L$^2$-COOH; and L$^2$ is —CH$_2$—; then X is not —CH$_3$;

(p) when L$^1$ is —CH$_2$—; Y is aryl substituted with A; and A is -L$^2$-COOH; and L$^2$ is —CH$_2$—; then X is not —CH$_3$, except when R$^{1a}$ comprises —COOH or —SO$_2$CH$_3$;

(q) when X is —CH$_3$; L$^1$ is —CH$_2$—; Y is aryl substituted with A; and A is -L$^2$-COOH; then L$^2$ is not —CH$_2$—;

(r) when X is —CH$_3$; L$^1$ is —CH$_2$—; Y is aryl substituted with A; and A is -L$^2$-COOH; then L$^2$ is not —CH$_2$—, except when R$^{1a}$ comprises —COOH or —SO$_2$CH$_3$;

(s) when X is —CH$_3$; Y is aryl substituted with A; and A is -L$^2$-COOH; and L$^2$ is —CH$_2$—; then L$^1$ is not —CH$_2$—;

(t) when X is —CH$_3$; Y is aryl substituted with A; and A is -L$^2$-COOH; and L$^2$ is —CH$_2$—; then L$^1$ is not —CH$_2$—, except when R$^{1a}$ comprises —COOH or —SO$_2$CH$_3$;

(u) when X is —CH$_3$; L$^1$ is —CH$_2$—; Y is aryl substituted with A; and A is -L$^2$-COOH; and L$^2$ is —CH$_2$—; then R$^{1a}$ comprises COOH or —SO$_2$CH$_3$;

(v) when X is —CH$_3$; L$^1$ is —CH$_2$—; Y is aryl substituted A and —OCH$_3$; and L$^2$ is —CH$_2$—; then A is not -L$^2$-COOH;

(w) when X is —CH$_3$; L$^1$ is —CH$_2$—; Y is aryl substituted A and —OCH$_3$; and L$^2$ is —CH$_2$—; then A is not -L$^2$-COOH, except when R$^{1a}$ comprises —COOH or —SO$_2$CH$_3$;

(x) when X is —CH$_3$; L$^1$ is —CH$_2$—; Y is aryl substituted A and —OCH$_3$; and L$^2$ is —CH$_2$—; and R$^{1a}$ does not comprise COOH or —SO$_2$CH$_3$; then A is not -L$^2$-COOH;

(y) when X is —CH$_3$; L$^1$ is —CH$_2$—; Y is aryl substituted with A; and A is -L$^2$-COOH; and L$^2$ is —CH$_2$—; then R$^{1a}$ is not H or alkyl substituted with —OH.

In certain embodiments, the compound having the structure of Formula (1) can have any one or more of the following features:

(aa) when X is —CH$_3$; L$^1$ is —CH$_2$—; Y is aryl substituted with A; L$^2$ is —CH$_2$—, —O—(CH$_2$)$_2$—O(CH$_2$)$_2$—, or —O—(CH$_2$)$_2$—O(CH$_2$)$_2$(CF$_2$)—; and A is

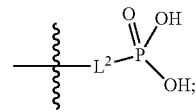

then A and L$^1$ are not in a para position with respect to each other;

(bb) when X is —CH$_3$; L$^1$ is —CH$_2$—; Y is aryl substituted with A; L$^2$ is —CH$_2$—; and A is

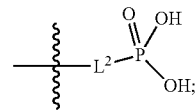

then A and L$^1$ are not in a para position with respect to each other;

(cc) when X is —CH$_3$; L$^1$ is —CH$_2$—; Y is aryl substituted with A and —OCH$_3$; L$^2$ is —CH$_2$—; and A is

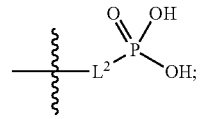

then A and L$^1$ are not in a para position with respect to each other;

(dd) when X is —CH$_3$; L$^1$ is —CH$_2$—; Y is aryl substituted with A; L$^2$ is —O—(CH$_2$)$_2$—O(CH$_2$)$_2$—; and A is

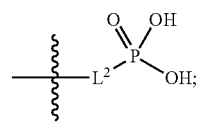

then A and L$^1$ are not in a para position with respect to each other;

(ee) when X is —CH$_3$; L$^1$ is —CH$_2$—; Y is aryl substituted with A; L$^2$ is —O—(CH$_2$)$_2$—O(CH$_2$)$_2$(CF$_2$)—; and A is

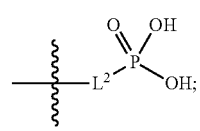

then A and L$^1$ are not in a para position with respect to each other;

(ff) when X is —CH$_3$; R$^{1a}$ is H; R$^{1b}$ is C$_4$alkyl; L$^1$ is —CH$_2$—; Y is aryl substituted with A; and L$^2$ is —CH$_2$—, —O—(CH$_2$)$_2$—O(CH$_2$)$_2$—, or —O—(CH$_2$)$_2$—O(CH$_2$)$_2$(CF$_2$)—; then A is not

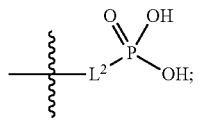

(gg) when X is —CH$_3$; R$^{1a}$ is H; R$^{1b}$ is C$_4$alkyl; L$^1$ is —CH$_2$—; Y is aryl substituted with A; and L$^2$ is —CH$_2$—; then A is not

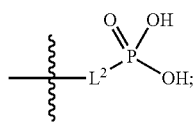

(hh) when X is —CH$_3$; R$^{1a}$ is H; R$^{1b}$ is C$_4$alkyl; L$^1$ is —CH$_2$—; Y is aryl substituted with A and —OCH$_3$; and L$^2$ is —CH$_2$—; then A is not

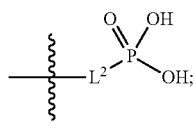

(ii) when X is —CH$_3$; R$^{1a}$ is H; R$^{1b}$ is C$_4$alkyl; L$^1$ is —CH$_2$—; Y is aryl substituted with A; and L$^2$ is —O—(CH$_2$)$_2$—O(CH$_2$)$_2$—; then A is not

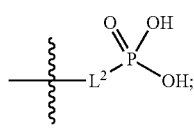

(jj) when X is —CH$_3$; R$^{1a}$ is H; R$^{1b}$ is C$_4$alkyl; L$^1$ is —CH$_2$—; Y is aryl substituted with A; and L$^2$ is —O—(CH$_2$)$_2$—O(CH$_2$)$_2$(CF$_2$)—; then A is not

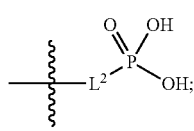

(kk) when X is —CH$_3$; R$^{1a}$ is H; R$^{1b}$ is C$_4$alkyl; L$^1$ is —CH$_2$—; Y is aryl substituted with A; L$^2$ is —CH$_2$—, —O—(CH$_2$)$_2$—O(CH$_2$)$_2$—, or —O—(CH$_2$)$_2$—O(CH$_2$)$_2$(CF$_2$)—; and A and L$^1$ are para position with respect to each other; then A is not

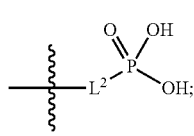

(ll) when X is —CH$_3$; R$^{1a}$ is H; R$^{1b}$ is C$_4$alkyl; L$^1$ is —CH$_2$—; Y is aryl substituted with A; L$^2$ is —CH$_2$—; and A and L$^1$ are para position with respect to each other; then A is not

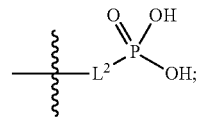

(mm) when X is —CH$_3$; R$^{1a}$ is H; R$^{1b}$ is C$_4$alkyl; L$^1$ is —CH$_2$—; Y is aryl substituted with A and —OCH$_3$; L$^2$ is —CH$_2$—; and A and L$^1$ are para position with respect to each other; then A is not

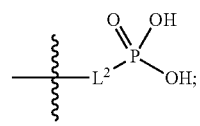

(nn) when X is —CH$_3$; R$^{1a}$ is H; R$^{1b}$ is C$_4$alkyl; L$^1$ is —CH$_2$—; Y is aryl substituted with A; L$^2$ is —O—(CH$_2$)$_2$—O(CH$_2$)$_2$—; and A and L$^1$ are para position with respect to each other; then A is not

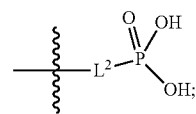

(oo) when X is —CH$_3$; R$^{1a}$ is H; R$^{1b}$ is C$_4$alkyl; L$^1$ is —CH$_2$—; Y is aryl substituted with A; L$^2$ is —O—(CH$_2$)$_2$—O(CH$_2$)$_2$(CF$_2$)—; and A and L$^1$ are para position with respect to each other; then A is not

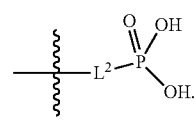

The present disclosure provides the compound of Formula (1) that is a compound of Formula (1a),

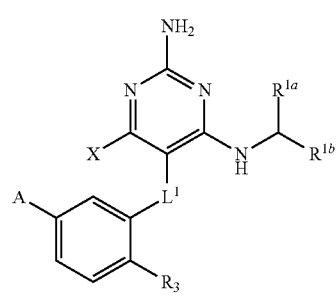

(1a)

wherein
X is H or CH$_3$;
L$^1$ is selected from the group consisting of a bond, —CH$_2$—, —O—, —S—, —CF$_2$—,

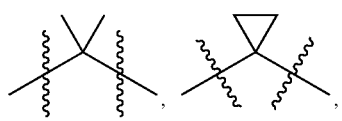

and —CH$_2$CH$_2$—;
A is selected from the group consisting of

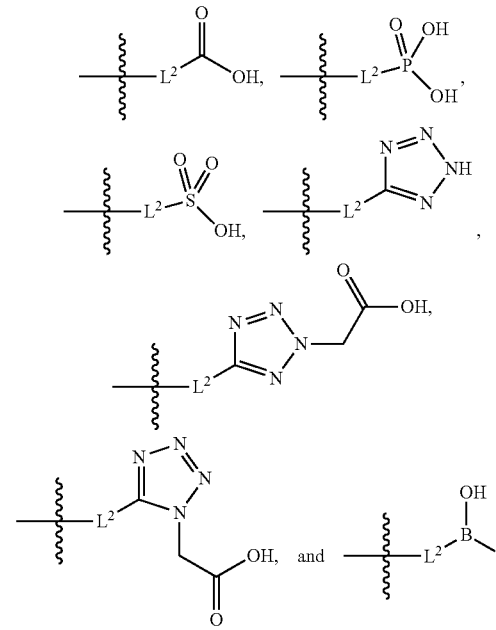

L$^2$ is selected from the group consisting of a bond, —CH$_2$—, —CH$_2$CH$_2$—,

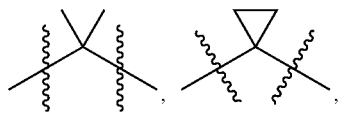

—C(O)NH(CH$_2$)$_n$—, —[O(CH$_2$CH$_2$)]$_n$—, —[O(C$_1$-C$_4$ alkylene)]-, and —[O(CH$_2$CH$_2$)]$_n$—OCH$_2$CH$_2$CF$_2$—; —C(O)NHCH$_2$CH$_2$—[O(CH$_2$CH$_2$)]$_m$—; and C(O)NHCH$_2$CH$_2$—[O(CH$_2$CH$_2$)]$_m$—OCH$_2$CH$_2$CF$_2$—; and R$^3$ is H, C$_1$-C$_3$ alkyl, or C$_1$-C$_3$ alkoxy.

The present disclosure provides the compound of Formula (1) that is a compound of Formula (1a),

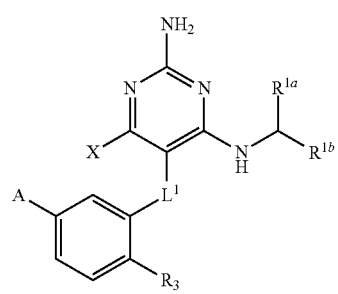

wherein
X is H or CH$_3$;
L$^1$ is selected from the group consisting of a bond, —CH$_2$—, —CF$_2$—,

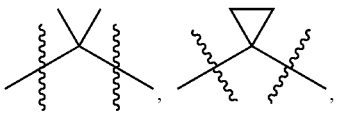

and —CH$_2$CH$_2$—;
A is selected from the group consisting of

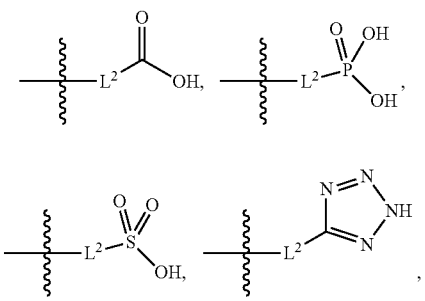

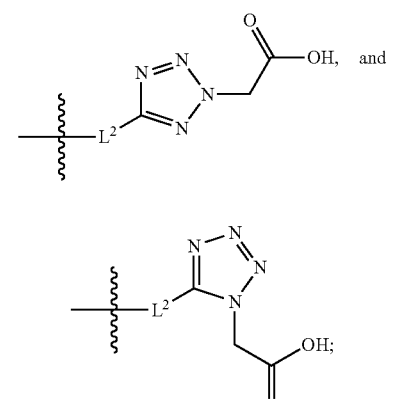

L$^2$ is selected from the group consisting of a bond, —CH$_2$—, —CH$_2$CH$_2$—,

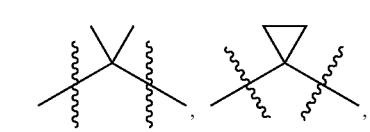

—C(O)NH(CH$_2$)$_n$—, —[O(CH$_2$CH$_2$)]$_n$—, —[O(C$_1$-C$_4$ alkylene)]-, and —[O(CH$_2$CH$_2$)]$_n$—OCH$_2$CH$_2$CF$_2$—; and R$^3$ is H, C$_1$-C$_3$ alkyl, or C$_1$-C$_3$ alkoxy.

The present disclosure provides the compound of Formula (1) that is a compound of Formula (1a),

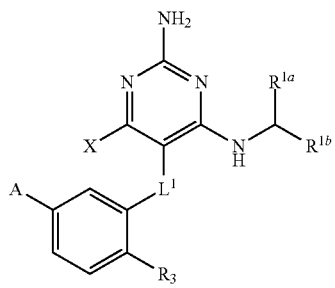

(1a)

wherein

X is —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$;

A$^{1a}$ is selected from the group consisting of

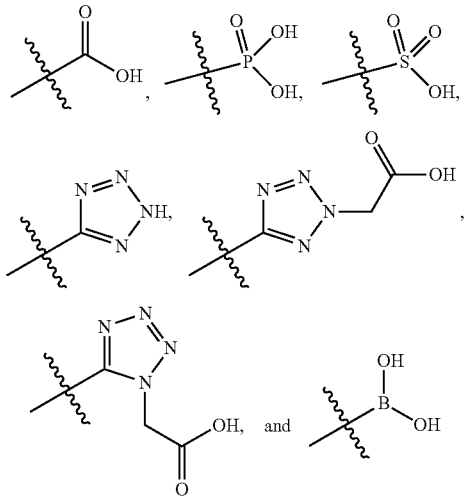

L$^1$ is selected from the group consisting of a bond, —CH$_2$—, —O—, —S—, —CF$_2$—,

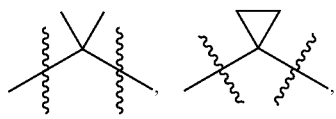

and —CH$_2$CH$_2$—;

A is selected from the group consisting of OH

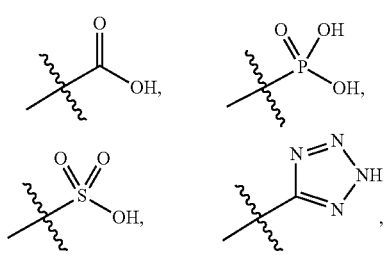

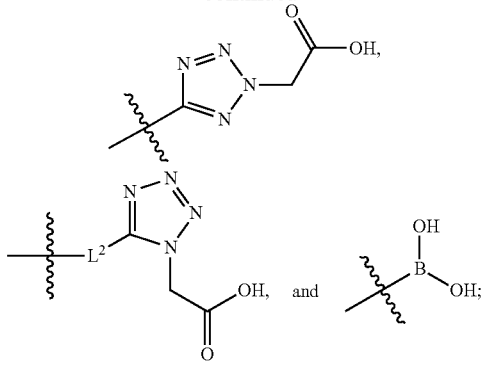

L$^2$ is selected from the group consisting of a bond, —CH$_2$—, —CH$_2$CH$_2$—,

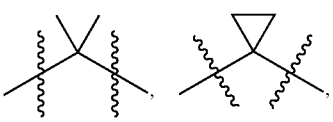

—C(O)NH(CH$_2$)$_n$—, —[O(CH$_2$CH$_2$)]$_n$—, —[O(C$_1$-C$_4$ alkylene)]-, and —[O(CH$_2$CH$_2$)]$_n$—OCH$_2$CH$_2$CF$_2$—; —C(O)NHCH$_2$CH$_2$—[O(CH$_2$CH$_2$)]$_m$—; and C(O)NHCH$_2$CH$_2$—[O(CH$_2$CH$_2$)]$_m$—OCH$_2$CH$_2$CF$_2$—; and R$^3$ is H, C$_1$-C$_3$ alkyl, or C$_1$-C$_3$ alkoxy.

The present disclosure provides the compound of Formula (1) that is a compound of Formula (1a),

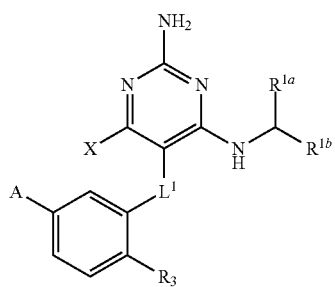

(1a)

wherein

X is —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$;

A$^{1a}$ is selected from the group consisting of

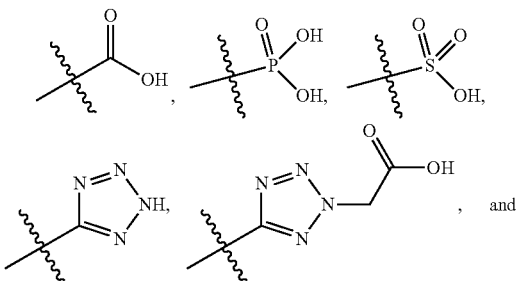

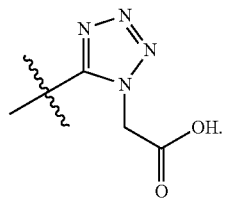

L¹ is selected from the group consisting of a bond, —CH$_2$—, —CF$_2$—,

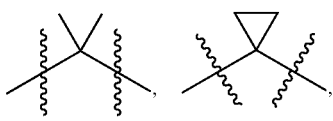

and —CH$_2$CH$_2$—;

A is selected from the group consisting of

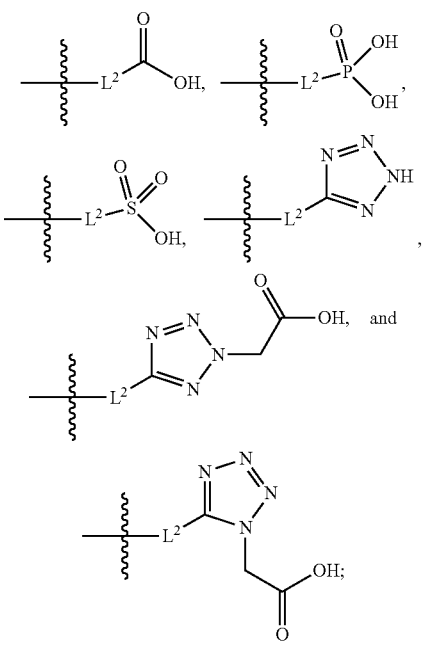

L² is selected from the group consisting of a bond, —CH$_2$—, —CH$_2$CH$_2$—,

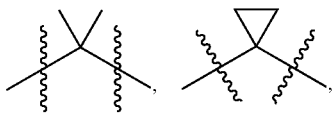

—C(O)NH(CH$_2$)$_n$—, —[O(CH$_2$CH$_2$)]$_n$—, —[O(C$_1$-C$_4$ alkylene)]-, and —[O(CH$_2$CH$_2$)]$_n$—OCH$_2$CH$_2$CF$_2$—; and R³ is H, C$_1$-C$_3$ alkyl, or C$_1$-C$_3$ alkoxy.

The present disclosure provides the compound of Formula (1) that is a compound of Formula (1b),

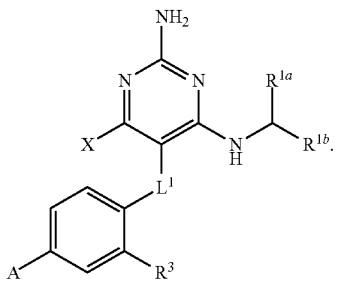

wherein

X is H or CH$_3$;

L¹ is selected from the group consisting of a bond, —CH$_2$—, —O—, —S—, —CF$_2$—,

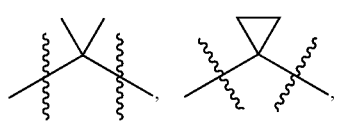

and —CH$_2$CH$_2$—;

A is selected from the group consisting of

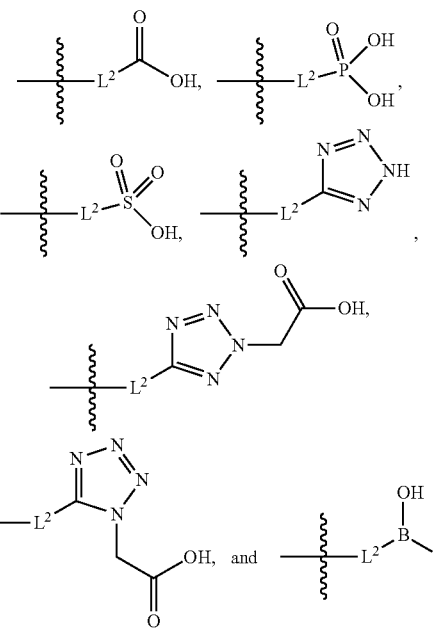

L² is selected from the group consisting of a bond, —CH$_2$—, —CH$_2$CH$_2$—,

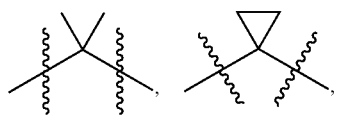

—C(O)NH(CH$_2$)$_n$—, —[O(CH$_2$CH$_2$)]$_n$—, —[O(C$_1$-C$_4$ alkylene)]-, and —[O(CH$_2$CH$_2$)]$_n$—OCH$_2$CH$_2$CF$_2$—;

—C(O)NHCH$_2$CH$_2$—[O(CH$_2$CH$_2$)]$_m$—; and —C(O)NHCH$_2$CH$_2$—[O(CH$_2$CH$_2$)]$_m$—OCH$_2$CH$_2$CF$_2$—; and R$^3$ is H, C$_1$-C$_3$ alkyl, or C$_1$-C$_3$ alkoxy.

The present disclosure provides the compound of Formula (1) that is a compound of Formula (1b),

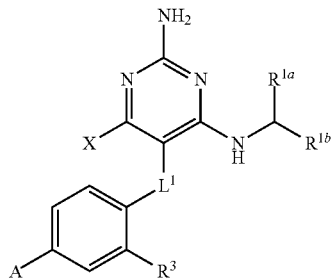

(1b)

wherein

X is H or CH$_3$;

L$^1$ is selected from the group consisting of a bond, —CH$_2$—, —CF$_2$—,

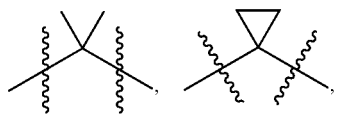

and —CH$_2$CH$_2$—;

A is selected from the group consisting of

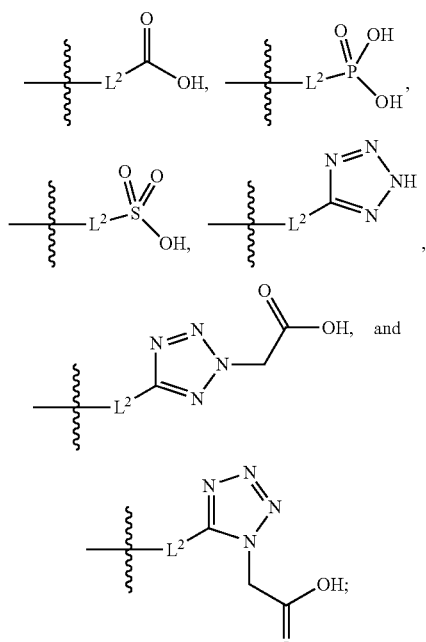

L$^2$ is selected from the group consisting of a bond, —CH$_2$—, —CH$_2$CH$_2$—,

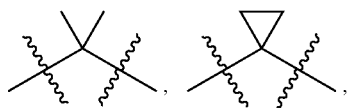

—C(O)NH(CH$_2$)$_n$—, —[O(CH$_2$CH$_2$)]$_n$—, —[O(C$_1$-C$_4$ alkylene)]-, and —[O(CH$_2$CH$_2$)]$_n$—OCH$_2$CH$_2$CF$_2$—; and R$^3$ is H, C$_1$-C$_3$ alkyl, or C$_1$-C$_3$ alkoxy.

The present disclosure provides the compound of Formula (1) that is a compound of Formula (1b),

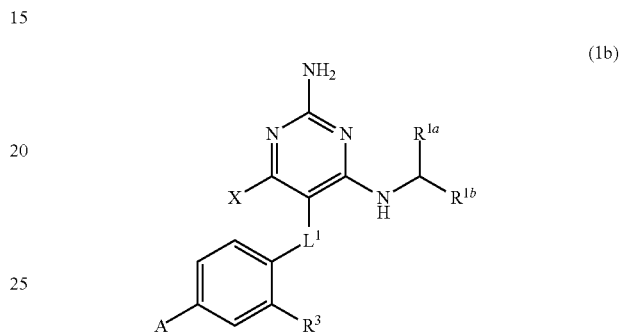

(1b)

wherein

X is —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$;

A$^{1a}$ is selected from the group consisting of

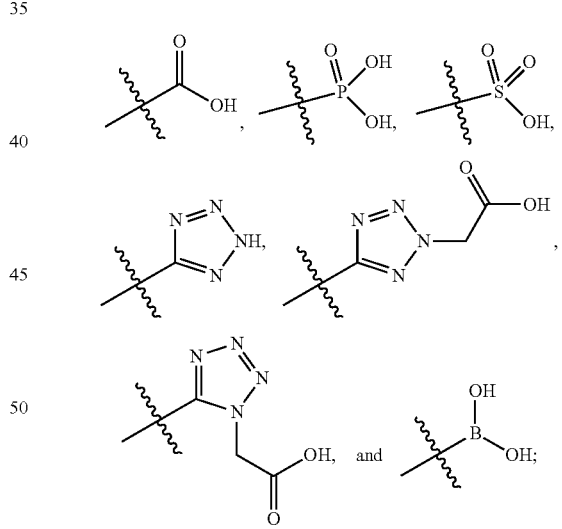

L$^1$ is selected from the group consisting of a bond, —CH$_2$—, —O—, —S—, —CF$_2$—,

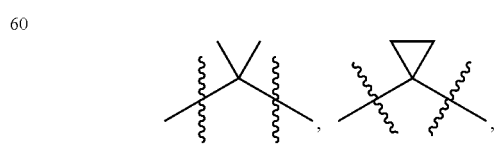

and —CH$_2$CH$_2$—;

A is selected from the group consisting of

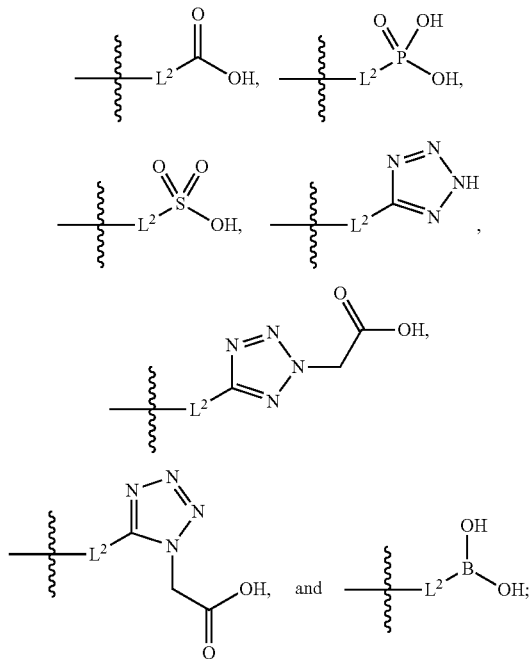

L² is selected from the group consisting of a bond, —CH₂—, —CH₂CH₂—,

—C(O)NH(CH₂)ₙ—, —[O(CH₂CH₂)]ₙ—, —[O(C₁-C₄ alkylene)]-, and —[O(CH₂CH₂)]ₙ—OCH₂CH₂CF₂—; —C(O)NHCH₂CH₂—[O(CH₂CH₂)]ₘ—; and C(O)NHCH₂CH₂—[O(CH₂CH₂)]ₘ—OCH₂CH₂CF₂—; and R³ is H, C₁-C₃ alkyl, or C₁-C₃ alkoxy.

The present disclosure provides the compound of Formula (1) that is a compound of Formula (1b),

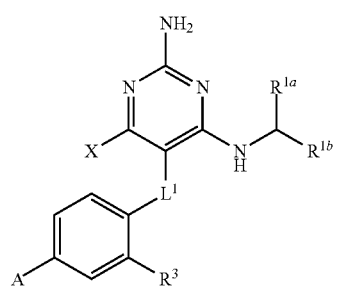

(1b)

wherein

X is —CH₂-A¹ᵃ, —CH₂CH₂-A¹ᵃ, —CH₂CH₂CH₂-A¹ᵃ, or —CH₂C(CH₃)₂-A¹ᵃ;

A¹ᵃ is selected from the group consisting of

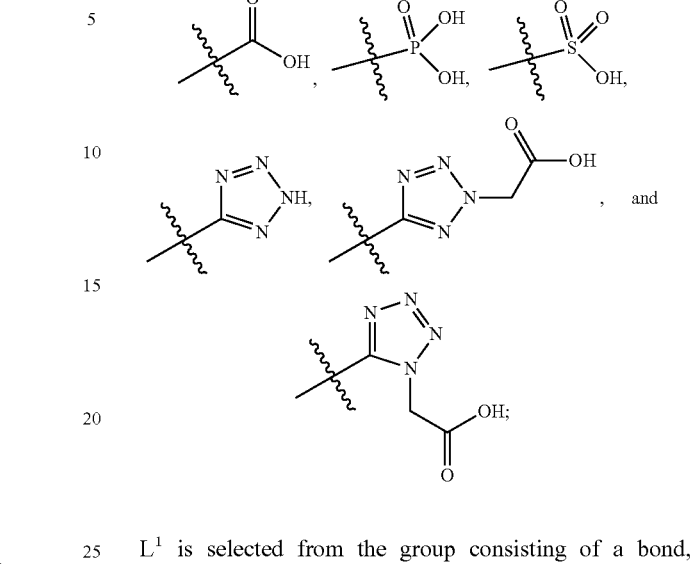

L¹ is selected from the group consisting of a bond, —CH₂—, —CF₂—,

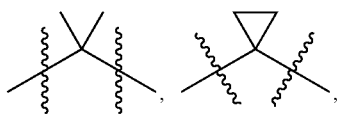

and —CH₂CH₂—;

A is selected from the group consisting of

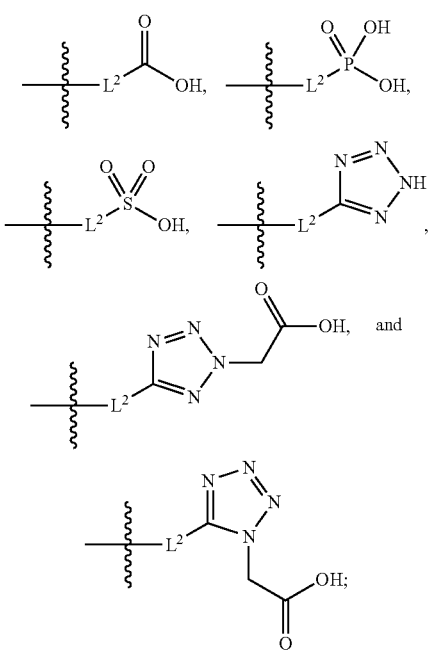

L² is selected from the group consisting of a bond, —CH₂—, —CH₂CH₂—,

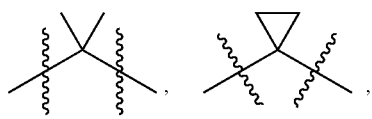

—C(O)NH(CH$_2$)$_n$—,   —[O(CH$_2$CH$_2$)]$_n$—,   —[O(C$_1$-C$_4$ alkylene)]-, and —[O(CH$_2$CH$_2$)]$_n$—OCH$_2$CH$_2$CF$_2$—; and
R$^3$ is H, C$_1$-C$_3$ alkyl, or C$_1$-C$_3$ alkoxy.

The present disclosure provides the compound of Formula (1) that is a compound of Formula (1c),

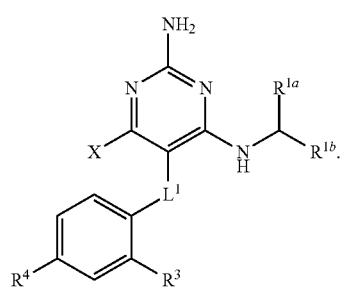
(1c)

wherein
X is —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$;
A$^{1a}$ is selected from the group consisting of

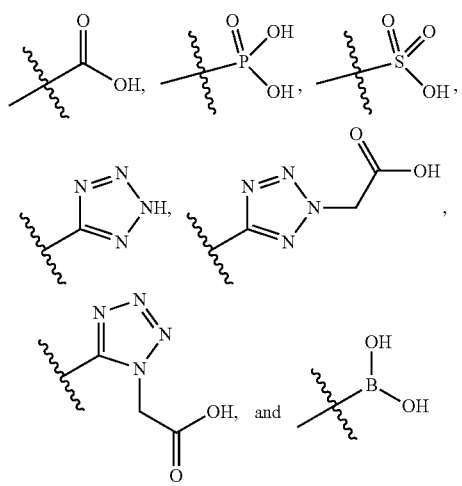

L$^1$ is selected from the group consisting of a bond, —CH$_2$—, —O—, —S—, —CF$_2$—,

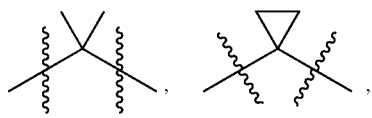

and —CH$_2$CH$_2$—;
R$^3$ is H, C$_1$-C$_3$ alkyl, or C$_1$-C$_3$ alkoxy; and
R$^4$ is H or C$_1$-C$_3$ alkoxy.

The present disclosure provides the compound of Formula (1) that is a compound of Formula (1c),

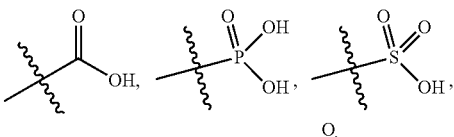
(1c)

wherein
X is —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$;
A$^{1a}$ is selected from the group consisting of

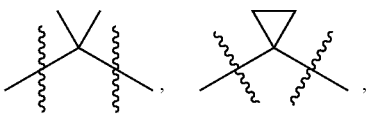

, and

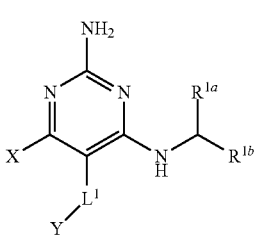

L$^1$ is selected from the group consisting of a bond, —CH$_2$—, —CF$_2$—, (and structures shown)

and —CH$_2$CH$_2$—;
R$^3$ is H, C$_1$-C$_3$ alkyl, or C$_1$-C$_3$ alkoxy; and
R$^4$ is H or C$_1$-C$_3$ alkoxy.

The present disclosure provides the compound of Formula (1) that is a compound of Formula (1d), (1d)

X is —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$;

A$^{1a}$ is selected from the group consisting of

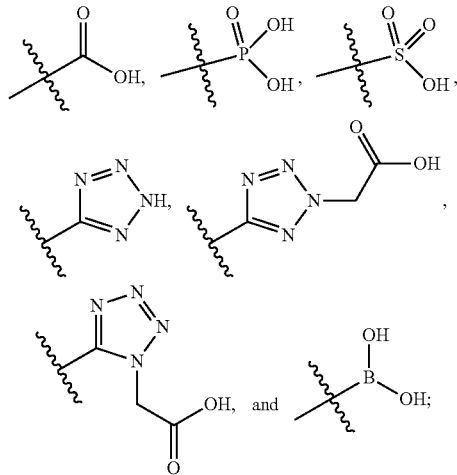

L$^1$ is selected from the group consisting of a bond, —CH$_2$—, —CF$_2$—,

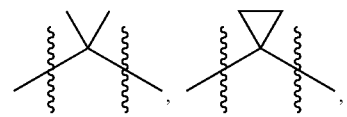

—O—, —CH$_2$CH$_2$, and —S—; and

Y is H or C$_1$-C$_3$ alkyl.

The present disclosure provides the compound of Formula (1) that is a compound of Formula (1d),

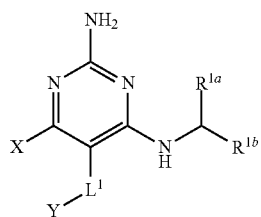

(1d)

X is —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$;

A$^{1a}$ is selected from the group consisting of

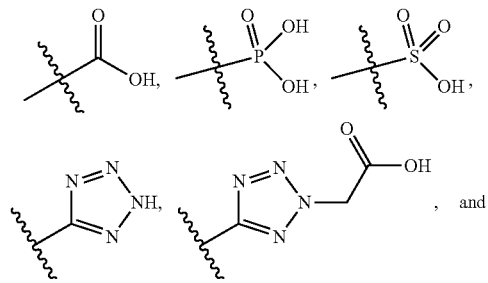

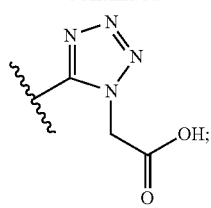

L$^1$ is selected from the group consisting of a bond, —CH$_2$—, —CF$_2$—,

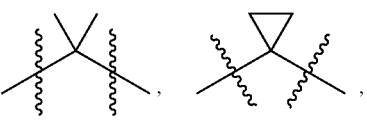

—O—, and —CH$_2$CH$_2$—; and

Y is H or C$_1$-C$_3$ alkyl.

The present disclosure provides the compound of Formula (1) that is a compound of Formula (1e),

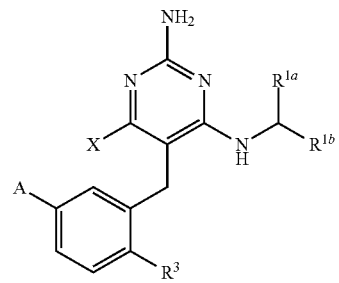

(1e)

wherein

R$^3$ is H, C$_1$-C$_3$ alkyl, or C$_1$-C$_3$ alkoxy.

The present disclosure provides the compound of Formula (1) that is a compound of Formula (1f),

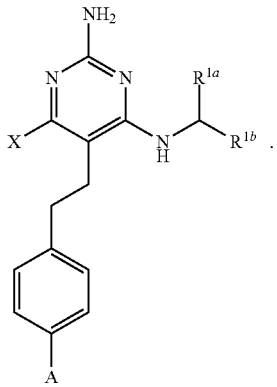

(1f)

The present disclosure provides the compound of Formula (1) that is a compound of Formula (1g),

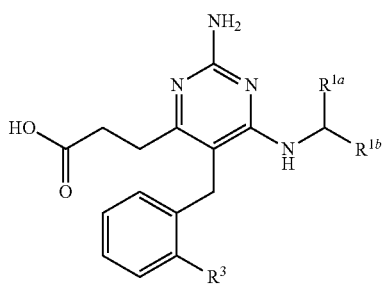
(1g)

wherein
R³ is H, $C_1$-$C_3$ alkyl, or $C_1$-$C_3$ alkoxy.

The present disclosure provides the compound of Formula (1) that is a compound of Formula (1h),

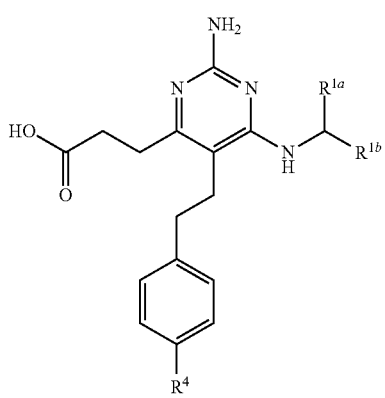
(1h)

wherein
R⁴ is H or $C_1$-$C_3$ alkoxy.

The present disclosure provides the compound of Formula (1) that is a compound of Formula (1i),

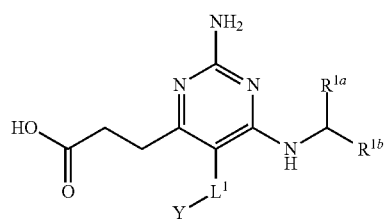
(1i)

wherein
L¹ is selected from the group consisting of a bond, —CH₂—, —CF₂—,

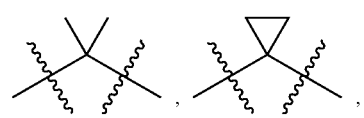

—O—, —CH₂CH₂—, and —S—; and
Y is H or $C_1$-$C_3$ alkyl.

The present disclosure provides the compound of Formula (1) that is a compound of Formula (1i),

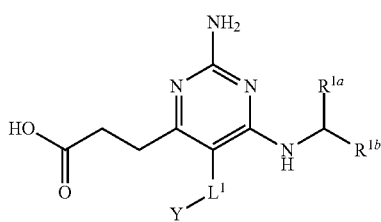
(1i)

wherein
L¹ is selected from the group consisting of a bond, —CH₂—, —CF₂—,

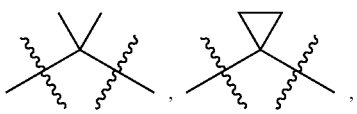

—O—, and —CH₂CH₂—; and
Y is H or $C_1$-$C_3$ alkyl.

The present disclosure provides the compound of Formula (1) that is a compound of Formula (1j),

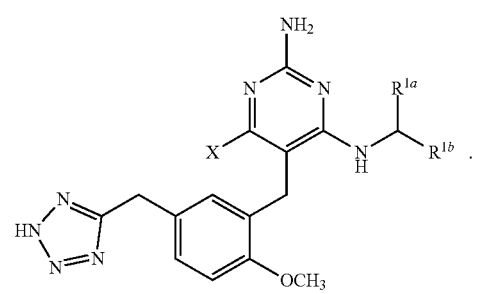
(1j)

The present disclosure provides the compound of Formula (1) that is a compound of Formula (1k),

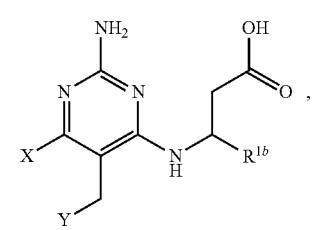
(1k)

The present disclosure provides pharmaceutical compositions comprising a compound of the present disclosure, or a pharmaceutically acceptable salt thereof, and a pharmaceutically acceptable carrier.

The present disclosure provides a method of treating a condition associated with TLR7 modulation in a subject in need thereof, comprising administering to the subject an effective amount of a compound of the present disclosure, or a pharmaceutically acceptable salt thereof. In certain embodiments, the condition is viral infection or cancer.

The present disclosure provides a compound of the present disclosure, or a pharmaceutically acceptable salt thereof, for use in treating a condition associated with TLR7 modulation. In certain embodiments, the condition is viral infection or cancer.

The present disclosure provides use of a compound of the present disclosure, or a pharmaceutically acceptable salt thereof, in the manufacture of a medicament for treating a condition associated with TLR7 modulation. In certain embodiments, the condition is viral infection or cancer.

DETAILED DESCRIPTION

Although specific embodiments of the present disclosure are herein illustrated and described in detail, the invention is not limited thereto. The detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

Definitions

The following definitions are meant to clarify, but not limit, the terms defined. If a particular term used herein is not specifically defined, such term should not be considered indefinite. Rather, terms are used within their accepted meanings.

The term "alkyl" as used herein refers to a straight or branched saturated hydrocarbon. For example, an alkyl group can have 1 to 8 carbon atoms (i.e., ($C_1$-$C_8$)alkyl) or 1 to 6 carbon atoms (i.e., ($C_1$-$C_6$ alkyl) or 1 to 4 carbon atoms.

The term "alkylene" as used herein refers to a straight or branched saturated hydrocarbon radical having two monovalent radical centers derived by the removal of two hydrogen atoms from the same or two different carbon atoms of a parent alkane. For example, an alkylene group can have 1 to 8 carbon atoms, 1 to 6 carbon atoms, or 1 to 4 carbon atoms.

The term "alkoxy" as used herein refers to an alkyl group attached to the parent molecular moiety through an oxygen atom.

The term "halo" or "halogen" as used herein refers to fluoro, chloro, bromo and iodo.

The term "aryl" as used herein refers to a single all carbon aromatic ring or a multiple condensed all carbon ring system wherein at least one of the rings is aromatic. For example, an aryl group can have 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems may be optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring.

The term "heteroaryl" as used herein refers to a single aromatic ring that has at least one atom other than carbon in the ring, wherein the atom is selected from the group consisting of oxygen, nitrogen and sulfur; the term also includes multiple condensed ring systems that have at least one such aromatic ring, which multiple condensed ring systems are further described below. Thus, the term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. The term also includes multiple condensed ring systems (e.g., ring systems comprising 2, 3 or 4 rings) wherein a heteroaryl group, as defined above, can be condensed with one or more rings selected from heteroaryls (to form for example a naphthyridinyl such as 1,8-naphthyridinyl), heterocycles, (to form for example a 1, 2, 3, 4-tetrahydronaphthyridinyl such as 1, 2, 3, 4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system and at any suitable atom of the multiple condensed ring system including a carbon atom and heteroatom (e.g., a nitrogen).

As used herein, the term "pharmaceutically acceptable" refers to carrier(s), diluent(s), excipient(s) or salt forms that are compatible with the other ingredients of the formulation and not deleterious to the recipient of the pharmaceutical composition.

As used herein, the term "pharmaceutical composition" refers to a compound of the present disclosure optionally admixed with one or more pharmaceutically acceptable carriers, diluents, excipients, or adjuvants. Pharmaceutical compositions preferably exhibit a degree of stability to environmental conditions so as to make them suitable for manufacturing and commercialization purposes.

As used herein, the terms "effective amount," "therapeutic amount," or "effective dose" refer to an amount of active ingredient sufficient to elicit the desired pharmacological or therapeutic effects, thus resulting in effective prevention or treatment of a disorder. Prevention of a disorder may be manifested by delaying or preventing the progression of the disorder, as well as delaying or preventing the onset of the symptoms associated with the disorder. Treatment of the disorder may be manifested by a decrease or elimination of symptoms, inhibition or reversal of the progression of the disorder, as well as any other contribution to the well-being of the patient.

The effective dose can vary, depending upon factors such as the condition of the patient, the severity of the symptoms of the disorder, and the manner in which the pharmaceutical composition is administered. Typically, to be administered in an effective dose, compounds are required to be administered in an amount of less than 30 mg/kg of patient weight. Often, the compounds may be administered in an amount from less than about 1 mg/kg patient weight to less than about 100 µg/kg of patient weight, and occasionally between about 10 µg/kg to less than 100 µg/kg of patient weight. The foregoing effective doses typically represent that amount administered as a single dose, or as one or more doses administered over a 24 hours period. For human patients, the effective dose of the compounds may require administering the compound in an amount of at least about 1 mg/24 hr/patient, but not more than about 2400 mg/24 hr/patient, and often not more than about 500 mg/24 hr/patient.

Compounds

The present disclosure provides a compound having the structure of Formula (1), and pharmaceutically acceptable salts thereof,

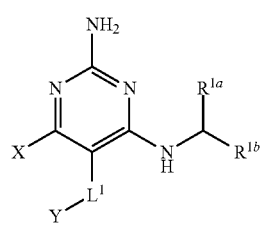

(1)

wherein
$R^{1a}$ is selected from the group consisting of H, $C_1$-$C_4$ alkyl, —$NH_2$, —NHAc, —COOH, —$SO_2CH_3$, —$SCH_3$, —$OCH_3$,

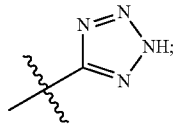 [SMILES: *c1nn[nH]n1]

and A,
wherein the alkyl is optionally substituted with —OH, —$NH_2$, —NHAc, —COOH, —$SO_2CH_3$, —$SCH_3$, —$OCH_3$,

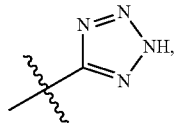 [SMILES: *c1nn[nH]n1]

or A;
$R^{1b}$ is $C_2$-$C_5$ alkyl;
X is selected from the group consisting of H and $C_1$-$C_4$ alkyl, wherein the alkyl is optionally substituted with A, —OH, or —C(CH$_3$)$_2$OH;
$L^1$ is selected from the group consisting of a bond, —$CH_2$—, —$CF_2$—,

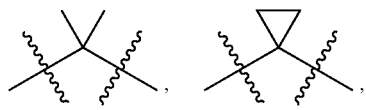

—O—, —S—, —$SO_2$—, —NH—, and —$CH_2CH_2$—;

Y is selected from the group consisting of $C_1$-$C_3$ alkyl, aryl, and heteroaryl, wherein the alkyl, aryl, and heteroaryl are optionally substituted with 1-5 substituents that are independently selected from A, $C_1$-$C_3$ alkyl, and $C_1$-$C_3$ alkoxy;

A is selected from the group consisting of

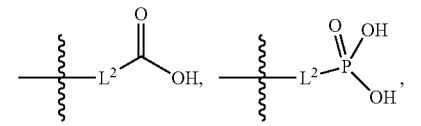

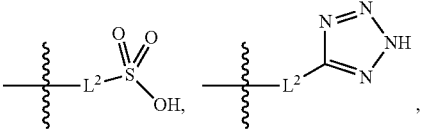

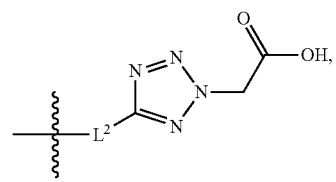

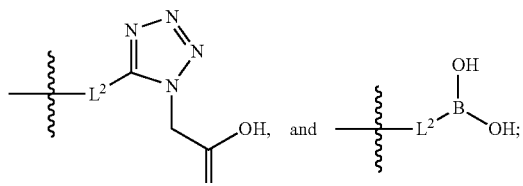

$L^2$ is selected from the group consisting of a bond, —(CH$_2$)$_n$—, —C(O)NH(CH$_2$)$_n$—,

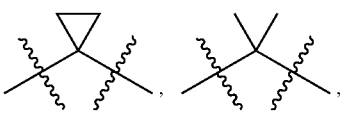

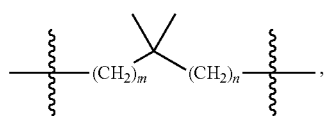

—[O(CH$_2$CH$_2$)]$_n$—, —[O(C$_1$-C$_4$ alkylene)]-, —[O(CH$_2$CH$_2$)]$_n$—OCH$_2$CH$_2$CF$_2$—; —C(O)NHCH$_2$CH$_2$—[O(CH$_2$CH$_2$)]$_m$—; and —C(O)NHCH$_2$CH$_2$—[O(CH$_2$CH$_2$)]$_m$—OCH$_2$CH$_2$CF$_2$—;

m is an integer from zero to four; and
n is an integer from one to four; and
wherein the compound is substituted with at least one A.

The present disclosure provides a compound having the structure of Formula (1), and pharmaceutically acceptable salts thereof,

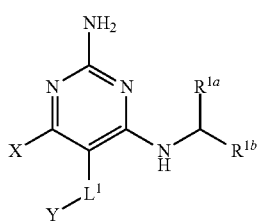

(1)

wherein
$R^{1a}$ is selected from the group consisting of H, $C_1$-$C_4$ alkyl, —$NH_2$, —NHAc, —COOH, —$SO_2CH_3$, —$SCH_3$, —$OCH_3$, and

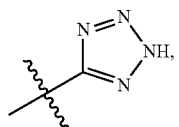 [SMILES: *c1nn[nH]n1]

wherein the alkyl is optionally substituted with —OH, —$NH_2$, —NHAc, —COOH, —$SO_2CH_3$, —$SCH_3$, —$OCH_3$, or

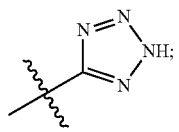 [SMILES: *c1nn[nH]n1]

$R^{1b}$ is $C_2$-$C_5$ alkyl;
X is selected from the group consisting of H and $C_1$-$C_4$ alkyl, wherein the alkyl is optionally substituted with A, —OH, or —$C(CH_3)_2OH$;
$L^1$ is selected from the group consisting of a bond, —$CH_2$—, —$CF_2$—,

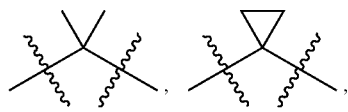

—O—, —S—, —$SO_2$—, —NH—, and —$CH_2CH_2$—;
Y is selected from the group consisting of $C_1$-$C_3$ alkyl, aryl, and heteroaryl, wherein the alkyl, aryl, and heteroaryl are optionally substituted with 1-5 substituents that are independently selected from A, $C_1$-$C_3$ alkyl, and $C_1$-$C_3$ alkoxy;
A is selected from the group consisting of

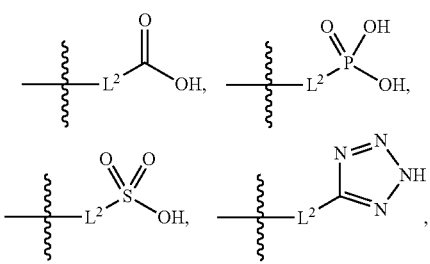

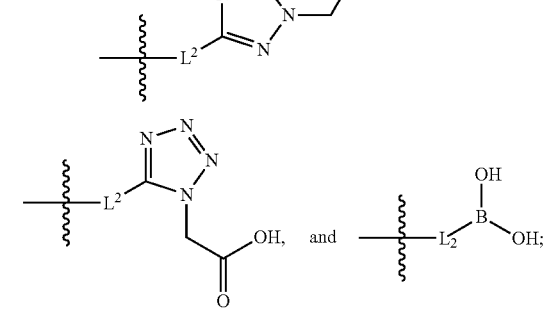

$L^2$ is selected from the group consisting of a bond, —$(CH_2)_n$—, —$C(O)NH(CH_2)_n$—,

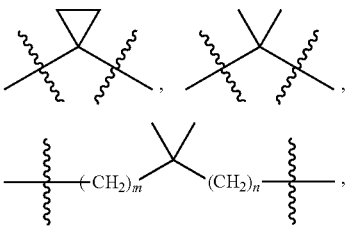

—[$O(CH_2CH_2)$]$_n$—, —[$O(C_1$-$C_4$ alkylene)]-, —[$O(CH_2CH_2)$]$_n$—$OCH_2CH_2CF_2$—; —$C(O)NHCH_2CH_2$—[$O(CH_2CH_2)$]$_m$—; and —$C(O)NHCH_2CH_2$—[$O(CH_2CH_2)$]$_m$—$OCH_2CH_2CF_2$—;

m is an integer from zero to four; and n is an integer from one to four; and wherein the compound is substituted with at least one A.

As disclosed above, $R^{1a}$ is selected from the group consisting of H, $C_1$-$C_4$ alkyl, —$NH_2$, —NHAc, —COOH, —$SO_2CH_3$, —$SCH_3$, —$OCH_3$, and

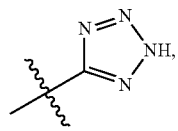

wherein the alkyl is optionally substituted with —OH, —$NH_2$, —NHAc, —COOH, —$SO_2CH_3$, —$SCH_3$, —$OCH_3$, or

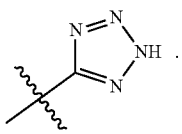 [SMILES: *c1nn[nH]n1]

In certain embodiments, $R^{1a}$ is —COOH, which is a selection among the substituents of A. In certain embodiments, $R^{1a}$ is

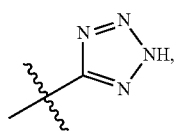

which is a selection among the substituents of A. In certain embodiments, $R^{1a}$ is $C_1$-$C_4$ alkyl, wherein the alkyl is substituted with —COOH, which is a selection among the substituents of A. In certain embodiments, $R^{1a}$ is $C_1$-$C_4$ alkyl, wherein the alkyl is substituted with

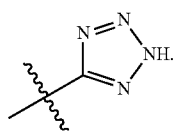

which is a selection among the substituents of A.

The present disclosure provides a compound having the structure of Formula (1), and pharmaceutically acceptable salts thereof,

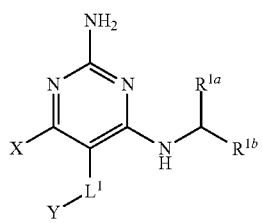

(1)

wherein $R^{1a}$ is selected from the group consisting of H, $C_1$-$C_4$ alkyl, —$NH_2$, —COOH, and —$SO_2CH_3$, wherein the alkyl is optionally substituted with —OH, —$NH_2$, —COOH, or —$SO_2CH_3$;

$R^{1b}$ is $C_2$-$C_5$ alkyl;

X is selected from the group consisting of H and $C_1$-$C_4$ alkyl, wherein the alkyl is optionally substituted with A;

$L^1$ is selected from the group consisting of a bond, —$CH_2$—, —$CF_2$—,

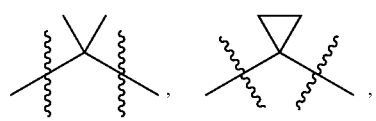

—O—, —S—, —$SO_2$—, —NH—, and —$CH_2CH_2$—;

Y is selected from the group consisting of $C_1$-$C_3$ alkyl, aryl, and heteroaryl, wherein the alkyl, aryl, and heteroaryl are optionally substituted with 1-5 substituents that are independently selected from A, $C_1$-$C_3$ alkyl, and $C_1$-$C_3$ alkoxy;

A is selected from the group consisting of

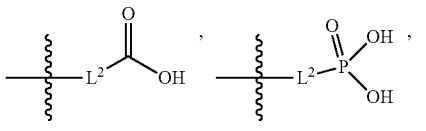

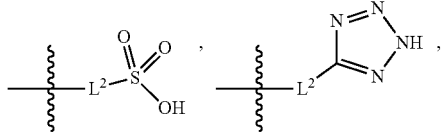

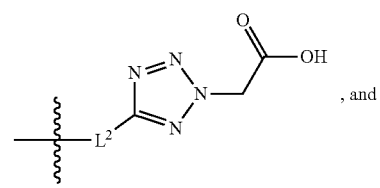

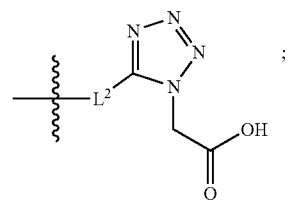

$L^2$ is selected from the group consisting of a bond, —$(CH_2)_n$—, —C(O)NH$(CH_2)_n$—,

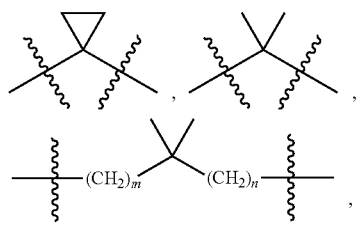

—[O$(CH_2CH_2)]_n$—, —[O($C_1$-$C_4$ alkylene)]-, and —[O$(CH_2CH_2)]_n$—OCH$_2$CH$_2$CF$_2$—;

m is an integer from zero to four; and n is an integer from one to four; and wherein the compound is substituted with at least one A.

In certain embodiments, $R^{1b}$ is $C_3$ alkyl, $C_4$ alkyl, or $C_5$ alkyl. In certain embodiments, $R^{1b}$ is —$(CH_2)_2CH_3$. In certain embodiments, $R^{1b}$ is —$(CH_2)_3CH_3$.

In certain embodiments, $R^{1a}$ is H. In certain embodiments, $R^{1a}$ is $C_1$-$C_4$ alkyl, optionally substituted with —OH. In certain embodiments, $R^{1a}$ is $C_1$-$C_3$ alkyl, optionally substituted with —OH. In certain embodiments, $R^{1a}$ is —$CH_2C(CH_3)_2OH$. In certain embodiments,

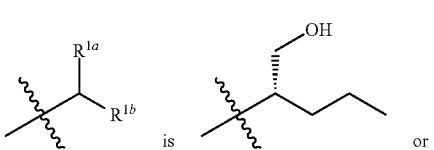

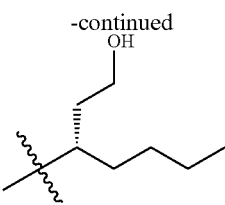

In certain embodiments,

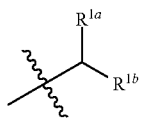

is

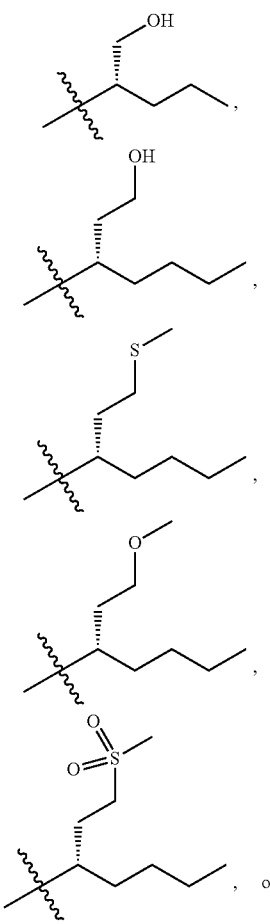

, or

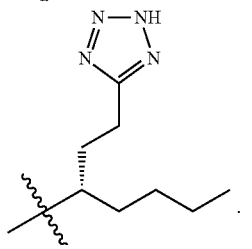

.

In certain embodiments, the stereocenter of the carbon bearing $R^{1A}$ and $R^{1B}$ is an (S)-configuration. In certain embodiments, the stereocenter of the carbon bearing $R^{1A}$ and $R^{1B}$ is an (R)-configuration.

In certain embodiments, $R^{1a}$ is $C_1$-$C_4$ alkyl, optionally substituted with —COOH. In certain embodiments, $R^{1a}$ is $C_1$-$C_3$ alkyl, optionally substituted with —COOH. In certain embodiments,

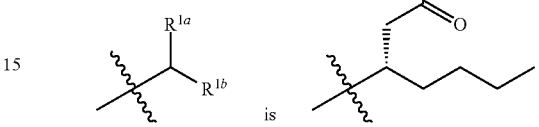

is

.

In certain embodiments, $R^{1a}$ is $C_1$-$C_4$ alkyl, wherein the alkyl is optionally substituted with —OH, —NH$_2$, —COOH, or —SO$_2$CH$_3$. In certain embodiments, $R^{1a}$ is —NH$_2$, —COOH, or —SO$_2$CH$_3$. In certain embodiments, $R^{1a}$ is $C_1$-$C_4$ alkyl, optionally substituted with —OH, —OCH$_3$, —SCH$_3$, or —SO$_2$CH$_3$.

In certain embodiments, X is $C_1$-$C_4$ alkyl, wherein the alkyl is substituted with A. In certain embodiments, X is $C_1$-$C_4$ alkyl, wherein the alkyl is substituted with

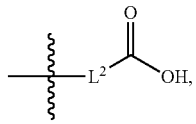

wherein $L^2$ is a bond. In certain embodiments, X is CH$_3$.

In certain embodiments, X is H. In certain embodiments, X is $C_1$-$C_4$ alkyl.

In certain embodiments, $L^1$ is —CH$_2$—, —CH$_2$CH$_2$—, or —O—. In certain embodiments, $L^1$ is —CH$_2$—. In certain embodiments, $L^1$ is —CH$_2$—, —CH$_2$CH$_2$—, —O—, or —S—.

In certain embodiments, $L^1$ is a bond, —CF$_2$—,

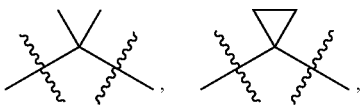

—S—, —SO$_2$—, or —NH—.

In certain embodiments, Y is $C_1$-$C_3$ alkyl or aryl. In certain embodiments, Y is aryl, wherein the aryl is substituted with $C_1$-$C_3$ alkoxy. In certain embodiments, Y is aryl, wherein the aryl is substituted with A. In certain embodiments, Y is aryl, wherein the aryl is substituted with $C_1$-$C_3$ alkoxy and A.

In certain embodiments, Y is heteroaryl, wherein the heteroaryl is optionally substituted with 1-5 substituents that are independently selected from A, $C_1$-$C_3$ alkyl, and $C_1$-$C_3$ alkoxy. In certain embodiments, Y is $C_1$-$C_3$ alkyl, wherein the alkyl is optionally substituted with 1-5 substituents that are independently selected from A, $C_1$-$C_3$ alkyl, and $C_1$-$C_3$ alkoxy. In certain embodiments, Y is aryl, wherein the aryl is optionally substituted with 1-5 substituents that are independently selected from A, $C_1$-$C_3$ alkyl, and $C_1$-$C_3$ alkoxy.

In certain embodiments, A is

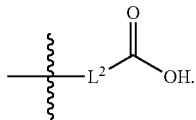

In certain embodiments, A is

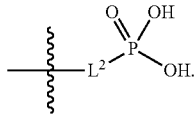

In certain embodiments, A is

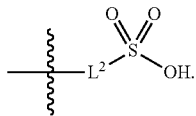

In certain embodiments, A is

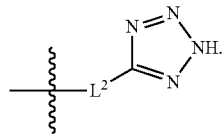

In certain embodiments, A is

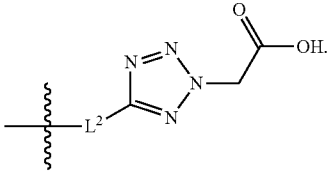

In certain embodiments, A is

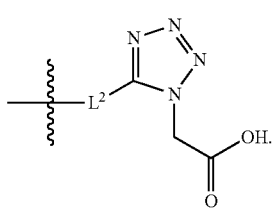

In certain embodiments, $L^2$ is —$(CH_2)_n$—. In certain embodiments, $L^2$ is

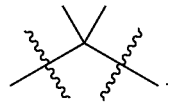 [SMILES: *C(*)(C)C]

In certain embodiments, $L^2$ is

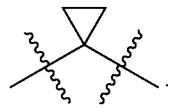 [SMILES: *C1(*)CC1]

In certain embodiments, $L^2$ is —C(O)NH(CH$_2$)$_n$—.

In certain embodiments, $L^2$ is a bond,

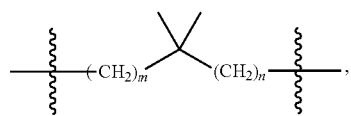

—[O(CH$_2$CH$_2$)]$_n$—, —[O(C$_1$-C$_4$ alkylene)]-, or —[O(CH$_2$CH$_2$)]$_n$—OCH$_2$CH$_2$CF$_2$—.

In certain embodiments, n is one or two. In certain embodiments, n is one. In certain embodiments, n is two. In certain embodiments, n is three. In certain embodiments, n is four.

In certain embodiments, m is zero. In certain embodiments, m is one. In certain embodiments, m is two. In certain embodiments, m is three. In certain embodiments, m is four.

The present disclosure provides a compound of Formula (1), having the structure of Formula (1a), and pharmaceutically acceptable salts thereof,

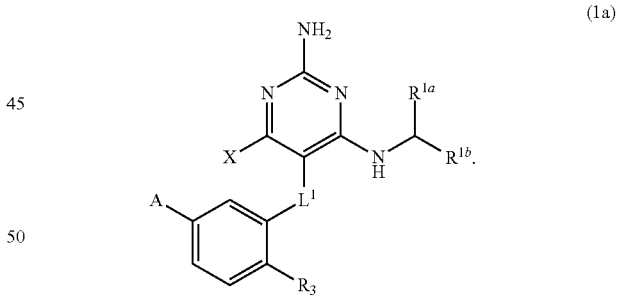

(1a)

In certain embodiment of Formula (1a),

X is H or CH$_3$;

$L^1$ is selected from the group consisting of a bond, —CH$_2$—, —O—, —S—, —CF$_2$—,

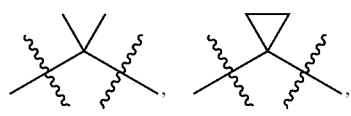

and —CH$_2$CH$_2$—;

A is selected from the group consisting of

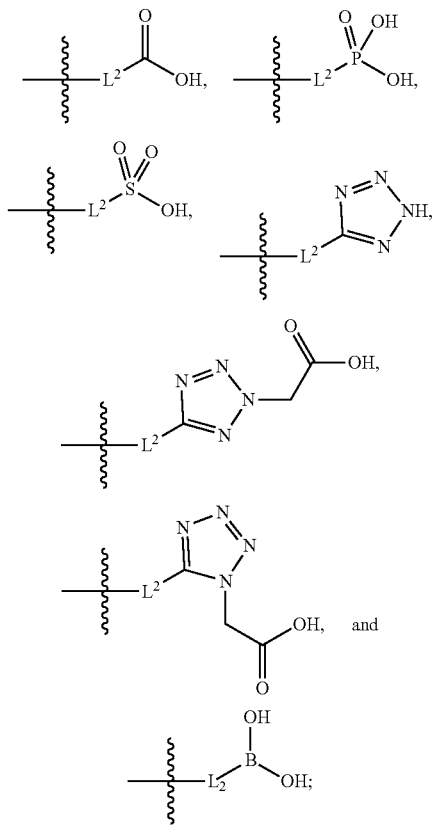

L² is selected from the group consisting of a bond, —CH₂—, —CH₂CH₂—,

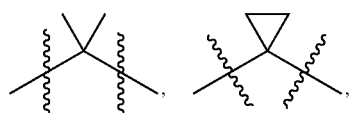

—C(O)NH(CH₂)$_n$—, —[O(CH₂CH₂)]$_n$—, —[O(C₁-C₄ alkylene)]-, and —[O(CH₂CH₂)]$_n$—OCH₂CH₂CF₂—; —C(O)NHCH₂CH₂—[O(CH₂CH₂)]$_m$—; and C(O)NHCH₂CH₂—[O(CH₂CH₂)]$_m$—OCH₂CH₂CF₂—; and R³ is H, C₁-C₃ alkyl, or C₁-C₃ alkoxy.

In another embodiment of Formula (1a),

X is H or CH₃;

L¹ is selected from the group consisting of a bond, —CH₂—, —CF₂—,

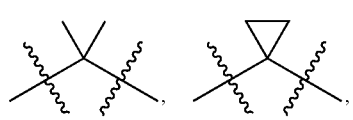

and —CH₂CH₂—;

A is selected from the group consisting of

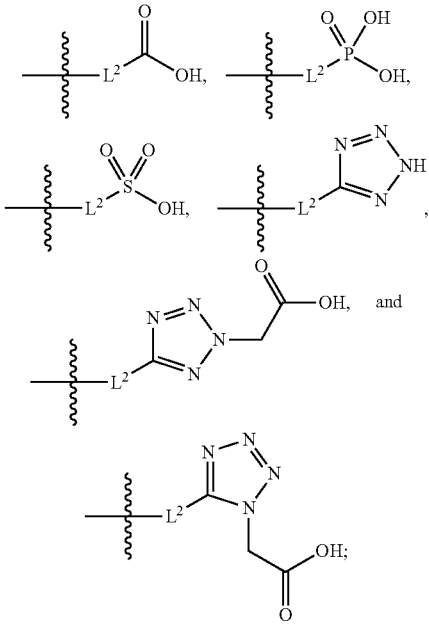

L² is selected from the group consisting of a bond, —CH₂—, —CH₂CH₂—,

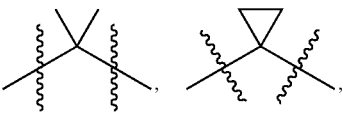

—C(O)NH(CH₂)$_n$—, —[O(CH₂CH₂)]$_n$—, —[O(C₁-C₄ alkylene)]-, and —[O(CH₂CH₂)]$_n$—OCH₂CH₂CF₂—; and R³ is H, C₁-C₃ alkyl, or C₁-C₃ alkoxy.

As disclosed above, in certain embodiments, X may be —CH₂-A$^{1a}$, —CH₂CH₂-A$^{1a}$, —CH₂CH₂CH₂-A$^{1a}$, or —CH₂C(CH₃)₂-A$^{1a}$; wherein A$^{1a}$ is selected from the group consisting of

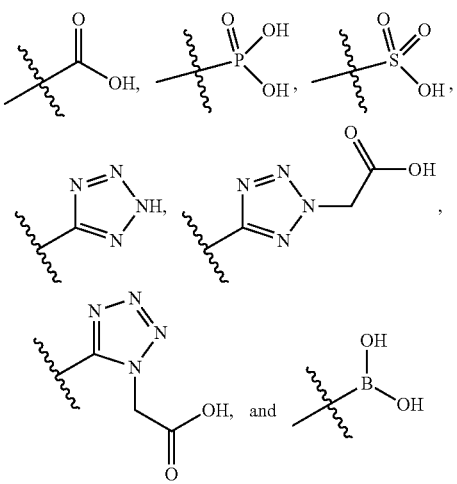

or $A^{1a}$ is selected from the group consisting of

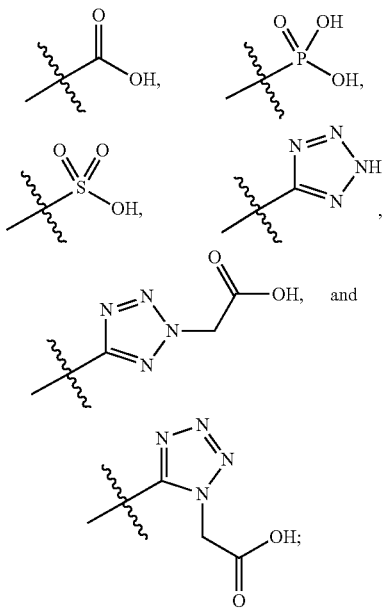

In the above, X comprises $A^{1a}$, which is a selection among the substituents of A.

Accordingly, in certain embodiments, X may be —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$; wherein A$^{1a}$ is A;

wherein A is selected from the group consisting of

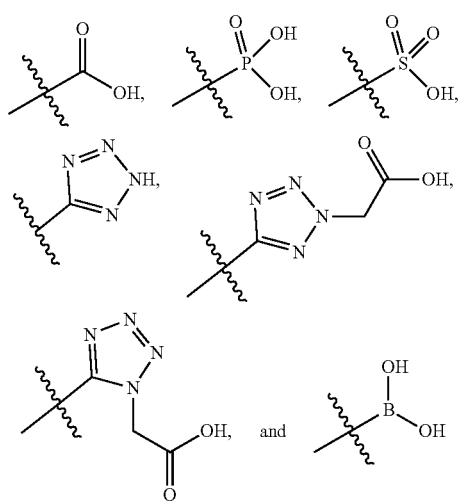

and $L^2$ is a bond.

Accordingly, in certain embodiments, X may be —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$; wherein A$^{1a}$ is A;

wherein A is selected from the group consisting of

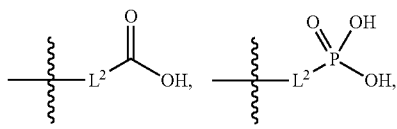

-continued

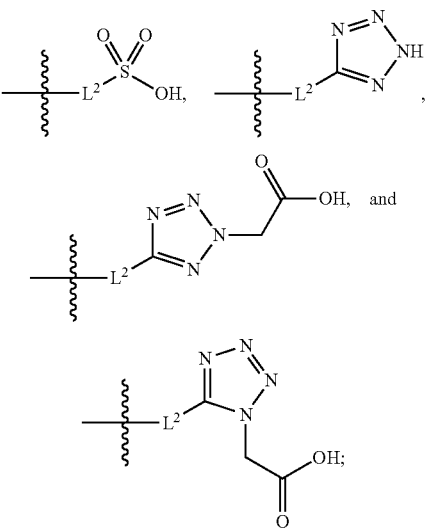

and $L^2$ is a bond.

In another embodiment of Formula (1a),

X is —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$;

$A^{1a}$ is selected from the group consisting of

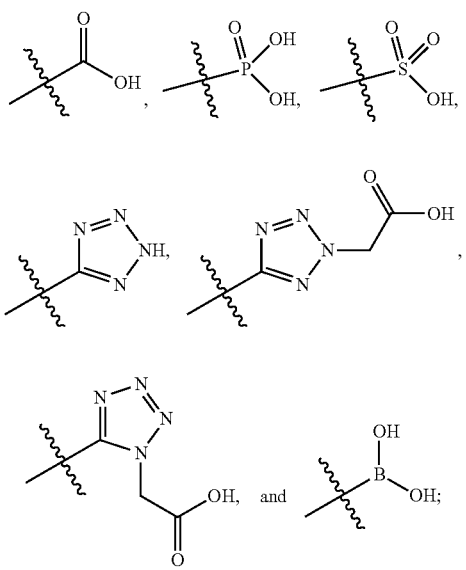

$L^1$ is selected from the group consisting of a bond, —CH$_2$—, —O—, —S—, —CF$_2$—,

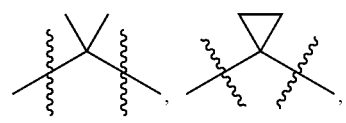

and —CH$_2$CH$_2$—;

A is selected from the group consisting of

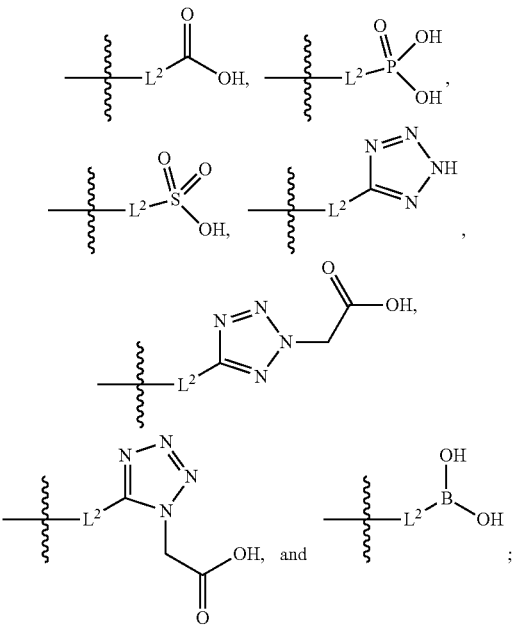

$L^2$ is selected from the group consisting of a bond, —CH$_2$—, —CH$_2$CH$_2$—,

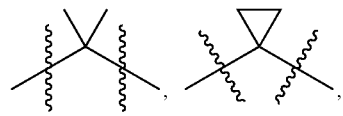

—C(O)NH(CH$_2$)$_n$—, —[O(CH$_2$CH$_2$)]$_n$—, —[O(C$_1$-C$_4$ alkylene)]-, and —[O(CH$_2$CH$_2$)]$_n$—OCH$_2$CH$_2$CF$_2$—; —C(O)NHCH$_2$CH$_2$—[O(CH$_2$CH$_2$)]$_m$—; and C(O)NHCH$_2$CH$_2$—[O(CH$_2$CH$_2$)]$_m$—OCH$_2$CH$_2$CF$_2$—; and $R^3$ is H, C$_1$-C$_3$ alkyl, or C$_1$-C$_3$ alkoxy.

In another embodiment of Formula (1a),

X is —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$;

A$^{1a}$ is selected from the group consisting of

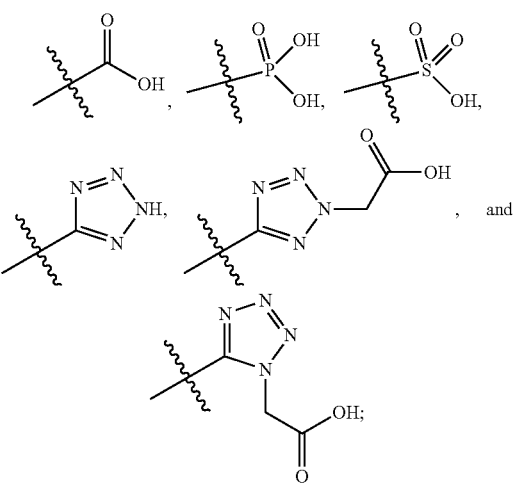

$L^1$ is selected from the group consisting of a bond, —CH$_2$—, —CF$_2$—,

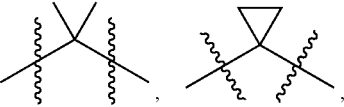

and —CH$_2$CH$_2$—;

A is selected from the group consisting of

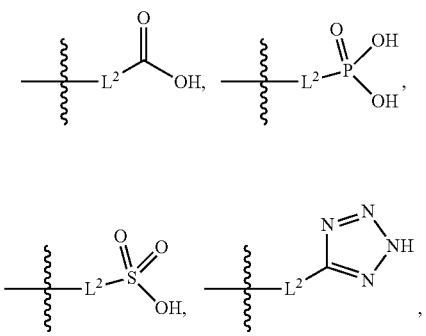

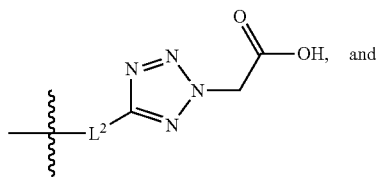

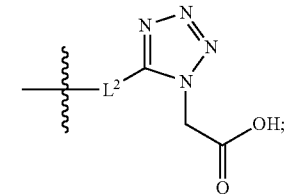

$L^2$ is selected from the group consisting of a bond, —CH$_2$—, —CH$_2$CH$_2$—,

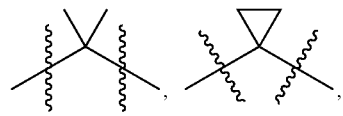

—C(O)NH(CH$_2$)$_n$—, —[O(CH$_2$CH$_2$)]$_n$—, —[O(C$_1$-C$_4$ alkylene)]-, and —[O(CH$_2$CH$_2$)]$_n$—OCH$_2$CH$_2$CF$_2$—; and $R^3$ is H, C$_1$-C$_3$ alkyl, or C$_1$-C$_3$ alkoxy.

The present disclosure provides a compound of Formula (1), having the structure of Formula (1b), and pharmaceutically acceptable salts thereof,

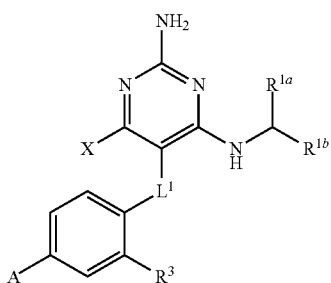 (1b)

In certain embodiment of Formula (1b),

X is H or CH$_3$;

L$^1$ is selected from the group consisting of a bond, —CH$_2$—, —O—, —S—, —CF$_2$—,

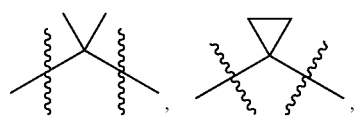

and —CH$_2$CH$_2$—;

A is selected from the group consisting of

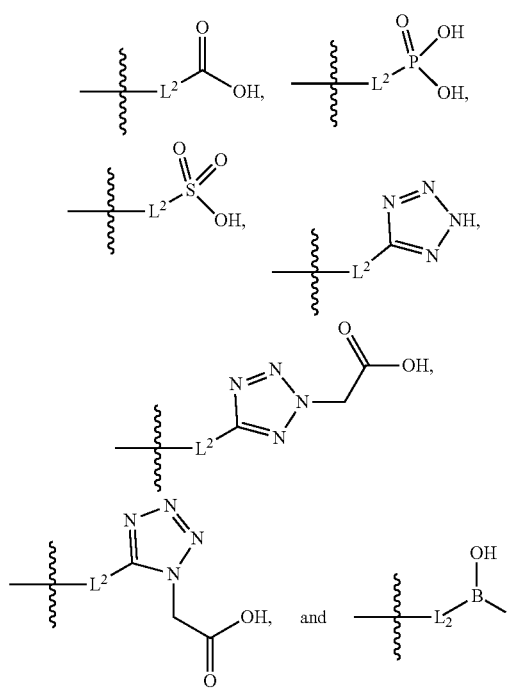

L$^2$ is selected from the group consisting of a bond, —CH$_2$—, —CH$_2$CH$_2$—,

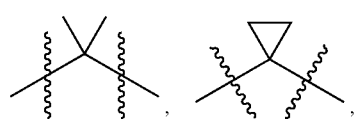

—C(O)NH(CH$_2$)$_n$—, —[O(CH$_2$CH$_2$)]$_n$—, —[O(C$_1$-C$_4$ alkylene)]-, and —[O(CH$_2$CH$_2$)]$_n$—OCH$_2$CH$_2$CF$_2$—; —C(O)NHCH$_2$CH$_2$—[O(CH$_2$CH$_2$)]$_m$—; and C(O)NHCH$_2$CH$_2$—[O(CH$_2$CH$_2$)]$_m$—OCH$_2$CH$_2$CF$_2$—; and R$^3$ is H, C$_1$-C$_3$ alkyl, or C$_1$-C$_3$ alkoxy.

In another embodiment of Formula (1b),

X is H or CH$_3$;

L$^1$ is selected from the group consisting of a bond, —CH$_2$—, —CF$_2$—,

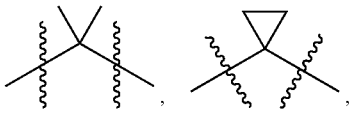

and —CH$_2$CH$_2$—;

A is selected from the group consisting of

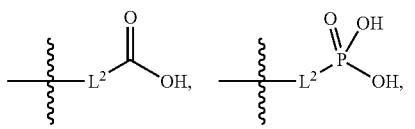

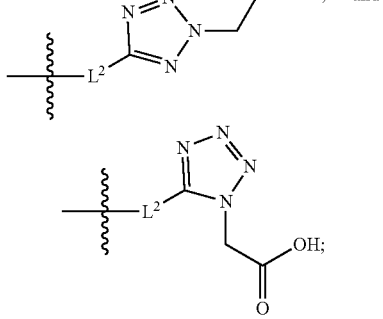

L$^2$ is selected from the group consisting of a bond, —CH$_2$—, —CH$_2$CH$_2$—,

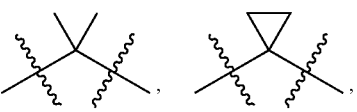

—C(O)NH(CH$_2$)$_n$—, —[O(CH$_2$CH$_2$)]$_n$—, —[O(C$_1$-C$_4$ alkylene)]-, and —[O(CH$_2$CH$_2$)]$_n$—OCH$_2$CH$_2$CF$_2$—; and R$^3$ is H, C$_1$-C$_3$ alkyl, or C$_1$-C$_3$ alkoxy.

As disclosed above, in certain embodiments, X may be —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$; wherein A$^{1a}$ is selected from the group consisting of

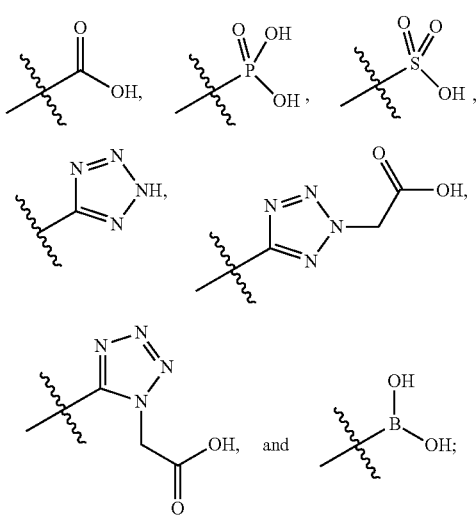

or $A^{1a}$ is selected from the group consisting of

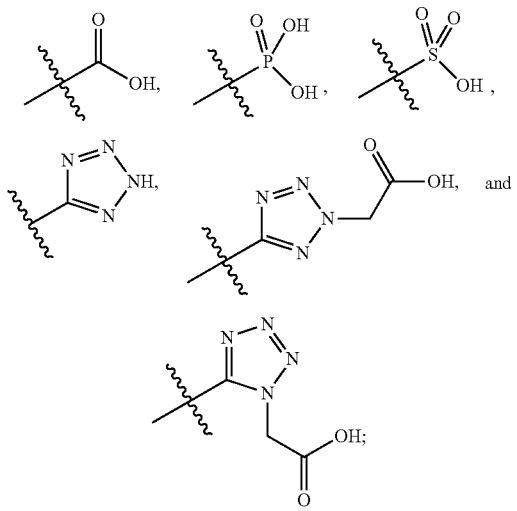

In the above, X comprises $A^{1a}$, which is a selection among the substituents of A.

Accordingly, in certain embodiments, X may be —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$; wherein A$^{1a}$ is A;

wherein A is selected from the group consisting of

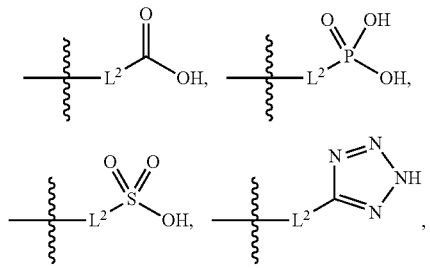

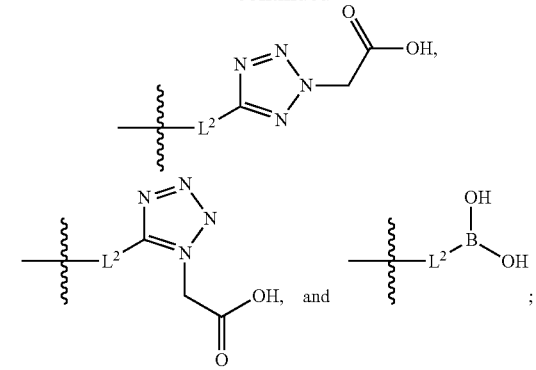

and $L^2$ is a bond.

Accordingly, in certain embodiments, X may be —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$; wherein A$^{1a}$ is A;

wherein A is selected from the group consisting of

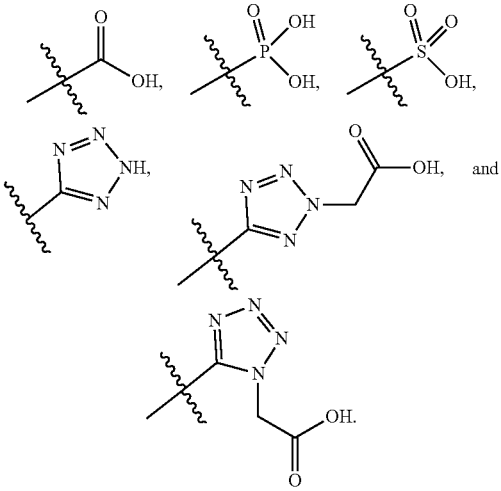

and $L^2$ is a bond.

In another embodiment of Formula (1b),

X is —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$;

$A^{1a}$ is selected from the group consisting of

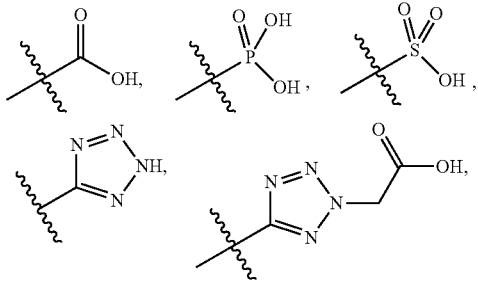

-continued

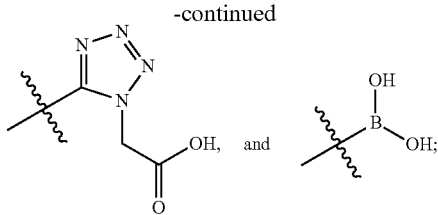

$L^1$ is selected from the group consisting of a bond, —CH$_2$—, —O—, —S—, —CF$_2$—,

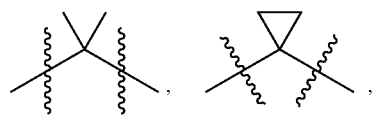

and —CH$_2$CH$_2$—;
A is selected from the group consisting of

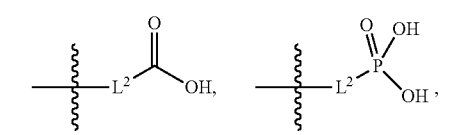

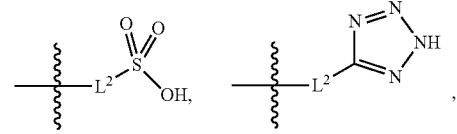

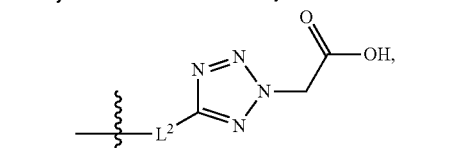

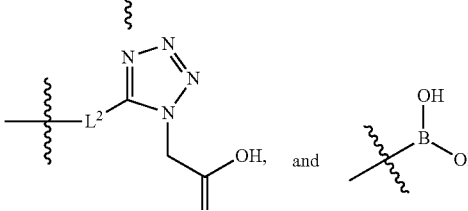

$L^2$ is selected from the group consisting of a bond, —CH$_2$—, —CH$_2$CH$_2$—,

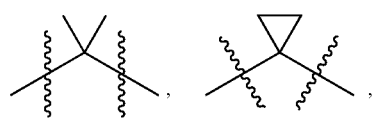

—C(O)NH(CH$_2$)$_n$—, —[O(CH$_2$CH$_2$)]$_n$—, —[O(C$_1$-C$_4$ alkylene)]-, and —[O(CH$_2$CH$_2$)]$_n$—OCH$_2$CH$_2$CF$_2$—; —C(O)NHCH$_2$CH$_2$—[O(CH$_2$CH$_2$)]$_m$—; and C(O)NHCH$_2$CH$_2$—[O(CH$_2$CH$_2$)]$_m$—OCH$_2$CH$_2$CF$_2$—; and
$R^3$ is H, C$_1$-C$_3$ alkyl, or C$_1$-C$_3$ alkoxy.

In another embodiment of Formula (1b),
X is —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$;

$A^{1a}$ is selected from the group consisting of

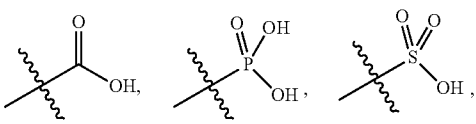

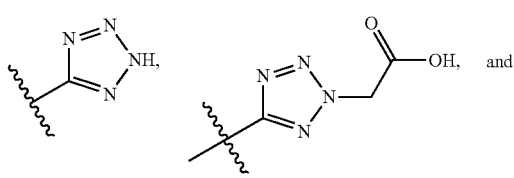

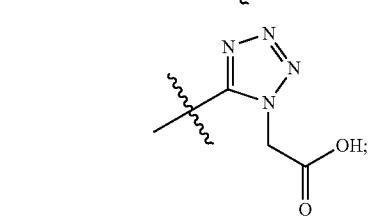

$L^1$ is selected from the group consisting of a bond, —CH$_2$—, —CF$_2$—,

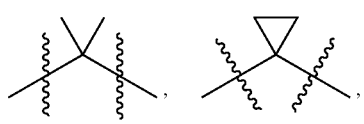

and —CH$_2$CH$_2$—;
A is selected from the group consisting of

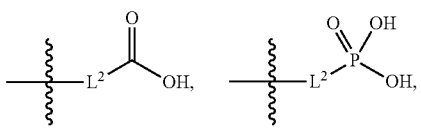

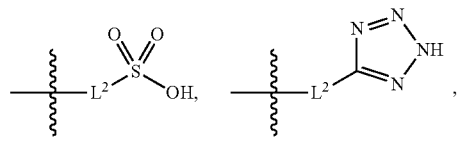

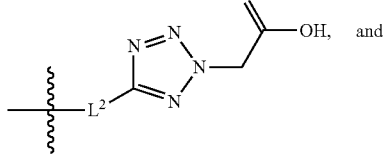

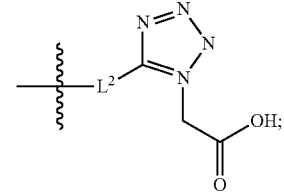

$L^2$ is selected from the group consisting of a bond, —CH$_2$—, —CH$_2$CH$_2$—,

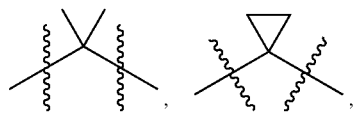

—C(O)NH(CH$_2$)$_n$—, —[O(CH$_2$CH$_2$)]$_n$—, —[O(C$_1$-C$_4$ alkylene)]-, and —[O(CH$_2$CH$_2$)]$_n$—OCH$_2$CH$_2$CF$_2$—; and R$^3$ is H, C$_1$-C$_3$ alkyl, or C$_1$-C$_3$ alkoxy.

The present disclosure provides a compound of Formula (1), having the structure of Formula (1c), and pharmaceutically acceptable salts thereof,

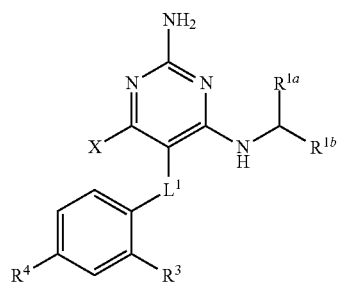

(1c)

As disclosed above, in certain embodiments, X may be —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$; wherein A$^{1a}$ is selected from the group consisting of

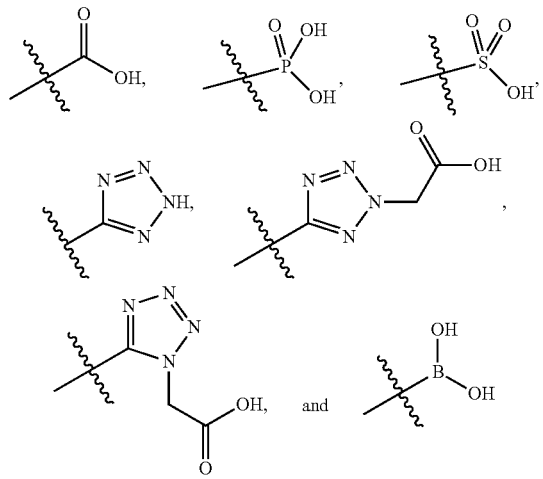

or A$^{1a}$ is selected from the group consisting of

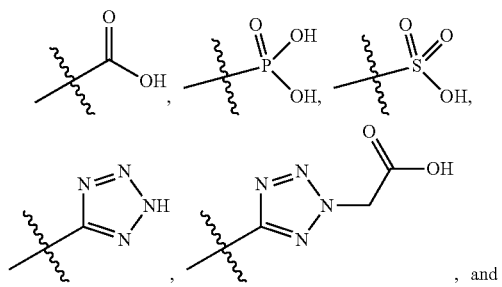

, and

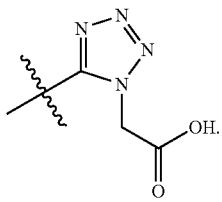

In the above, X comprises A$^{1a}$, which is a selection among the substituents of A.

Accordingly, in certain embodiments, X may be —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$; wherein A$^{1a}$ is A;

wherein A is selected from the group consisting of

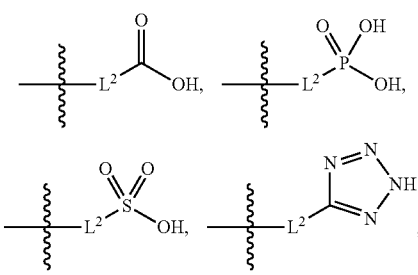

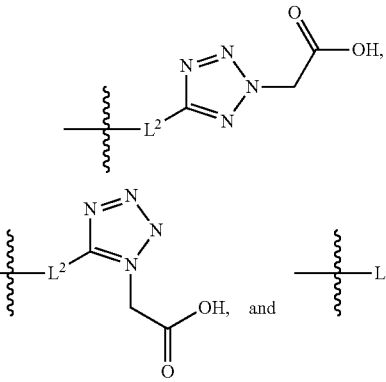

and

L$^2$ is a bond.

Accordingly, in certain embodiments, X may be —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$; wherein A$^{1a}$ is A;

wherein A is selected from the group consisting of

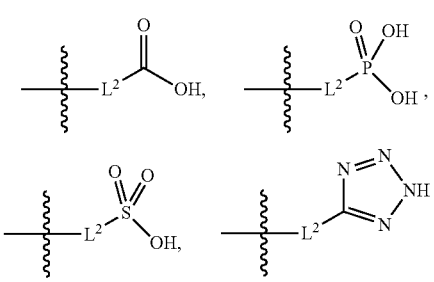

53

-continued

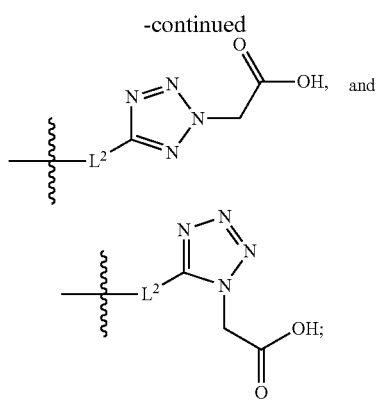

and
L² is a bond.
In certain embodiment of Formula (1c),
X is —CH₂-A¹ᵃ, —CH₂CH₂-A¹ᵃ, —CH₂CH₂CH₂-A¹ᵃ, or —CH₂C(CH₃)₂-A¹ᵃ;
A¹ᵃ is selected from the group consisting of

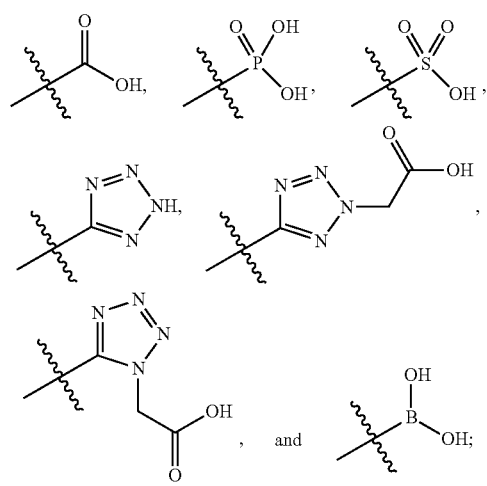

L¹ is selected from the group consisting of a bond, —CH₂—, —O—, —S—, —CF₂—,

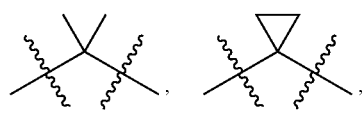

and —CH₂CH₂—;
R³ is H, C₁-C₃ alkyl, or C₁-C₃ alkoxy; and
R⁴ is H or C₁-C₃ alkoxy.
In another embodiment of Formula (1c),
X is —CH₂-A¹ᵃ, —CH₂CH₂-A¹ᵃ, —CH₂CH₂CH₂-A¹ᵃ, or —CH₂C(CH₃)₂-A¹ᵃ;
A¹ᵃ is selected from the group consisting of

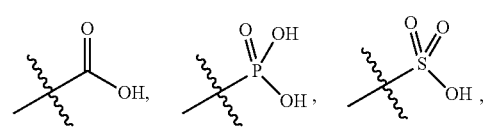

54

-continued

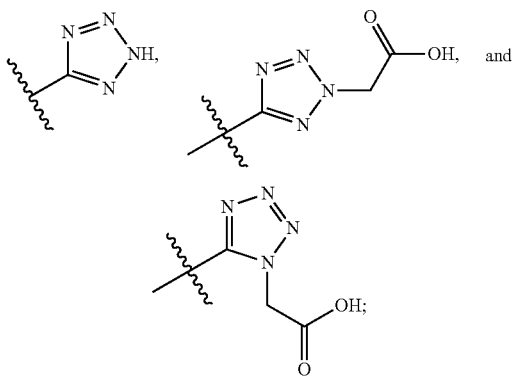

L¹ is selected from the group consisting of a bond, —CH₂—, —CF₂—,

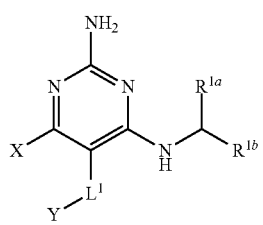

and —CH₂CH₂—;
R³ is H, C₁-C₃ alkyl, or C₁-C₃ alkoxy; and
R⁴ is H or C₁-C₃ alkoxy.

The present disclosure provides a compound of Formula (1), having the structure of Formula (1d), and pharmaceutically acceptable salts thereof, (1d)

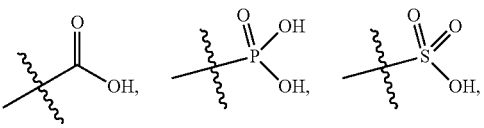

As disclosed above, in certain embodiments, X may be —CH₂-A¹ᵃ, —CH₂CH₂-A¹ᵃ, —CH₂CH₂CH₂-A¹ᵃ, or —CH₂C(CH₃)₂-A¹ᵃ; wherein A¹ᵃ is selected from the group consisting of

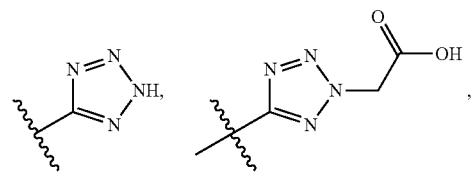

-continued

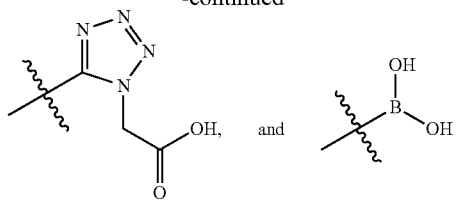

or $A^{1a}$ is selected from the group consisting of

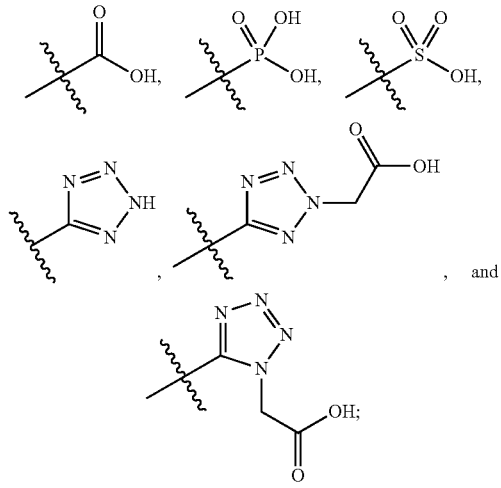

In the above, X comprises $A^{1a}$, which is a selection among the substituents of A.

Accordingly, in certain embodiments, X may be —$CH_2$-$A^{1a}$, —$CH_2CH_2$-$A^{1a}$, —$CH_2CH_2CH_2$-$A^{1a}$, or —$CH_2C(CH_3)_2$-$A^{1a}$; wherein $A^{1a}$ is A;

wherein A is selected from the group consisting of

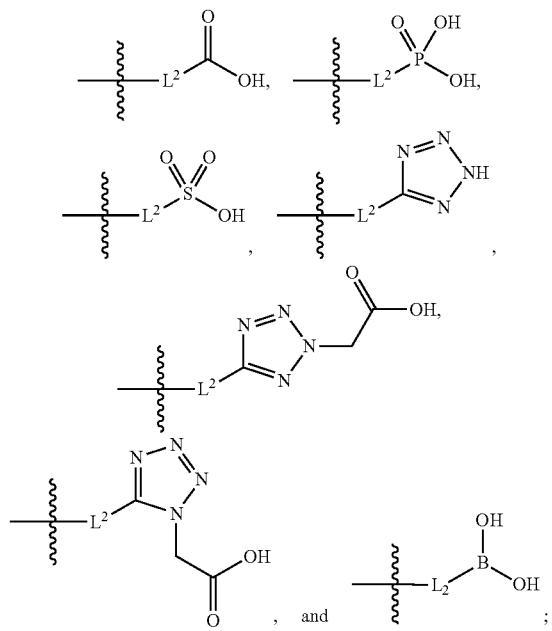

and $L^2$ is a bond.

Accordingly, in certain embodiments, X may be —$CH_2$-$A^{1a}$, —$CH_2CH_2$-$A^{1a}$, —$CH_2CH_2CH_2$-$A^{1a}$, or —$CH_2C(CH_3)_2$-$A^{1a}$; wherein $A^{1a}$ is A;

wherein A is selected from the group consisting of

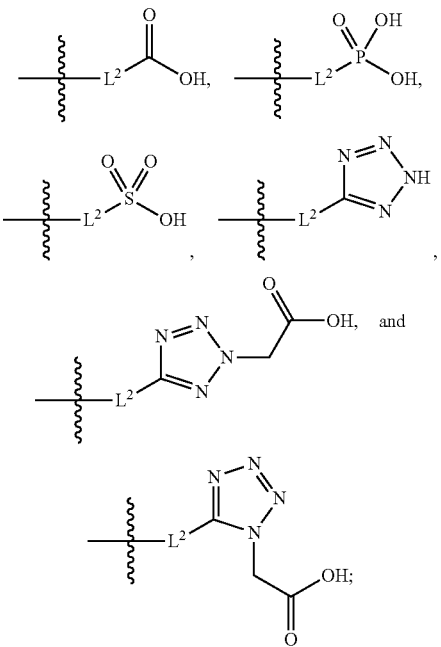

and $L^2$ is a bond.

In certain embodiment of Formula (1d),

X is —$CH_2$-$A^{1a}$, —$CH_2CH_2$-$A^{1a}$, —$CH_2CH_2CH_2$-$A^{1a}$, or —$CH_2C(CH_3)_2$-$A^{1a}$;

$A^{1a}$ is selected from the group consisting of

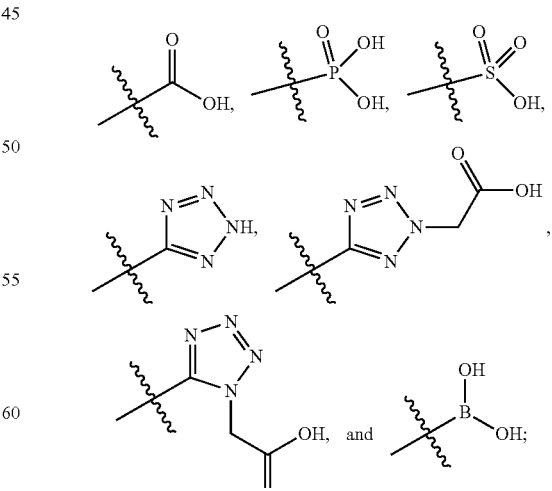

$L^1$ is selected from the group consisting of a bond, —$CH_2$—, —$CF_2$—,

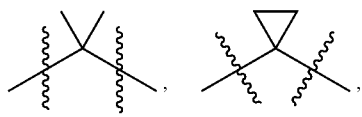

—O—, —CH$_2$CH$_2$, and —S—; and
Y is H or C$_1$-C$_3$ alkyl.

In another embodiment of Formula (1d),
X is —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$;
A$^{1a}$ is selected from the group consisting of

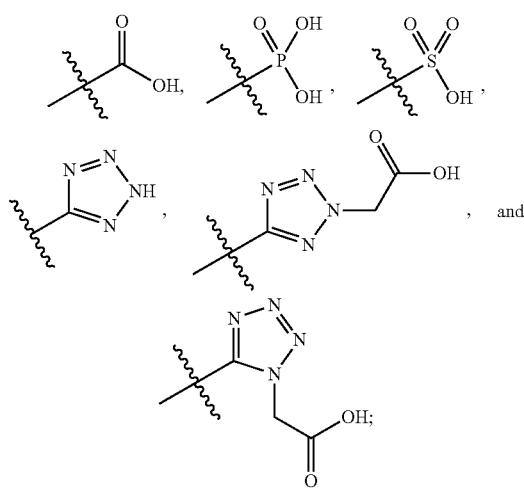

, and

L$^1$ is selected from the group consisting of a bond, —CH$_2$—, —CF$_2$—,

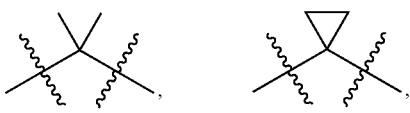

—O—, and —CH$_2$CH$_2$—; and
Y is H or C$_1$-C$_3$ alkyl.

The present disclosure provides a compound of Formula (1), having the structure of Formula (1e), and pharmaceutically acceptable salts thereof,

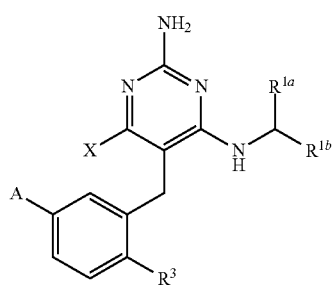

(1e)

wherein R$^3$ is H, C$_1$-C$_3$ alkyl, or C$_1$-C$_3$ alkoxy.

The present disclosure provides a compound of Formula (1), having the structure of Formula (1f), and pharmaceutically acceptable salts thereof,

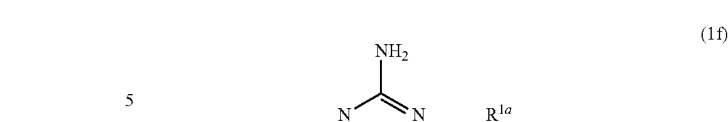

(1f)

The present disclosure provides a compound of Formula (1), having the structure of Formula (1g), and pharmaceutically acceptable salts thereof,

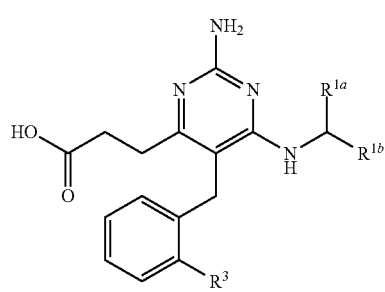

(1g)

wherein R$^3$ is H, C$_1$-C$_3$ alkyl, or C$_1$-C$_3$ alkoxy.

The present disclosure provides a compound of Formula (1), having the structure of Formula (1h), and pharmaceutically acceptable salts thereof,

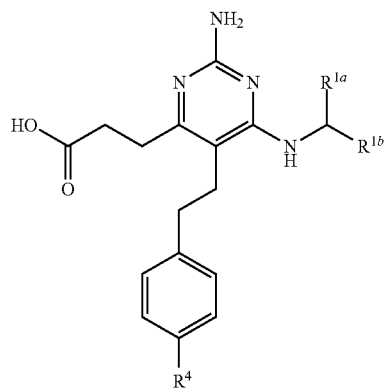

(1h)

wherein R$^4$ is H or C$_1$-C$_3$ alkoxy.

The present disclosure provides a compound of Formula (1), having the structure of Formula (1i), and pharmaceutically acceptable salts thereof,

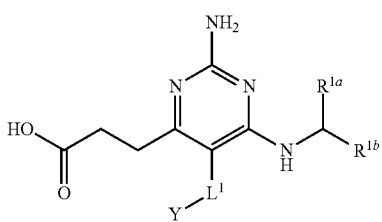

(1i)

wherein
L¹ is selected from the group consisting of a bond, —CH₂—, —CF₂—,

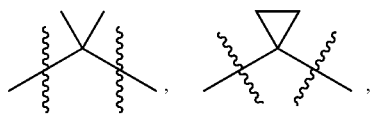

—O—, —CH₂CH₂—, and —S—; and
Y is H or $C_1$-$C_3$ alkyl.
In another embodiment of Formula (1i),
L¹ is selected from the group consisting of a bond, —CH₂—, —CF₂—,

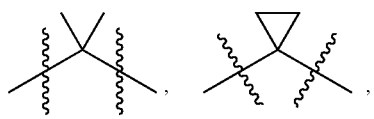

—O—, and —CH₂CH₂—; and
Y is H or $C_1$-$C_3$ alkyl.

The present disclosure provides a compound of Formula (1), having the structure of Formula (1j), and pharmaceutically acceptable salts thereof,

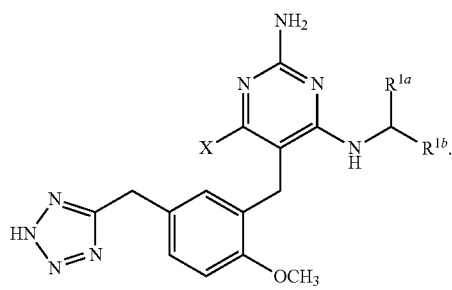

(1j)

In certain embodiment of Formula (1j), X is H or CH₃.
In certain embodiment of Formula (1j), $R^{1a}$ is selected from the group consisting of H and $C_1$-$C_4$ alkyl, wherein the alkyl is optionally substituted with —OH, —NH₂, —NHAc, —COOH, —SO₂CH₃, —SCH₃, —OCH₃, or

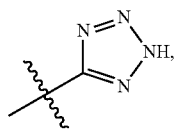 [SMILES: *c1nn[nH]n1]

In certain embodiment of Formula (1j), $R^{1a}$ is selected from the group consisting of H and $C_1$-$C_4$ alkyl, wherein the alkyl is optionally substituted with —COOH.

The present disclosure provides a compound of Formula (1), having the structure of Formula (1k), and pharmaceutically acceptable salts thereof,

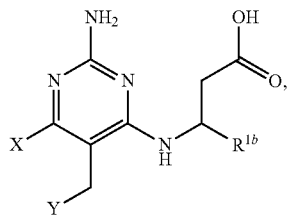

(1k)

In certain embodiment of Formula (1k), X is H or CH₃.
In certain embodiment of Formula (1k), $R^{1b}$ is $C_4$ alkyl.
In certain embodiment of Formula (1k),
Y is aryl or heteroaryl, wherein the aryl and heteroaryl are optionally substituted with 1-5 substituents that are independently selected from A, $C_1$-$C_3$ alkyl, and $C_1$-$C_3$ alkoxy;
A is selected from the group consisting of

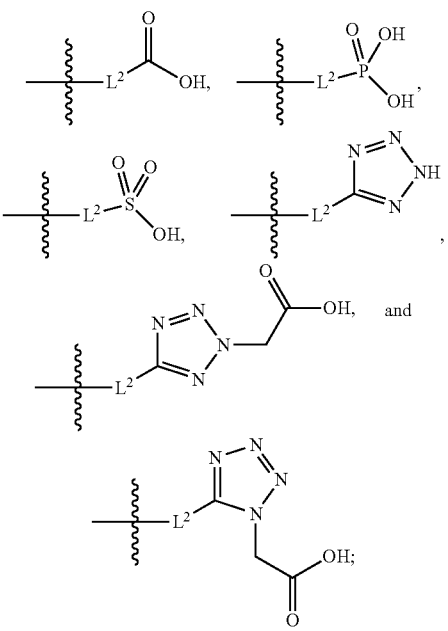

and
$L^2$ is selected from the group consisting of a bond, —(CH₂)ₙ—, —C(O)NH(CH₂)ₙ—,

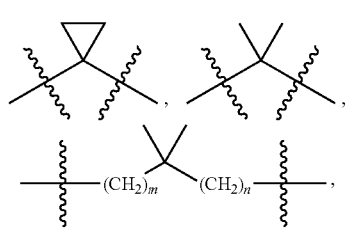

—[O(CH$_2$CH$_2$)]$_n$—, —[O(C$_1$-C$_4$ alkylene)]-, and —[O(CH$_2$CH$_2$)]$_n$—OCH$_2$CH$_2$CF$_2$.

In certain embodiment of Formula (1k),

Y is aryl, wherein the aryl is optionally substituted with 1-5 substituents that are independently selected from A, C$_1$-C$_3$ alkyl, and C$_1$-C$_3$ alkoxy;

A is selected from the group consisting of

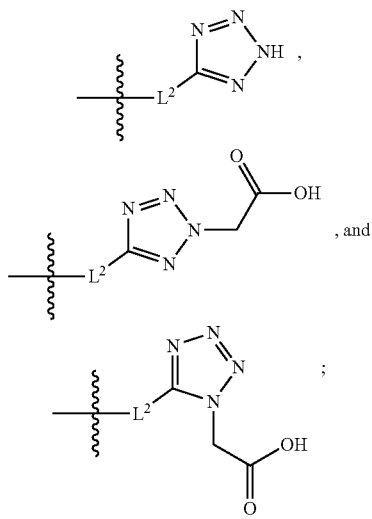

, and

L$^2$ is selected from the group consisting of a bond, —(CH$_2$)$_n$—, —C(O)NH(CH$_2$)$_n$—,

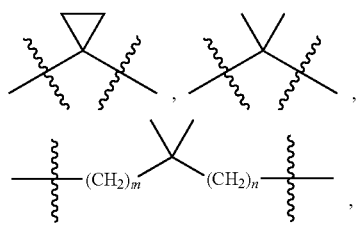

,

—[O(CH$_2$CH$_2$)]$_n$—, —[O(C$_1$-C$_4$ alkylene)]-, and —[O(CH$_2$CH$_2$)]$_n$—OCH$_2$CH$_2$CF$_2$.

In certain embodiment of Formula (1k),

Y is aryl, wherein the aryl is optionally substituted with 1-5 substituents that are independently selected from A, C$_1$-C$_3$ alkyl, and C$_1$-C$_3$ alkoxy;

A is

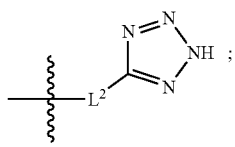

and

L$^2$ is selected from the group consisting of a bond, —(CH$_2$)$_n$—,

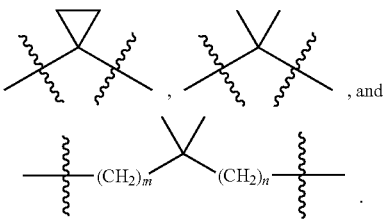

.

In one variation of Formula (1), R$^{1b}$ is —(CH$_2$)$_2$CH$_3$ and R$^{1a}$ is H. In one variation of Formula (1), R$^{1b}$ is —(CH$_2$)$_2$CH$_3$ and R$^{1a}$ is C$_1$-C$_4$ alkyl, optionally substituted with —OH. In one variation of Formula (1), R$^{1b}$ is —(CH$_2$)$_2$CH$_3$ and R$^{1a}$ is —CH$_2$C(CH$_3$)$_2$OH. In one variation of Formula (1),

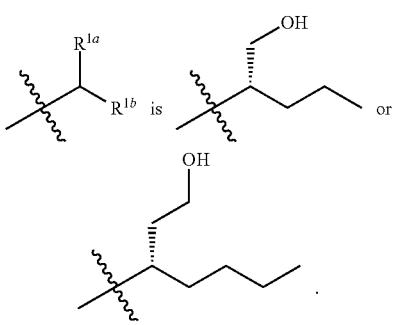

In one variation of Formula (1), Y is aryl, wherein the aryl is substituted with C$_1$-C$_3$ alkoxy and A. In one variation of Formula (1), Y is aryl, wherein the aryl is substituted with —OCH$_3$ and A.

In one variation of Formula (1), R$^{1b}$ is —(CH$_2$)$_3$CH$_3$ and R$^{1a}$ is C$_1$-C$_4$ alkyl, optionally substituted with —COOH. In one variation of Formula (1), R$^{1b}$ is —(CH$_2$)$_2$CH$_3$ and R$^{1a}$ is —CH$_2$COOH.

The present disclosure provides a compound of formula (1),

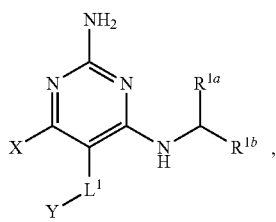

(1)

having one, two, three, or more of the following features:
a) R$^{1b}$ is —(CH$_2$)$_2$CH$_3$;
b) R$^{1a}$ is H;
c) X is —CH$_3$;
d) L$^1$ is —CH$_2$—; and
e) Y is aryl, optionally substituted with 1-5 substituents that are independently selected from A, C$_1$-C$_3$ alkyl, and C$_1$-C$_3$ alkoxy.

The present disclosure provides a compound of formula (1),

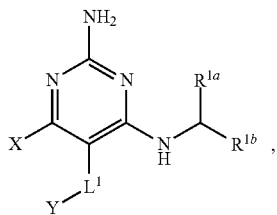 (1)

having one, two, or three of the following features:
a) $R^{1b}$ is —$(CH_2)_2CH_3$ or —$(CH_2)_3CH_3$;
b) $R^{1a}$ is H; and
c) X is $C_1$-$C_4$ alkyl, wherein the alkyl is substituted with A.

The present disclosure provides a compound of formula (1),

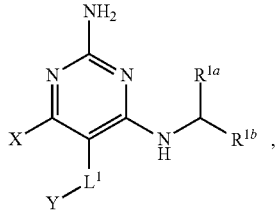 (1)

having one, two, or three of the following features:
a) $R^{1b}$ is —$(CH_2)_2CH_3$ or —$(CH_2)_3CH_3$;
b) $R^{1a}$ is $C_1$-$C_4$ alkyl, substituted with —OH, —$NH_2$, —COOH, or —$SO_2CH$; and
c) X is $C_1$-$C_4$ alkyl, wherein the alkyl is substituted with A.

The present disclosure provides a compound of formula (1),

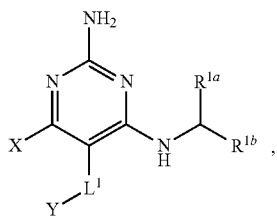 (1)

having one, two, three, or more of the following features:
a) $R^{1b}$ is —$(CH_2)_2CH_3$ or —$(CH_2)_3CH_3$;
b) $R^{1a}$ is $C_1$-$C_4$ alkyl, optionally substituted with —COOH;
c) X is —$CH_3$;
d) $L^1$ is —$CH_2$—; and
e) Y is aryl, optionally substituted with 1-5 substituents that are independently selected from A, $C_1$-$C_3$ alkyl, and $C_1$-$C_3$ alkoxy.

The present disclosure provides a compound of formula (1),

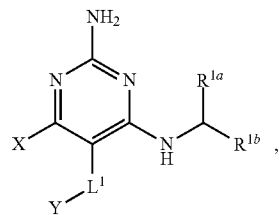 (1)

having one, two, three, or more of the following features:
a) $R^{1b}$ is —$(CH_2)_2CH_3$ or —$(CH_2)_3CH_3$;
b) $R^{1a}$ is H or $C_1$-$C_4$ alkyl, optionally substituted with —COOH;
c) X is —$CH_3$;
d) $L^1$ is —$CH_2$—; and
e) Y is aryl, optionally substituted with 1-5 substituents that are independently selected from

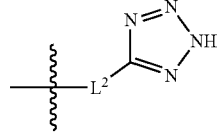

and $C_1$-$C_3$ alkoxy.

The present disclosure provides a compound having the structure of Formula (1), and pharmaceutically acceptable salts thereof,

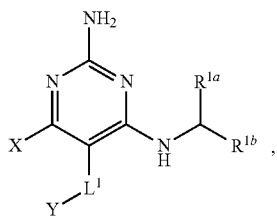 (1)

wherein $R^{1a}$ is selected from the group consisting of H, $C_1$-$C_4$ alkyl, —$NH_2$, —COOH, and —$SO_2CH_3$, wherein the alkyl is optionally substituted with —OH, —$NH_2$, —COOH, or —$SO_2CH_3$;

$R^{1b}$ is $C_2$-$C_5$ alkyl;

X is selected from the group consisting of H and $C_1$-$C_4$ alkyl, wherein the alkyl is optionally substituted with A or halogen;

$L^1$ is selected from the group consisting of a bond, —$CH_2$—, —$CF_2$—,

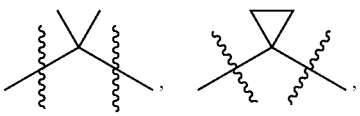

—O—, —S—, —$SO_2$—, —NH—, and —$CH_2CH_2$—;

Y is selected from the group consisting of $C_1$-$C_3$ alkyl, aryl, and heteroaryl, wherein the alkyl, aryl, and heteroaryl are optionally substituted with 1-5 substituents that are independently selected from A, $C_1$-$C_3$ alkyl, and $C_1$-$C_3$ alkoxy;

A is selected from the group consisting of

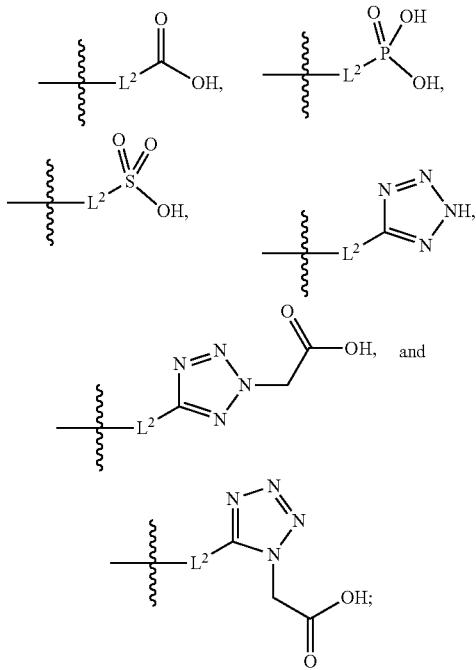

$L^2$ is selected from the group consisting of a bond, —$(CH_2)_n$—, —C(O)NH$(CH_2)_n$—,

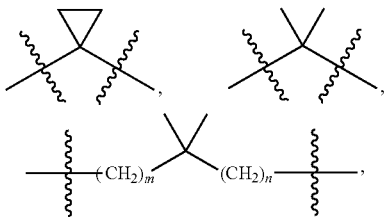

—[O($CH_2CH_2$)]$_n$—, —[O($C_1$-$C_4$ alkylene)]-, and —[O($CH_2CH_2$)]$_n$—O$CH_2CH_2CF_2$—;

m is an integer from zero to four; and n is an integer from one to four; and wherein the compound is substituted with at least one A, with any one or more of the following features, (a) when X is —$CH_3$; $L^1$ is —$CH_2$—; Y is aryl substituted with A; and $L^2$ is —$CH_2$—; then A is not -$L^2$-COOH;

(b) when X is —$CH_3$; $L^1$ is —$CH_2$—; Y is aryl substituted with A; and $L^2$ is —$CH_2$—; then A is not -$L^2$-COOH, except when $R^{1a}$ comprises —COOH;

(c) when $L^1$ is —$CH_2$—; Y is aryl substituted with A; and A is -$L^2$-COOH; and $L^2$ is —$CH_2$—; then X is not —$CH_3$;

(d) when $L^1$ is —$CH_2$—; Y is aryl substituted with A; and A is -$L^2$-COOH; and $L^2$ is —$CH_2$—; then X is not —$CH_3$, except when $R^{1a}$ comprises —COOH;

(e) when X is —$CH_3$; $L^1$ is —$CH_2$—; Y is aryl substituted with A; and A is -$L^2$-COOH; then $L^2$ is not —$CH_2$—;

(f) when X is —$CH_3$; $L^1$ is —$CH_2$—; Y is aryl substituted with A; and A is -$L^2$-COOH; then $L^2$ is not —$CH_2$—, except when $R^{1a}$ comprises —COOH;

(g) when X is —$CH_3$; Y is aryl substituted with A; and A is -$L^2$-COOH; and $L^2$ is —$CH_2$—; then $L^1$ is not —$CH_2$—;

(h) when X is —$CH_3$; Y is aryl substituted with A; and A is -$L^2$-COOH; and $L^2$ is —$CH_2$—; then $L^1$ is not —$CH_2$—, except when $R^{1a}$ comprises —COOH;

(i) when X is —$CH_3$; $L^1$ is —$CH_2$—; Y is aryl substituted with A; and A is -$L^2$-COOH; and $L^2$ is —$CH_2$—; then $R^{1a}$ comprises COOH;

(j) when X is —$CH_3$; $L^1$ is —$CH_2$—; Y is aryl substituted A and —$OCH_3$; and $L^2$ is —$CH_2$—; then A is not -$L^2$-COOH;

(k) when X is —$CH_3$; $L^1$ is —$CH_2$—; Y is aryl substituted A and —$OCH_3$; and $L^2$ is —$CH_2$—; then A is not -$L^2$-COOH, except when $R^{1a}$ comprises —COOH;

(l) when X is —$CH_3$; $L^1$ is —$CH_2$—; Y is aryl substituted A and —$OCH_3$; and $L^2$ is —$CH_2$—; and $R^{1a}$ does not comprise COOH; then A is not -$L^2$-COOH.

In certain embodiments, the compound having the structure of Formula (1) can have any one or more of the following features, (m) when X is —$CH_3$; $L^1$ is —$CH_2$—; Y is aryl substituted with A; and $L^2$ is —$CH_2$—; then A is not -$L^2$-COOH;

(n) when X is —$CH_3$; $L^1$ is —$CH_2$—; Y is aryl substituted with A; and $L^2$ is —$CH_2$—; then A is not -$L^2$-COOH, except when $R^{1a}$ comprises —COOH or —$SO_2CH_3$;

(o) when $L^1$ is —$CH_2$—; Y is aryl substituted with A; and A is -$L^2$-COOH; and $L^2$ is —$CH_2$—; then X is not —$CH_3$;

(p) when $L^1$ is —$CH_2$—; Y is aryl substituted with A; and A is -$L^2$-COOH; and $L^2$ is —$CH_2$—; then X is not —$CH_3$, except when $R^{1a}$ comprises —COOH or —$SO_2CH_3$;

(q) when X is —$CH_3$; $L^1$ is —$CH_2$—; Y is aryl substituted with A; and A is -$L^2$-COOH; then $L^2$ is not —$CH_2$—;

(r) when X is —$CH_3$; $L^1$ is —$CH_2$—; Y is aryl substituted with A; and A is -$L^2$-COOH; then $L^2$ is not —$CH_2$—, except when $R^{1a}$ comprises —COOH or —$SO_2CH_3$;

(s) when X is —$CH_3$; Y is aryl substituted with A; and A is -$L^2$-COOH; and $L^2$ is —$CH_2$—; then $L^1$ is not —$CH_2$—;

(t) when X is —$CH_3$; Y is aryl substituted with A; and A is -$L^2$-COOH; and $L^2$ is —$CH_2$—; then $L^1$ is not —$CH_2$—, except when $R^{1a}$ comprises —COOH or —$SO_2CH_3$;

(u) when X is —$CH_3$; $L^1$ is —$CH_2$—; Y is aryl substituted with A; and A is -$L^2$-COOH; and $L^2$ is —$CH_2$—; then $R^{1a}$ comprises COOH or —$SO_2CH_3$;

(v) when X is —$CH_3$; $L^1$ is —$CH_2$—; Y is aryl substituted A and —$OCH_3$; and $L^2$ is —$CH_2$—; then A is not -$L^2$-COOH;

(w) when X is —$CH_3$; $L^1$ is —$CH_2$—; Y is aryl substituted A and —$OCH_3$; and $L^2$ is —$CH_2$—; then A is not -$L^2$-COOH, except when $R^{1a}$ comprises —COOH or —$SO_2CH_3$;

(x) when X is —$CH_3$; $L^1$ is —$CH_2$—; Y is aryl substituted A and —$OCH_3$; and $L^2$ is —$CH_2$—; and $R^{1a}$ does not comprise COOH or —$SO_2CH_3$; then A is not -$L^2$-COOH;

(y) when X is —$CH_3$; $L^1$ is —$CH_2$—; Y is aryl substituted with A; and A is -$L^2$-COOH; and $L^2$ is —$CH_2$—; then $R^{1a}$ is not H or alkyl substituted with —OH.

In certain embodiments, the compound having the structure of Formula (1) can have any one or more of the following features:

(aa) when X is —CH$_3$; L$^1$ is —CH$_2$—; Y is aryl substituted with A; L$^2$ is —CH$_2$—, —O—(CH$_2$)$_2$—O(CH$_2$)$_2$—, or —O—(CH$_2$)$_2$—O(CH$_2$)$_2$(CF$_2$)—; and A is

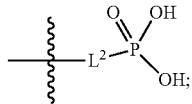

then A and L$^1$ are not in a para position with respect to each other;

(bb) when X is —CH$_3$; L$^1$ is —CH$_2$—; Y is aryl substituted with A; L$^2$ is —CH$_2$—; and A is

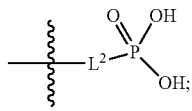

then A and L$^1$ are not in a para position with respect to each other;

(cc) when X is —CH$_3$; L$^1$ is —CH$_2$—; Y is aryl substituted with A and —OCH$_3$; L$^2$ is —CH$_2$—; and A is

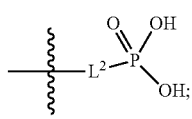

then A and L$^1$ are not in a para position with respect to each other;

(dd) when X is —CH$_3$; L$^1$ is —CH$_2$—; Y is aryl substituted with A; L$^2$ is —O—(CH$_2$)$_2$—O(CH$_2$)$_2$—; and A is

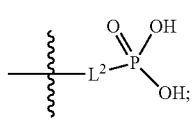

then A and L$^1$ are not in a para position with respect to each other;

(ee) when X is —CH$_3$; L$^1$ is —CH$_2$—; Y is aryl substituted with A; L$^2$ is —O—(CH$_2$)$_2$—O(CH$_2$)$_2$(CF$_2$)—; and A is

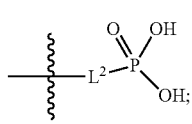

then A and L$^1$ are not in a para position with respect to each other;

(ff) when X is —CH$_3$; R$^{1a}$ is H; R$^{1b}$ is C$_4$alkyl; L$^1$ is —CH$_2$—; Y is aryl substituted with A; and L$^2$ is —CH$_2$—, —O—(CH$_2$)$_2$—O(CH$_2$)$_2$—, or —O—(CH$_2$)$_2$—O(CH$_2$)$_2$(CF$_2$)—; then A is not

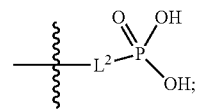

(gg) when X is —CH$_3$; R$^{1a}$ is H; R$^{1b}$ is C$_4$alkyl; L$^1$ is —CH$_2$—; Y is aryl substituted with A; and L$^2$ is —CH$_2$—; then A is not

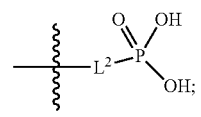

(hh) when X is —CH$_3$; R$^{1a}$ is H; R$^{1b}$ is C$_4$alkyl; L$^1$ is —CH$_2$—; Y is aryl substituted with A and —OCH$_3$; and L$^2$ is —CH$_2$—; then A is not

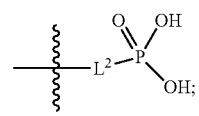

(ii) when X is —CH$_3$; R$^{1a}$ is H; R$^{1b}$ is C$_4$alkyl; L$^1$ is —CH$_2$—; Y is aryl substituted with A; and L$^2$ is —O—(CH$_2$)$_2$—O(CH$_2$)$_2$—; then A is not

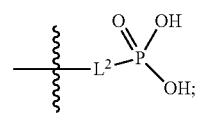

(jj) when X is —CH$_3$; R$^{1a}$ is H; R$^{1b}$ is C$_4$alkyl; L$^1$ is —CH$_2$—; Y is aryl substituted with A; and L$^2$ is —O—(CH$_2$)$_2$—O(CH$_2$)$_2$(CF$_2$)—; then A is not

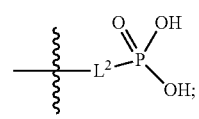

(kk) when X is —CH$_3$; R$^{1a}$ is H; R$^{1b}$ is C$_4$alkyl; L$^1$ is —CH$_2$—; Y is aryl substituted with A; L$^2$ is —CH$_2$—, —O—(CH$_2$)$_2$—O(CH$_2$)$_2$—, or —O—(CH$_2$)$_2$—O(CH$_2$)$_2$(CF$_2$)—; and A and L$^1$ are para position with respect to each other; then A is not

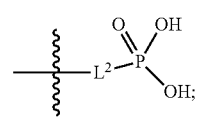

(ll) when X is —CH$_3$; R$^{1a}$ is H; R$^{1b}$ is C$_4$alkyl; L$^1$ is —CH$_2$—; Y is aryl substituted with A; L$^2$ is —CH$_2$—; and A and L$^1$ are para position with respect to each other; then A is not

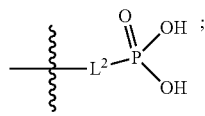

(mm) when X is —CH₃; $R^{1a}$ is H; $R^{1b}$ is C₄alkyl; $L^1$ is —CH₂—; Y is aryl substituted with A and —OCH₃; $L^2$ is —CH₂—; and A and $L^1$ are para position with respect to each other; then A is not

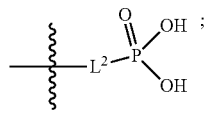

(nn) when X is —CH₃; $R^{1a}$ is H; $R^{1b}$ is C₄alkyl; $L^1$ is —CH₂—; Y is aryl substituted with A; $L^2$ is —O—(CH₂)₂—O(CH₂)₂—; and A and $L^1$ are para position with respect to each other; then A is not

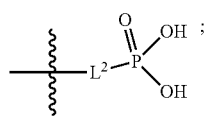

(oo) when X is —CH₃; $R^{1a}$ is H; $R^{1b}$ is C₄alkyl; $L^1$ is —CH₂—; Y is aryl substituted with A; $L^2$ is —O—(CH₂)₂—O(CH₂)₂(CF₂)—; and A and $L^1$ are para position with respect to each other; then A is not

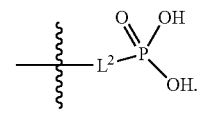

In certain embodiments, the present disclosure provides a compound of formula (1) that is not disclosed in WO 2009/067081 (PCT/SE2008/051334). In certain embodiments, the present disclosure provides a compound of formula (1) that is not disclosed in WO 2012/031140 (PCT/US2011/050231).

In certain embodiments, the present disclosure provides a compound of formula (1) that is not

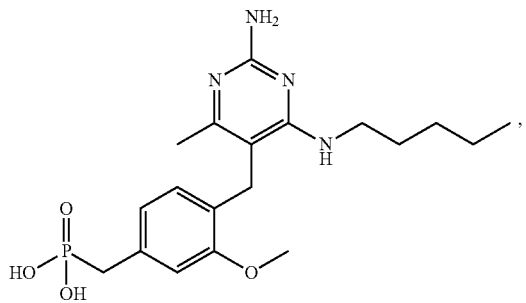

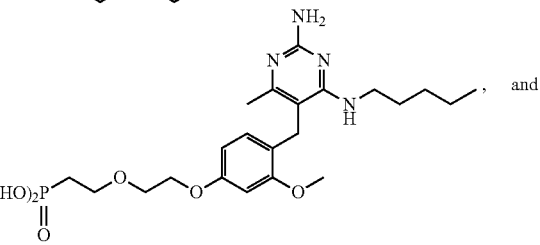

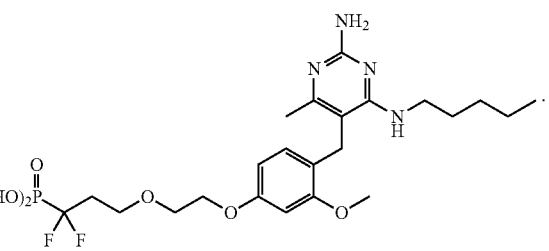

The present disclosure provides for the following compounds and pharmaceutically acceptable salts thereof.

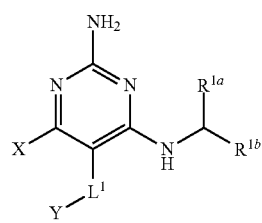

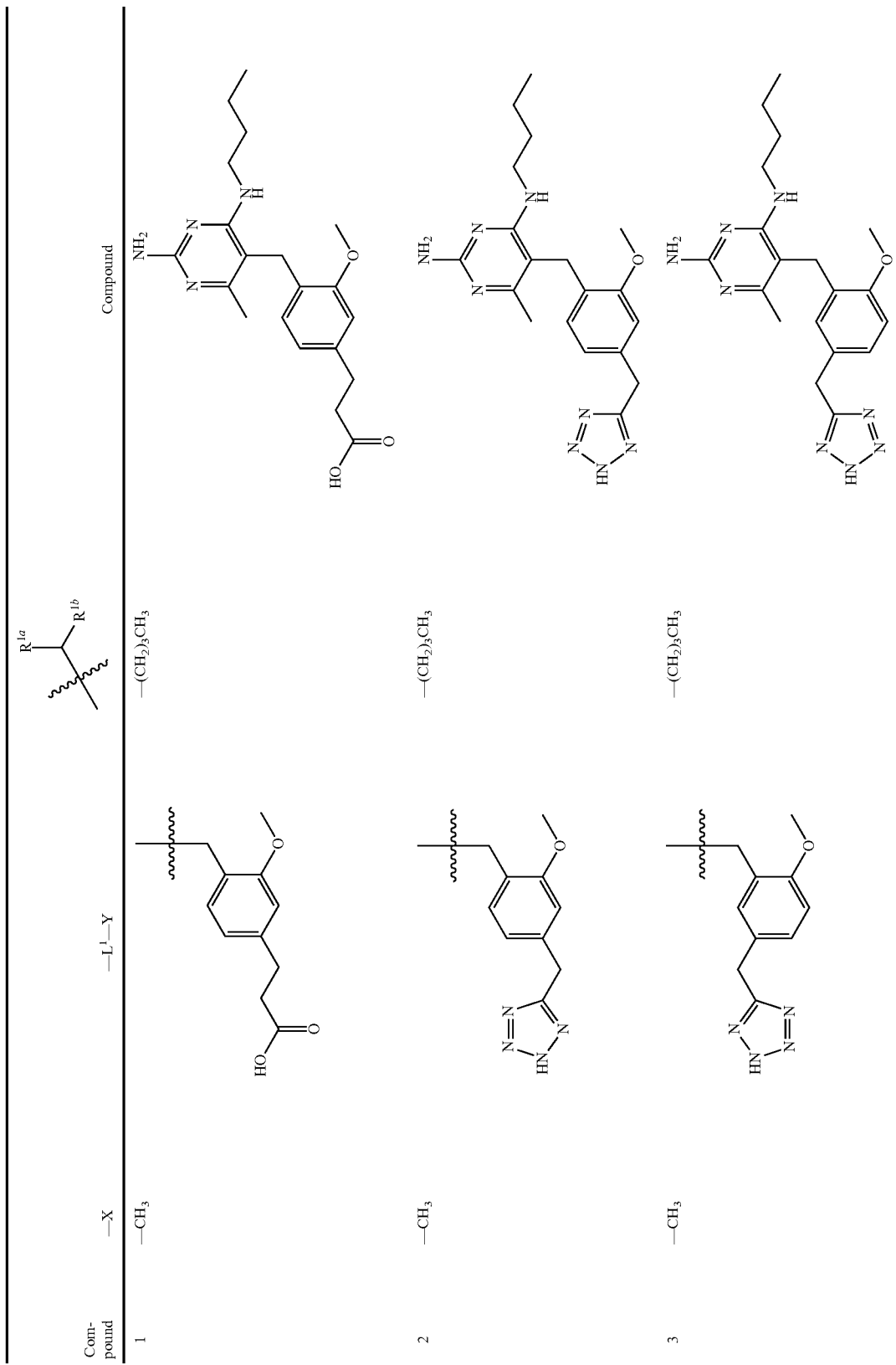

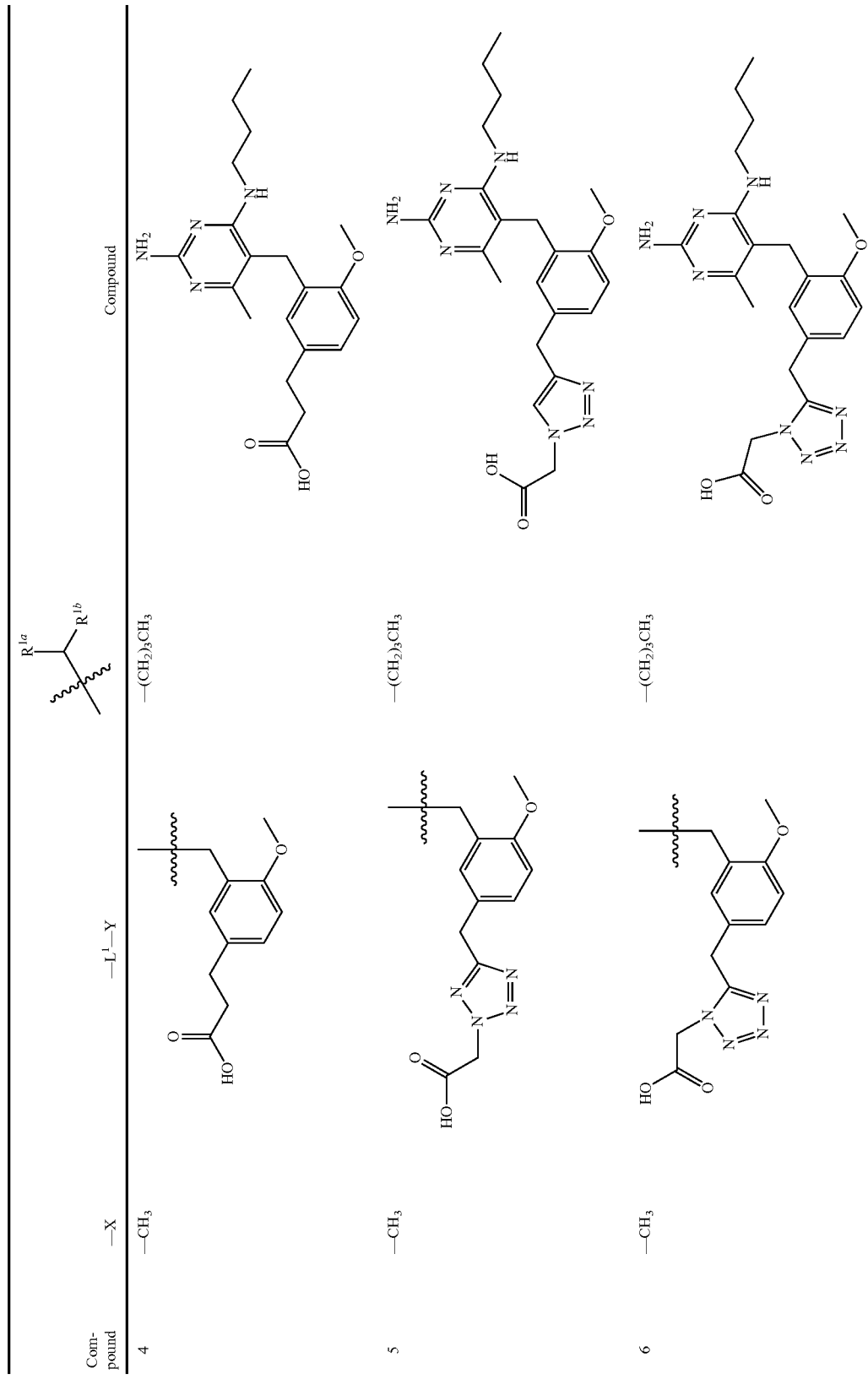

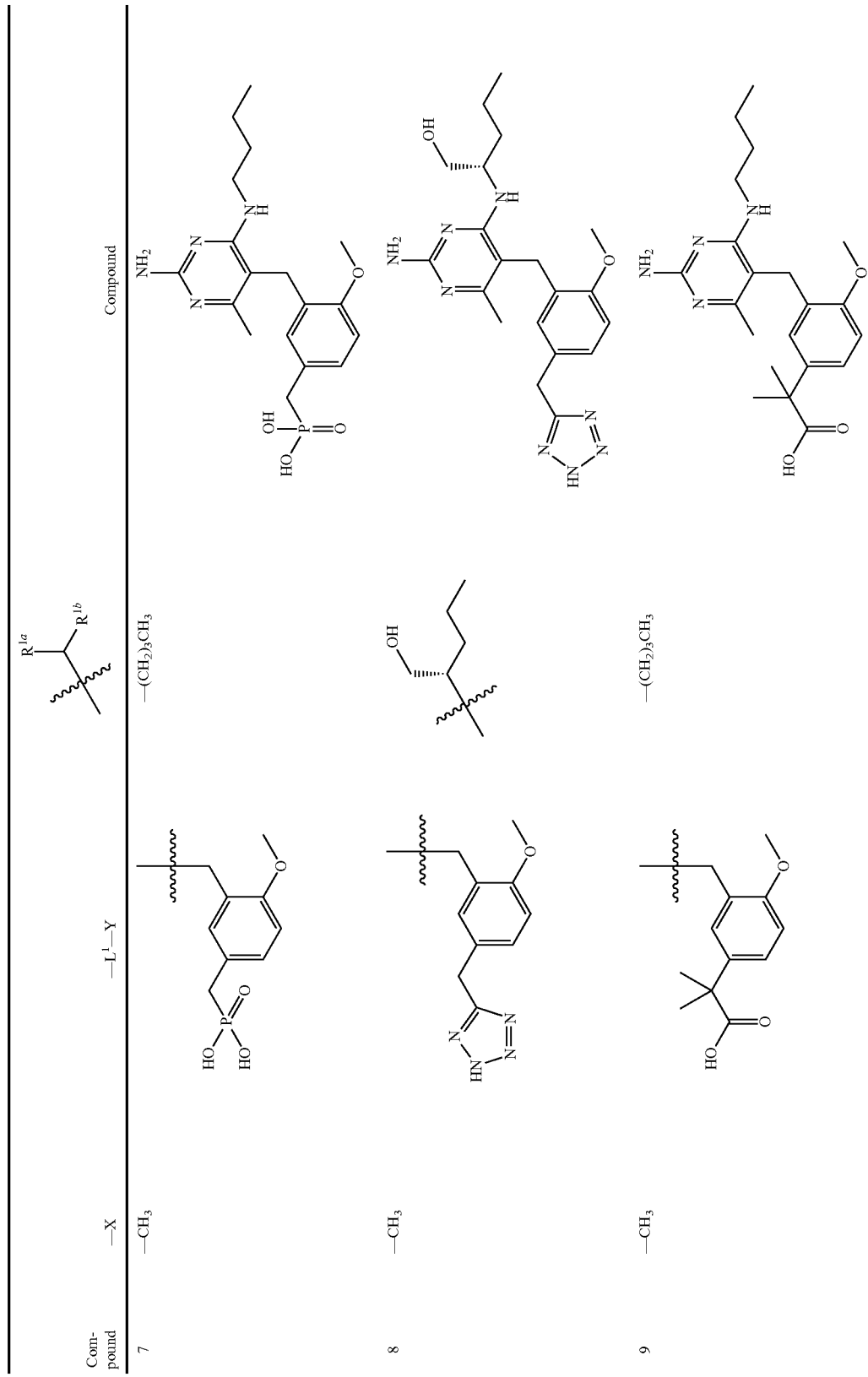

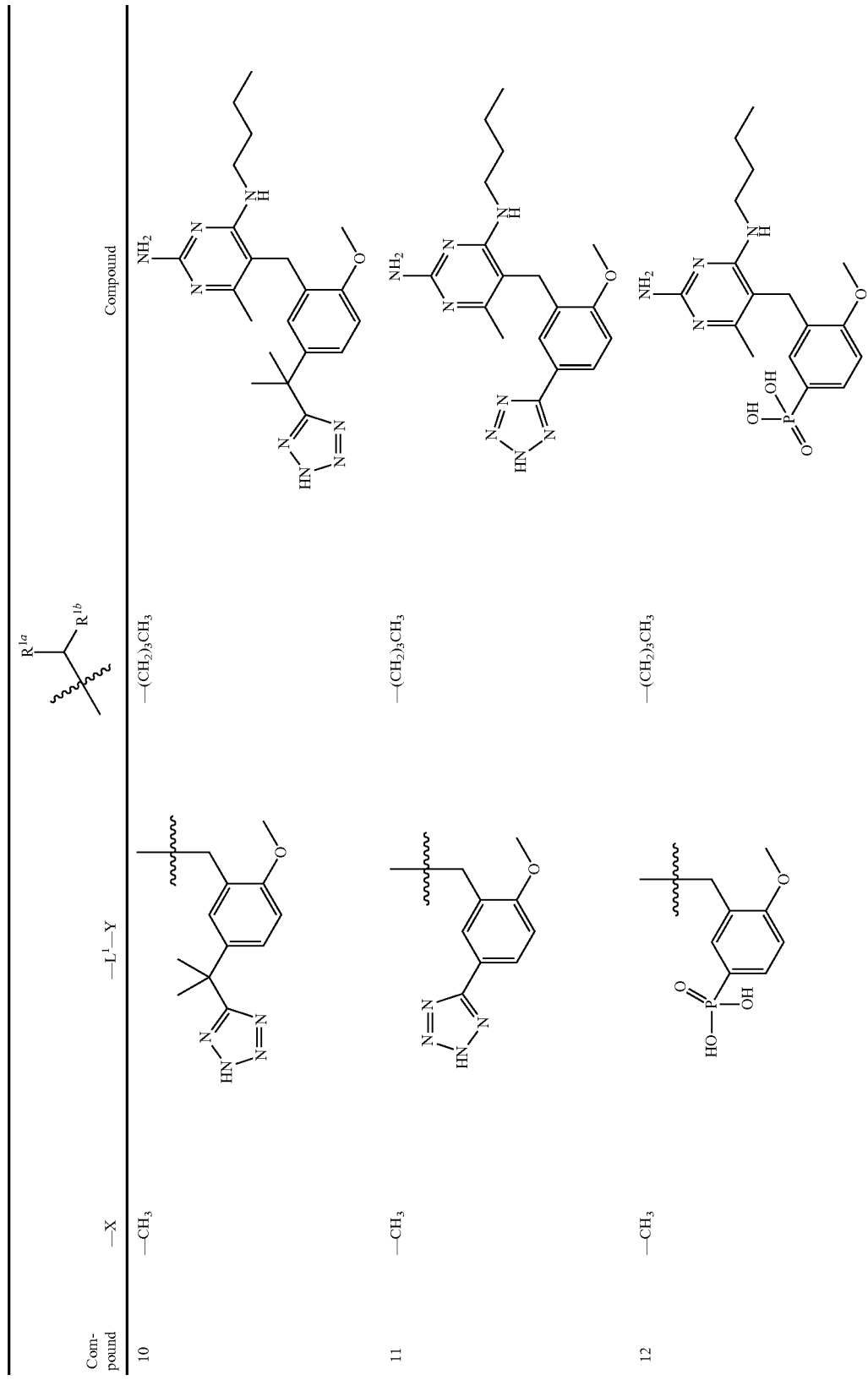

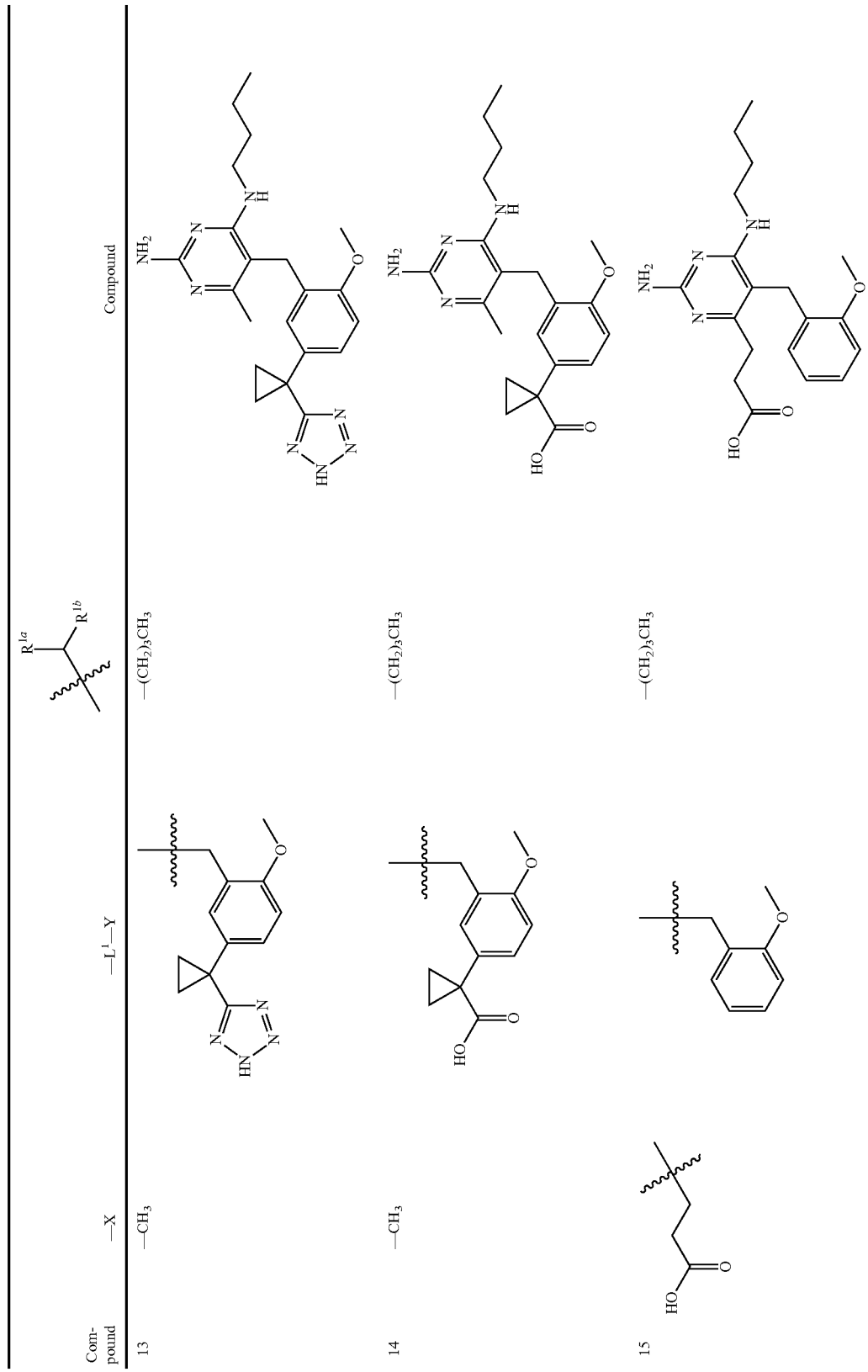

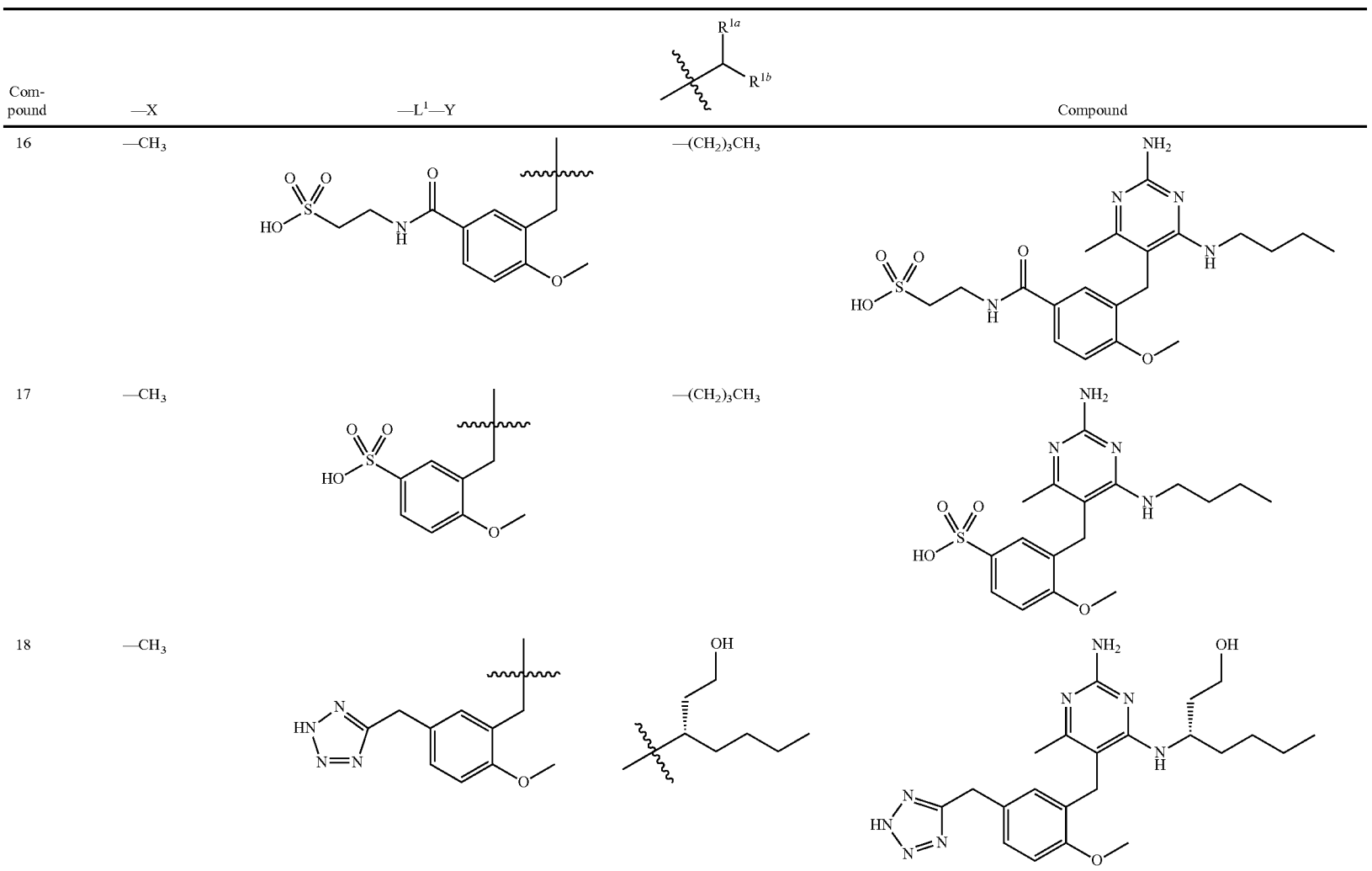

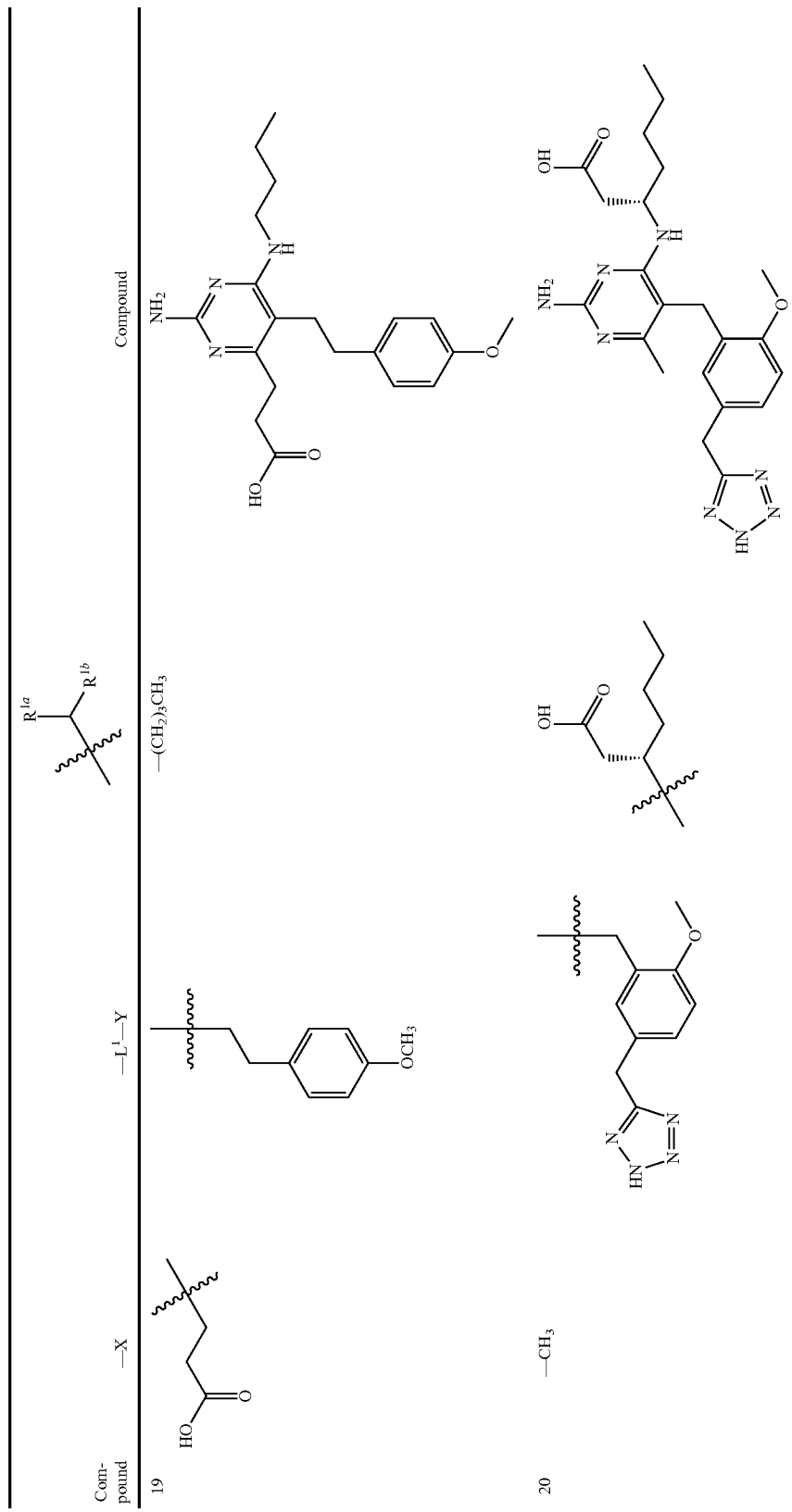

| Compound | —X | —L¹—Y | R¹ᵃ⟩−⟨R¹ᵇ | Compound |
|---|---|---|---|---|
| 20C | —CH₃ | 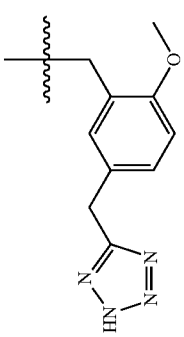 | 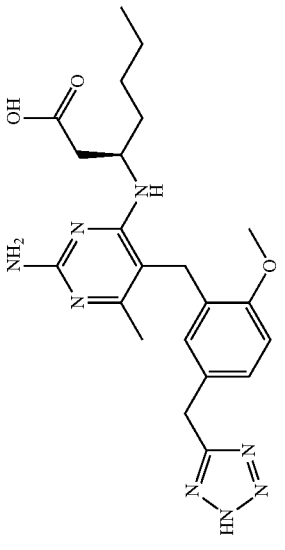 | 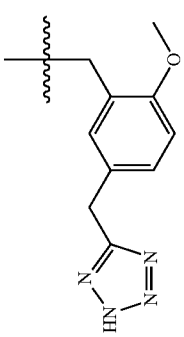 |
| 21 | 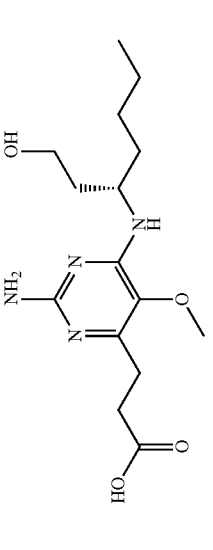 | —OCH₃ | 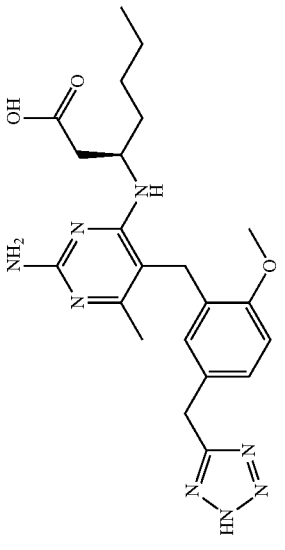 | 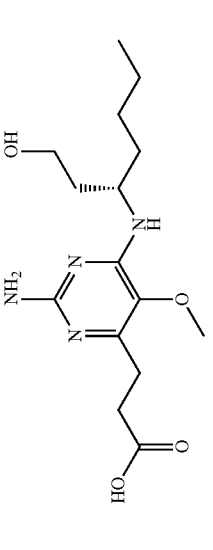 |

The present disclosure provides for the following compounds and pharmaceutically acceptable salts thereof.
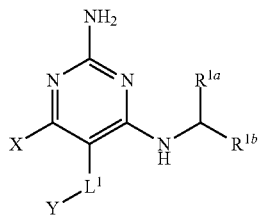

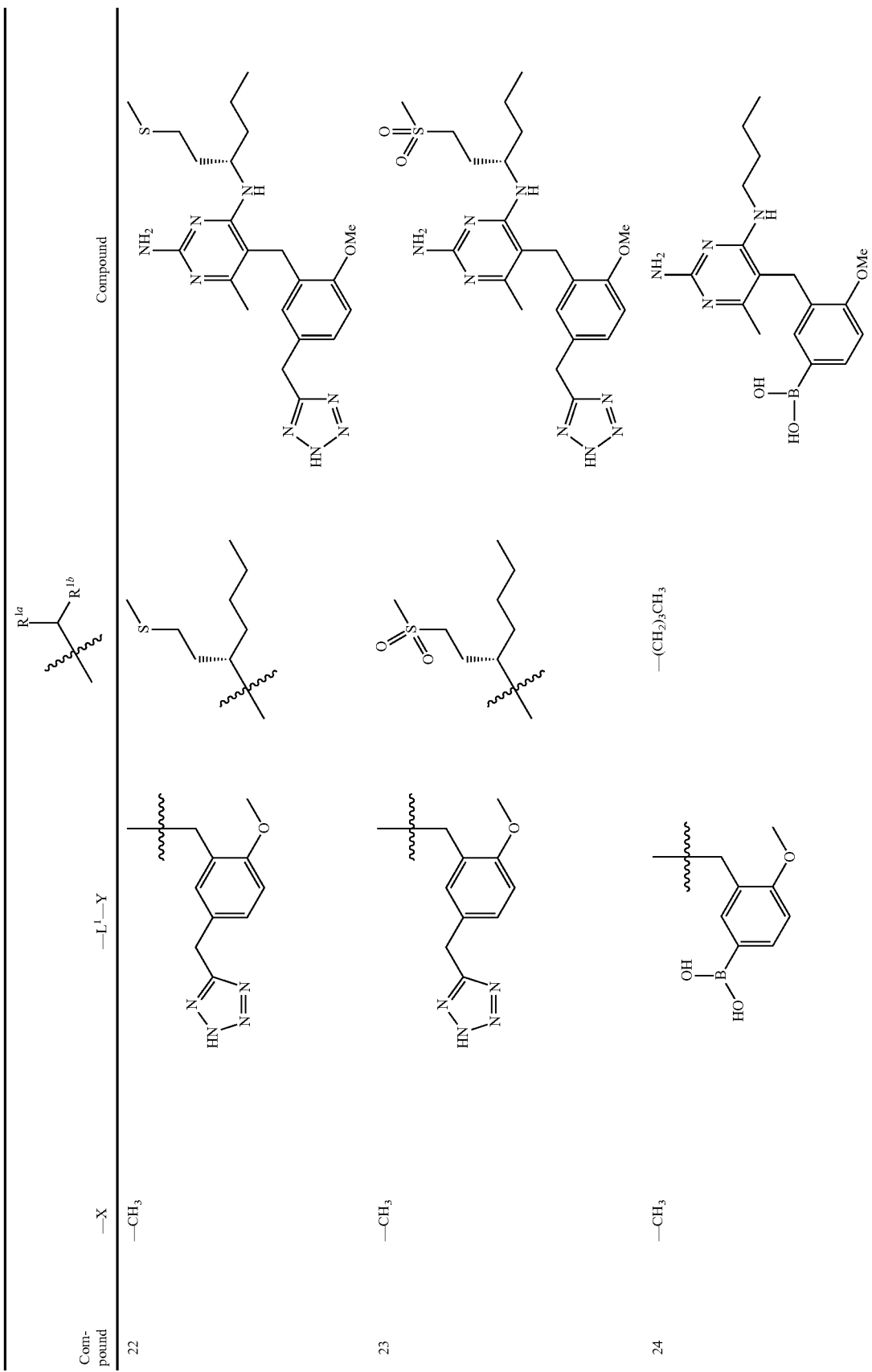

-continued

| Compound | —X | —L¹—Y | R¹ᵃ⧸R¹ᵇ | Compound |
|---|---|---|---|---|
| 25 | —CH₃ | (methoxyphenyl-benzamide-butanoic acid group) | —(CH₂)₃CH₃ | (structure shown) |
| 26 | —CH₃ | (methoxybenzyl-tetrazole group) | —(CH₂)₄CH₃ | (structure shown) |
| 27 | (butanoic acid group) | (methoxybenzyl group) | (hydroxyethyl-pentyl group) | (structure shown) |

-continued
| Compound | —X | —L¹—Y | R¹ᵃ⤳R¹ᵇ | Compound |
|---|---|---|---|---|
| 28 | —CH₃ | 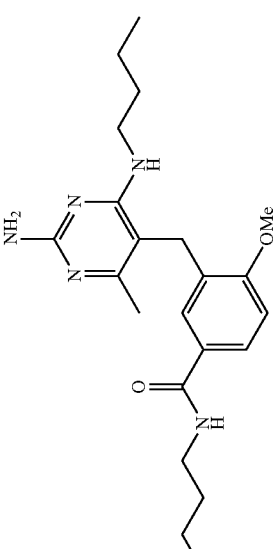 | —(CH₂)₃CH₃ | 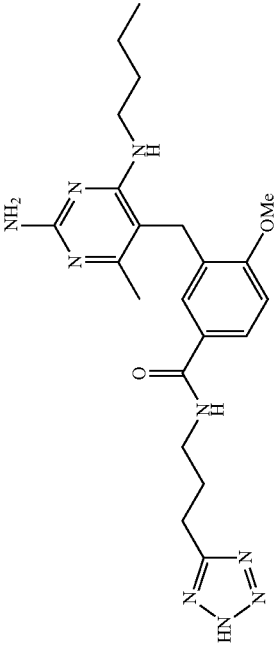 |
| 29 |  | 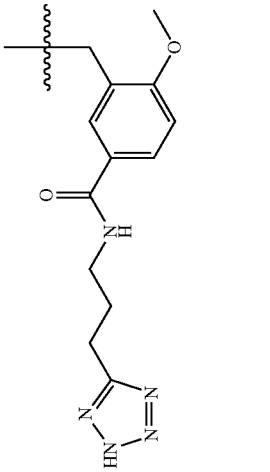 | 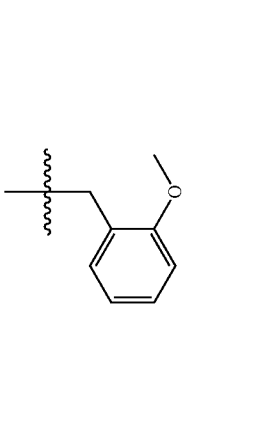 | 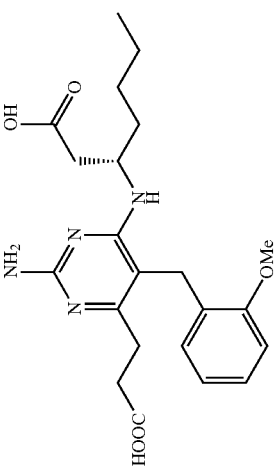 |
| 30 | —CH₃ | 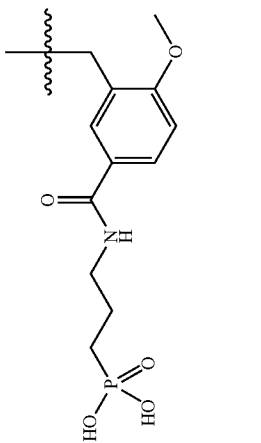 | —(CH₂)₃CH₃ | 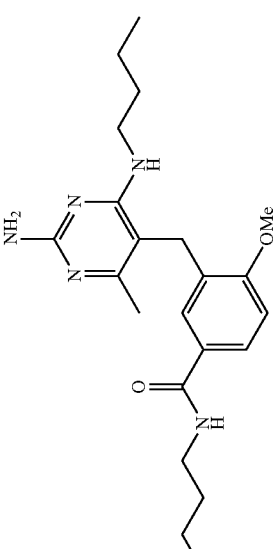 |

| Compound | —X | —L¹—Y | R^{1a}⧫R^{1b} | Compound |
|---|---|---|---|---|
| 31 | —CH₃ | (thiomethoxyphenyl-tetrazole group) | —(CH₂)₃CH₃ | (structure 31) |
| 32 | —CH₃ | (methylene-methoxyphenyl-tetrazole group) | (methoxyethyl hexyl group) | (structure 32) |
| 33 | —CH₃ | (methylene-methoxyphenyl-dimethylacetic acid group) | (methylthioethyl hexyl group) | (structure 33) |

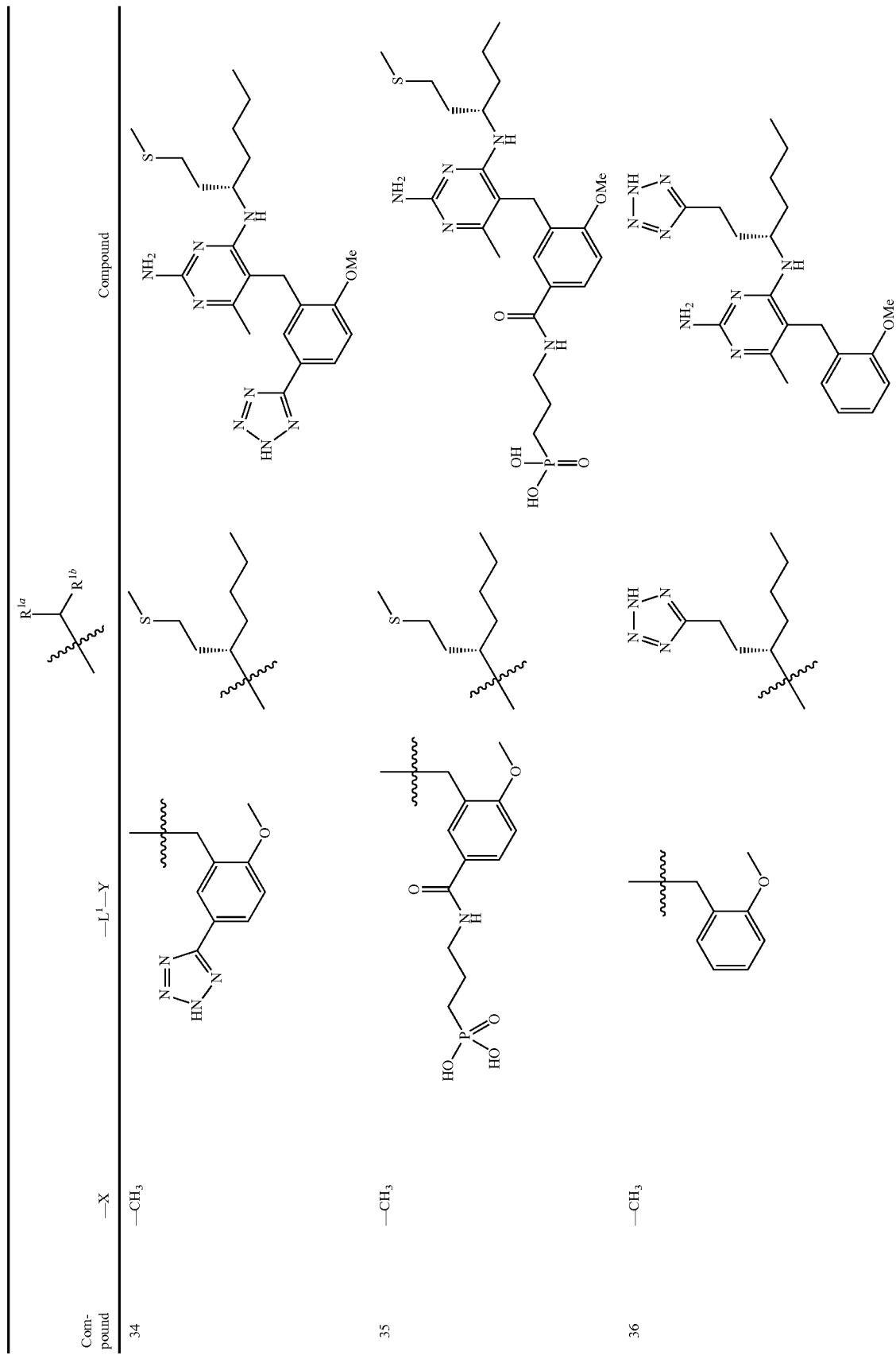

-continued

| Compound | $R^{1a}\!\!\diagdown\!\!\diagup\!\!R^{1b}$ | —L¹—Y | —X |
|---|---|---|---|
| 37 | —(CH₂)₃CH₃ | 2-methoxybenzyl | tetrazol-5-yl-ethyl |
| 38 | (S)-1-(2-methylthioethyl)pentyl | 2-methoxybenzyl | 2-carboxyethyl |
| 39 | sec-pentyl (1-methylbutyl) | 4-methoxy-3-(tetrazol-5-ylmethyl)benzyl | —CH₃ |

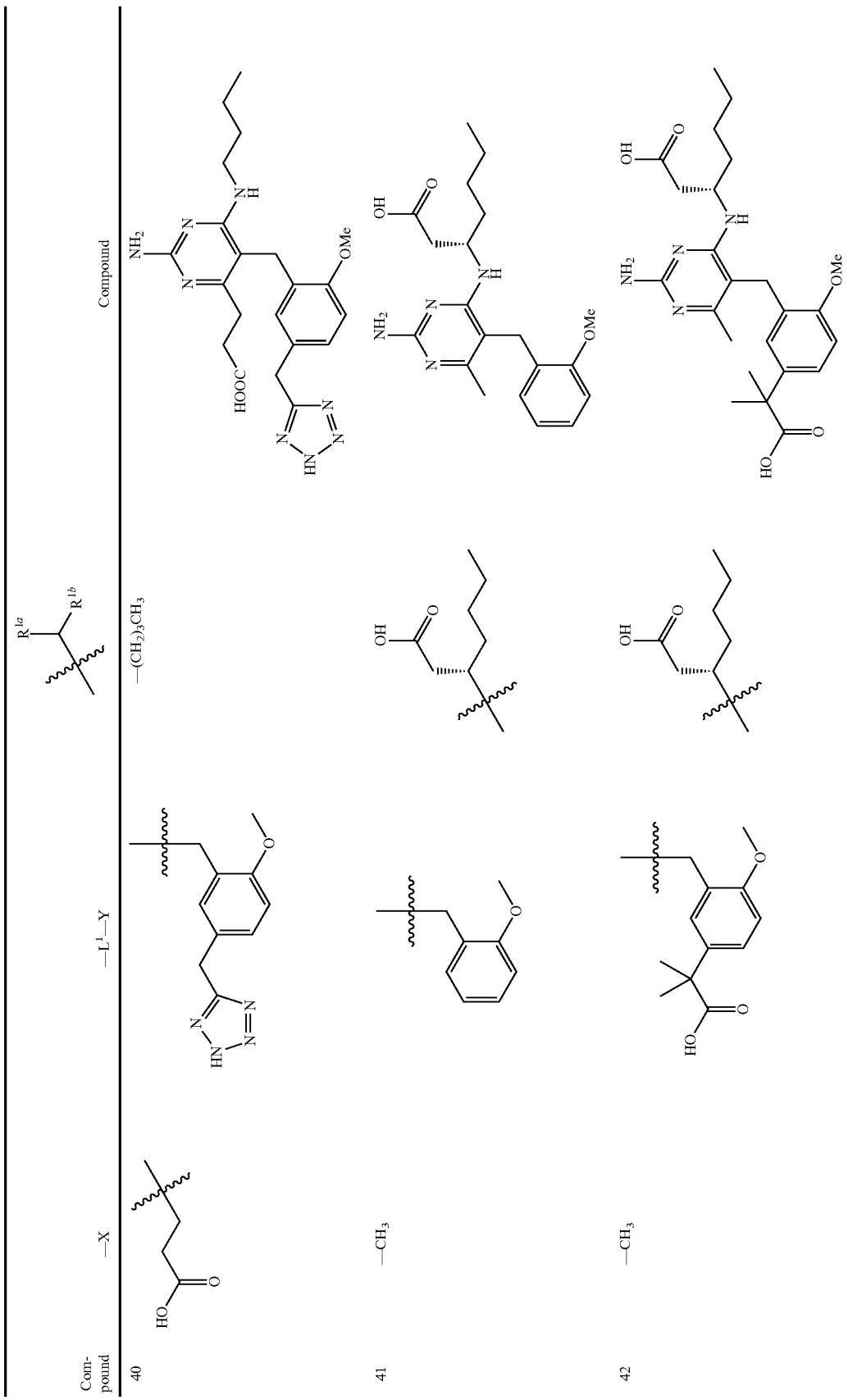

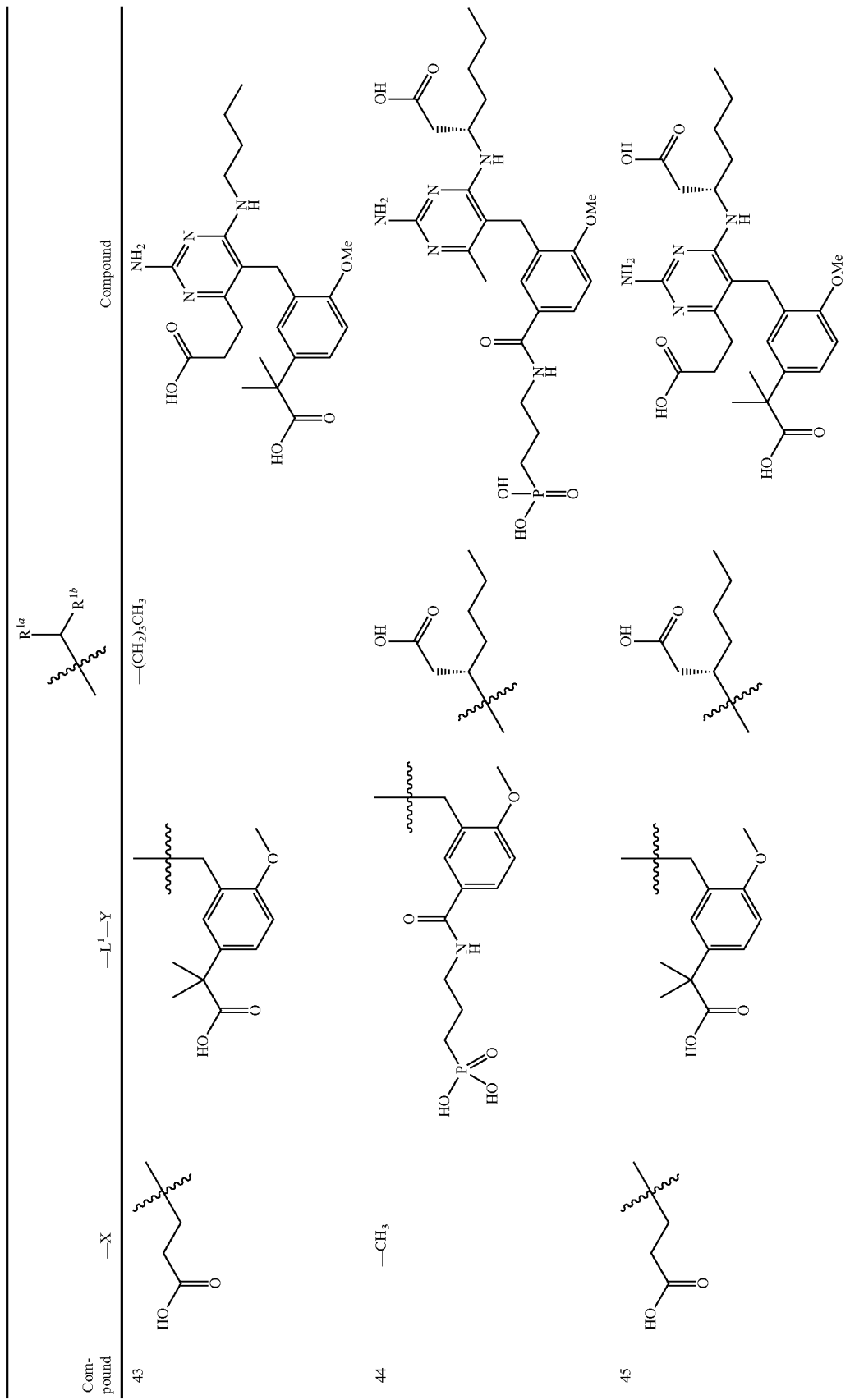

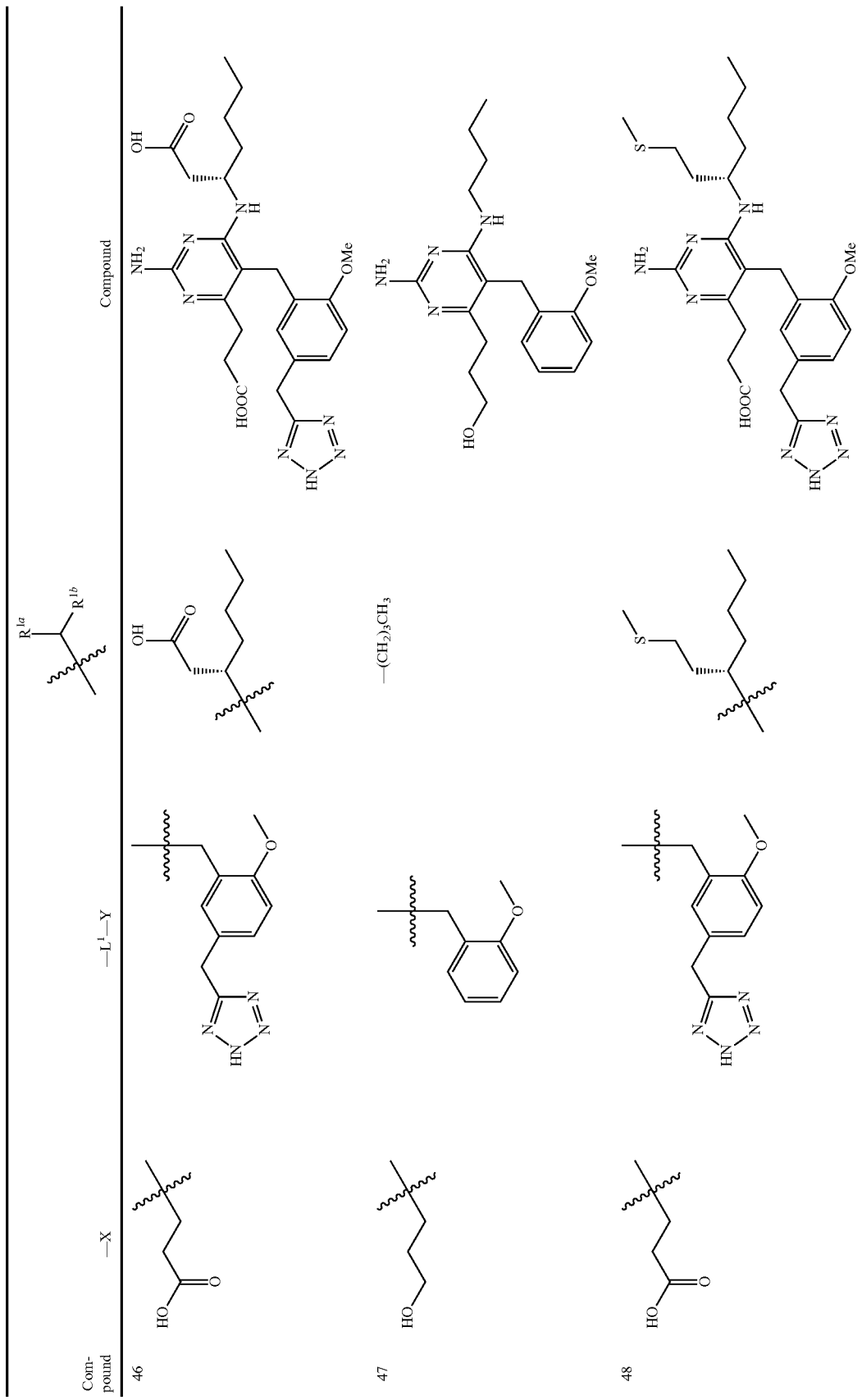

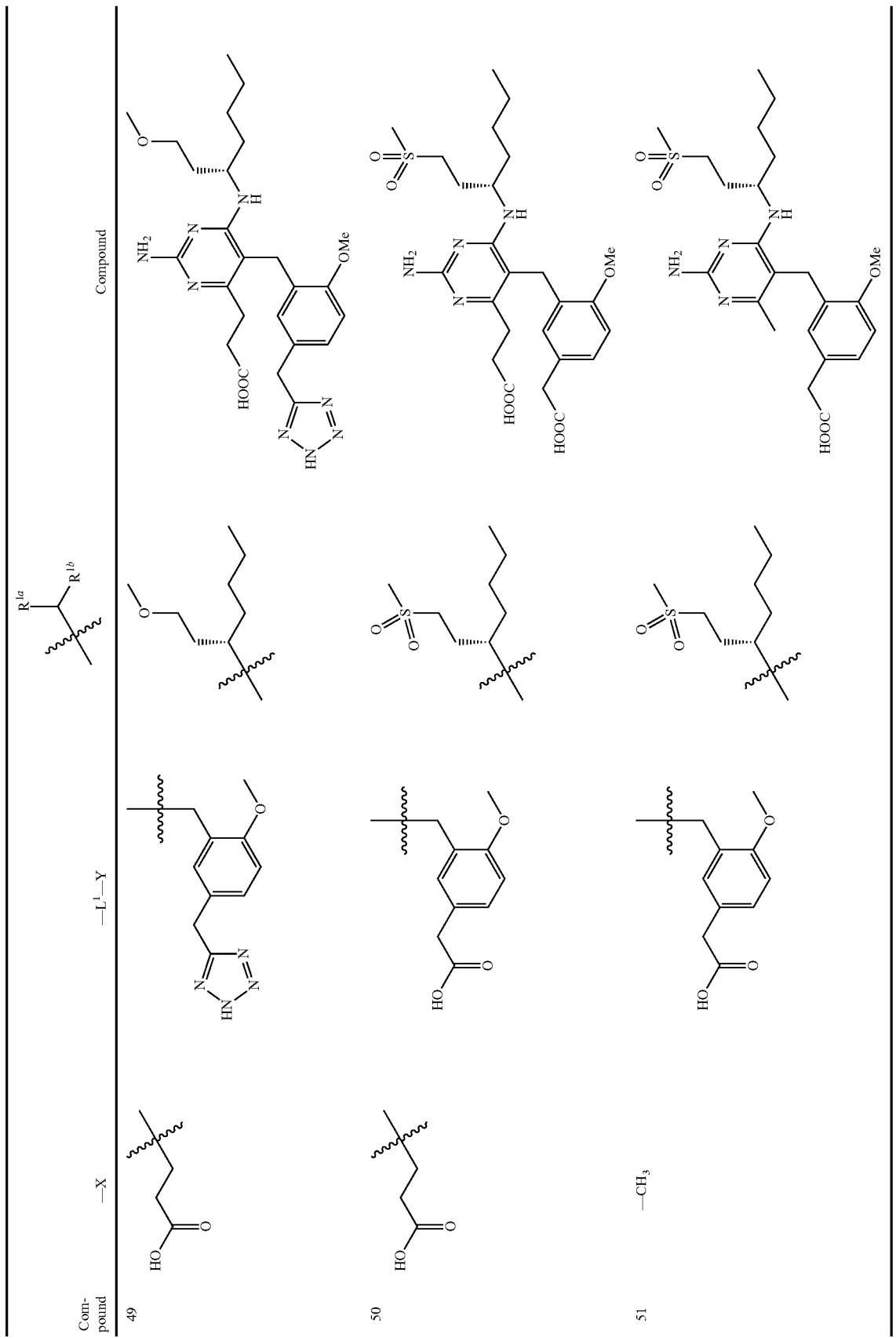

Unless otherwise stated, structures depicted herein are also meant to include compounds which differ only in the presence of one or more isotopically enriched atoms. For example, compounds having the present structure except for the replacement of a hydrogen atom by deuterium or tritium, or the replacement of a carbon atom by $^{13}C$ or $^{14}C$, or the replacement of a nitrogen atom by $^{15}N$, or the replacement of an oxygen atom with $^{17}O$ or $^{18}O$ are within the scope of the present disclosure. Such isotopically labeled compounds are useful as research or diagnostic tools.

General Synthetic Methods

As noted herein, the present disclosure includes specific representative compounds, which are identified herein with particularity. The compounds of the present disclosure may be made by a variety of methods, including well-known standard synthetic methods. Illustrative general synthetic methods are set out below and then specific compounds of the present disclosure are prepared in the working Examples.

In all of the examples described below, protecting groups for sensitive or reactive groups are employed where necessary in accordance with general principles of synthetic chemistry. Protecting groups are manipulated according to standard methods of organic synthesis (T. W. Green and P. G. M. Wuts, *Protecting Groups in Organic Synthesis*, 3rd Edition, John Wiley & Sons, New York (1999)). These groups are removed at a convenient stage of the compound synthesis using methods that are readily apparent to those skilled in the art. The selection of processes as well as the reaction conditions and order of their execution shall be consistent with the preparation of compounds of the present disclosure.

A representative synthesis for subject compounds is shown in Scheme 1.

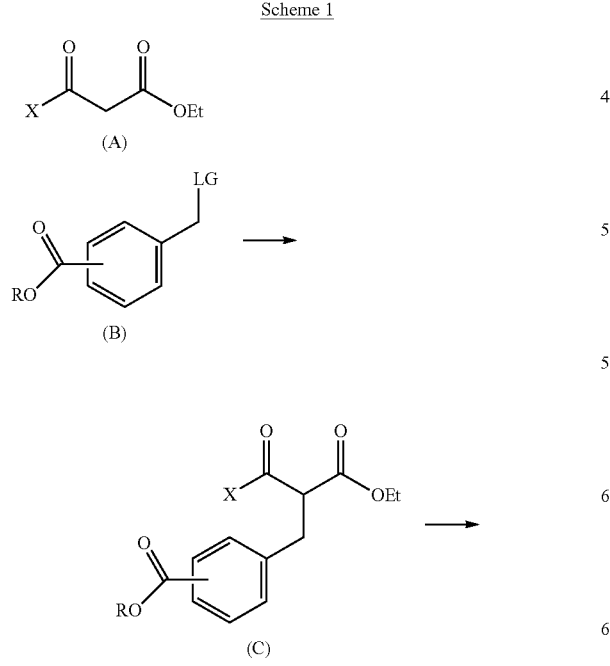

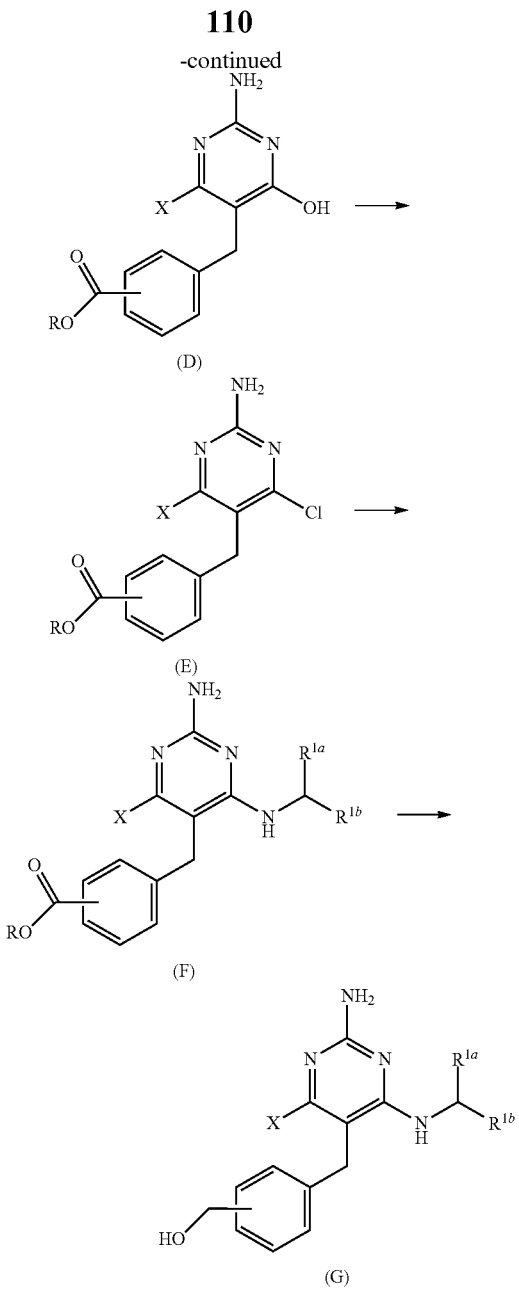

In Scheme 1, compound of formula (G) is an embodiment wherein $L^1$ is —$CH_2$— and Y is aryl, which is appropriately substituted. Also in Scheme 1, LG is a leaving group; and R is H or alkyl. Compounds of formula (A) and (B) are commercially available starting materials. Alternatively, compounds of formula (A) and (B) can be synthesized via a variety of different synthetic routes using commercially available starting materials and/or starting materials prepared by conventional synthetic methods.

With continued reference to Scheme 1, compounds of formula (C) may be prepared by reacting a compound of formula (A) with a base, such as sodium hydride, in a suitable solvent such as tetrahydrofuran or N,N-dimethylformamide at a temperature, for example, from 0° C. to room temperature (20° C.), followed by addition of a compound of formula (B). The reaction is then preferably heated at a temperature, for example, from 50° C. to 100° C., optionally in the presence of an additive such as potassium iodide.

Compounds of formula (D) may be prepared by reacting a compound of formula (C) with guanidine or guanidine carbonate in a suitable solvent such as methanol or ethanol at a temperature, for example, in the range from 50° C. to 150° C.

Compounds of formula (E) may be prepared by reacting a compound of formula (D) with phosphorous oxychloride, at a temperature, for example, from 50° C. to 110° C.

Compounds of formula (F) may be prepared by reacting a compound of formula (E) with excess of an amine of formula $R^{1a}R^{1b}NH$, in a suitable solvent such as NMP, butanol or 1,2-dioxane at a temperature, for example, from 50° C. to 150° C. Alternatively, the reaction can be performed in a microwave at a temperature, for example, from 50° C. to 200° C.

Compounds of formula (G) may be prepared by reacting a compound of formula (F) with a reducing agent, such as lithium aluminum hydride, in a suitable solvent such as tetrahydrofuran at a temperature, for example, from 0° C. to 60° C.

A representative synthesis for subject compounds is shown in Scheme 2.

Scheme 2

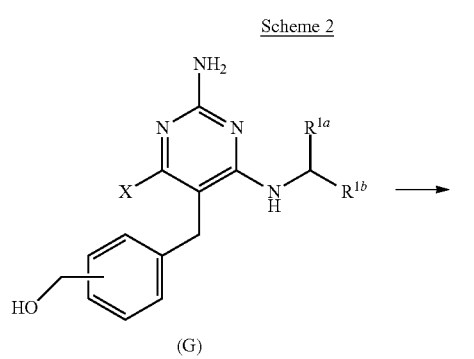

(G)

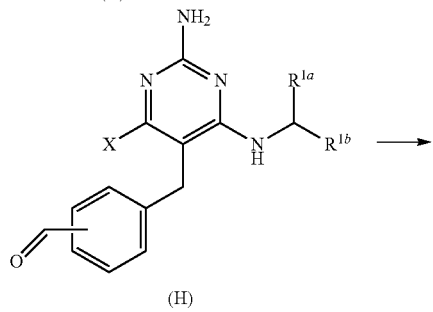

(H)

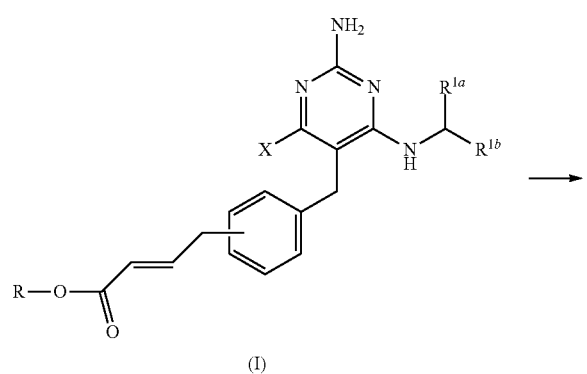

(I)

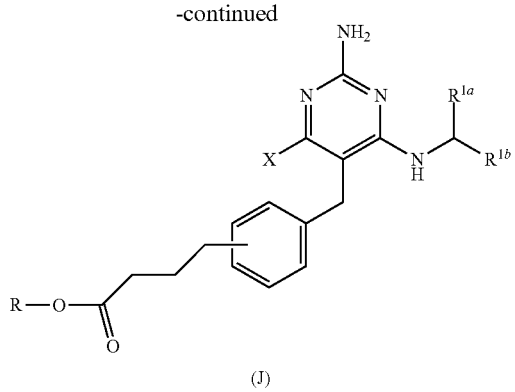

(J)

In Scheme 2, compound of formula (G) is an embodiment wherein $L^1$ is —$CH_2$— and Y is aryl, which is appropriately substituted. Also in Scheme 2, R is H or alkyl.

With continued reference to Scheme 2, compounds of formula (H) may be prepared by reacting a compound of formula (G) with an oxidizing agent, such as manganese oxide, in a suitable solvent such as tetrahydrofuran or N,N-dimethylformamide at a temperature, for example, from 40° C. to 100° C.

Compounds of formula (I) may be prepared by reacting a compound of formula (H) via a Wittig reaction with RO—C(O)—CH=PPh$_3$. The reaction may be carried out in a suitable solvent, such as tetrahydrofuran, at a temperature, for example, from 50° C. to 150° C.

Compounds of formula (J) may be prepared by the reduction of a compound of formula (I) under hydrogenation conditions. The reaction may be carried out with a catalyst such as palladium on carbon under a hydrogen atmosphere in a suitable solvent such as ethyl acetate at a temperature, for example, from 20° C. to 100° C.

A representative synthesis for subject compounds is shown in Scheme 3.

Scheme 3

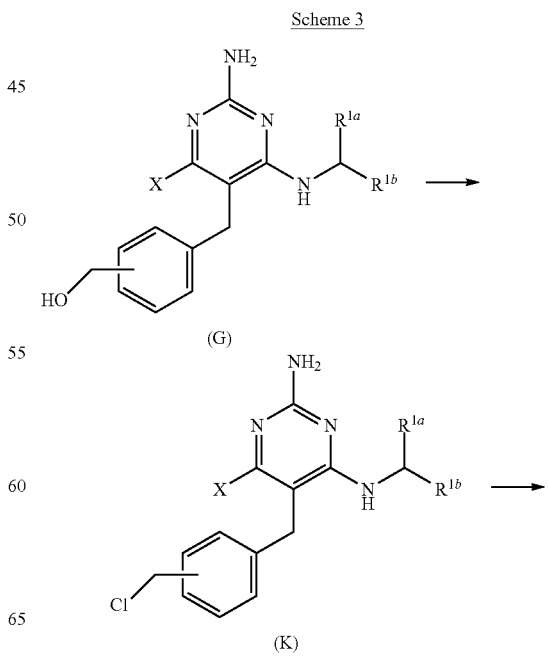

(G)

(K)

Scheme 4

(G) → (K) → (L) → (O)

In Scheme 3, compound of formula (G) is an embodiment wherein L¹ is —CH₂— and Y is aryl, which is appropriately substituted.

With continued reference to Scheme 3, compounds of formula (K) may be prepared by reacting a compound of formula (G) with a chlorinating reagent, such as thionyl chloride in a suitable solvent such as methylene chloride at a temperature, for example, from room temperature to 50° C.

Compounds of formula (L) may be prepared by reacting a compound of formula (K) with a cyanide salt, such as potassium cyanide, in a suitable solvent such as dimethylsulfoxide or N,N-dimethylformamide (or a mixture of both solvents) at a temperature, for example, from room temperature to 50° C.

Compounds of formula (M) may be prepared by reacting a compound of formula (L) with an azido reagent, such as trimethylsilyl azide, in an azide-nitrile cycloaddition. The reaction can be run in a suitable solvent such as NMP or dioxane at a temperature, for example, from 50° C. to 150° C. The reaction may be done in the presence of catalyst, such as dibutyltin oxide.

Compounds of formula (N) may be prepared by reacting a compound of formula (M) with an alkylating agent, such as 2-bromoacetate, in a suitable solvent such as acetone at a temperature, for example, from 0° C. to 60° C.

In Scheme 4, compound of formula (G) is an embodiment wherein L¹ is —CH₂— and Y is aryl, which is appropriately substituted. Preparation of compounds of formula (K) and (L) are described above.

With continued reference to Scheme 4, compounds of formula (O) may be prepared by hydrolyzing a compound of formula (L), such as with use of a base, such as potassium hydroxide, in a suitable solvent such as ethane-1,2-diol and water (or mixtures thereof) at a temperature, for example, from 50° C. to 200° C.

A representative synthesis for subject compounds is shown in Scheme 5.

Scheme 5

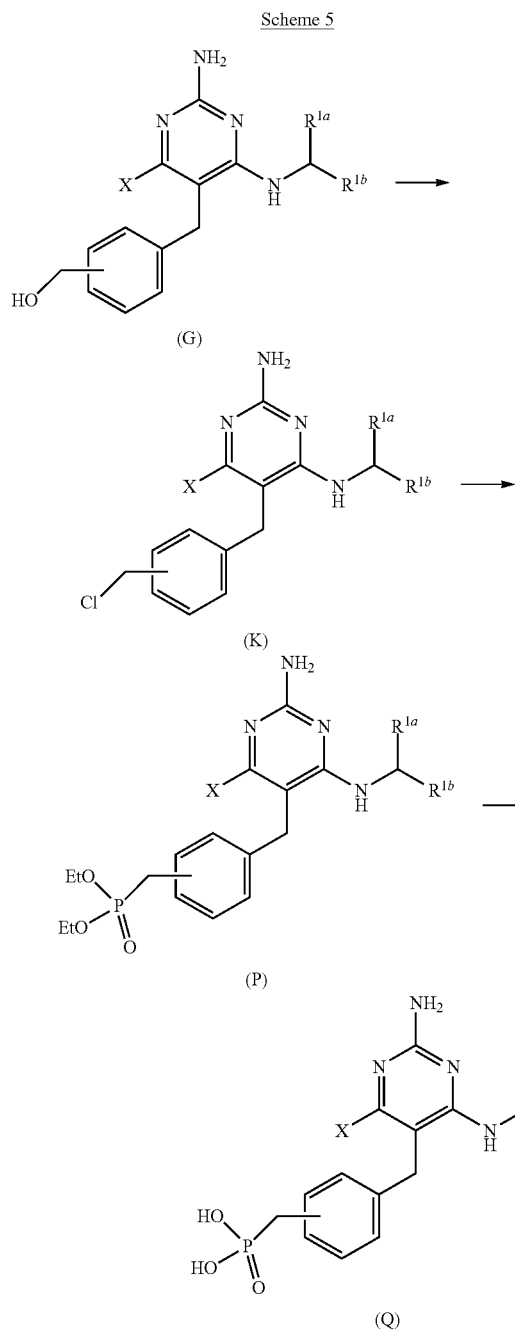

Scheme 6

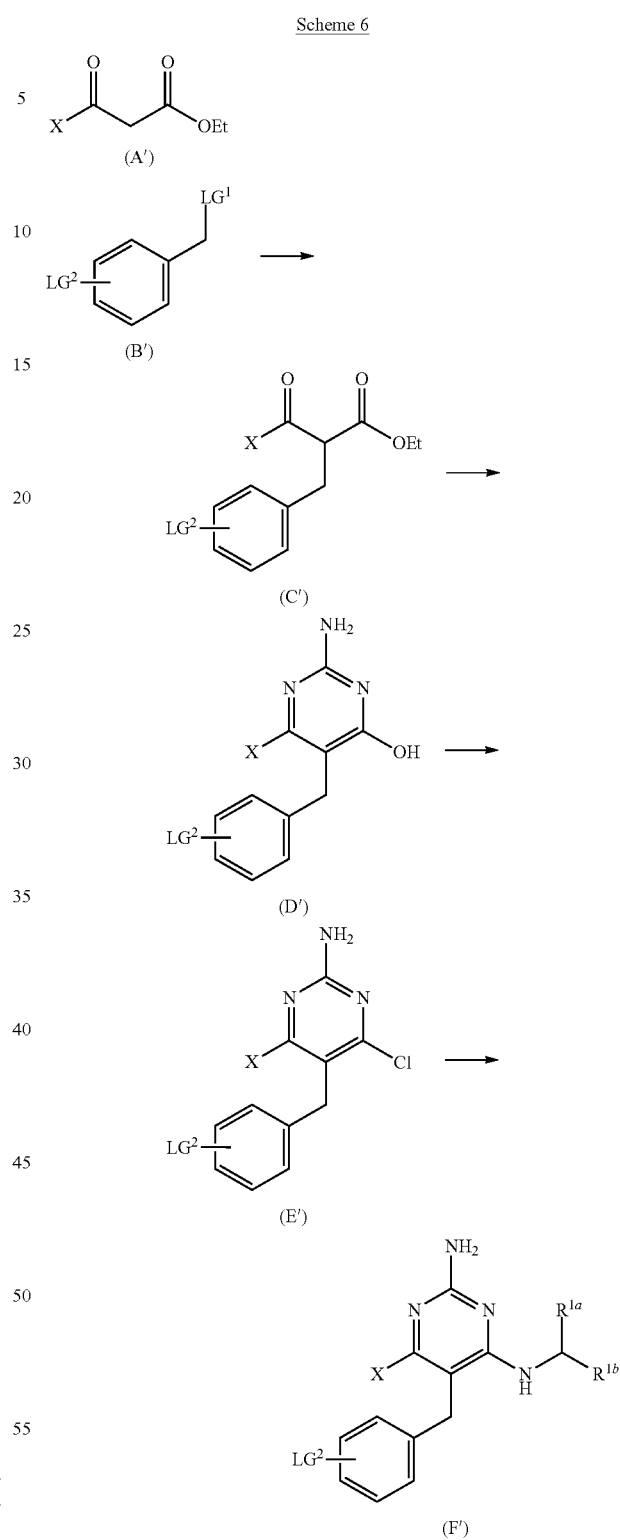

In Scheme 5, compound of formula (G) is an embodiment wherein $L^1$ is —$CH_2$— and Y is aryl, which is appropriately substituted. Preparation of compound of formula (K) is described above.

With continued reference to Scheme 5, compounds of formula (P) may be prepared by reacting a compound of formula (K) with triethylphosphite, in a suitable solvent or neatly at a temperature, for example, from 50° C. to 150° C.

Compounds of formula (Q) may be prepared by reacting a compound of formula (P) with reagents to remove the ethyl groups, such as bromotrimethylsilane, in a suitable solvent such as methylene chloride at a temperature, for example, from room temperature to 60° C.

A representative synthesis for subject compounds is shown in Scheme 6.

In Scheme 6, compound of formula (F') is an embodiment wherein $L^1$ is —$CH_2$— and Y is aryl, which is appropriately substituted. Also in Scheme 6, $LG^1$ and $LG^2$ are leaving groups. Compounds of formula (A') and (B') are commercially available starting materials. Alternatively, compounds of formula (A') and (B') can be synthesized via a variety of different synthetic routes using commercially available starting materials and/or starting materials prepared by conventional synthetic methods.

With continued reference to Scheme 6, compounds of formula (C') may be prepared by reacting a compound of formula (A') with a base, such as sodium hydride, in a suitable solvent such as tetrahydrofuran or N,N-dimethylformamide at a temperature, for example, from 0° C. to room temperature (20° C.), followed by addition of a compound of formula (B). The reaction is then preferably heated at a temperature, for example, from 50° C. to 100° C., optionally in the presence of an additive such as potassium iodide.

Compounds of formula (D') may be prepared by reacting a compound of formula (C') with guanidine or guanidine carbonate in a suitable solvent such as methanol or ethanol at a temperature, for example, in the range from 50° C. to 150° C.

Compounds of formula (E') may be prepared by reacting a compound of formula (D') with phosphorous oxychloride, at a temperature, for example, from 50° C. to 110° C.

Compounds of formula (F') may be prepared by reacting a compound of formula (E') with excess of an amine of formula $R^{1a}R^{1b}NH$, in a suitable solvent such as NMP, butanol or 1,2-dioxane at a temperature, for example, from 50° C. to 150° C. Alternatively, the reaction can be performed in a microwave at a temperature, for example, from 50° C. to 200° C.

A representative synthesis for subject compounds is shown in Scheme 7.

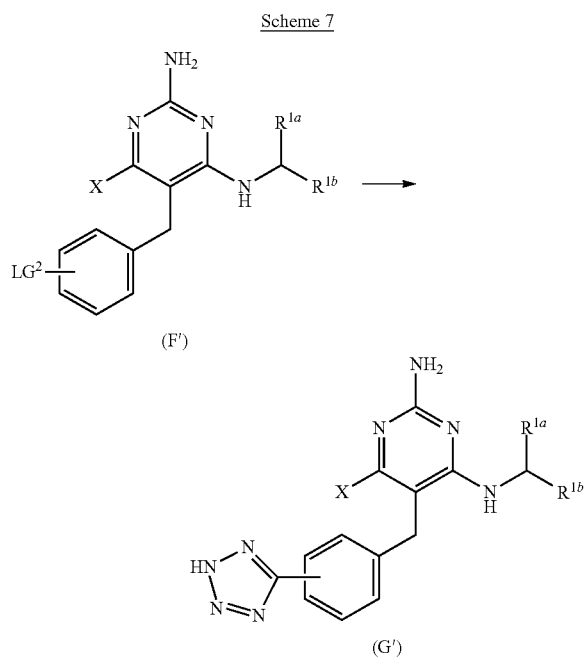

In Scheme 7, compound of formula (F') is an embodiment wherein $L^1$ is —CH$_2$— and Y is aryl, which is appropriately substituted. Also in Scheme 7, LG$^2$ is a leaving group.

With continued reference to Scheme 7, compounds of formula (G') may be prepared by reacting a compound of formula (F') with an azido reagent, such as trimethylsilyl azide, in an azide-nitrile cycloaddition. The reaction can be run in a suitable solvent such as NMP or dioxane at a temperature, for example, from 50° C. to 150° C. The reaction may be done in the presence of catalyst, such as dibutyltin oxide.

A representative synthesis for subject compounds is shown in Scheme 8.

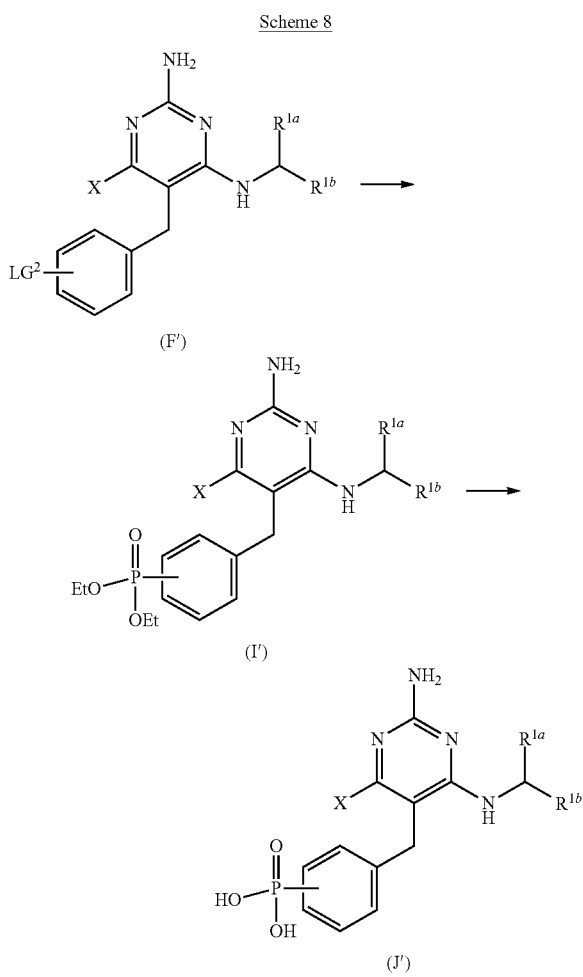

In Scheme 8, compound of formula (F') is an embodiment wherein $L^1$ is —CH$_2$— and Y is aryl, which is appropriately substituted. Also in Scheme 8, LG$^2$ is a leaving group.

With continued reference to Scheme 8, compounds of formula (I') may be prepared by reacting a compound of formula (F') with triethylphosphite, in a suitable solvent or neatly at a temperature, for example, from 50° C. to 150° C.

Compounds of formula (J') may be prepared by reacting a compound of formula (I') with reagents to remove the ethyl groups, such as bromotrimethylsilane, in a suitable solvent such as methylene chloride at a temperature, for example, from room temperature to 60° C.

Method of Treatment

The compounds of formula (1) and their pharmaceutically acceptable salts have activity as pharmaceuticals, in particular as modulators of toll-like receptor (especially TLR7) activity, and thus may be used in the treatment of:
1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;
2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions, non-malignant skin cancer, basal cell carcinoma; actinic keratosis; drug-induced disorders including fixed drug eruptions;
3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;
4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvovaginitis; Peyronie's disease; erectile dysfunction (both male and female);
5. allograft rejection: acute and chronic following, for example, transplantation of kidney, heart, liver, lung, bone marrow, skin or cornea or following blood transfusion; or chronic graft versus host disease;
6. other auto-immune and allergic disorders including rheumatoid arthritis, irritable bowel syndrome, inflammatory bowel syndrome, colitis, Crohn's disease, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;
7. oncology: treatment of common cancers including liver, lung, bladder, gastrointestinal (including gastric, colorectal, esophageal, and rectal), head and neck, prostate, breast, lung, ovarian, pancreatic, bowel and colon, stomach, skin, and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and
8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, parainfluenza; bacterial diseases such as tuberculosis and *mycobacterium avium*, leprosy; other infectious diseases, such as fungal diseases, *chlamydia, Candida, aspergillus*, cryptococcal meningitis, *Pneumocystis* carnii, cryptosporidiosis, histoplasmosis, toxoplasmosis, trypanosome infection and leishmaniasis.

The present disclosure provides the use of a compound of formula (1) or a pharmaceutically acceptable salt thereof as a vaccine adjuvant, used together with one or more antigens against the following diseases: HBV, HPV, meningitis, TDaP, flu, rabies, tuberculosis, malaria, *Staphylococcus aureus* infection, and cancers (tumor-associated antigen or neo-antigen).

Thus, the present disclosure provides a compound of formula (1) or a pharmaceutically-acceptable salt thereof as hereinbefore defined for use in therapy.

In a further aspect, the present disclosure provides the use of a compound of formula (1) or a pharmaceutically acceptable salt thereof as hereinbefore defined in the manufacture of a medicament for use in therapy.

The present disclosure provides a method of treating a condition associated with TLR7 modulation in a subject in need thereof, comprising administering to the subject an effective amount of a compound of the present disclosure, or a pharmaceutically acceptable salt thereof. The present disclosure also provides a compound of the present disclosure, or a pharmaceutically acceptable salt thereof, for use in treating a condition associated with TLR7 modulation. The present disclosure provides use of a compound of the present disclosure, or a pharmaceutically acceptable salt thereof, in the manufacture of a medicament for treating a condition associated with TLR7 modulation. In certain embodiments, the condition is viral infection or cancer.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

In particular, the compounds of the present disclosure (including pharmaceutically acceptable salts) may be used in the treatment of asthma, COPD, allergic rhinitis, allergic conjunctivitis, atopic dermatitis, cancer, hepatitis B, hepatitis C, HIV, HPV, bacterial infections and dermatosis.

The present disclosure still further provides a method of treating, or reducing the risk of, a disease or condition comprising or arising from abnormal cell growth (e.g. a cancer), which method comprises administering to a patient in need thereof a therapeutically effective amount of a compound of formula (1) or a pharmaceutically acceptable salt thereof as hereinbefore defined.

The present disclosure also provides a method of treating, or reducing the risk of, an obstructive airways disease or condition (e.g. asthma or COPD) which comprises administering to a patient in need thereof a therapeutically effective amount of a compound of formula (1) or a pharmaceutically acceptable salt thereof as hereinbefore defined.

For the above-mentioned therapeutic uses the dosage administered will, of course, vary with the compound employed, the mode of administration, the treatment desired and the disorder indicated. For example, the daily dosage of the compound of the present disclosure, if inhaled, may be in the range from about 0.05 micrograms per kilogram body weight (μg/kg) to about 100 micrograms per kilogram body weight (μg/kg). Alternatively, if the compound is administered orally, then the daily dosage of the compound of the present disclosure may be in the range from about 0.01 micrograms per kilogram body weight (μg/kg) to about 100 milligrams per kilogram body weight (mg/kg).

Pharmaceutical Compositions

The compounds of formula (1) and pharmaceutically acceptable salts thereof may be used on their own but will generally be administered in the form of a pharmaceutical composition in which the formula (1) compound/salt (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

In certain embodiments, the administration can be oral, intravenous, subcutaneous, intramuscular, intratumoral, intradermal, intranasal, inhaled, intravesicle, topical, sublingual, bucchal, intrarectal, intrathecal, intracranial, or other forms of local delivery.

Depending on the mode of administration, the pharmaceutical composition will comprise from about 0.05 to about 99% w (percent by weight), more particularly from about 0.05 to about 80% w, still more particularly from about 0.10 to about 70% w, and even more particularly from about 0.10 to about 50% w, of active ingredient, all percentages by weight being based on total composition.

The present disclosure also provides a pharmaceutical composition comprising a compound of formula (1) or a pharmaceutically acceptable salt thereof as hereinbefore defined, in association with a pharmaceutically acceptable adjuvant, diluent or carrier.

The present disclosure further provides a process for the preparation of a pharmaceutical composition of the present disclosure which comprises mixing a compound of formula (1) or a pharmaceutically acceptable salt thereof as hereinbefore defined with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); or by rectal administration in the form of suppositories.

Dry powder formulations and pressurized HFA aerosols of the compounds of the present disclosure (including pharmaceutically acceptable salts) may be administered by oral or nasal inhalation. For inhalation, the compound is desirably finely divided. The finely divided compound preferably has a mass median diameter of less than 10 micrometers (μm), and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

The compounds of the present disclosure may also be administered by means of a dry powder inhaler. The inhaler may be a single or a multi dose inhaler, and may be a breath actuated dry powder inhaler.

One possibility is to mix the finely divided compound of the present disclosure with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. Alternatively the finely divided compound may be coated by another substance. The powder mixture may also be dispensed into hard gelatin capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

For oral administration the compound of the present disclosure may be admixed with an adjuvant or a carrier, for example, lactose, saccharose, sorbitol, mannitol; a starch, for example, potato starch, corn starch or amylopectin; a cellulose derivative; a binder, for example, gelatin or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatin, talcum and titanium dioxide. Alternatively, the tablet may be coated with a suitable polymer dissolved in a readily volatile organic solvent.

For the preparation of soft gelatin capsules, the compound of the present disclosure may be admixed with, for example, a vegetable oil or polyethylene glycol. Hard gelatin capsules may contain granules of the compound using either the above-mentioned excipients for tablets. Also liquid or semi-solid formulations of the compound of the present disclosure may be filled into hard gelatin capsules.

Liquid preparations for oral application may be in the form of syrups or suspensions, for example, solutions containing the compound of the present disclosure, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

Combination Therapy

The compounds of the present disclosure (that is, compounds of formula (1) and pharmaceutically acceptable salts thereof) may also be administered in conjunction with other compounds used for the treatment of the above conditions.

The present disclosure therefore further relates to combination therapies wherein a compound of the present disclosure or a pharmaceutical composition or formulation comprising a compound of the present disclosure is administered concurrently or sequentially or as a combined preparation with another therapeutic agent or agents, for the treatment of one or more of the conditions listed.

The anti-cancer treatment defined hereinbefore may be applied as a sole therapy or may involve, in addition to the compound of the present disclosure, conventional surgery or radiotherapy or chemotherapy. Such chemotherapy may include one or more of the following categories of anti-tumour agents:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example *vinca* alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem. 2004, 47, 6658-6661), and metalloproteinase inhibitors like marimastat, inhibitors of urokinase plasminogen activator receptor function or antibodies to Heparanase);

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp1 1-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD 1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)quinazoline (AZD2171; Example 240 within WO 00/47212), vatalanib (PTK787; WO 98/35985) and SU11248 (sunitinib; WO 01/60814), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies;

(x) Checkpoint inhibitors, including but not limited to antibodies to PD-1/PD-L1, CTLA-4, TIM-3, LAG-3, OX-40, GITR, VISTA, 4-1BB, CD40, TIGIT, BTLA;

(xi) Kinase inhibitors, including but not limited to small molecule or monoclonal antibody inhibitors of BRAF, EGFR, ALK, RAS, RAF, VEGF, HER, c-MET, MEK, FGFR, BCR-ABL, PI3K;

(xii) Inhibitors of cancer/immune metabolism, including but not limited to inhibitors of IDO, TDO, GLS, IDH, arginase, adenosine receptor, CD73, CD39;

(xiii) Epigenetic modulators, including but not limited to inhibitors of HDAC, bromodomain, methyl transferase;

(xiv) Developmental pathway modulator, including but not limited to Smo, Wnt, YAP;

(xv) Other anti-cancer or immune-oncology biologics including but not limited to oncolytic virus, BCG, CART, cytokines; and (xv) Antibodies including but not limited to PD-1 antibody and PD-L1 antibody.

Furthermore, for the treatment of the inflammatory diseases, COPD, asthma and allergic rhinitis the compounds of the present disclosure may be combined with agents such as tumour necrosis factor alpha (TNF-alpha) inhibitors such as anti-TNF monoclonal antibodies (for example Remicade, CDP-870 and adalimumab) and TNF receptor immunoglobulin molecules (such as Enbrel); non-selective cyclooxygenase COX-1/COX-2 inhibitors whether applied topically or systemically (such as piroxicam, diclofenac, propionic acids such as naproxen, flubiprofen, fenoprofen, ketoprofen and ibuprofen, fenamates such as mefenamic acid, indomethacin, sulindac, azapropazone, pyrazolones such as phenylbutazone, salicylates such as aspirin), COX-2 inhibitors (such as meloxicam, celecoxib, rofecoxib, valdecoxib, lumarocoxib, parecoxib and etoricoxib); corticosteroids; glucocorticosteroids (whether administered by topical, oral, intramuscular, intravenous, or intra-articular routes); beta agonists; anti-histamines; methotrexate, lefunomide; hydroxychloroquine, d-penicillamine, auranofin or other parenteral or oral gold preparations.

For the treatment of the infectious diseases, the compounds of the present disclosure may be combined with agents such as nucleoside antivirals; non-nucleoside antivirals, including but not limited inhibitors of entry, polymerase, reverse transcriptase, protease, integrase; monoclonal antibodies against specific viruses; siRNA therapies; antibiotics; and antifungals.

For the treatment of HBV, the compounds of the present disclosure may be combined with agents such as antiviral nucleosides.

The present disclosure still further relates to other innate immune agonists targeting the following classes of receptors, including, but not limited to, TLRs (Toll-like receptor); NLRs (Nod-like receptor); CLRs (C-type lectin receptor); RLRs (RIG-I like receptor); and STING (stimulator of interferon gene).

The present disclosure still further relates to the combination of a compound of the present disclosure and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; an N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; or an indole or quinoline compound such as MK-591, MK-886, and BAY× 1005.

The present disclosure further relates to the combination of a compound of the present disclosure and a receptor antagonist for leukotrienes (LTB4, LTC4, LTD4, and LTE4) selected from the group consisting of the phenothiazin-3-ones such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY×7195.

The present disclosure still further relates to the combination of a compound of the present disclosure and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present disclosure further relates to the combination of a compound of the present disclosure and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present disclosure still further relates to the combination of a compound of the present disclosure and a gastroprotective histamine type 2 receptor antagonist.

The present disclosure further relates to the combination of a compound of the present disclosure and an antagonist of the histamine type 4 receptor.

The present disclosure still further relates to the combination of a compound of the present disclosure and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present disclosure further relates to the combination of a compound of the present disclosure and an anticholinergic agent including muscarinic receptor (M1, M2, and M3) antagonists such as atropine, hyoscine, glycopyrrrolate, ipratropium bromide, tiotropium bromide, oxitropium bromide, pirenzepine or telenzepine.

The present disclosure still further relates to the combination of a compound of the present disclosure together with a beta-adrenoceptor agonist (including beta receptor subtypes 1-4) such as isoprenaline, salbutamol, formoterol, salmeterol, terbutaline, orciprenaline, bitolterol mesylate, and pirbuterol.

The present disclosure further relates to the combination of a compound of the present disclosure and a chromone, such as sodium cromoglycate or nedocromil sodium.

The present disclosure still further relates to the combination of a compound of the present disclosure together with an insulin-like growth factor type I (IGF-I) mimetic.

The present disclosure still further relates to the combination of a compound of the present disclosure and a glucocorticoid, such as flunisolide, triamcinolone acetonide, beclomethasone dipropionate, budesonide, fluticasone propionate, ciclesonide or mometasone furoate.

The present disclosure still further relates to the combination of a compound of the present disclosure together with an inhibitor of matrix metalloproteases (MMPs), i.e., the stromelysins, the collagenases, and the gelatinases, as well as aggrecanase; especially collagenase-1 (MMP-I), collagenase-2 (MMP-8), collagenase-3 (MMP-13), stromelysin-1 (MMP-3), stromelysin-2 (MMP-IO), and stromelysin-3 (MMP-11) and MMP-9 and MMP-12.

The present disclosure still further relates to the combination of a compound of the present disclosure together with modulators of chemokine receptor function such as antagonists of CCR1, CCR2, CCR2A, CCR2B, CCR3, CCR4, CCR5, CCR6, CCR7, CCR8, CCR9, CCR1O and CCR11 (for the C—C family); CXCR1, CXCR2, CXCR3, CXCR4 and CXCR5 (for the C—X—C family) and CX3CR1 for the C—X3-C family.

The present disclosure still further relates to the combination of a compound of the present disclosure together with a cytokine or modulator of cytokine function, including alpha-, beta-, and gamma-interferon; interleukins (IL) including IL1 to 15, and interleukin antagonists or inhibitors, including agents which act on cytokine signalling pathways.

The present disclosure still further relates to the combination of a compound of the present disclosure together with an immunoglobulin (Ig) or Ig preparation or an antagonist or antibody modulating Ig function such as anti-IgE (omalizumab).

The present disclosure further relates to the combination of a compound of the present disclosure and another systemic or topically-applied anti-inflammatory agent, such as thalidomide or a derivative thereof, a retinoid, dithranol or calcipotriol.

The present disclosure further relates to the combination of a compound of the present disclosure together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

In a further aspect the present disclosure provides a combination (for example for the treatment of COPD, asthma or allergic rhinitis) of a compound of formula (1) or a pharmaceutically acceptable salt thereof as hereinbefore defined and one or more agents independently selected from:

a non-steroidal glucocorticoid receptor (GR-receptor) agonist;

a selective β2 adrenoceptor agonist (such as metaproterenol, isoproterenol, isoprenaline, albuterol, salbutamol, formoterol, salmeterol, terbutaline, orciprenaline, bitolterol mesylate, pirbuterol or indacaterol);

a phosphodiesterase inhibitor (such as a PDE4 inhibitor);

a protease inhibitor (such as a neutrophil elastase or matrix metalloprotease MMP-12 inhibitor);

a glucocorticoid;

an anticholinergic agent;

a modulator of chemokine receptor function (such as a CCR1 receptor antagonist); and an inhibitor of kinase function (such as the kinases p38 or IKK).

The present disclosure also provides a pharmaceutical product comprising, in combination, a preparation of a first active ingredient which is a compound of formula (1) or a pharmaceutically acceptable salt thereof as hereinbefore defined, and a preparation of a second active ingredient which is a non-steroidal glucocorticoid receptor (GR-receptor) agonist;

a selective β2 adrenoceptor agonist;

a phosphodiesterase inhibitor;

a protease inhibitor;

a glucocorticoid;

an anticholinergic agent;

a modulator of chemokine receptor function; or an inhibitor of kinase function;

for simultaneous, sequential or separate use in therapy.

In another aspect, the present disclosure provides a kit comprising a preparation of a first active ingredient which is a compound of formula (1) or a pharmaceutically acceptable salt thereof as hereinbefore defined, and a preparation of a second active ingredient which is a non-steroidal glucocorticoid receptor (GR-receptor) agonist;

a selective β2 adrenoceptor agonist;

a phosphodiesterase inhibitor;

a protease inhibitor;

a glucocorticoid;

an anticholinergic agent;

a modulator of chemokine receptor function; or an inhibitor of kinase function;

and instructions for the simultaneous, sequential or separate administration of the preparations to a patient in need thereof.

EXEMPLARY EMBODIMENTS

Embodiment I-1

A compound having the structure of Formula (1), or a pharmaceutically acceptable salt thereof,

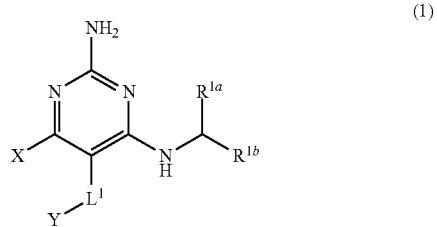

(1)

wherein $R^{1a}$ is selected from the group consisting of H, $C_1$-$C_4$ alkyl, —$NH_2$, —COOH, and —$SO_2CH_3$, wherein the alkyl is optionally substituted with —OH, —$NH_2$, —COOH, or —$SO_2CH_3$;

$R^{1b}$ is $C_2$-$C_5$ alkyl;

X is selected from the group consisting of H and $C_1$-$C_4$ alkyl, wherein the alkyl is optionally substituted with A;

$L^1$ is selected from the group consisting of a bond, —$CH_2$—, —$CF_2$—,

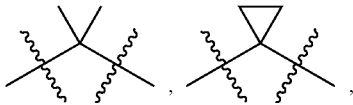

—O—, —S—, —$SO_2$—, —NH—, and —$CH_2CH_2$—;

Y is selected from the group consisting of $C_1$-$C_3$ alkyl, aryl, and heteroaryl, wherein the alkyl, aryl, and heteroaryl are optionally substituted with 1-5 substituents that are independently selected from A, $C_1$-$C_3$ alkyl, and $C_1$-$C_3$ alkoxy;

A is selected from the group consisting of

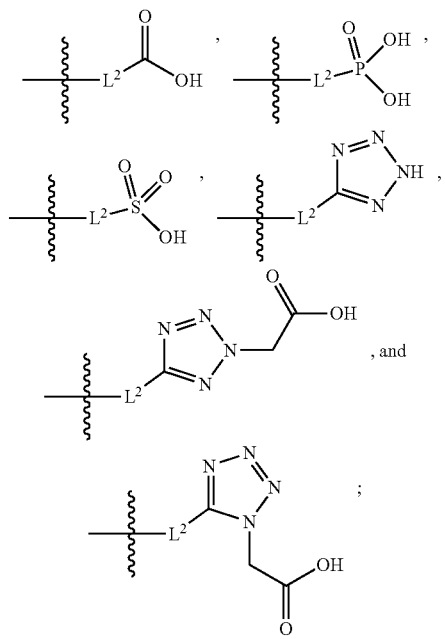

$L^2$ is selected from the group consisting of a bond, —(CH$_2$)$_n$—, —C(O)NH(CH$_2$)$_n$—,

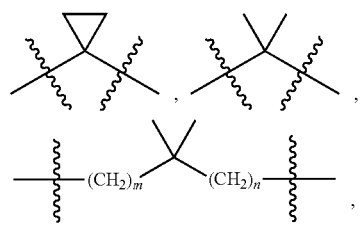

—[O(CH$_2$CH$_2$)]$_n$—, —[O(C$_1$-C$_4$ alkylene)]-, and —[O(CH$_2$CH$_2$)]$_n$—OCH$_2$CH$_2$CF$_2$—;

m is an integer from zero to four; and n is an integer from one to four; and wherein the compound is substituted with at least one A; and when X is —CH$_3$; $L^1$ is —CH$_2$—; Y is aryl substituted with A; and $L^2$ is —CH$_2$—; then A is not -$L^2$-COOH, except when $R^{1a}$ comprises —COOH.

Embodiment I-2

The compound of Embodiment I-1, or a pharmaceutically acceptable salt thereof, wherein $R^{1b}$ is —(CH$_2$)$_2$CH$_3$.

Embodiment I-3

The compound of Embodiment I-1, or a pharmaceutically acceptable salt thereof, wherein $R^{1b}$ is —(CH$_2$)$_3$CH$_3$.

Embodiment I-4

The compound of any one of Embodiments I-1 to I-3, or a pharmaceutically acceptable salt thereof, wherein $R^{1a}$ is $C_1$-$C_4$ alkyl, optionally substituted with —OH.

Embodiment I-5

The compound of any one of Embodiments I-1 to I-4, or a pharmaceutically acceptable salt thereof, wherein $R^{1a}$ is —CH$_2$C(CH$_3$)$_2$OH.

Embodiment I-6

The compound of any one of Embodiments I-1 to I-4, or a pharmaceutically acceptable salt thereof, wherein

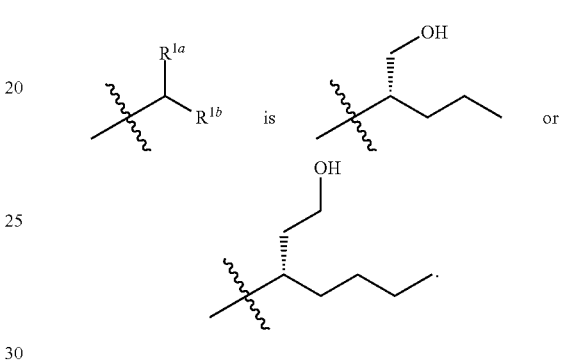

Embodiment I-7

The compound of any one of Embodiments I-1 to I-3, or a pharmaceutically acceptable salt thereof, wherein $R^{1a}$ is $C_1$-$C_4$ alkyl, optionally substituted with —COOH.

Embodiment I-8

The compound of any one of Embodiments I-1 to I-3 and I-7, or a pharmaceutically acceptable salt thereof, wherein

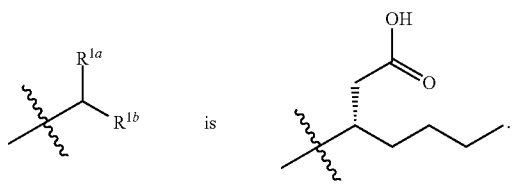

Embodiment I-9

The compound of any one of Embodiments I-1 to I-3, or a pharmaceutically acceptable salt thereof, wherein $R^{1a}$ is H.

Embodiment I-10

The compound of any one of Embodiments I-1 to I-9, or a pharmaceutically acceptable salt thereof, wherein X is $C_1$-$C_4$ alkyl, wherein the alkyl is substituted with A.

Embodiment I-11

The compound of any one of Embodiments I-1 to I-10, or a pharmaceutically acceptable salt thereof, wherein X is $C_1$-$C_4$ alkyl, wherein the alkyl is substituted with

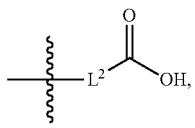

wherein $L^2$ is a bond.

Embodiment I-12

The compound of any one of Embodiments I-1 to I-9, or a pharmaceutically acceptable salt thereof, wherein X is $CH_3$.

Embodiment I-13

The compound of any one of Embodiments I-1 to I-9, or a pharmaceutically acceptable salt thereof, wherein X is H.

Embodiment I-14

The compound of any one of Embodiments I-1 to I-13, or a pharmaceutically acceptable salt thereof, wherein $L^1$ is —$CH_2$—, —$CH_2CH_2$—, or —O—.

Embodiment I-15

The compound of any one of Embodiments I-1 to I-14, or a pharmaceutically acceptable salt thereof, wherein $L^1$ is —$CH_2$—.

Embodiment I-16

The compound of any one of Embodiments I-1 to I-15, or a pharmaceutically acceptable salt thereof, wherein Y is $C_1$-$C_3$ alkyl or aryl.

Embodiment I-17

The compound of any one of Embodiments I-1 to I-16, or a pharmaceutically acceptable salt thereof, wherein Y is aryl, wherein the aryl is substituted with $C_1$-$C_3$ alkoxy.

Embodiment I-18

The compound of any one of Embodiments I-1 to I-17, or a pharmaceutically acceptable salt thereof, wherein Y is aryl, wherein the aryl is substituted with A.

Embodiment I-19

The compound of any one of Embodiments I-1 to I-18, or a pharmaceutically acceptable salt thereof, wherein A is

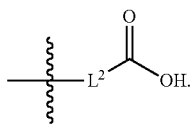

Embodiment I-20

The compound of any one of Embodiments I-1 to I-18, or a pharmaceutically acceptable salt thereof, wherein A is

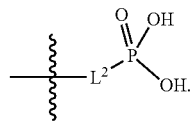

Embodiment I-21

The compound of any one of Embodiments I-1 to I-18, or a pharmaceutically acceptable salt thereof, wherein A is

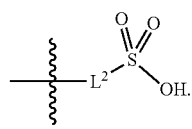

Embodiment I-22

The compound of any one of Embodiments I-1 to I-18, or a pharmaceutically acceptable salt thereof, wherein A is

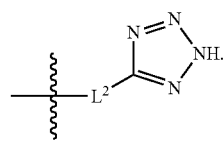

Embodiment I-23

The compound of any one of Embodiments I-1 to I-18, or a pharmaceutically acceptable salt thereof, wherein A is

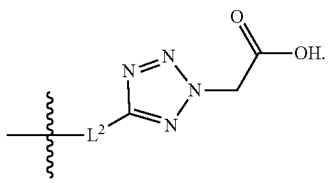

Embodiment I-24

The compound of any one of Embodiments I-1 to I-18, or a pharmaceutically acceptable salt thereof, wherein A is

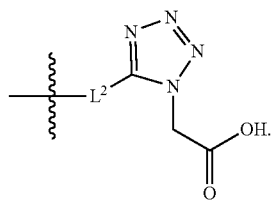

Embodiment I-25

The compound of any one of Embodiments I-1 to I-24, or a pharmaceutically acceptable salt thereof, wherein $L^2$ is $-(CH_2)_n-$.

Embodiment I-26

The compound of any one of Embodiments I-1 to I-25, or a pharmaceutically acceptable salt thereof, wherein n is one or two.

Embodiment I-27

The compound of any one of Embodiments I-1 to I-24, or a pharmaceutically acceptable salt thereof, wherein $L^2$ is

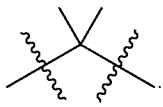 [SMILES: *C(*)(C)C]

Embodiment I-28

The compound of any one of Embodiments I-1 to I-24, or a pharmaceutically acceptable salt thereof, wherein $L^2$ is

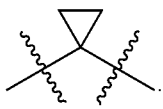

Embodiment I-29

The compound of any one of Embodiments I-1 to I-24, or a pharmaceutically acceptable salt thereof, wherein $L^2$ is $-C(O)NH(CH_2)_n-$.

Embodiment I-30

A compound of Embodiment I-1, or a pharmaceutically acceptable salt thereof, wherein the compound of Formula (1) is a compound of Formula (1a),

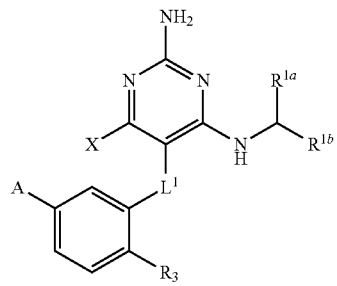

wherein
X is H or $CH_3$
$L^1$ is selected from the group consisting of a bond, $-CH_2-$, $-CF_2-$,

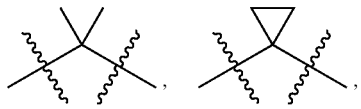

and $-CH_2CH_2-$;
A is selected from the group consisting of

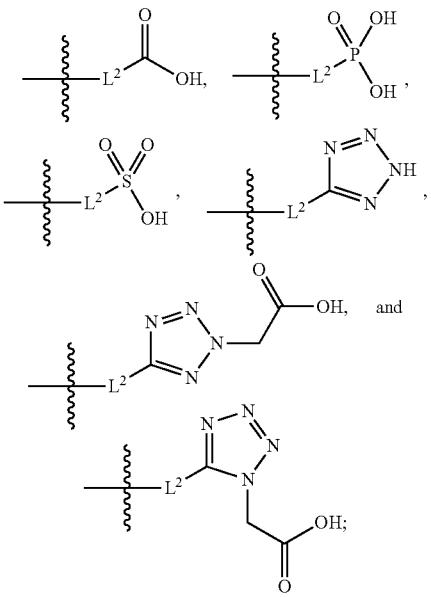

$L^2$ is selected from the group consisting of a bond, $-CH_2-$, $-CH_2CH_2-$,

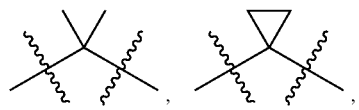

$-C(O)NH(CH_2)_n-$, $-[O(CH_2CH_2)]_n-$, $-[O(C_1-C_4 \text{ alkylene})]-$, and $-[O(CH_2CH_2)]_n-OCH_2CH_2CF_2-$; and
$R^3$ is H, $C_1-C_3$ alkyl, or $C_1-C_3$ alkoxy.

Embodiment I-31

A compound of Embodiment I-1, or a pharmaceutically acceptable salt thereof, wherein the compound of Formula (1) is a compound of Formula (1a),

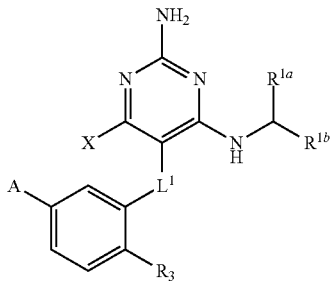

wherein
X is $-CH_2-A^{1a}$, $-CH_2CH_2-A^{1a}$, $-CH_2CH_2CH_2-A^{1a}$, or $-CH_2C(CH_3)_2-A^{1a}$;

$A^{1a}$ is selected from the group consisting of

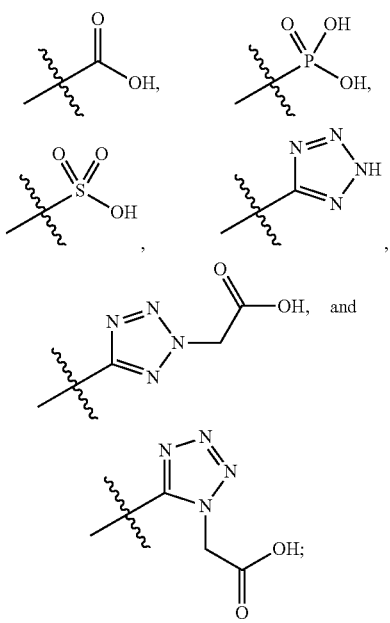

$L^1$ is selected from the group consisting of a bond, —CH$_2$—, —CF$_2$—,

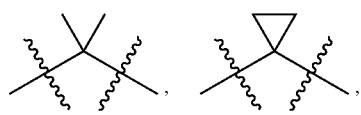

and —CH$_2$CH$_2$—;
A is selected from the group consisting of

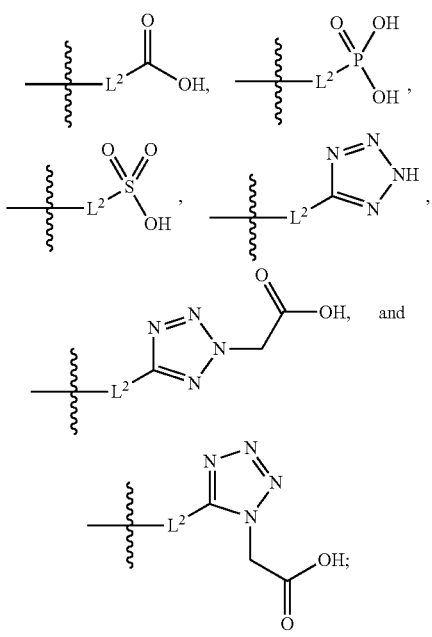

$L^2$ is selected from the group consisting of a bond, —CH$_2$—, —CH$_2$CH$_2$—,

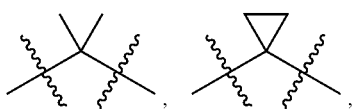

—C(O)NH(CH$_2$)$_n$—, —[O(CH$_2$CH$_2$)]$_n$—, —[O(C$_1$-C$_4$ alkylene)]-, and —[O(CH$_2$CH$_2$)]$_n$—OCH$_2$CH$_2$CF$_2$—; and
$R^3$ is H, C$_1$-C$_3$ alkyl, or C$_1$-C$_3$ alkoxy.

Embodiment I-32

A compound of Embodiment I-1, or a pharmaceutically acceptable salt thereof, wherein the compound of Formula (1) is a compound of Formula (1b),

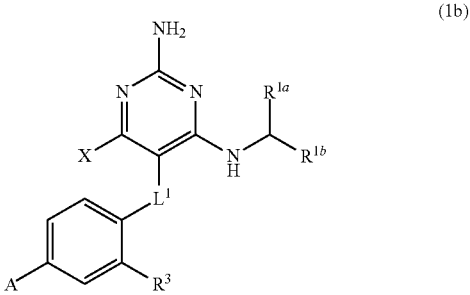

(1b)

wherein
X is H or CH$_3$;
$L^1$ is selected from the group consisting of a bond, —CH$_2$—, —CF$_2$—,

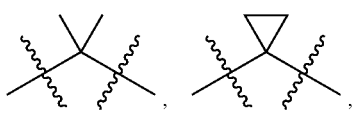

and —CH$_2$CH$_2$—;
A is selected from the group consisting of

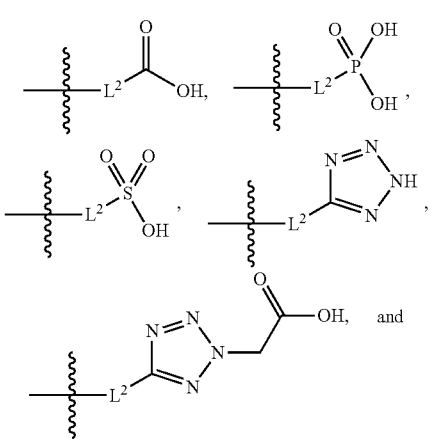

-continued

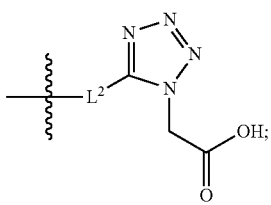

$L^2$ is selected from the group consisting of a bond, —CH₂—, —CH₂CH₂—,

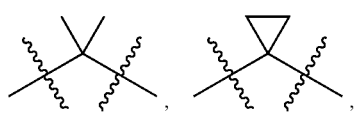

—C(O)NH(CH₂)$_n$—, —[O(CH₂CH₂)]$_n$—, —[O(C₁-C₄ alkylene)]-, and —[O(CH₂CH₂)]$_n$—OCH₂CH₂CF₂—; and $R^3$ is H, C₁-C₃ alkyl, or C₁-C₃ alkoxy.

Embodiment I-33

A compound of Embodiment I-1, or a pharmaceutically acceptable salt thereof, wherein the compound of Formula (1) is a compound of Formula (1b), (1b)

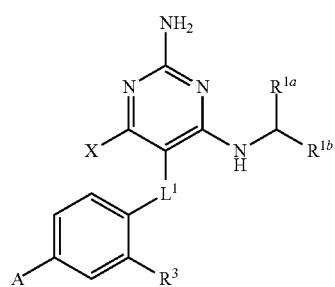

wherein

X is —CH₂-A$^{1a}$, —CH₂CH₂-A$^{1a}$, —CH₂CH₂CH₂-A$^{1a}$, or —CH₂C(CH₃)₂-A$^{1a}$;

A$^{1a}$ is selected from the group consisting of

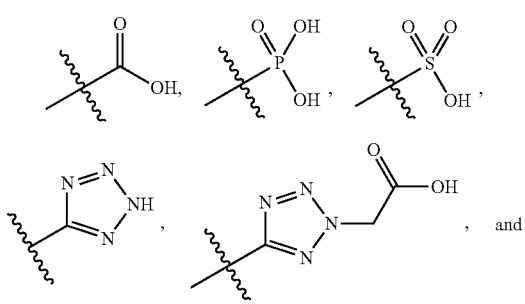

-continued

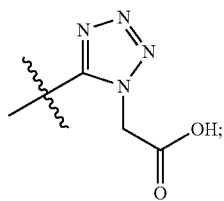

$L^1$ is selected from the group consisting of a bond, —CH₂—, —CF₂—,

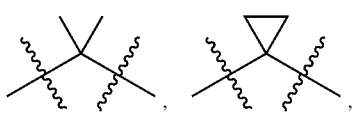

and —CH₂CH₂—;

A is selected from the group consisting of

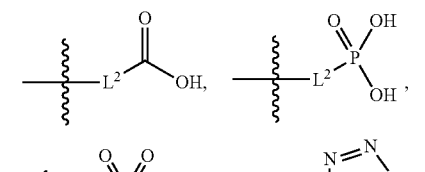

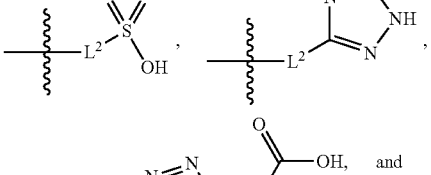

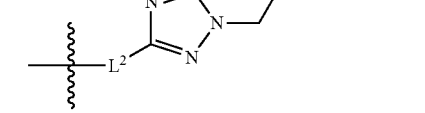, and

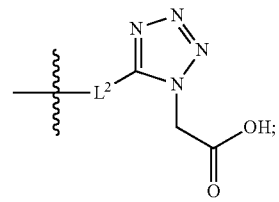

$L^2$ is selected from the group consisting of a bond, —CH₂—, —CH₂CH₂—,

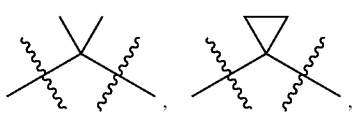

—C(O)NH(CH₂)$_n$—, —[O(CH₂CH₂)]$_n$—, —[O(C₁-C₄ alkylene)]-, and —[O(CH₂CH₂)]$_n$—OCH₂CH₂CF₂—; and $R^3$ is H, C₁-C₃ alkyl, or C₁-C₃ alkoxy.

Embodiment I-34

A compound of Embodiment I-1, or a pharmaceutically acceptable salt thereof, wherein the compound of Formula (1) is a compound of Formula (1c),

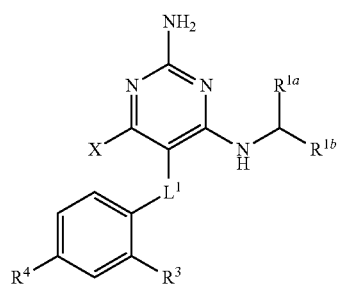
(1c)

wherein

X is —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$;

A$^{1a}$ is selected from the group consisting of

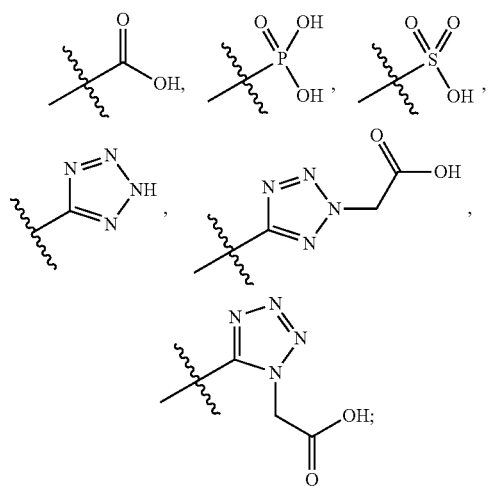

, and

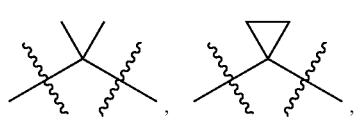

L$^1$ is selected from the group consisting of a bond, —CH$_2$—, —CF$_2$—,

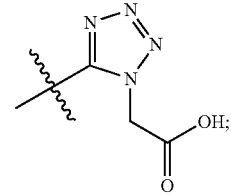

and —CH$_2$CH$_2$—;

R$^3$ is H, C$_1$-C$_3$ alkyl, or C$_1$-C$_3$ alkoxy; and
R$^4$ is H or C$_1$-C$_3$ alkoxy.

Embodiment I-35

A compound of Embodiment I-1, or a pharmaceutically acceptable salt thereof, wherein the compound of Formula (1) is a compound of Formula (1d),

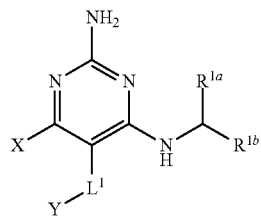
(1d)

X is —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$;

A$^{1a}$ is selected from the group consisting of

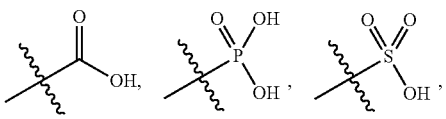

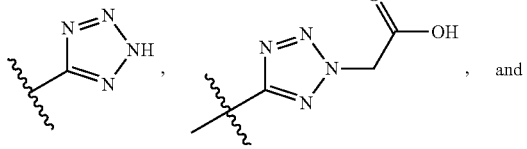
, and

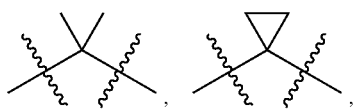

L$^1$ is selected from the group consisting of a bond, —CH$_2$—, —CF$_2$—,

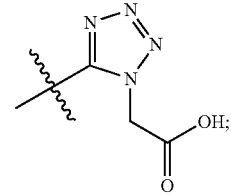

—O—, and —CH$_2$CH$_2$—; and
Y is H or C$_1$-C$_3$ alkyl.

Embodiment I-36

A compound of Embodiment I-1, or a pharmaceutically acceptable salt thereof, wherein the compound of Formula (1) is a compound of Formula (1e),

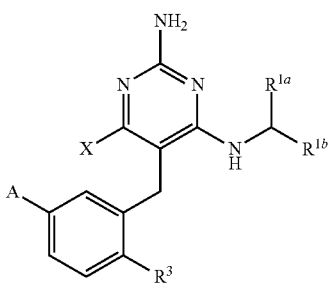
(1e)

wherein
$R^3$ is H, $C_1$-$C_3$ alkyl, or $C_1$-$C_3$ alkoxy.

Embodiment I-37

A compound of Embodiment I-1, or a pharmaceutically acceptable salt thereof, wherein the compound of Formula (1) is a compound of Formula (1f),

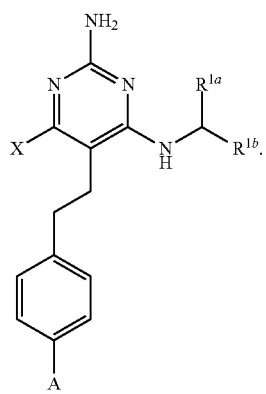

(1f)

Embodiment I-38

A compound of Embodiment I-1, or a pharmaceutically acceptable salt thereof, wherein the compound of Formula (1) is a compound of Formula (1g),

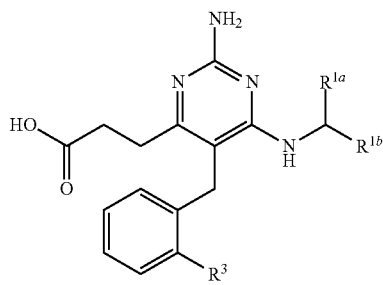

(1g)

wherein
$R^3$ is H, $C_1$-$C_3$ alkyl, or $C_1$-$C_3$ alkoxy.

Embodiment I-39

A compound of Embodiment I-1, or a pharmaceutically acceptable salt thereof, wherein the compound of Formula (1) is a compound of Formula (1h),

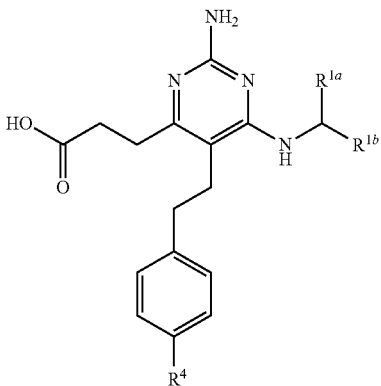

(1h)

wherein
$R^4$ is H or $C_1$-$C_3$ alkoxy.

Embodiment I-40

A compound of Embodiment I-1, or a pharmaceutically acceptable salt thereof, wherein the compound of Formula (1) is a compound of Formula (1i),

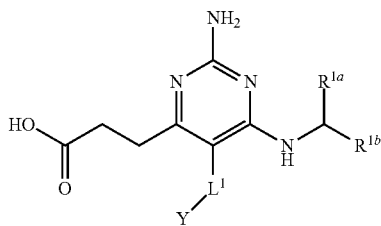

(1i)

wherein
$L^1$ is selected from the group consisting of a bond, —$CH_2$—, —$CF_2$—,

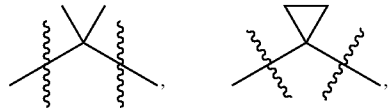

—O—, and —$CH_2CH_2$—; and
Y is H or $C_1$-$C_3$ alkyl.

Embodiment I-41

A compound, or a pharmaceutically acceptable salt, selected from the group consisting of:

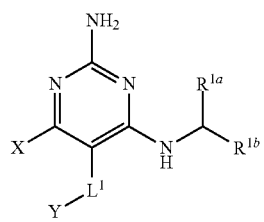

| Compound | —X | —L¹—Y | 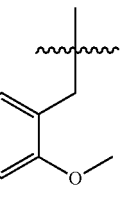 |
|---|---|---|---|
| 1 | —CH₃ | 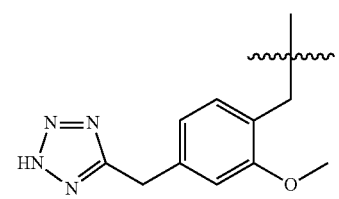 [SMILES: *Cc1ccc(Cc2nn[nH]n2)cc1OC] | —(CH₂)₃CH₃ |
| 2 | —CH₃ | 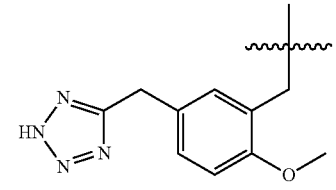 [SMILES: *Cc1cc(Cc2nn[nH]n2)ccc1OC] | —(CH₂)₃CH₃ |
| 3 | —CH₃ | 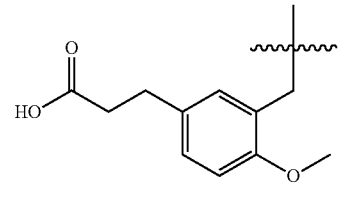 [SMILES: *Cc1cc(CCC(=O)O)ccc1OC] | —(CH₂)₃CH₃ |
| 4 | —CH₃ | 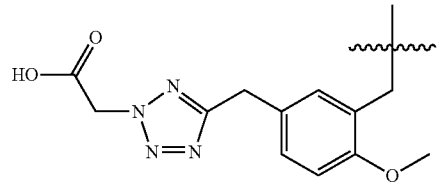 [SMILES: *Cc1cc(Cc2nnn(CC(=O)O)n2)ccc1OC] | —(CH₂)₃CH₃ |
| 5 | —CH₃ | 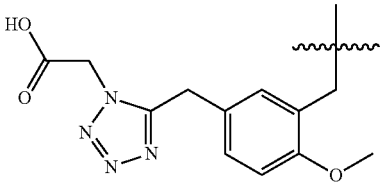 [SMILES: *Cc1cc(Cc2nnnn2CC(=O)O)ccc1OC] | —(CH₂)₃CH₃ |
| 6 | —CH₃ | 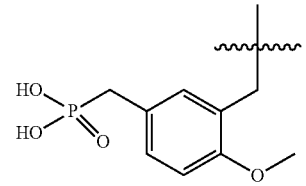 [SMILES: *Cc1cc(CP(=O)(O)O)ccc1OC] | —(CH₂)₃CH₃ |
| 7 | —CH₃ |  | —(CH₂)₃CH₃ |

-continued

| Compound | —X | —L¹—Y | ![structure](Rᴬ/Rᴮ branch) |
|---|---|---|---|
| 8 | —CH₃ | 5-(2H-tetrazol-5-ylmethyl)-2-methoxyphenyl, CH₂ linker | (S)-2-(hydroxymethyl)pentyl (—CH(CH₂OH)CH₂CH₂CH₃) |
| 9 | —CH₃ | 5-(2-hydroxy-2-oxopropan-2-yl)... 2-(4-methoxy-3-substituted phenyl)-2-methylpropanoic acid | —(CH₂)₃CH₃ |
| 10 | —CH₃ | 5-[2-(2H-tetrazol-5-yl)propan-2-yl]-2-methoxyphenyl | —(CH₂)₃CH₃ |
| 11 | —CH₃ | 5-(2H-tetrazol-5-yl)-2-methoxyphenyl | —(CH₂)₃CH₃ |
| 12 | —CH₃ | 5-phosphono-2-methoxyphenyl | —(CH₂)₃CH₃ |
| 13 | —CH₃ | 5-[1-(2H-tetrazol-5-yl)cyclopropyl]-2-methoxyphenyl | —(CH₂)₃CH₃ |
| 14 | —CH₃ | 5-(1-carboxycyclopropyl)-2-methoxyphenyl | —(CH₂)₃CH₃ |

-continued

| Compound | —X | —L¹—Y | ![R1a/R1b structure] |
|---|---|---|---|
| 15 | HOOC-CH₂CH₂-C(CH₃)- (4-carbon chain with COOH) | benzyl with 2-OMe | —(CH₂)₃CH₃ |
| 16 | —CH₃ | HO₃S-CH₂CH₂-NH-C(O)-phenyl(4-OMe)-CH₂- | —(CH₂)₃CH₃ |
| 17 | —CH₃ | HO₃S-phenyl(4-OMe)-CH₂- | —(CH₂)₃CH₃ |
| 18 | —CH₃ | tetrazol-5-yl-CH₂-phenyl(4-OMe)-CH₂- | (S)-2-(hydroxyethyl)hexyl |
| 19 | HOOC-CH₂CH₂-C(CH₃)- | 4-methoxyphenethyl | —(CH₂)₃CH₃ |
| 20 | —CH₃ | tetrazol-5-yl-CH₂-phenyl(4-OMe)-CH₂- | (S)-2-(carboxymethyl)hexyl |
| 21 | HOOC-CH₂CH₂-C(CH₃)- | —OCH₃ | (S)-2-(hydroxyethyl)hexyl |

Embodiment I-42

A pharmaceutical composition comprising a compound of any one of Embodiments I-1 to I-41, or a pharmaceutically acceptable salt thereof, and a pharmaceutically acceptable carrier.

Embodiment I-43

A method of treating a condition associated with TLR7 modulation in a subject in need thereof, comprising administering to the subject an effective amount of a compound of any one of Embodiments I-1 to I-41, or a pharmaceutically acceptable salt thereof.

Embodiment I-44

The method of Embodiment I-43, wherein the condition is viral infection or cancer.

Embodiment I-45

A compound of any one of Embodiments I-1 to I-41, or a pharmaceutically acceptable salt thereof, for use in treating a condition associated with TLR7 modulation.

Embodiment I-46

The compound of Embodiment I-45, wherein the condition is viral infection or cancer.

Embodiment I-47

Use of a compound of any one of Embodiments I-1 to I-41, or a pharmaceutically acceptable salt thereof, in the manufacture of a medicament for treating a condition associated with TLR7 modulation.

Embodiment I-48

The use of Embodiment I-47, wherein the condition is viral infection or cancer.

Embodiment II-1

A compound having the structure of Formula (1), or a pharmaceutically acceptable salt thereof,

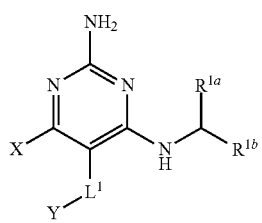

(1)

wherein
$R^{1a}$ is selected from the group consisting of H, $C_1$-$C_4$ alkyl, —$NH_2$, —NHAc, —COOH, —$SO_2CH_3$, —$SCH_3$, —$OCH_3$, and

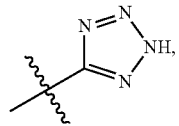 [SMILES: *c1nn[nH]n1]

wherein the alkyl is optionally substituted with —OH, —$NH_2$, —NHAc, —COOH, —$SO_2CH_3$, —$SCH_3$, —$OCH_3$, or

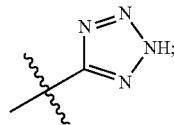 [SMILES: *c1nn[nH]n1]

$R^{1b}$ is $C_2$-$C_5$ alkyl;
X is selected from the group consisting of H and $C_1$-$C_4$ alkyl, wherein the alkyl is optionally substituted with A, —OH, or —$C(CH_3)_2OH$;
$L^1$ is selected from the group consisting of a bond, —$CH_2$—, —$CF_2$—,

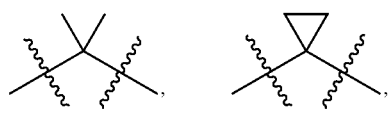

—O—, —S—, —$SO_2$—, —NH—, and —$CH_2CH_2$—;
Y is selected from the group consisting of $C_1$-$C_3$ alkyl, aryl, and heteroaryl, wherein the alkyl, aryl, and heteroaryl are optionally substituted with 1-5 substituents that are independently selected from A, $C_1$-$C_3$ alkyl, and $C_1$-$C_3$ alkoxy;
A is selected from the group consisting of

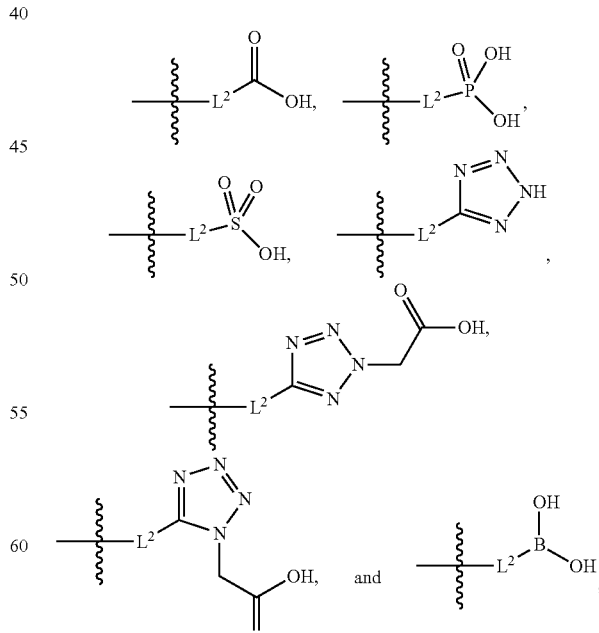

$L^2$ is selected from the group consisting of a bond, —$(CH_2)_n$—, —$C(O)NH(CH_2)_n$—,

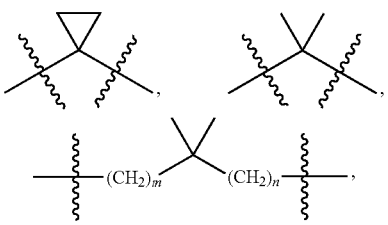

—[O(CH$_2$CH$_2$)]$_n$—, —[O(C$_1$-C$_4$ alkylene)]-, —[O(CH$_2$CH$_2$)]$_n$—OCH$_2$CH$_2$CF$_2$—; —C(O)NHCH$_2$CH$_2$—[O(CH$_2$CH$_2$)]$_m$—; and —C(O)NHCH$_2$CH$_2$—[O(CH$_2$CH$_2$)]$_m$—OCH$_2$CH$_2$CF$_2$—;

m is an integer from zero to four; and n is an integer from one to four; and wherein the compound is substituted with at least one A; and when X is —CH$_3$; L$^1$ is —CH$_2$—; Y is aryl substituted with A; and L$^2$ is —CH$_2$—; then A is not -L$^2$-COOH, except when R$^{1a}$ comprises —COOH.

Embodiment II-2

The compound of Embodiment II-1, or a pharmaceutically acceptable salt thereof, wherein R$^{1b}$ is —(CH$_2$)$_2$CH$_3$.

Embodiment II-3

The compound of Embodiment II-1, or a pharmaceutically acceptable salt thereof, wherein R$^{1b}$ is —(CH$_2$)$_3$CH$_3$.

Embodiment II-4

The compound of any one of Embodiments II-1 to II-3, or a pharmaceutically acceptable salt thereof, wherein R$^{1a}$ is C$_1$-C$_4$ alkyl, optionally substituted with —OH, —OCH$_3$, —SCH$_3$, —SO$_2$CH$_3$ Embodiment II-5

The compound of any one of Embodiments II-1 to II-4, or a pharmaceutically acceptable salt thereof, wherein R$^{1a}$ is —CH$_2$C(CH$_3$)$_2$OH.

Embodiment II-6

The compound of any one of Embodiments II-1 to II-4, or a pharmaceutically acceptable salt thereof, wherein

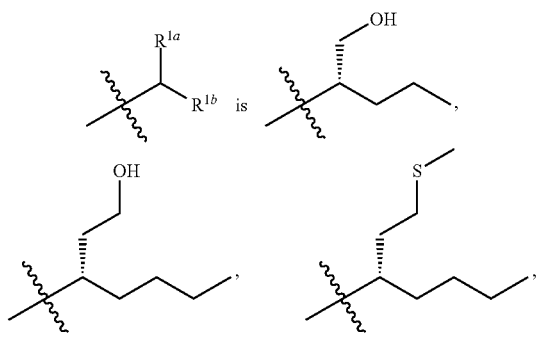

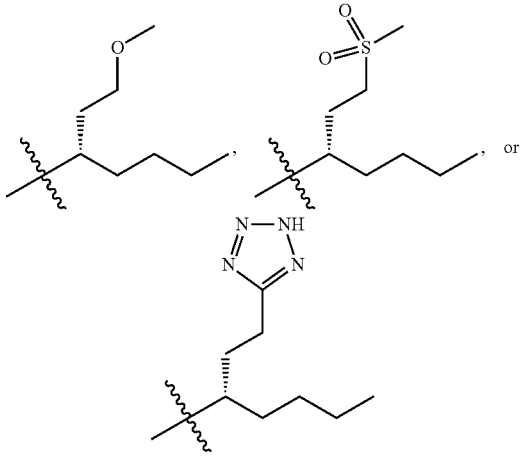

Embodiment II-7

The compound of any one of Embodiments II-1 to II-3, or a pharmaceutically acceptable salt thereof, wherein R$^{1a}$ is C$_1$-C$_4$ alkyl, optionally substituted with —COOH.

Embodiment II-8

The compound of any one of Embodiments II-1 to II 3 and II-7, or a pharmaceutically acceptable salt thereof, wherein

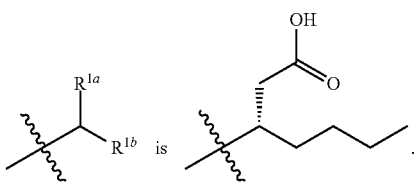

Embodiment II-9

The compound of any one of Embodiments II-1 to II-3, or a pharmaceutically acceptable salt thereof, wherein R$^{1a}$ is H.

Embodiment II-10

The compound of any one of Embodiments II-1 to II-9, or a pharmaceutically acceptable salt thereof, wherein X is C$_1$-C$_4$ alkyl, wherein the alkyl is substituted with A.

Embodiment II-11

The compound of any one of Embodiments II-1 to II-10, or a pharmaceutically acceptable salt thereof, wherein X is C$_1$-C$_4$ alkyl, wherein the alkyl is substituted with

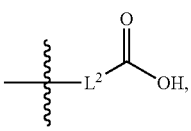

wherein L$^2$ is a bond.

Embodiment II-12

The compound of any one of Embodiments II-1 to II-9, or a pharmaceutically acceptable salt thereof, wherein X is $CH_3$.

Embodiment II-13

The compound of any one of Embodiments II-1 to II-9, or a pharmaceutically acceptable salt thereof, wherein X is H.

Embodiment II-14

The compound of any one of Embodiments II-1 to II-13, or a pharmaceutically acceptable salt thereof, wherein $L^1$ is —$CH_2$—, —$CH_2CH_2$—, —O—, or —S—.

Embodiment II-15

The compound of any one of Embodiments II-1 to II-14, or a pharmaceutically acceptable salt thereof, wherein $L^1$ is —$CH_2$—.

Embodiment II-16

The compound of any one of Embodiments II-1 to II-15, or a pharmaceutically acceptable salt thereof, wherein Y is $C_1$-$C_3$ alkyl or aryl.

Embodiment II-17

The compound of any one of Embodiments II-1 to II-16, or a pharmaceutically acceptable salt thereof, wherein Y is aryl, wherein the aryl is substituted with $C_1$-$C_3$ alkoxy.

Embodiment II-18

The compound of any one of Embodiments II-1 to II-17, or a pharmaceutically acceptable salt thereof, wherein Y is aryl, wherein the aryl is substituted with A.

Embodiment II-19

The compound of any one of Embodiments II-1 to II-18, or a pharmaceutically acceptable salt thereof, wherein A is

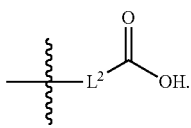

Embodiment II-20

The compound of any one of Embodiments II-1 to II-18, or a pharmaceutically acceptable salt thereof, wherein A is

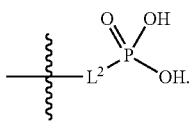

Embodiment II-21

The compound of any one of Embodiments II-1 to II-18, or a pharmaceutically acceptable salt thereof, wherein A is

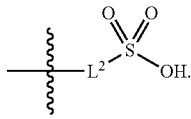

Embodiment II-22

The compound of any one of Embodiments II-1 to II-18, or a pharmaceutically acceptable salt thereof, wherein A is

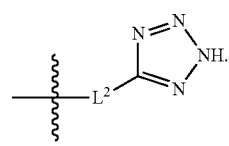

Embodiment II-23

The compound of any one of Embodiments II-1 to II-18, or a pharmaceutically acceptable salt thereof, wherein A is

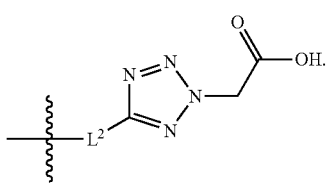

Embodiment II-24

The compound of any one of Embodiments II-1 to II-18, or a pharmaceutically acceptable salt thereof, wherein A is

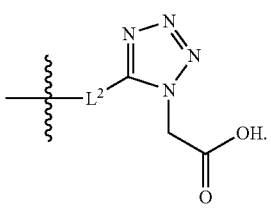

Embodiment II-25

The compound of any one of Embodiments II-1 to II-18, or a pharmaceutically acceptable salt thereof, wherein A is

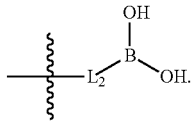

Embodiment II-26

The compound of any one of Embodiments II-1 to II-25, or a pharmaceutically acceptable salt thereof, wherein $L^2$ is —(CH$_2$)$_n$—.

Embodiment II-27

The compound of any one of Embodiments II-1 to II-26, or a pharmaceutically acceptable salt thereof, wherein n is one or two.

Embodiment II-28

The compound of any one of Embodiments II-1 to II-25, or a pharmaceutically acceptable salt thereof, wherein $L^2$ is

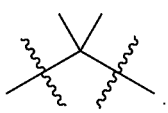 [SMILES: *C(*)(C)C].

Embodiment II-29

The compound of any one of Embodiments II-1 to II-25, or a pharmaceutically acceptable salt thereof, wherein $L^2$ is

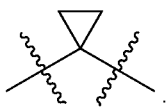 [SMILES: *C1(*)CC1].

Embodiment II-30

The compound of any one of Embodiments II-1 to II-25, or a pharmaceutically acceptable salt thereof, wherein $L^2$ is —C(O)NH(CH$_2$)$_n$—.

Embodiment II-31

A compound of Embodiment II-1, or a pharmaceutically acceptable salt thereof, wherein the compound of Formula (1) is a compound of Formula (1a),

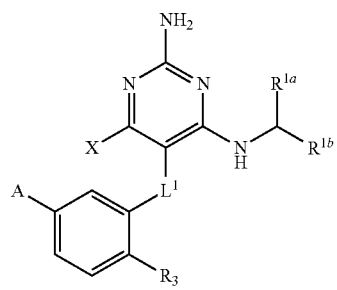

(1a)

wherein

X is H or CH$_3$ $L^1$ is selected from the group consisting of a bond, —CH$_2$—, —O—, —S—, —CF$_2$—,

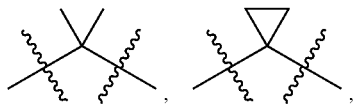

and —CH$_2$CH$_2$—;

A is selected from the group consisting of

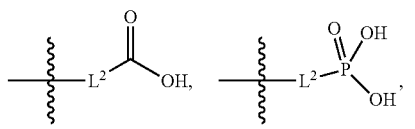

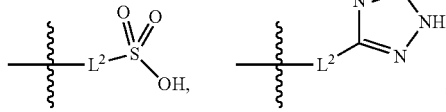

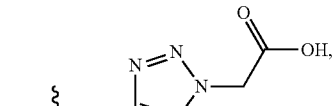

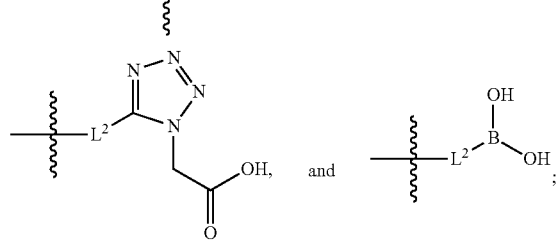

$L^2$ is selected from the group consisting of a bond, —CH$_2$—, —CH$_2$CH$_2$—,

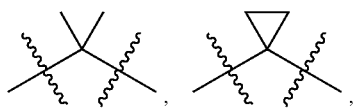

—C(O)NH(CH$_2$)$_n$—, —[O(CH$_2$CH$_2$)]$_n$—, —[O(C$_1$-C$_4$ alkylene)]-, and —[O(CH$_2$CH$_2$)]$_n$—OCH$_2$CH$_2$CF$_2$—; —C(O)NHCH$_2$CH$_2$—[O(CH$_2$CH$_2$)]$_m$; C(O)NHCH$_2$CH$_2$—[O(CH$_2$CH$_2$)]$_m$—OCH$_2$CH$_2$CF$_2$—; and $R^3$ is H, C$_1$-C$_3$ alkyl, or C$_1$-C$_3$ alkoxy.

Embodiment II-32

A compound of Embodiment II-1, or a pharmaceutically acceptable salt thereof, wherein the compound of Formula (1) is a compound of Formula (1a), (1a)

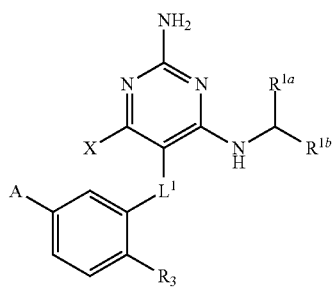

wherein
X is —CH₂-A¹ᵃ, —CH₂CH₂-A¹ᵃ, —CH₂CH₂CH₂-A¹ᵃ, or —CH₂C(CH₃)₂-A¹ᵃ;
A¹ᵃ is selected from the group consisting of

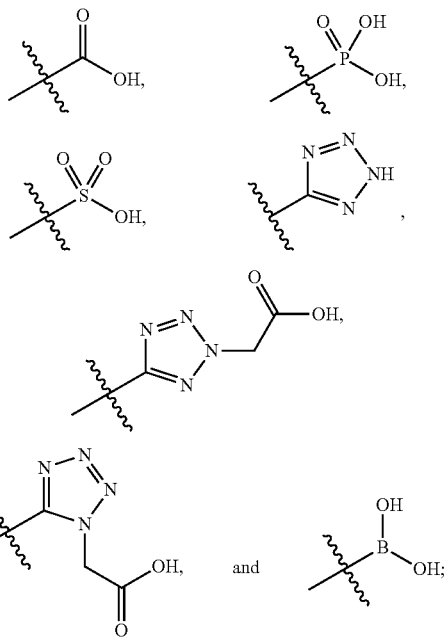

L¹ is selected from the group consisting of a bond, —CH₂—, —O—, —S—, —CF₂—,

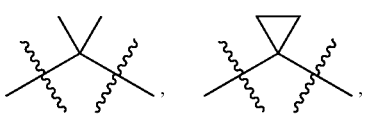

and —CH₂CH₂—;
A is selected from the group consisting of

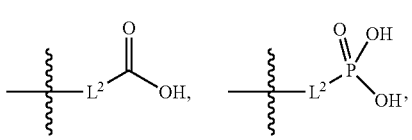

-continued

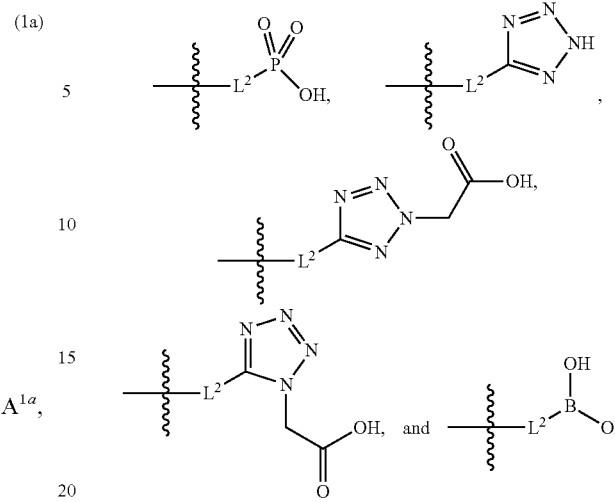

L² is selected from the group consisting of a bond, —CH₂—, —CH₂CH₂—,

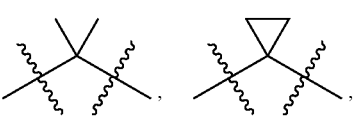

—C(O)NH(CH₂)ₙ—, —[O(CH₂CH₂)]ₙ—, —[O(C₁-C₄ alkylene)]-, and —[O(CH₂CH₂)]ₙ—OCH₂CH₂CF₂—; —C(O)NHCH₂CH₂—[O(CH₂CH₂)]ₘ; C(O)NHCH₂CH₂—[O(CH₂CH₂)]ₘ—OCH₂CH₂CF₂—; and
R³ is H, C₁-C₃ alkyl, or C₁-C₃ alkoxy.

Embodiment II-33

A compound of Embodiment II-1, or a pharmaceutically acceptable salt thereof, wherein the compound of Formula (1) is a compound of Formula (1b), (1b)

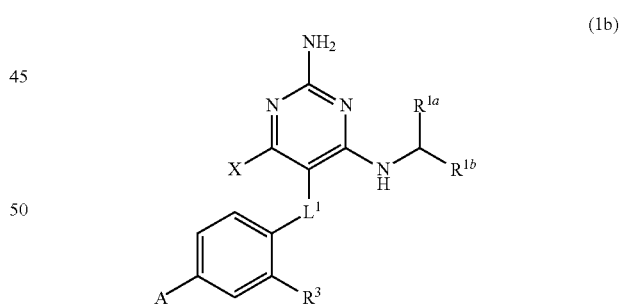

wherein
X is H or CH₃;
L¹ is selected from the group consisting of a bond, —CH₂—, —O—, —S—, —CF₂—,

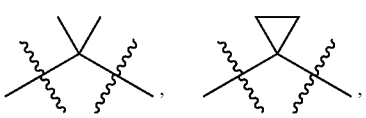

and —CH₂CH₂—;

A is selected from the group consisting of

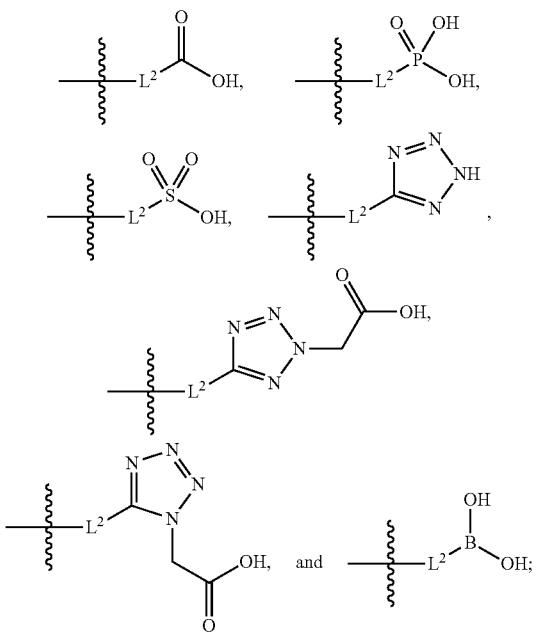

L² is selected from the group consisting of a bond, —CH₂—, —CH₂CH₂—,

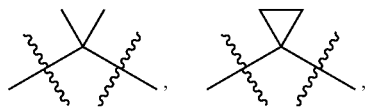

—C(O)NH(CH₂)$_n$—, —[O(CH₂CH₂)]$_n$—, —[O(C₁-C₄ alkylene)]-, and —[O(CH₂CH₂)]$_n$—OCH₂CH₂CF₂—; —C(O)NHCH₂CH₂—[O(CH₂CH₂)]$_m$; C(O)NHCH₂CH₂—[O(CH₂CH₂)]$_m$—OCH₂CH₂CF₂—; and
R³ is H, C₁-C₃ alkyl, or C₁-C₃ alkoxy.

Embodiment II-34

A compound of Embodiment II-1, or a pharmaceutically acceptable salt thereof, wherein the compound of Formula (1) is a compound of Formula (1b),

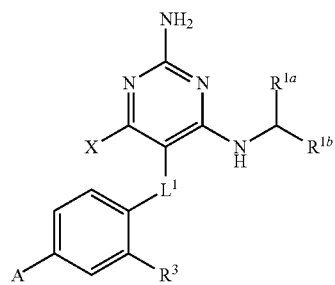

(1b)

wherein
X is —CH₂-A¹ᵃ, —CH₂CH₂-A¹ᵃ, —CH₂CH₂CH₂-A¹ᵃ, or —CH₂C(CH₃)₂-A¹ᵃ;

A¹ᵃ is selected from the group consisting of

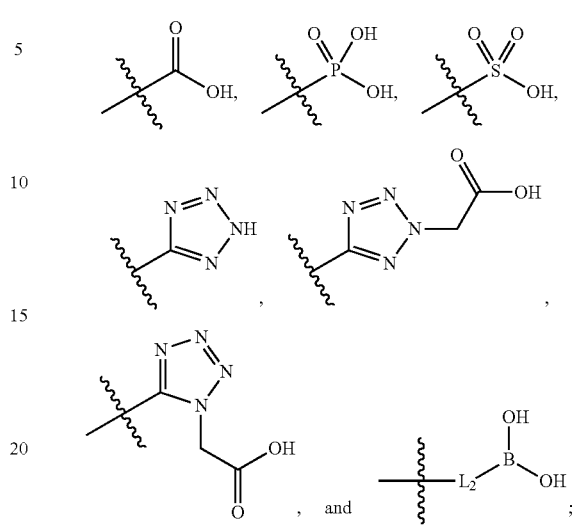

L¹ is selected from the group consisting of a bond, —CH₂—, —O—, —S—, —CF₂—,

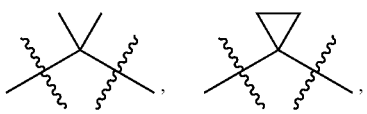

and —CH₂CH₂—;
A is selected from the group consisting of

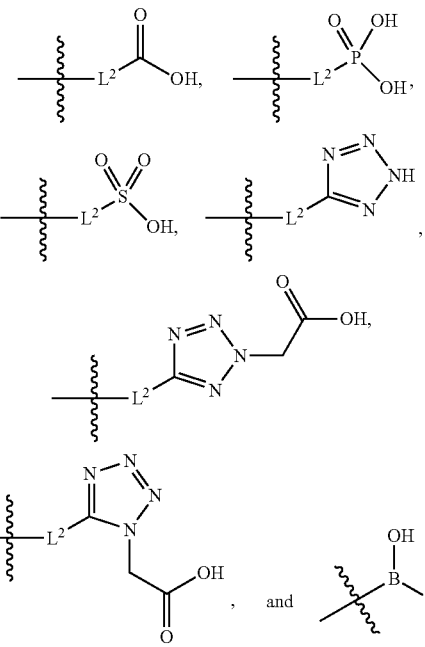

L² is selected from the group consisting of a bond, —CH₂—, —CH₂CH₂—,

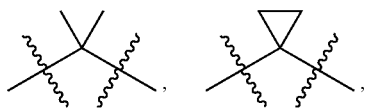,

—C(O)NH(CH$_2$)$_n$—, —[O(CH$_2$CH$_2$)]$_n$—, —[O(C$_1$-C$_4$ alkylene)]-, and —[O(CH$_2$CH$_2$)]$_n$—OCH$_2$CH$_2$CF$_2$—; —C(O)NHCH$_2$CH$_2$—[O(CH$_2$CH$_2$)]$_m$; C(O)NHCH$_2$CH$_2$—[O(CH$_2$CH$_2$)]$_m$—OCH$_2$CH$_2$CF$_2$—; and R$^3$ is H, C$_1$-C$_3$ alkyl, or C$_1$-C$_3$ alkoxy.

Embodiment II-35

A compound of Embodiment II-1, or a pharmaceutically acceptable salt thereof, wherein the compound of Formula (1) is a compound of Formula (1c),

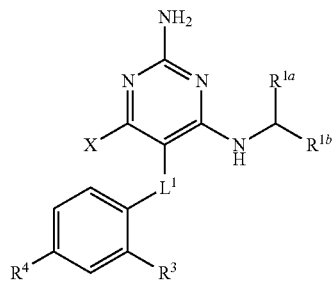

(1c)

wherein
X is —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$;
A$^{1a}$ is selected from the group consisting of

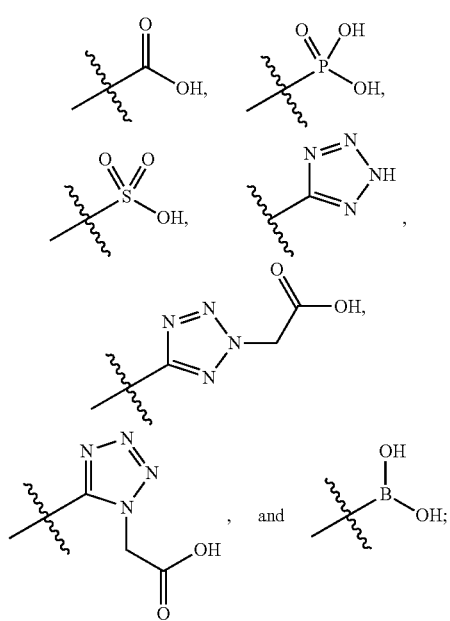

L$^1$ is selected from the group consisting of a bond, —CH$_2$—, —O—, —S—, —CF$_2$—,

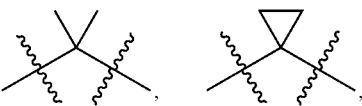, and —CH$_2$CH$_2$—;
R$^3$ is H, C$_1$-C$_3$ alkyl, or C$_1$-C$_3$ alkoxy; and
R$^4$ is H or C$_1$-C$_3$ alkoxy.

Embodiment II-36

A compound of Embodiment II-1, or a pharmaceutically acceptable salt thereof, wherein the compound of Formula (1) is a compound of Formula (1d),

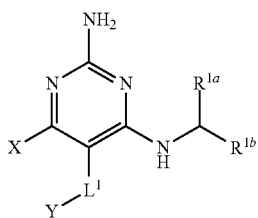

(1d)

X is —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$;
A$^{1a}$ is selected from the group consisting of

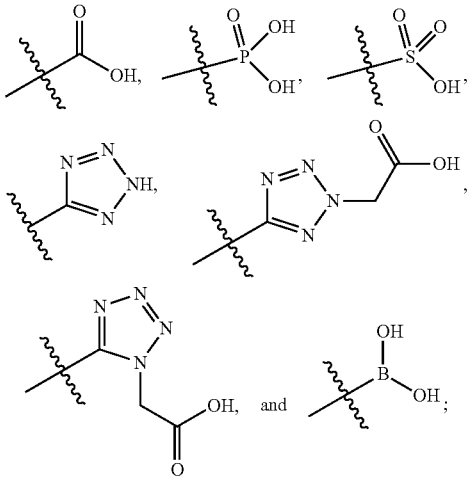

L$^1$ is selected from the group consisting of a bond, —CH$_2$—, —CF$_2$—,

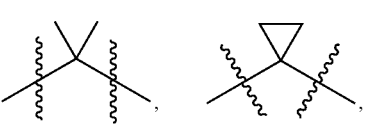,

—O—, and —CH$_2$CH$_2$, —S—; and
Y is H or C$_1$-C$_3$ alkyl.

Embodiment II-37

A compound of Embodiment II-1, or a pharmaceutically acceptable salt thereof, wherein the compound of Formula (1) is a compound of Formula (1e),

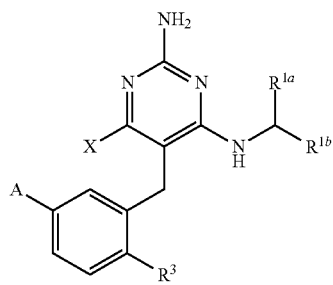

wherein $R^3$ is H, $C_1$-$C_3$ alkyl, or $C_1$-$C_3$ alkoxy.

Embodiment II-38

A compound of Embodiment II-1, or a pharmaceutically acceptable salt thereof, wherein the compound of Formula (1) is a compound of Formula (1f),

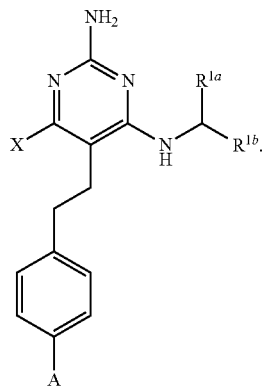

Embodiment II-39

A compound of Embodiment II-1, or a pharmaceutically acceptable salt thereof, wherein the compound of Formula (1) is a compound of Formula (1g),

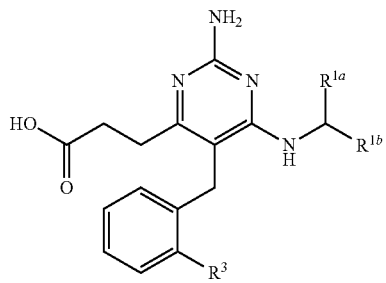

wherein $R^3$ is H, $C_1$-$C_3$ alkyl, or $C_1$-$C_3$ alkoxy.

Embodiment II-40

A compound of Embodiment II-1, or a pharmaceutically acceptable salt thereof, wherein the compound of Formula (1) is a compound of Formula (1h),

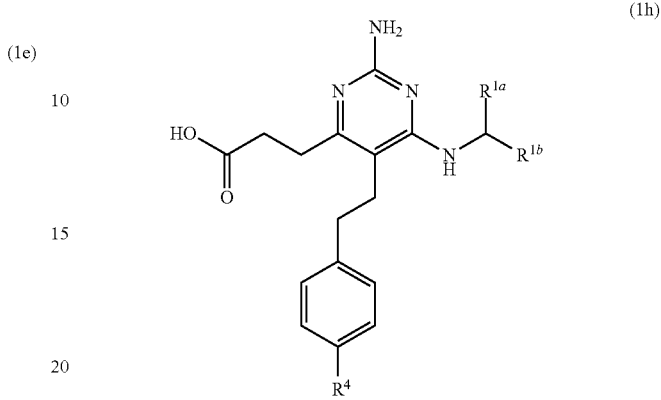

wherein $R^4$ is H or $C_1$-$C_3$ alkoxy.

Embodiment II-41

A compound of Embodiment II-1, or a pharmaceutically acceptable salt thereof, wherein the compound of Formula (1) is a compound of Formula (1i),

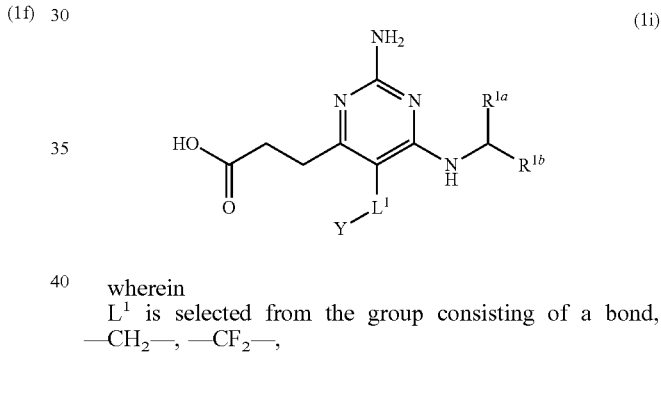

wherein
$L^1$ is selected from the group consisting of a bond, —CH$_2$—, —CF$_2$—,

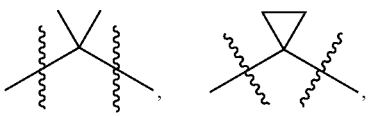

—O—, —CH$_2$CH$_2$—, and —S—; and
Y is H or $C_1$-$C_3$ alkyl.

Embodiment II-42

A compound, or a pharmaceutically acceptable salt, selected from the group consisting of:

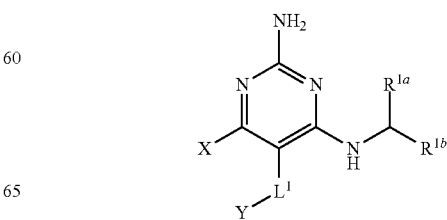

| Compound | —X | —L¹—Y | ![](R1a/R1b branch) |
|---|---|---|---|
| 1 | —CH₃ | 4-(2-carboxyethyl)-2-methoxybenzyl group | —(CH₂)₃CH₃ |
| 2 | —CH₃ | 4-(1H-tetrazol-5-yl)methyl-2-methoxybenzyl group | —(CH₂)₃CH₃ |
| 3 | —CH₃ | 3-(1H-tetrazol-5-yl)methyl-4-methoxybenzyl group | —(CH₂)₃CH₃ |
| 4 | —CH₃ | 3-(2-carboxyethyl)-4-methoxybenzyl group | —(CH₂)₃CH₃ |
| 5 | —CH₃ | 2-(carboxymethyl)-2H-tetrazol-5-yl linked 4-methoxybenzyl | —(CH₂)₃CH₃ |
| 6 | —CH₃ | 1-(carboxymethyl)-1H-tetrazol-5-yl linked 4-methoxybenzyl | —(CH₂)₃CH₃ |
| 7 | —CH₃ | 3-(phosphonomethyl)-4-methoxybenzyl group | —(CH₂)₃CH₃ |

US 10,287,253 B2
167                                                                    168
-continued
| Compound | —X | —L¹—Y | ⸺⸺C(R^{1a})(R^{1b})⸺ |
|---|---|---|---|
| 8 | —CH₃ | 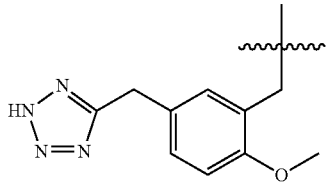 [SMILES: *Cc1cc(Cc2nn[nH]n2)ccc1OC] | 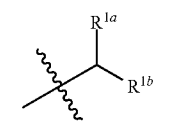 |
| 9 | —CH₃ | 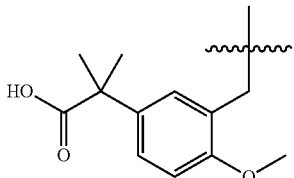 | —(CH₂)₃CH₃ |
| 10 | —CH₃ | 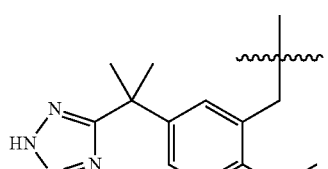 | —(CH₂)₃CH₃ |
| 11 | —CH₃ | 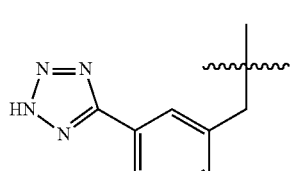 | —(CH₂)₃CH₃ |
| 12 | —CH₃ | 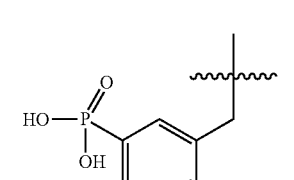 | —(CH₂)₃CH₃ |
| 13 | —CH₃ | 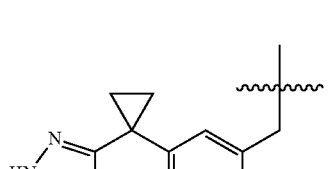 | —(CH₂)₃CH₃ |
| 14 | —CH₃ | 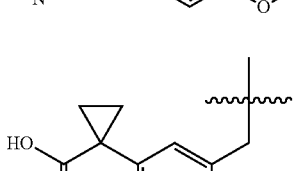 | —(CH₂)₃CH₃ |

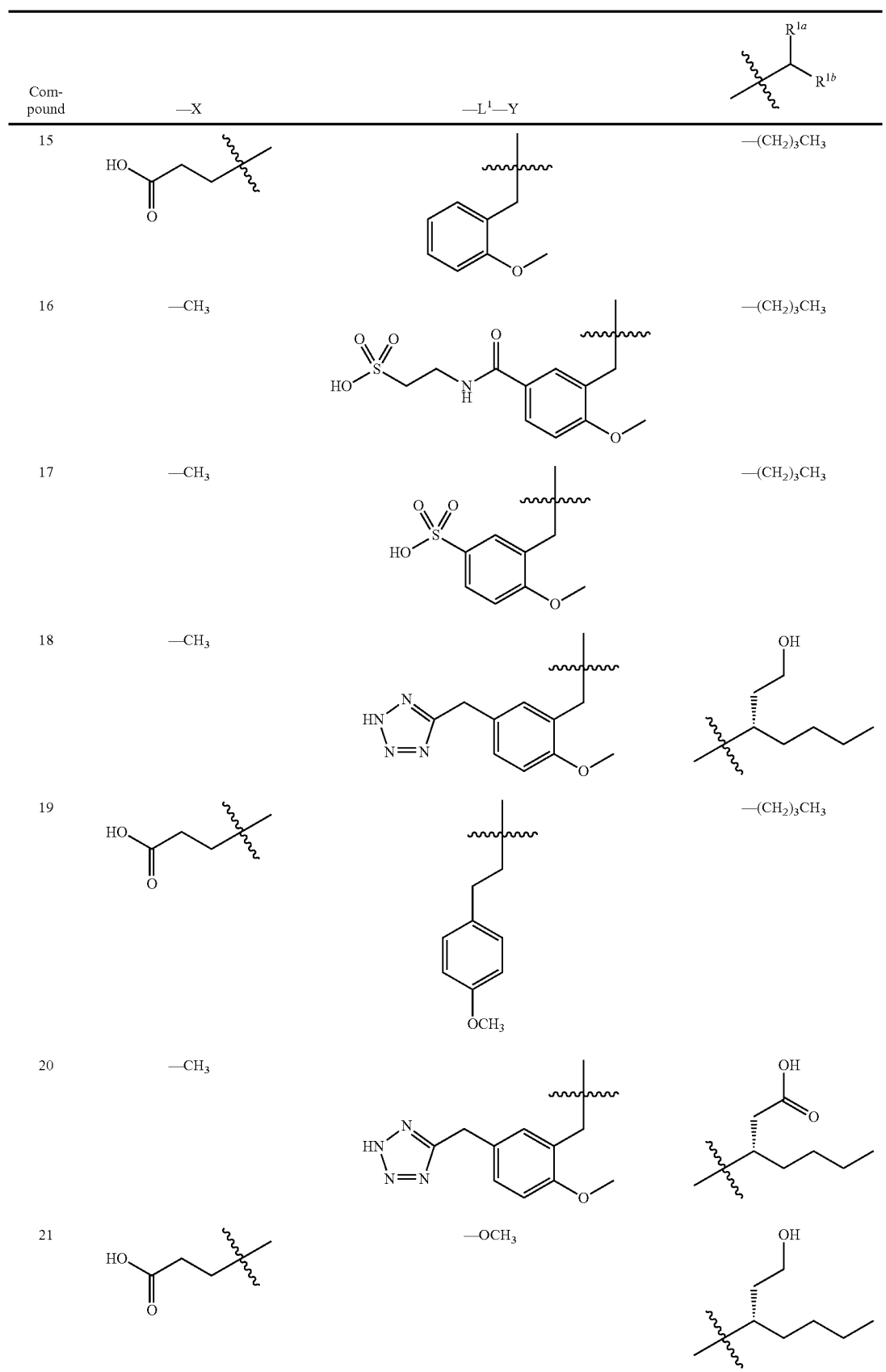

-continued
| Compound | —X | —L¹—Y | 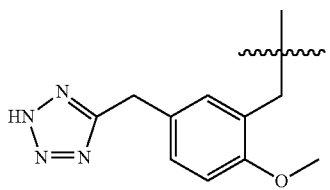 |
|---|---|---|---|
| 22 | —CH₃ | 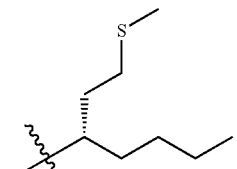 | 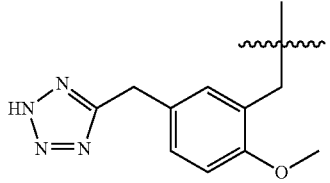 |
| 23 | —CH₃ | 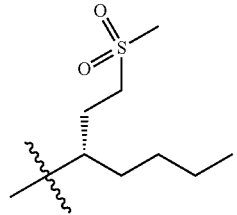 [SMILES: *[C@@H](CCCC)CCS(C)(=O)=O] | 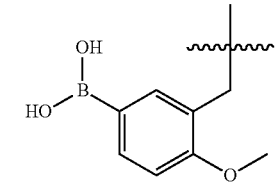 |
| 24 | —CH₃ | 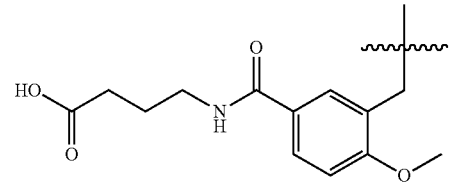 [SMILES: *Cc1cc(C(=O)NCCCC(=O)O)ccc1OC] | —(CH₂)₃CH₃ |
| 25 | —CH₃ | 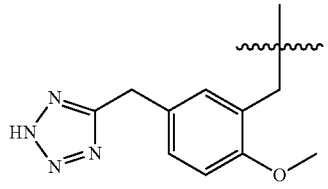 [SMILES: *Cc1cc(Cc2nn[nH]n2)ccc1OC] | —(CH₂)₃CH₃ |
| 26 | —CH₃ | 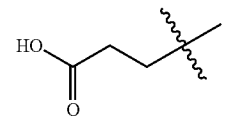 [SMILES: *CCC(=O)O] | —(CH₂)₄CH₃ |
| 27 | 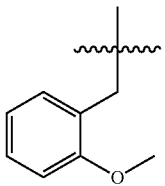 [SMILES: *Cc1ccccc1OC] | 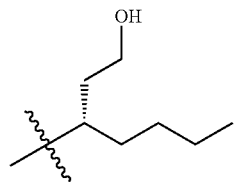 [SMILES: *[C@H](CCO)CCCC] | 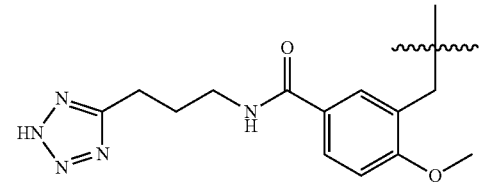 [SMILES: *Cc1cc(C(=O)NCCCc2nn[nH]n2)ccc1OC] |
| 28 | —CH₃ | | —(CH₂)₃CH₃ |

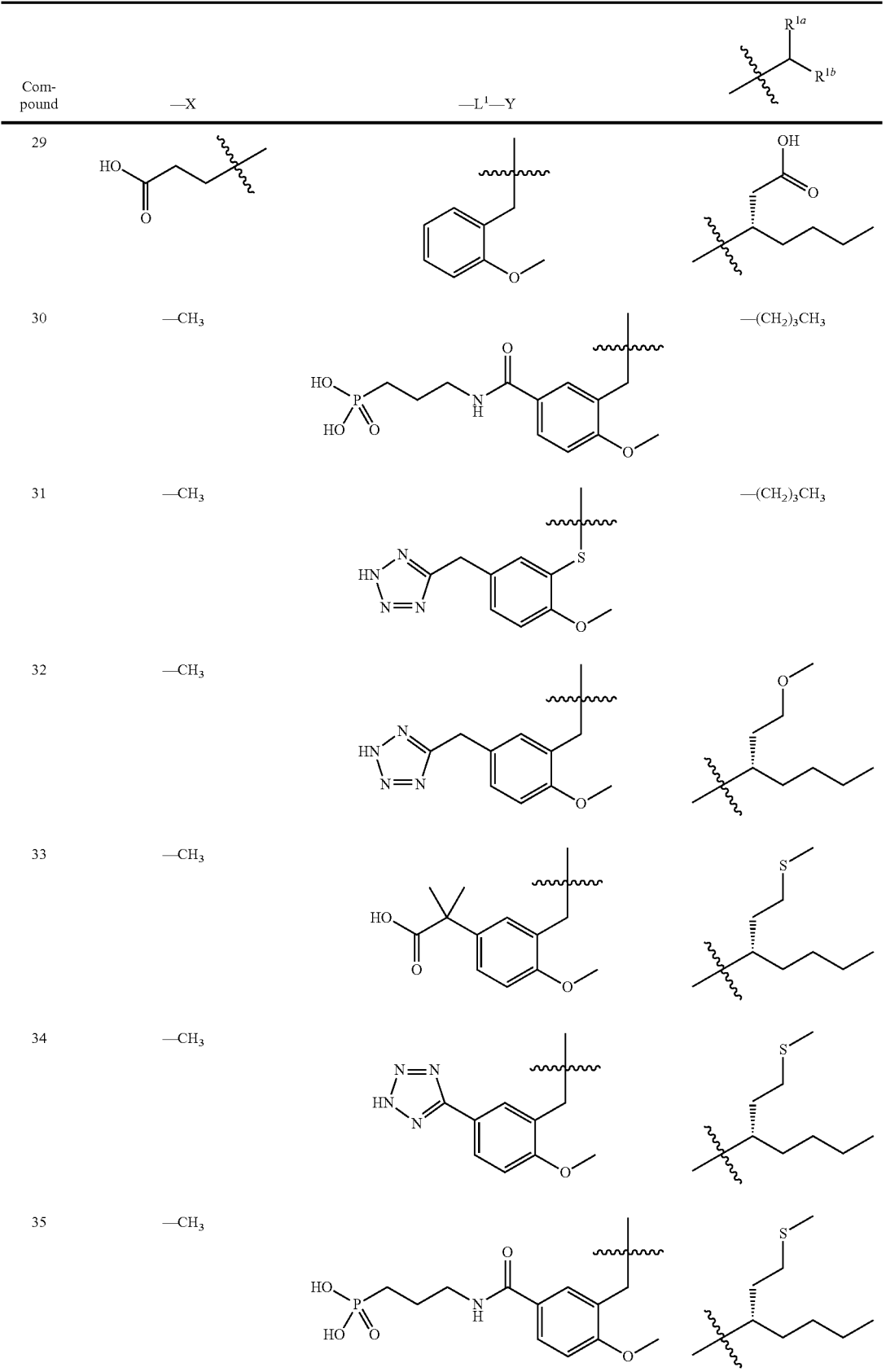

US 10,287,253 B2
175                                176
-continued
| Compound | —X | —L¹—Y | 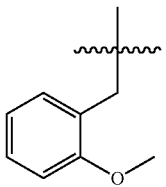 [SMILES: *Cc1ccccc1OC] |
|---|---|---|---|
| 36 | —CH₃ | 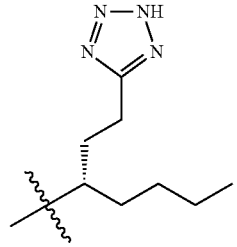 [SMILES: *[C@@H](CCCC)CCc1nn[nH]n1] |  |
| 37 | 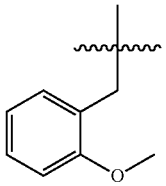 | 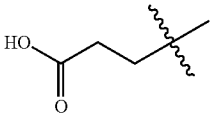 [SMILES: *CCC(=O)O] | —(CH₂)₃CH₃ |
| 38 | 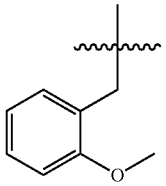 [SMILES: *Cc1ccccc1OC] | 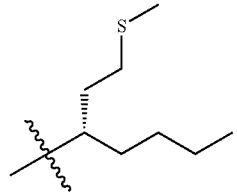 [SMILES: *[C@@H](CCCC)CCSC] | 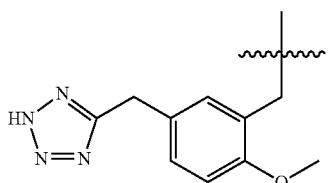 |
| 39 | —CH₃ | 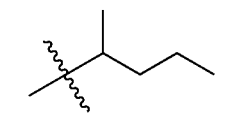 [SMILES: *C(C)CCC] | 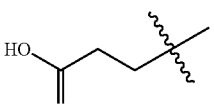 |
| 40 | 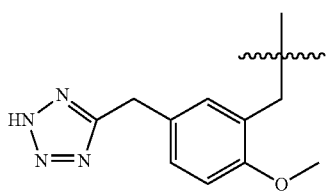 [SMILES: *Cc1cc(Cc2nn[nH]n2)ccc1OC] | 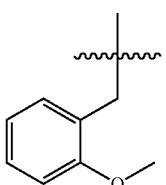 | —(CH₂)₃CH₃ |
| 41 | —CH₃ | 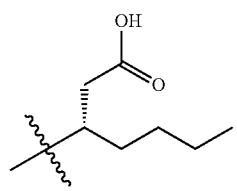 [SMILES: *[C@@H](CCCC)CC(=O)O] | 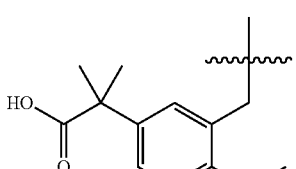 |
| 42 | —CH₃ | 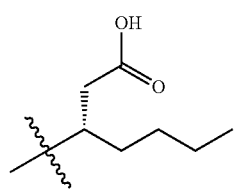 [SMILES: *[C@@H](CCCC)CC(=O)O] |  |

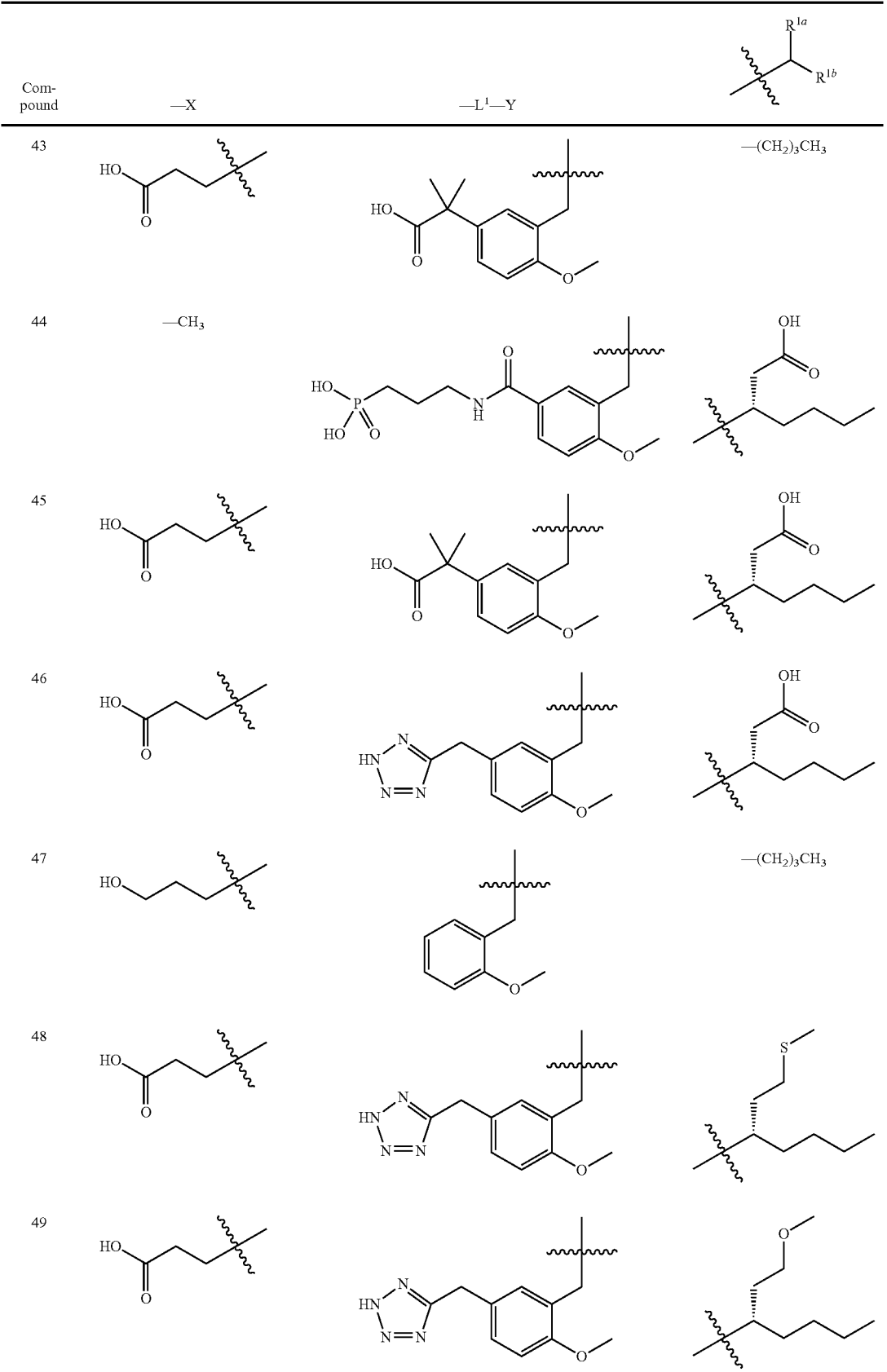

-continued

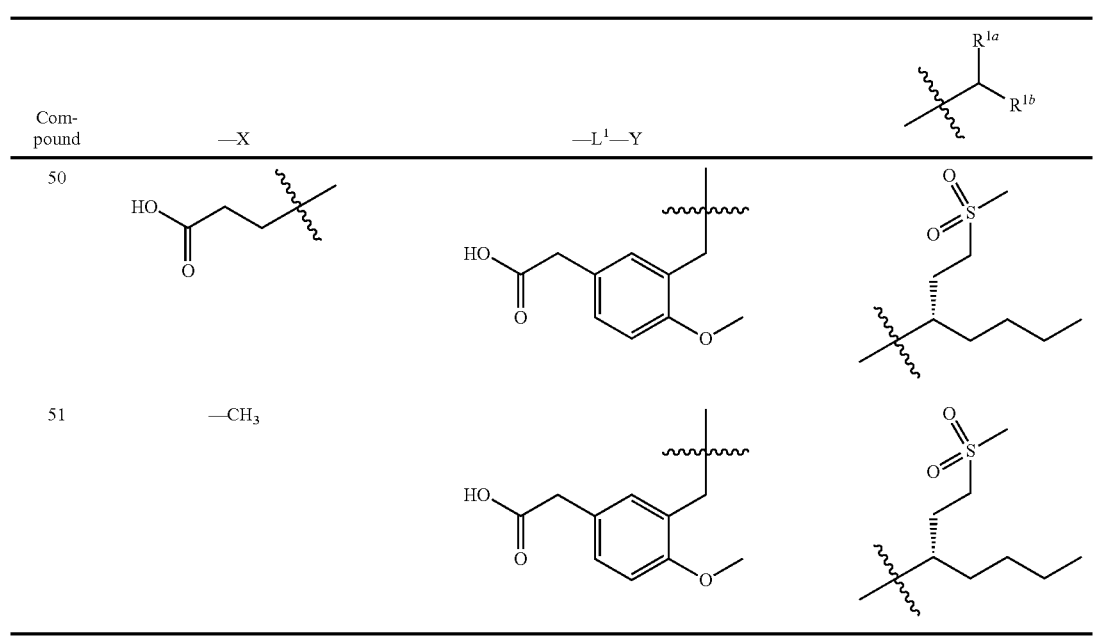

Embodiment II-43

A pharmaceutical composition comprising a compound of any one of Embodiments II-1 to II-42, or a pharmaceutically acceptable salt thereof, and a pharmaceutically acceptable carrier.

Embodiment II-44

A method of treating a condition associated with TLR7 modulation in a subject in need thereof, comprising administering to the subject an effective amount of a compound of any one of Embodiments II-1 to II-42, or a pharmaceutically acceptable salt thereof.

Embodiment II-45

The method of Embodiment II-44, wherein the condition is viral infection or cancer.

Embodiment II-46

The method of Embodiment II-45, wherein the administration is oral, intravenous, subcutaneous, intramuscular, intratumoral, intradermal, intranasal, inhaled, intravesicle, topical, sublingual, bucchal, intrarectal, intrathecal, intracranial, or other forms of local delivery.

Embodiment II-47

A compound of any one of Embodiments II-1 to II-42, or a pharmaceutically acceptable salt thereof, for use as a medicament.

Embodiment II-48

A compound of any one of Embodiments II-1 to II-42, or a pharmaceutically acceptable salt thereof, for use in treating a condition associated with TLR7 modulation.

Embodiment II-49

The compound of Embodiments II-48, wherein the condition is viral infection or cancer.

Embodiment II-50

Use of a compound of any one of Embodiments II-1 to II-42, or a pharmaceutically acceptable salt thereof, in the manufacture of a medicament for treating a condition associated with TLR7 modulation.

Embodiment II-51

The use of Embodiment II-50, wherein the condition is viral infection or cancer.

Embodiment II-52

A pharmaceutical composition of Embodiment II-43, further comprising at least one or more additional therapeutic agents.

Embodiment II-53

The pharmaceutical composition of Embodiment II-52, wherein the at least one or more additional therapeutic agent is antiviral nucleoside.

Embodiment II-54

The pharmaceutical composition of Embodiment II-52, wherein the at least one or more additional therapeutic agent is PD-1 antibody or PD-L1 antibody.

Embodiment II-55

A method of treating HBV in a subject in need thereof, comprising administering a compound of any one of Embodiments II-1 to II-42, or a pharmaceutically acceptable salt thereof, in combination with an antiviral nucleoside.

Embodiment II-56

A method of treating cancer in a subject in need thereof, comprising administering a compound of any one of Embodiments II-1 to II-42, or a pharmaceutically acceptable salt thereof, in combination with a PD-1 antibody or PD-L1 antibody.

Embodiment III-1

A compound having the structure of Formula (1), or a pharmaceutically acceptable salt thereof,

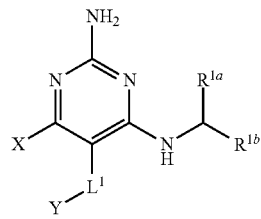

(1)

wherein
$R^{1a}$ is selected from the group consisting of H, $C_1$-$C_4$ alkyl, —$NH_2$, —NHAc, —COOH, —$SO_2CH_3$, —$SCH_3$, —$OCH_3$,

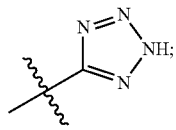 [SMILES: *c1nn[nH]n1]

and A,
wherein the alkyl is optionally substituted with —OH, —$NH_2$, —NHAc, —COOH, —$SO_2CH_3$, —$SCH_3$, —$OCH_3$,

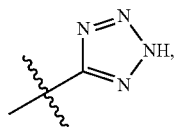

or A;
$R^{1b}$ is $C_2$-$C_5$ alkyl;
X is selected from the group consisting of H and $C_1$-$C_4$ alkyl, wherein the alkyl is optionally substituted with A, —OH, or —$C(CH_3)_2OH$;
$L^1$ is selected from the group consisting of a bond, —$CH_2$—, —$CF_2$—,

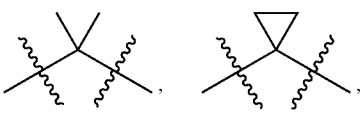

—O—, —S—, —$SO_2$—, —NH—, and —$CH_2CH_2$—;

Y is selected from the group consisting of $C_1$-$C_3$ alkyl, aryl, and heteroaryl, wherein the alkyl, aryl, and heteroaryl are optionally substituted with 1-5 substituents that are independently selected from A, $C_1$-$C_3$ alkyl, and $C_1$-$C_3$ alkoxy;

A is selected from the group consisting of

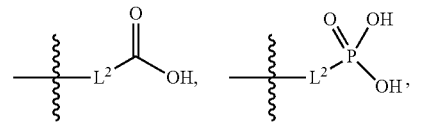

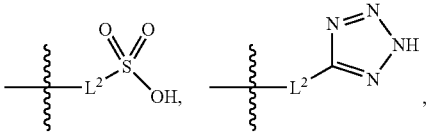

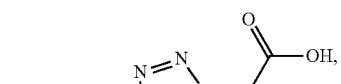

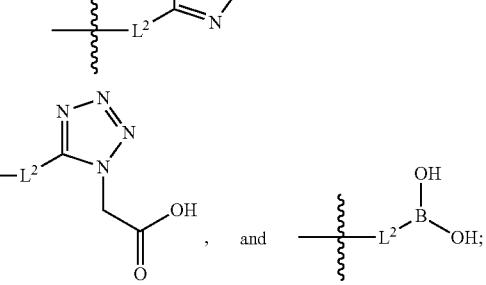

$L^2$ is selected from the group consisting of a bond, —$(CH_2)_n$—, —$C(O)NH(CH_2)_n$—,

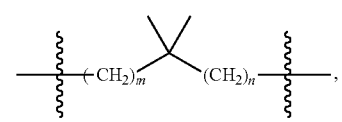

—[$O(CH_2CH_2)]_n$—, —[$O(C_1$-$C_4$ alkylene)]—, —[$O(CH_2CH_2)]_n$—$OCH_2CH_2CF_2$—; —$C(O)NHCH_2CH_2$—[$O(CH_2CH_2)]_m$—; and —$C(O)NHCH_2CH_2$—[$O(CH_2CH_2)]_m$—$OCH_2CH_2CF_2$—;

m is an integer from zero to four;

n is an integer from one to four;

wherein the compound is substituted with at least one A; and when X is —$CH_3$; $L^1$ is —$CH_2$—; Y is aryl substituted with A; and $L^2$ is —$CH_2$—; then A is not -$L^2$-COOH, except when $R^{1a}$ comprises —COOH or —$SO_2CH_3$, and when X is —$CH_3$; $L^1$ is —$CH_2$—; Y is aryl substituted with A; $L^2$ is —$CH_2$—, —O—$(CH_2)_2$—$O(CH_2)_2$—, or —O—$(CH_2)_2$—$O(CH_2)_2(CF_2)$—; and A is

183

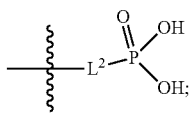

then A and $L^1$ are not in a para position with respect to each other.

Embodiment III-2

A compound having the structure of Formula (1), or a pharmaceutically acceptable salt thereof,

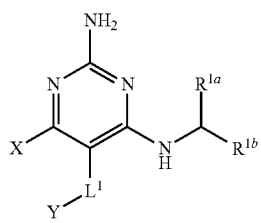

wherein
$R^{1a}$ is selected from the group consisting of H, $C_1$-$C_4$ alkyl, —$NH_2$, —NHAc, —COOH, —$SO_2CH_3$, —$SCH_3$, —$OCH_3$, and

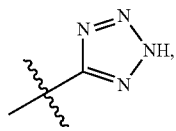 [SMILES: *c1nn[nH]n1]

wherein the alkyl is optionally substituted with —OH, —$NH_2$, —NHAc, —COOH, —$SO_2CH_3$, —$SCH_3$, —$OCH_3$, or

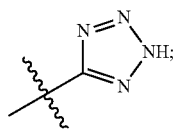

$R^{1b}$ is $C_2$-$C_5$ alkyl;
X is selected from the group consisting of H and $C_1$-$C_4$ alkyl, wherein the alkyl is optionally substituted with A, —OH, or —$C(CH_3)_2OH$;
$L^1$ is selected from the group consisting of a bond, —$CH_2$—, —$CF_2$—,

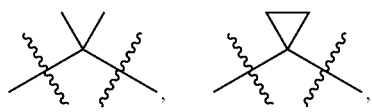

—O—, —S—, —$SO_2$—, —NH—, and —$CH_2CH_2$—;
Y is selected from the group consisting of $C_1$-$C_3$ alkyl, aryl, and heteroaryl, wherein the alkyl, aryl, and heteroaryl

184 are optionally substituted with 1-5 substituents that are independently selected from A, $C_1$-$C_3$ alkyl, and $C_1$-$C_3$ alkoxy;
A is selected from the group consisting of

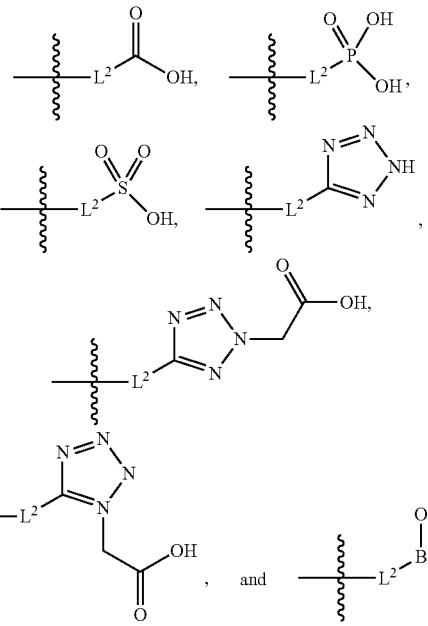

$L^2$ is selected from the group consisting of a bond, —$(CH_2)_n$—, —$C(O)NH(CH_2)_n$—,

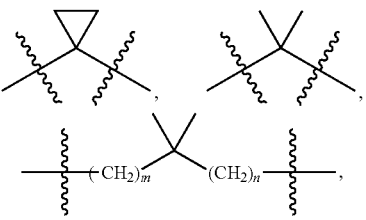

—[O($CH_2CH_2$)]$_n$—, —[O($C_1$-$C_4$ alkylene)]—, —[O($CH_2CH_2$)]$_n$—$OCH_2CH_2CF_2$—; —$C(O)NHCH_2CH_2$—[O($CH_2CH_2$)]$_m$—; and —$C(O)NHCH_2CH_2$—[O($CH_2$ $CH_2$)]$_m$—$OCH_2CH_2CF_2$—;
m is an integer from zero to four; and
n is an integer from one to four; and
wherein the compound is substituted with at least one A; and
when X is —$CH_3$; $L^1$ is —$CH_2$—; Y is aryl substituted with A; and $L^2$ is —$CH_2$—; then A is not -$L^2$-COOH, except when $R^{1a}$ comprises —COOH or —$SO_2CH_3$; and
when X is —$CH_3$; $L^1$ is —$CH_2$—; Y is aryl substituted with A; $L^2$ is —$CH_2$—, —O—$(CH_2)_2$—O$(CH_2)_2$—, or —O—$(CH_2)_2$—O$(CH_2)_2(CF_2)$—; and A is

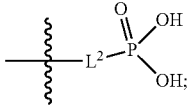

then A and $L^1$ are not in a para position with respect to each other.

Embodiment III-3

The compound of Embodiment III-1 or III-2, or a pharmaceutically acceptable salt thereof, wherein $R^{1b}$ is —(CH$_2$)$_2$CH$_3$.

Embodiment III-4

The compound of Embodiment III-1 or III-2, or a pharmaceutically acceptable salt thereof, wherein $R^{1b}$ is —(CH$_2$)$_3$CH$_3$.

Embodiment III-5

The compound of any one of Embodiments III-1 to III-4, or a pharmaceutically acceptable salt thereof, wherein $R^{1a}$ is $C_1$-$C_4$ alkyl, optionally substituted with —OH, —OCH$_3$, —SCH$_3$, or —SO$_2$CH$_3$.

Embodiment III-6

The compound of any one of Embodiments III-1 to III-5, or a pharmaceutically acceptable salt thereof, wherein $R^{1a}$ is —CH$_2$C(CH$_3$)$_2$OH.

Embodiment III-7

The compound of any one of Embodiments III-1 to III-6, or a pharmaceutically acceptable salt thereof, wherein

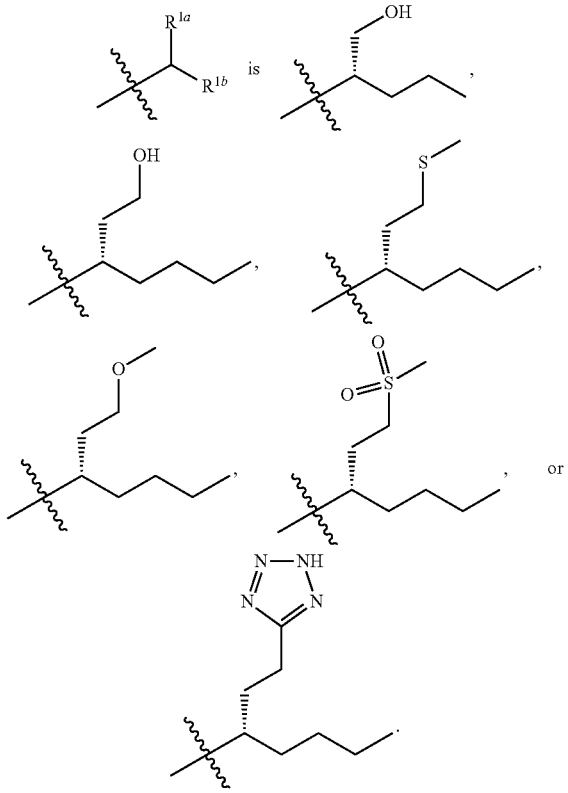

Embodiment III-8

The compound of any one of Embodiments III-1 to III-4, or a pharmaceutically acceptable salt thereof, wherein $R^{1a}$ is $C_1$-$C_4$ alkyl, optionally substituted with —COOH.

Embodiment III-9

The compound of any one of Embodiments III-1 to III-4 and III-8, or a pharmaceutically acceptable salt thereof, wherein

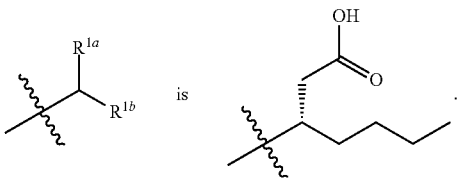

Embodiment III-10

The compound of any one of Embodiments III-1 to IIII-4, or a pharmaceutically acceptable salt thereof, wherein $R^{1a}$ is H.

Embodiment III-11

The compound of any one of Embodiments III-1 to III-10, or a pharmaceutically acceptable salt thereof, wherein X is $C_1$-$C_4$ alkyl, wherein the alkyl is substituted with A.

Embodiment III-12

The compound of any one of Embodiments III-1 to III-11, or a pharmaceutically acceptable salt thereof, wherein X is $C_1$-$C_4$ alkyl, wherein the alkyl is substituted with

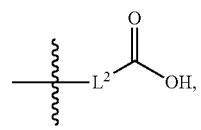

wherein $L^2$ is a bond.

Embodiment III-13

The compound of any one of Embodiments III-1 to III-10, or a pharmaceutically acceptable salt thereof, wherein X is CH$_3$.

Embodiment III-14

The compound of any one of Embodiments III-1 to III-10, or a pharmaceutically acceptable salt thereof, wherein X is H.

Embodiment III-15

The compound of any one of Embodiments III-1 to III-14, or a pharmaceutically acceptable salt thereof, wherein $L^1$ is —CH$_2$—, —CH$_2$CH$_2$—, —O—, or —S—.

Embodiment III-16

The compound of any one of Embodiments III-1 to III-15, or a pharmaceutically acceptable salt thereof, wherein $L^1$ is —CH$_2$—.

Embodiment III-17

The compound of any one of Embodiments III-1 to III-16, or a pharmaceutically acceptable salt thereof, wherein Y is $C_1$-$C_3$ alkyl or aryl.

Embodiment III-18

The compound of any one of Embodiments III-1 to III-17, or a pharmaceutically acceptable salt thereof, wherein Y is aryl, wherein the aryl is substituted with C1-C3 alkoxy.

Embodiment III-19

The compound of any one of Embodiments III-1 to III-18, or a pharmaceutically acceptable salt thereof, wherein Y is aryl, wherein the aryl is substituted with A.

Embodiment III-20

The compound of any one of Embodiments III-1 to III-19, or a pharmaceutically acceptable salt thereof, wherein A is

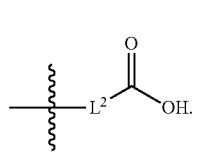

Embodiment III-21

The compound of any one of Embodiments III-1 to III-19, or a pharmaceutically acceptable salt thereof, wherein A is

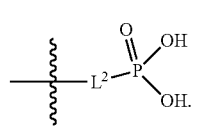

Embodiment III-22

The compound of any one of Embodiments III-1 to III-19, or a pharmaceutically acceptable salt thereof, wherein A is

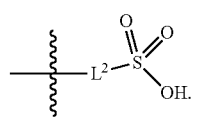

Embodiment III-23

The compound of any one of Embodiments III-1 to III-19, or a pharmaceutically acceptable salt thereof, wherein A is

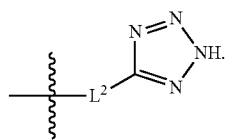

Embodiment III-24

The compound of any one of Embodiments III-1 to III-19, or a pharmaceutically acceptable salt thereof, wherein A is

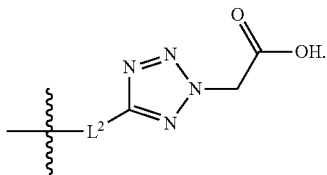

Embodiment III-25

The compound of any one of Embodiments III-1 to III-19, or a pharmaceutically acceptable salt thereof, wherein A is

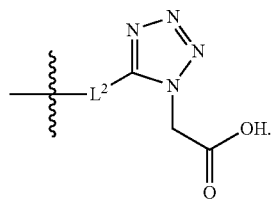

Embodiment III-26

The compound of any one of Embodiments III-1 to III-19, or a pharmaceutically acceptable salt thereof, wherein A is

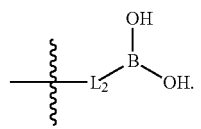

Embodiment III-27

The compound of any one of Embodiments III-1 to III-26, or a pharmaceutically acceptable salt thereof, wherein $L^2$ is —(CH$_2$)$_n$—.

Embodiment III-28

The compound of any one of Embodiments III-1 to III-27, or a pharmaceutically acceptable salt thereof, wherein n is one or two.

Embodiment III-29

The compound of any one of Embodiments III-1 to III-26, or a pharmaceutically acceptable salt thereof, wherein $L^2$ is

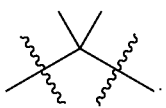 [SMILES: *C(*)(C)C]

Embodiment III-30

The compound of any one of Embodiments III-1 to III-26, or a pharmaceutically acceptable salt thereof, wherein $L^2$ is

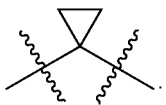 [SMILES: *C1(*)CC1]

Embodiment III-31

The compound of any one of Embodiments III-1 to III-26, or a pharmaceutically acceptable salt thereof, wherein $L^2$ is —C(O)NH(CH$_2$)$_n$—.

Embodiment III-32

A compound of Embodiment III-1 or III-2, or a pharmaceutically acceptable salt thereof, wherein the compound of Formula (1) is a compound of Formula (1a),

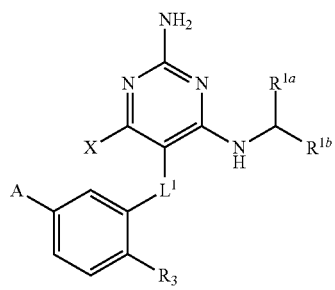

(1a)

wherein
X is H or CH$_3$
$L^1$ is selected from the group consisting of a bond, —CH$_2$—, —O—, —S—, —CF$_2$—,

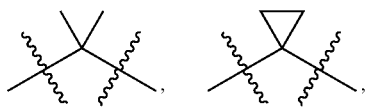

and —CH$_2$CH$_2$—;
A is selected from the group consisting of

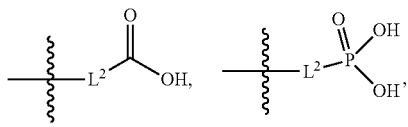

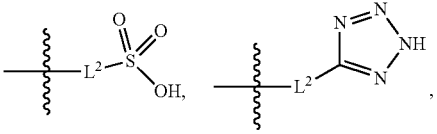

$L^2$ is selected from the group consisting of a bond, —CH$_2$—, —CH$_2$CH$_2$—,

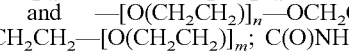

—C(O)NH(CH$_2$)$_n$—, —[O(CH$_2$CH$_2$)]$_n$—, —[O(C$_1$-C$_4$ alkylene)]-, and —[O(CH$_2$CH$_2$)]$_n$—OCH$_2$CH$_2$CF$_2$—; —C(O)NHCH$_2$CH$_2$—[O(CH$_2$CH$_2$)]$_m$; C(O)NHCH$_2$CH$_2$— [O(CH$_2$CH$_2$)]$_m$—OCH$_2$CH$_2$CF$_2$—; and
$R^3$ is H, C$_1$-C$_3$ alkyl, or C$_1$-C$_3$ alkoxy.

Embodiment III-33

A compound of Embodiment III-1 or III-2, or a pharmaceutically acceptable salt thereof, wherein the compound of Formula (1) is a compound of Formula (1a),

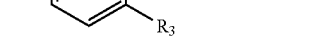

(1a)

wherein
X is —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$;
A$^{1a}$ is selected from the group consisting of

-continued

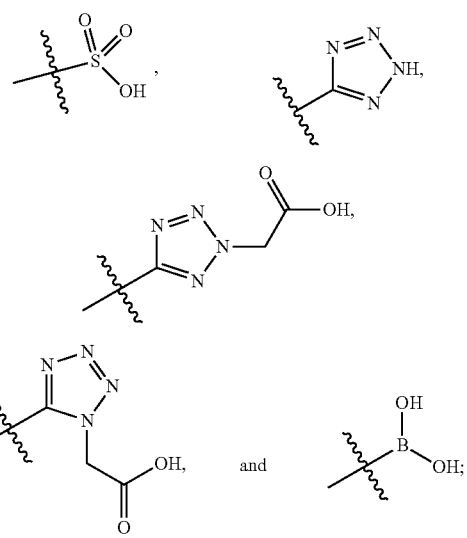

L¹ is selected from the group consisting of a bond, —CH₂—, —O—, —S—, —CF₂—,

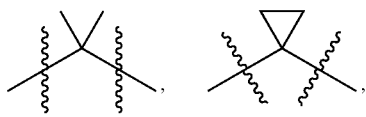

and —CH₂CH₂—;

A is selected from the group consisting of

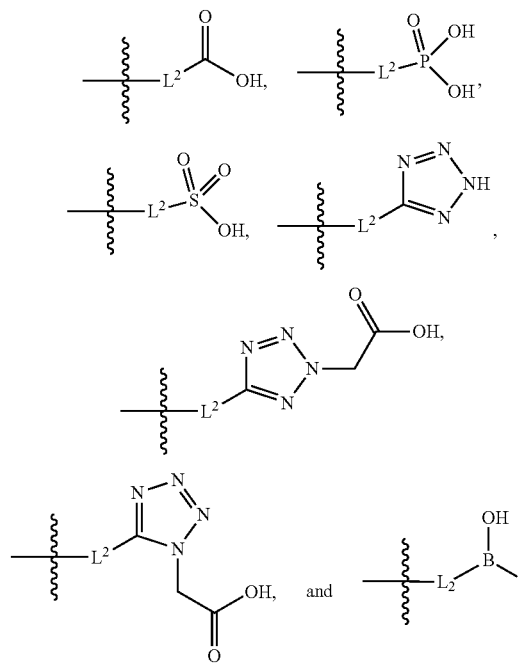

L² is selected from the group consisting of a bond, —CH₂—, —CH₂CH₂—,

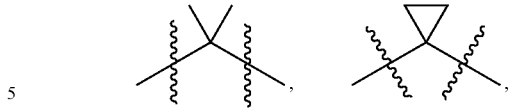

—C(O)NH(CH₂)ₙ—, —[O(CH₂CH₂)]ₙ—, —[O(C₁-C₄ alkylene)]-, and —[O(CH₂CH₂)]ₙ—OCH₂CH₂CF₂—; —C(O)NHCH₂CH₂—[O(CH₂CH₂)]ₘ; C(O)NHCH₂CH₂—[O(CH₂CH₂)]ₘ—OCH₂CH₂CF₂—; and R³ is H, C₁-C₃ alkyl, or C₁-C₃ alkoxy.

Embodiment III-34

A compound of Embodiment III-1 or III-2, or a pharmaceutically acceptable salt thereof, wherein the compound of Formula (1) is a compound of Formula (1b), (1b)

[Structure of Formula (1b)]

wherein
X is H or CH₃;
L¹ is selected from the group consisting of a bond, —CH₂—, —O—, —S—, —CF₂—,

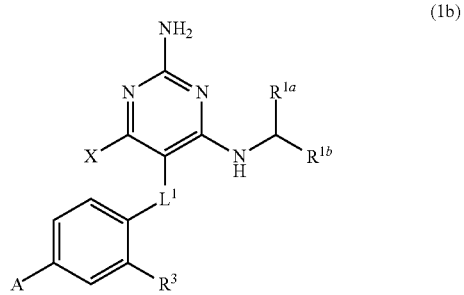

and —CH₂CH₂—;
A is selected from the group consisting of

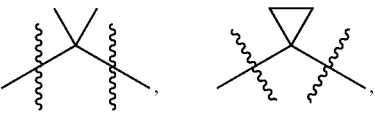

-continued

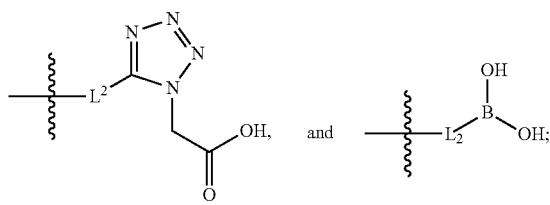

$L^2$ is selected from the group consisting of a bond, —CH$_2$—, —CH$_2$CH$_2$—,

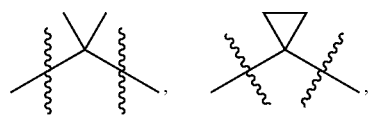

—C(O)NH(CH$_2$)$_n$—, —[O(CH$_2$CH$_2$)]$_n$—, —[O(C$_1$-C$_4$ alkylene)]—, and —[O(CH$_2$CH$_2$)]$_n$—OCH$_2$CH$_2$CF$_2$—; —C(O)NHCH$_2$CH$_2$—[O(CH$_2$CH$_2$)]$_m$; C(O)NHCH$_2$CH$_2$—[O(CH$_2$CH$_2$)]$_m$—OCH$_2$CH$_2$CF$_2$—; and $R^3$ is H, C$_1$-C$_3$ alkyl, or C$_1$-C$_3$ alkoxy.

Embodiment III-35

A compound of Embodiment III-1 or III-2, or a pharmaceutically acceptable salt thereof, wherein the compound of Formula (1) is a compound of Formula (1b),

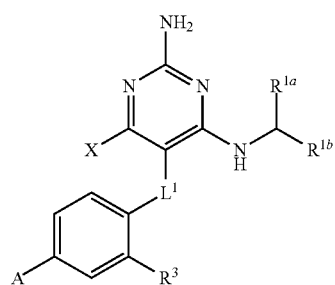

(1b)

wherein

X is —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$;

A$^{1a}$ is selected from the group consisting of

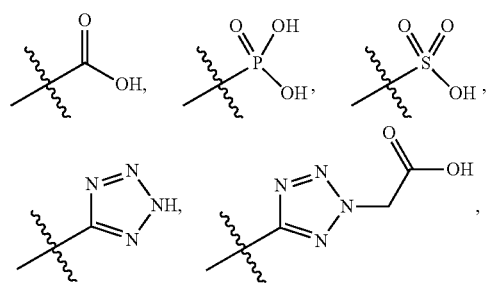

-continued

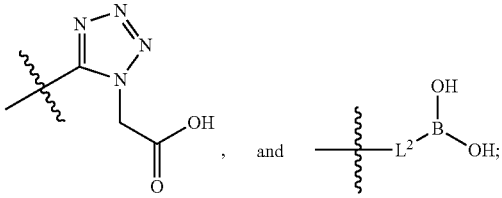

$L^1$ is selected from the group consisting of a bond, —CH$_2$—, —O—, —S—, —CF$_2$—,

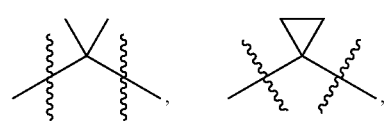

and —CH$_2$CH$_2$—;

A is selected from the group consisting of

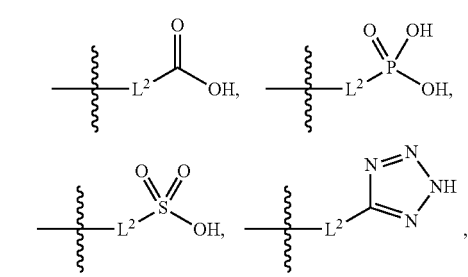

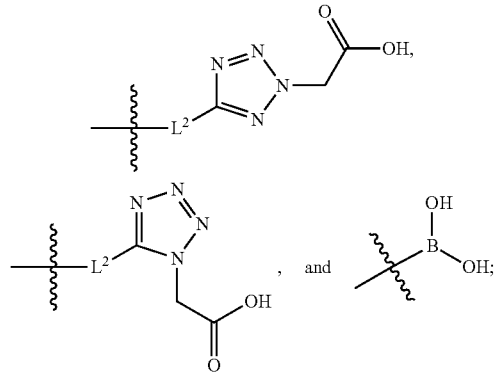

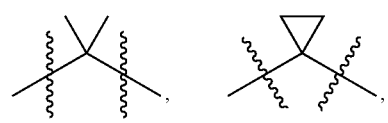

$L^2$ is selected from the group consisting of a bond, —CH$_2$—, —CH$_2$CH$_2$—,

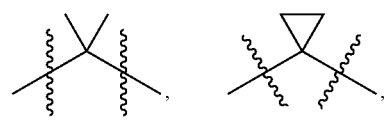

—C(O)NH(CH$_2$)$_n$—, —[O(CH$_2$CH$_2$)]$_n$—, —[O(C$_1$-C$_4$ alkylene)]—, and —[O(CH$_2$CH$_2$)]$_n$—OCH$_2$CH$_2$CF$_2$—; —C(O)NHCH$_2$CH$_2$—[O(CH$_2$CH$_2$)]$_m$; C(O)NHCH$_2$CH$_2$—[O(CH$_2$CH$_2$)]$_m$—OCH$_2$CH$_2$CF$_2$—; and $R^3$ is H, C$_1$-C$_3$ alkyl, or C$_1$-C$_3$ alkoxy.

Embodiment III-36

A compound of Embodiment III-1 or III-2, or a pharmaceutically acceptable salt thereof, wherein the compound of Formula (1) is a compound of Formula (1c),

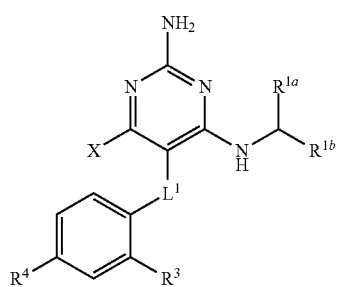

wherein

X is —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$;

A$^{1a}$ is selected from the group consisting of

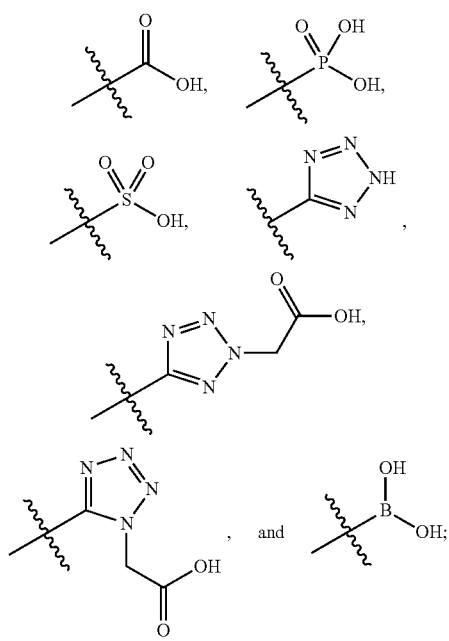

L$^1$ is selected from the group consisting of a bond, —CH$_2$—, —O—, —S—, —CF$_2$—,

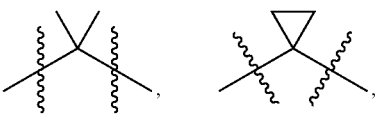

and —CH$_2$CH$_2$—;

R$^3$ is H, C$_1$-C$_3$ alkyl, or C$_1$-C$_3$ alkoxy; and

R$^4$ is H or C$_1$-C$_3$ alkoxy.

Embodiment III-37

A compound of Embodiment III-1 or III-2, or a pharmaceutically acceptable salt thereof, wherein the compound of Formula (1) is a compound of Formula (1d),

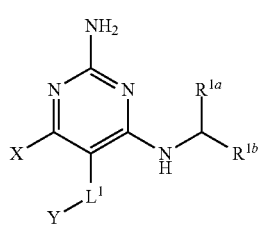

X is —CH$_2$-A$^{1a}$, —CH$_2$CH$_2$-A$^{1a}$, —CH$_2$CH$_2$CH$_2$-A$^{1a}$, or —CH$_2$C(CH$_3$)$_2$-A$^{1a}$;

A$^{1a}$ is selected from the group consisting of

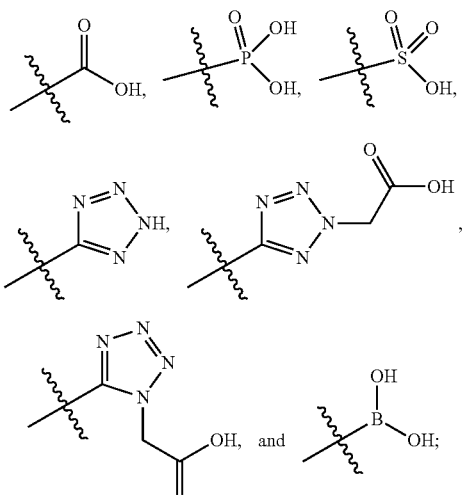

L$^1$ is selected from the group consisting of a bond, —CH$_2$—, —CF$_2$—,

—O—, and —CH$_2$CH$_2$, —S—; and

Y is H or C$_1$-C$_3$ alkyl.

Embodiment III-38

A compound of Embodiment III-1 or III-2, or a pharmaceutically acceptable salt thereof, wherein the compound of Formula (1) is a compound of Formula (1e),

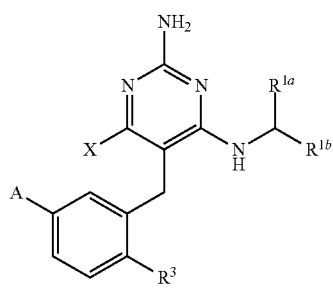
(1e)

wherein R³ is H, $C_1$-$C_3$ alkyl, or $C_1$-$C_3$ alkoxy.

Embodiment III-39

A compound of Embodiment III-1 or III-22, or a pharmaceutically acceptable salt thereof, wherein the compound of Formula (1) is a compound of Formula (1f),

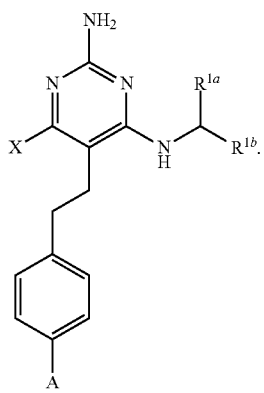
(1f)

Embodiment III-40

A compound of Embodiment III-1 or III-22, or a pharmaceutically acceptable salt thereof, wherein the compound of Formula (1) is a compound of Formula (1g),

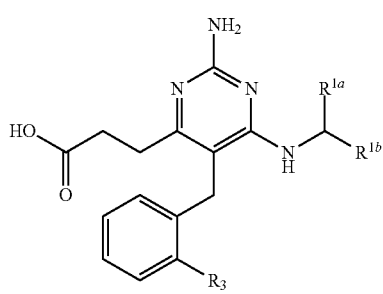
(1g)

wherein R³ is H, $C_1$-$C_3$ alkyl, or $C_1$-$C_3$ alkoxy.

Embodiment III-41

A compound of Embodiment III-1 or III-2, or a pharmaceutically acceptable salt thereof, wherein the compound of Formula (1) is a compound of Formula (1h),

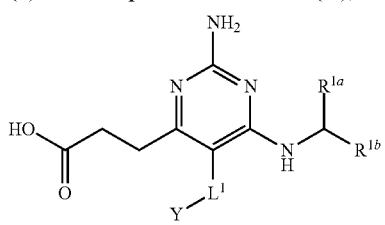
(1h)

wherein R⁴ is H or $C_1$-$C_3$ alkoxy.

Embodiment III-42

A compound of Embodiment III-1 or III-2, or a pharmaceutically acceptable salt thereof, wherein the compound of Formula (1) is a compound of Formula (1i), (1i)

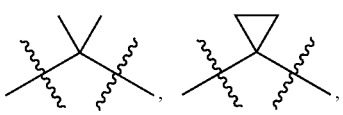

wherein
L¹ is selected from the group consisting of a bond, —CH₂—, —CF₂—,

—O—, —CH₂CH₂—, and —S—; and
Y is H or $C_1$-$C_3$ alkyl.

Embodiment III-43

A compound of Embodiment III-1 or III-2, or a pharmaceutically acceptable salt thereof, wherein the compound of Formula (1) is a compound of Formula (1j), (1j)

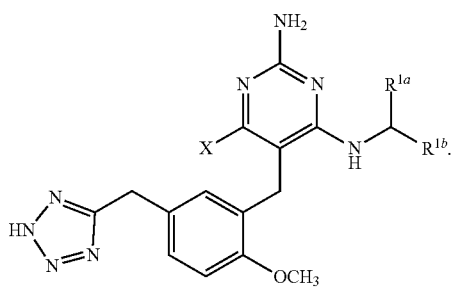

Embodiment III-44
A compound of Embodiment III-1 or III-2, or a pharmaceutically acceptable salt thereof, wherein the compound of Formula (1) is a compound of Formula (1k),
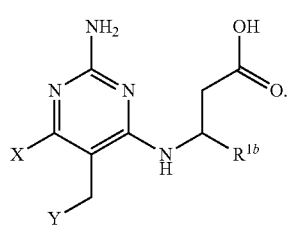
(1k)
Embodiment III-45
A compound, or a pharmaceutically acceptable salt, selected from the group consisting of:
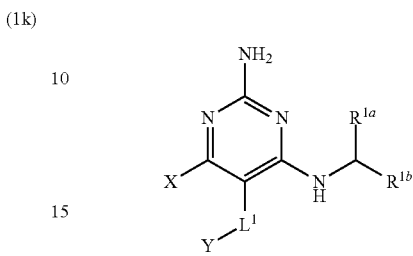

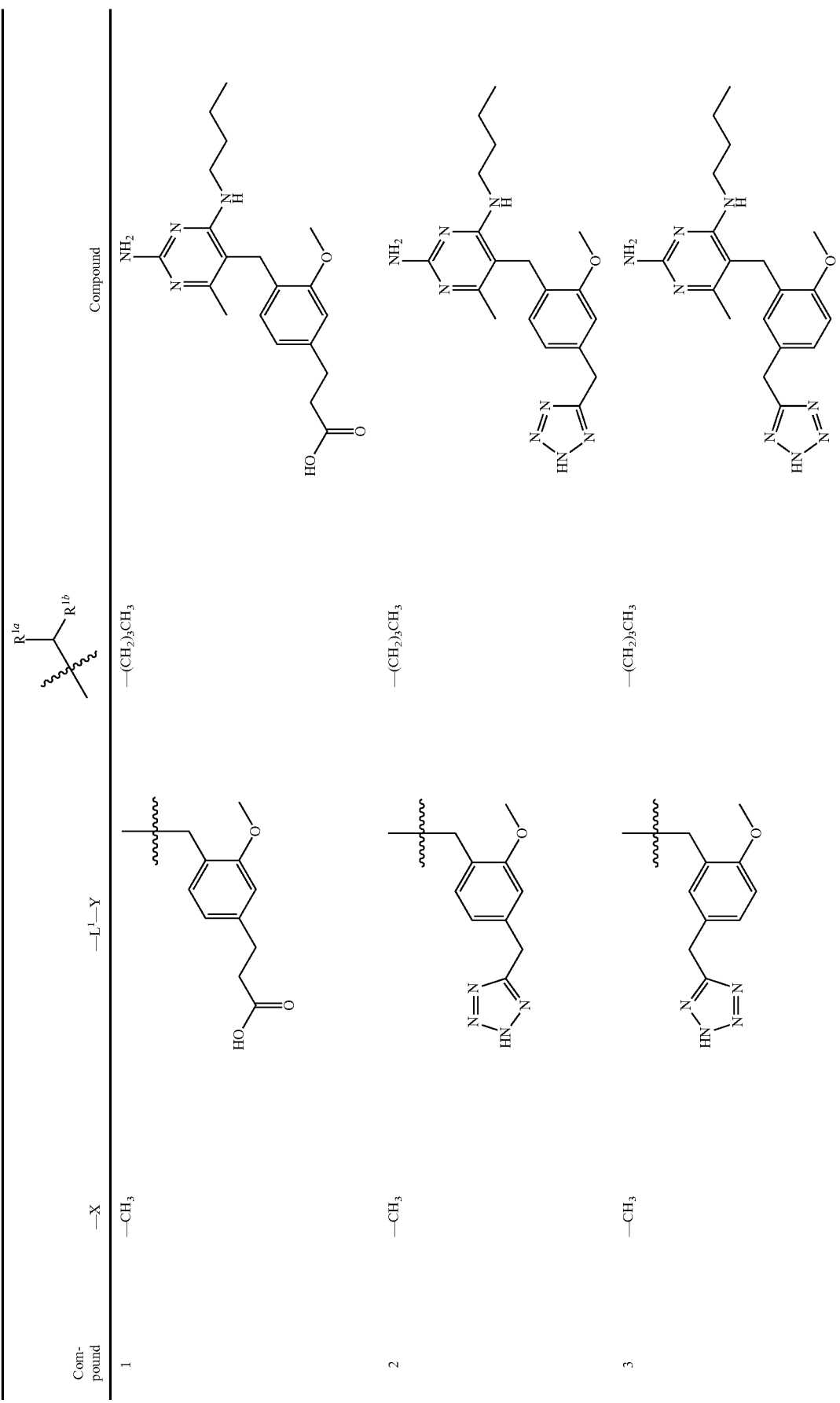

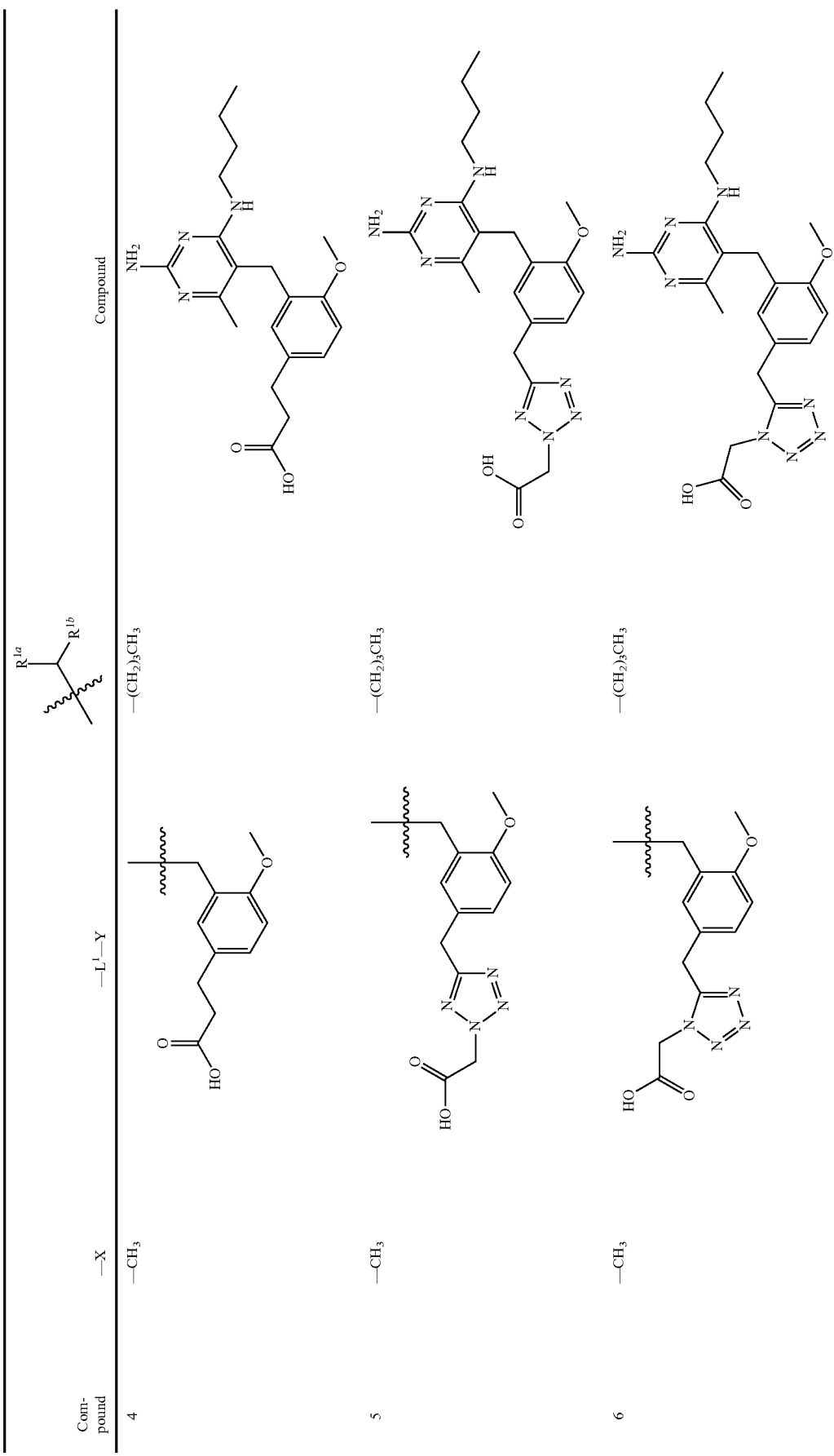

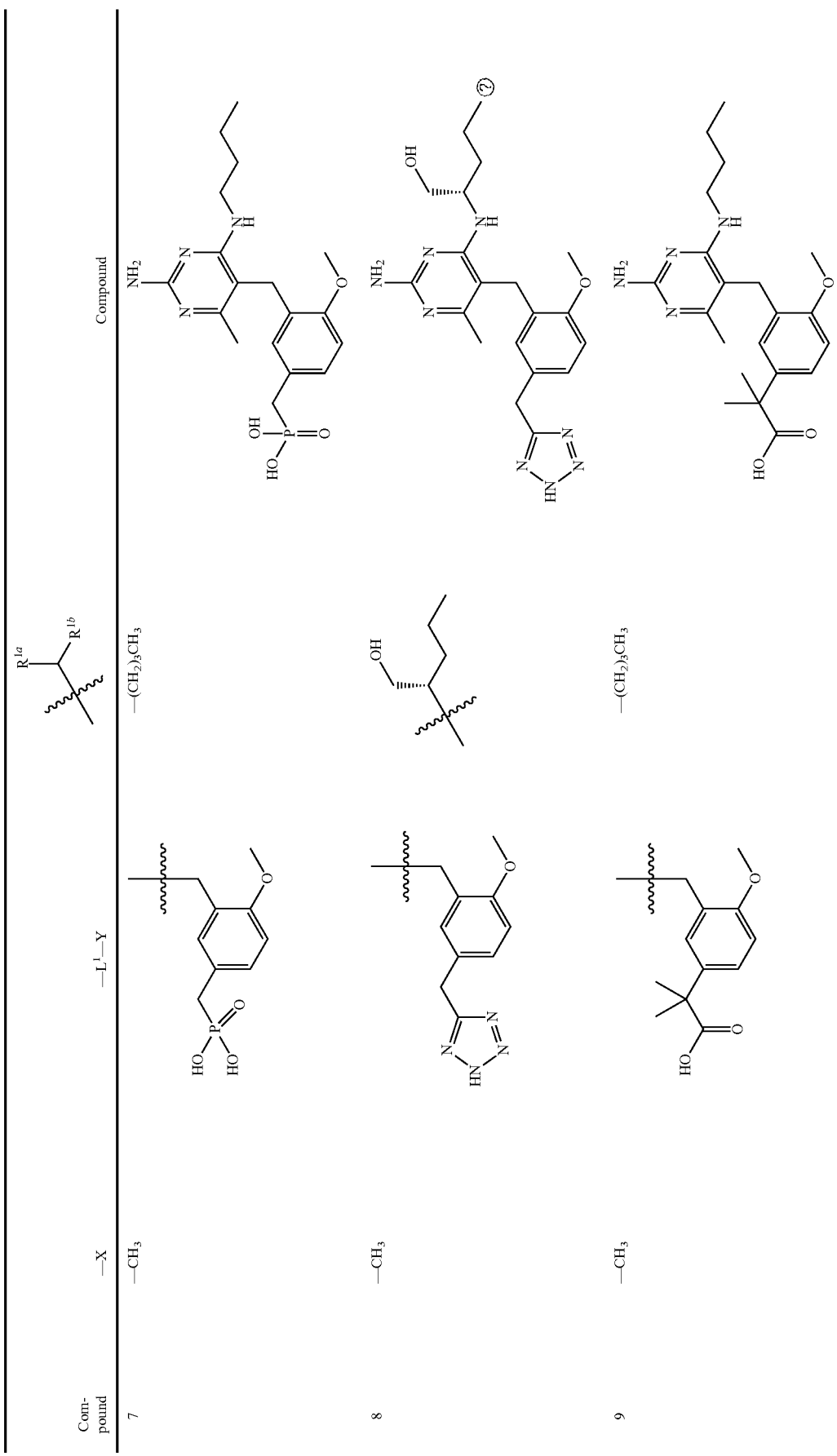

-continued

| Compound | —X | —L¹—Y | Compound R¹ᵃ⟨⟩R¹ᵇ |
|---|---|---|---|
| 10 | —CH₃ | (3-methoxy-4-... with tetrazole-substituted benzyl group) | —(CH₂)₃CH₃ |
| 11 | —CH₃ | (4-methoxy-3-... with tetrazole-substituted benzyl group) | —(CH₂)₃CH₃ |
| 12 | —CH₃ | (4-methoxy-3-... with phosphonic acid-substituted benzyl group) | —(CH₂)₃CH₃ |

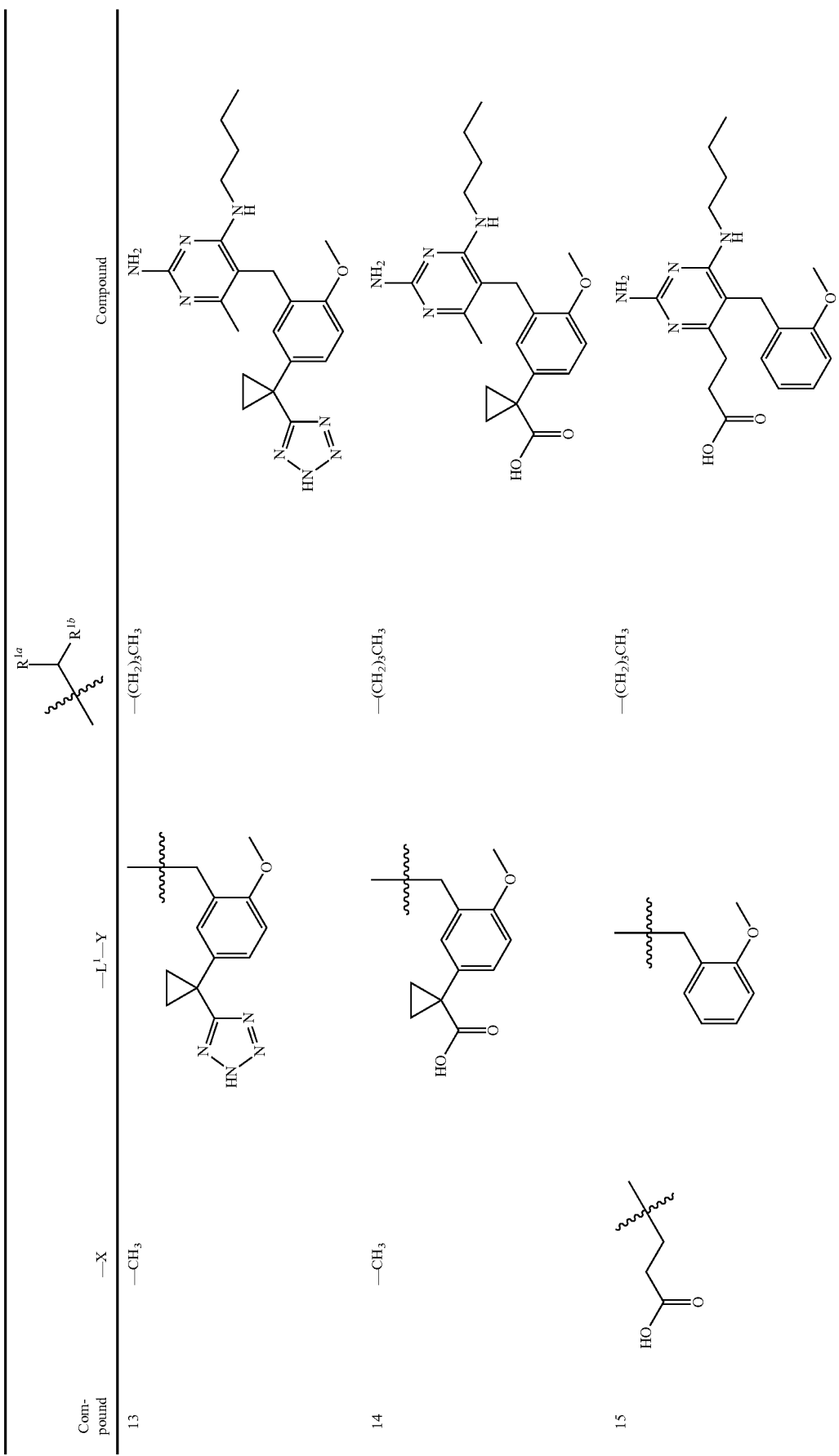

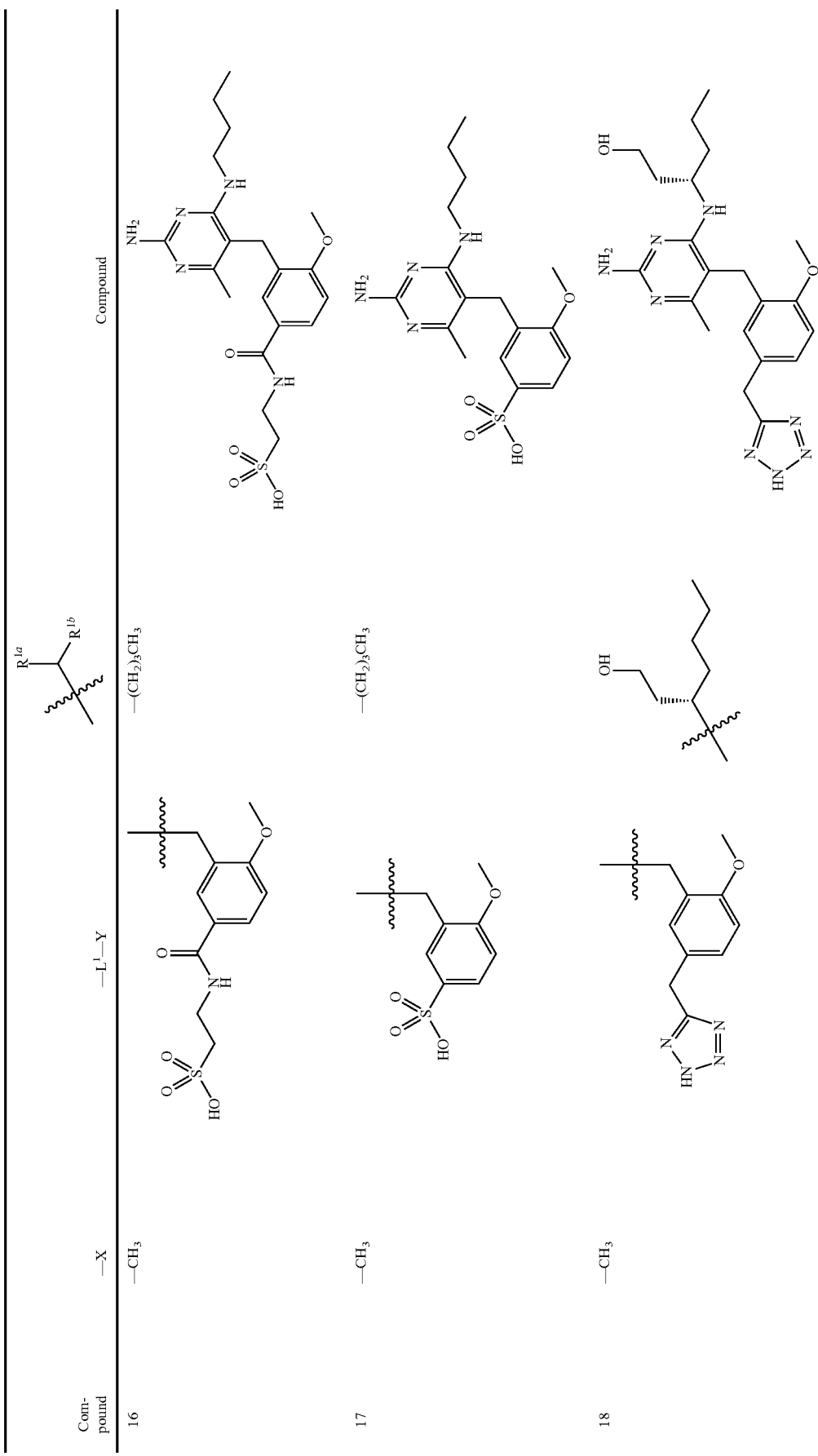

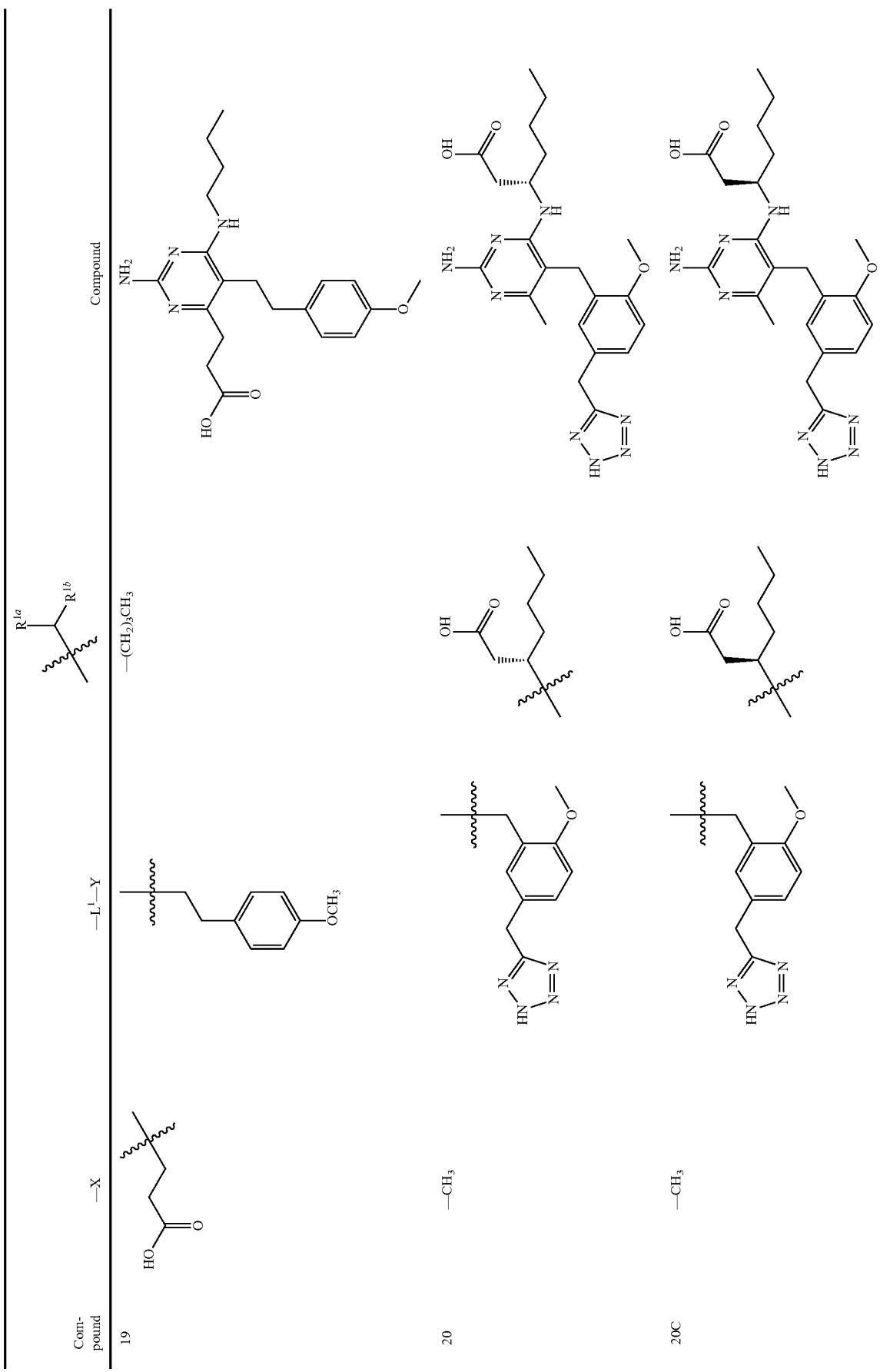

-continued

| Compound | —X | —L¹—Y | R¹ᵃ⧸R¹ᵇ | Compound |
|---|---|---|---|---|
| 21 | -CH₂CH₂COOH | —OCH₃ | -CH₂CH₂OH (with butyl branch) | 215 structure |
| 22 | —CH₃ | -CH₂-(2-OMe-phenyl)-5-CH₂-tetrazole | -CH₂CH₂SMe (with butyl branch) | 216 structure |
| 23 | —CH₃ | -CH₂-(2-OMe-phenyl)-5-CH₂-tetrazole | -CH₂CH₂S(O)₂Me (with butyl branch) | |

-continued

| Compound | —X | —L¹—Y | R¹ᵃ  R¹ᵇ | Compound |
|---|---|---|---|---|
| 24 | —CH₃ | (3-boronic acid-4-methoxybenzyl) | —(CH₂)₃CH₃ | 217 |
| 25 | —CH₃ | (3-(N-(3-carboxypropyl)carbamoyl)-4-methoxybenzyl) | —(CH₂)₄CH₃ | |
| 26 | —CH₃ | (3-((2H-tetrazol-5-yl)methyl)-4-methoxybenzyl variant) | —(CH₂)₄CH₃ | 218 |

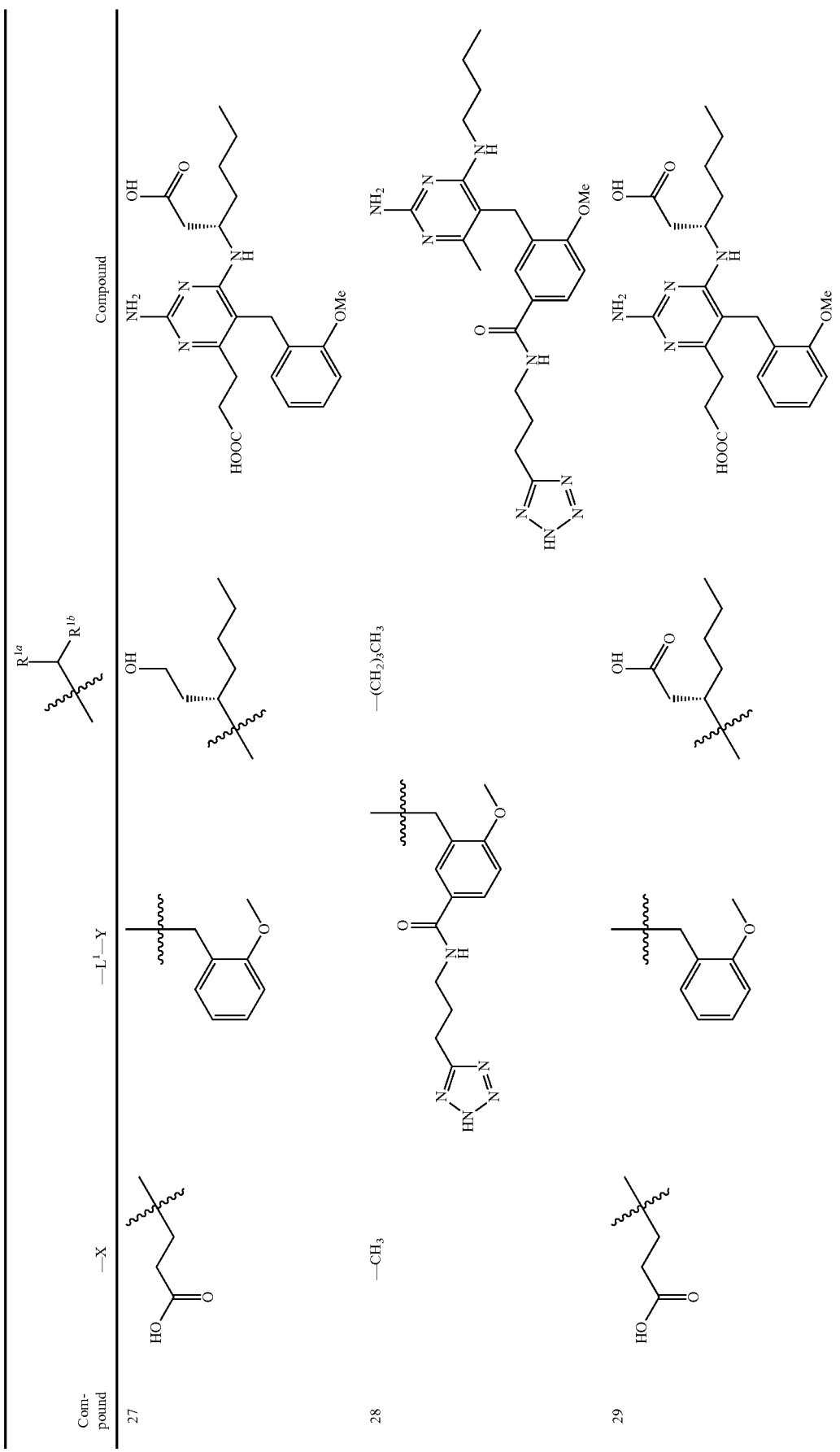

-continued

| Compound | —X | —L¹—Y | R¹ᵃ⤬R¹ᵇ | Compound |
|---|---|---|---|---|
| 30 | —CH₃ | (3-carbamoyl-4-methoxybenzyl with N-(3-phosphonopropyl) group) | —(CH₂)₃CH₃ | 221 |
| 31 | —CH₃ | (2-methoxy-5-((2H-tetrazol-5-yl)methyl)phenylthio) | —(CH₂)₃CH₃ | |
| 32 | —CH₃ | (2-methoxy-5-((2H-tetrazol-5-yl)methyl)benzyl) | (3-methoxypropyl-hexyl branched) | 222 |

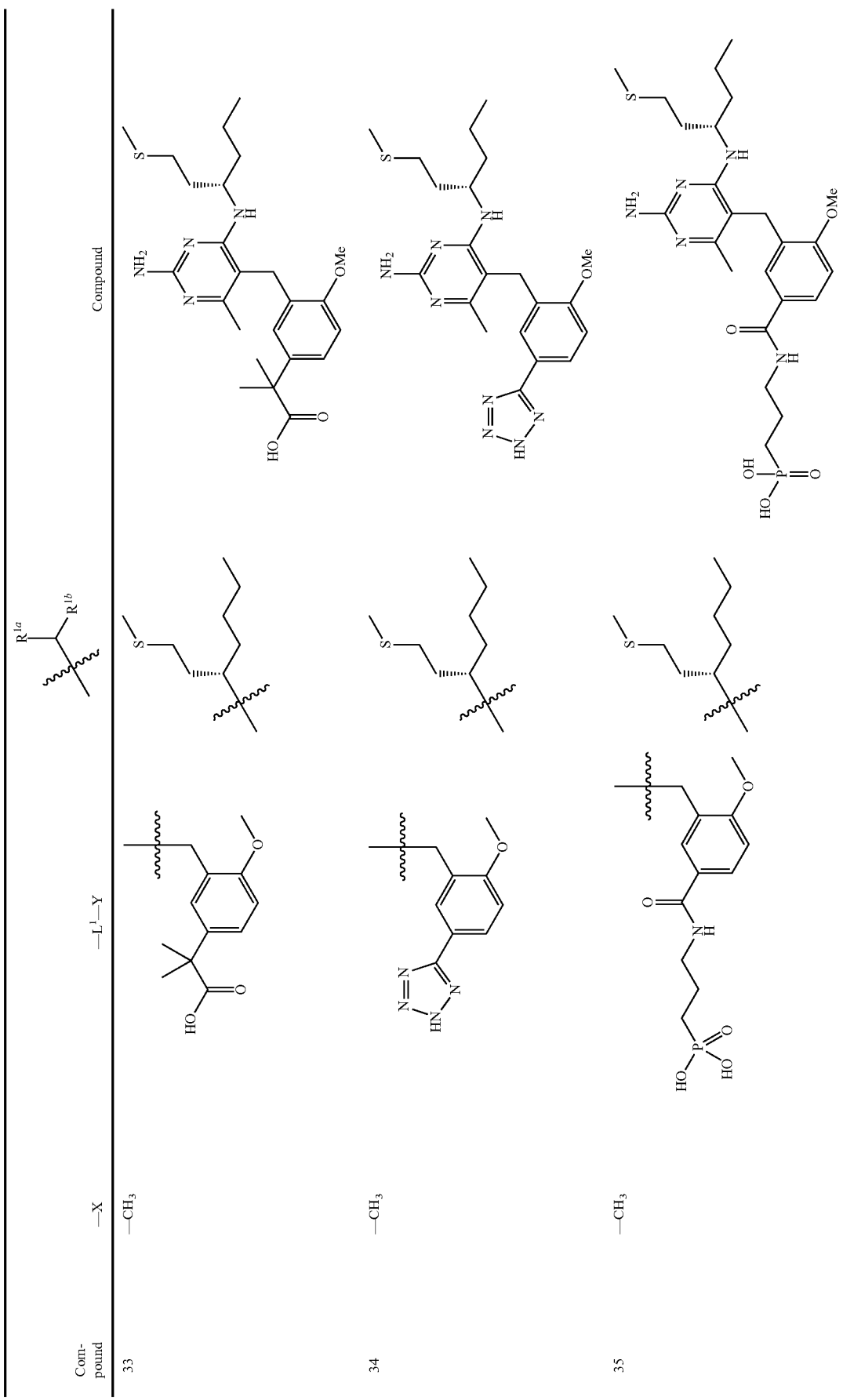

| Compound | —X | —L¹—Y | R¹ᵃ\R¹ᵇ | Compound |
|---|---|---|---|---|
| 36 | —CH₃ | (2-methoxybenzyl) | (tetrazolylmethyl-hexyl branched) | (structure 225 top) |
| 37 | (CH₂)₂-tetrazole | (2-methoxybenzyl) | —(CH₂)₃CH₃ | (structure middle) |
| 38 | (CH₂)₂COOH | (2-methoxybenzyl) | (methylthioethyl-hexyl branched) | (structure 226 bottom) |

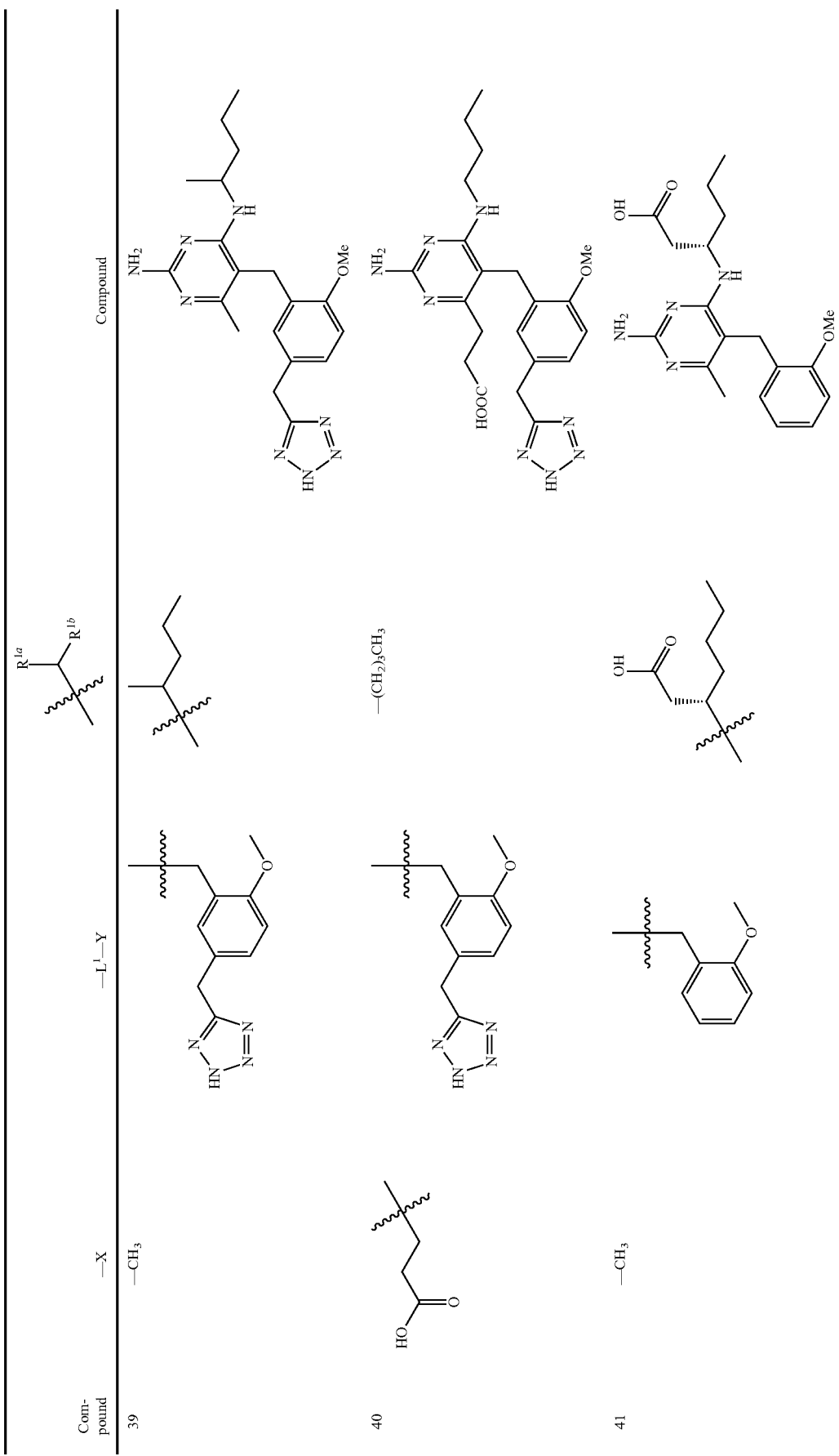

-continued

| Compound | —X | —L¹—Y | R¹ᵃ  R¹ᵇ | Compound |
|---|---|---|---|---|
| 42 | —CH₃ | (4-methoxy-3-methylene-phenyl with C(CH₃)₂COOH) | (CH(CH₂CH₂CH₂CH₃)CH₂COOH) | 2-amino-4-[NH-CH(butyl)CH₂COOH]-6-methyl-5-[(4-methoxy-3-C(CH₃)₂COOH-benzyl)]pyrimidine |
| 43 | (CH₂CH₂COOH) | (4-methoxy-3-methylene-phenyl with C(CH₃)₂COOH) | —(CH₂)₃CH₃ | 2-amino-4-(butylamino)-5-[(4-methoxy-3-C(CH₃)₂COOH-benzyl)]-6-(CH₂CH₂COOH)pyrimidine |
| 44 | —CH₃ | (3-methylene-4-methoxy-phenyl-C(O)NH-(CH₂)₃-P(O)(OH)₂) | (CH(CH₂CH₂CH₂CH₃)CH₂COOH) | 2-amino-4-[NH-CH(butyl)CH₂COOH]-6-methyl-5-[(4-methoxy-3-substituted-benzyl)]pyrimidine with phosphonate amide |

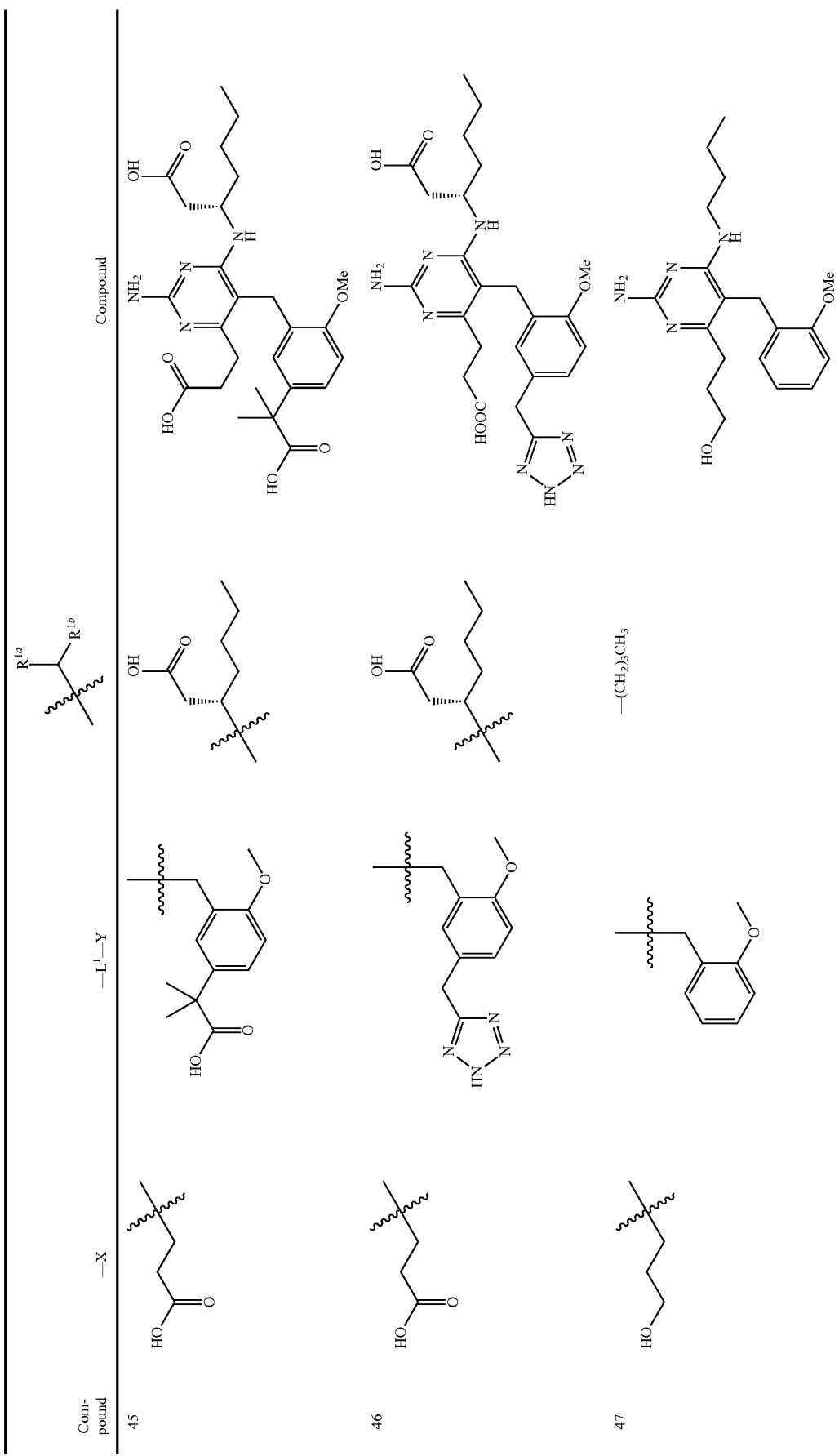

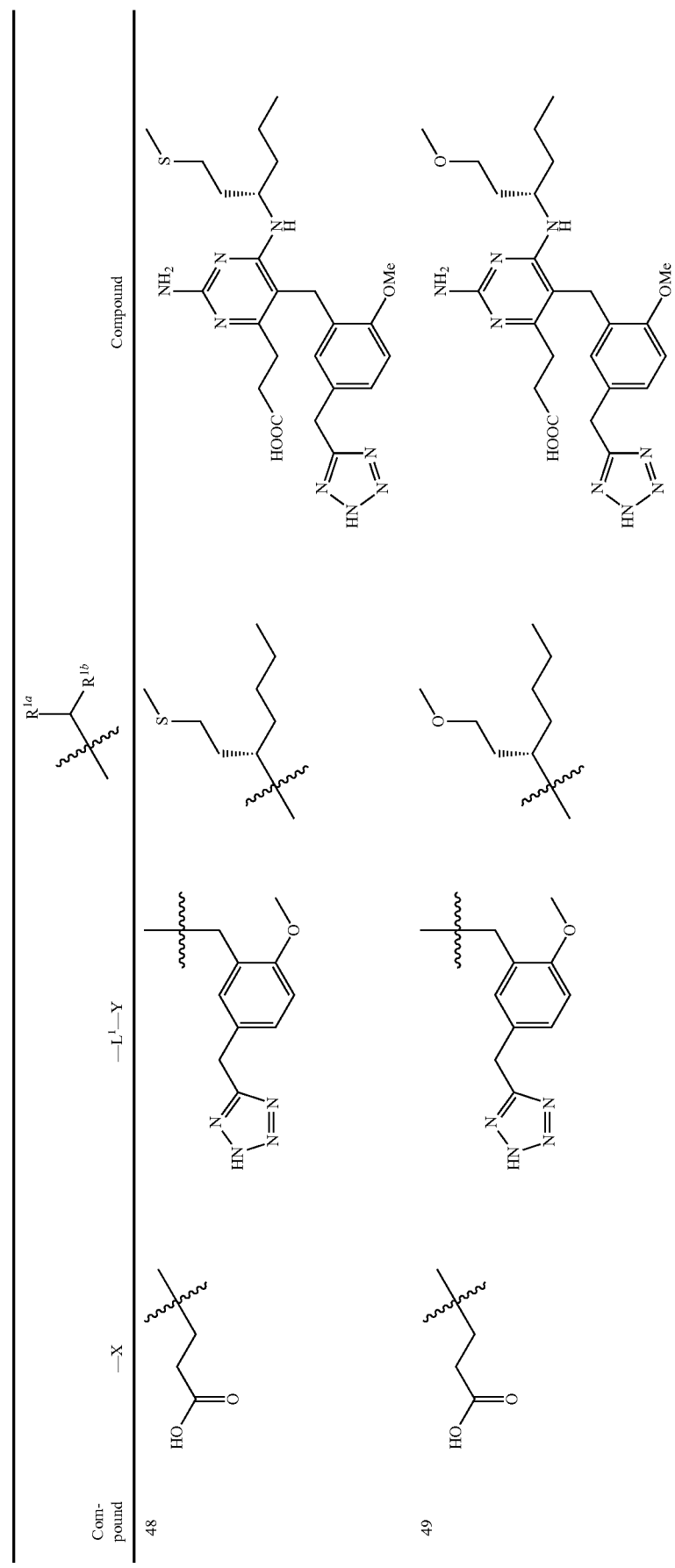

-continued
| Compound | —X | —L¹—Y | R¹ᵃ⤫R¹ᵇ | Compound |
|---|---|---|---|---|
| 50 | 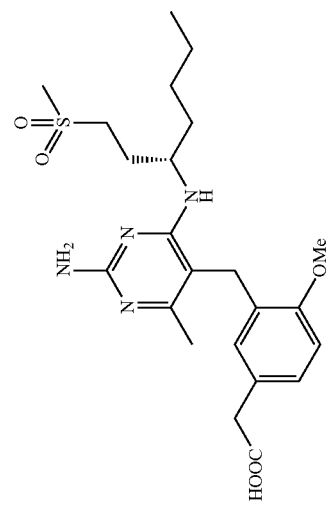 | 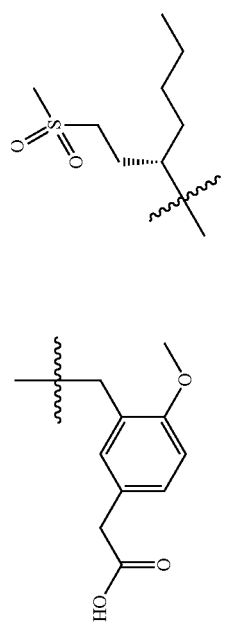 | 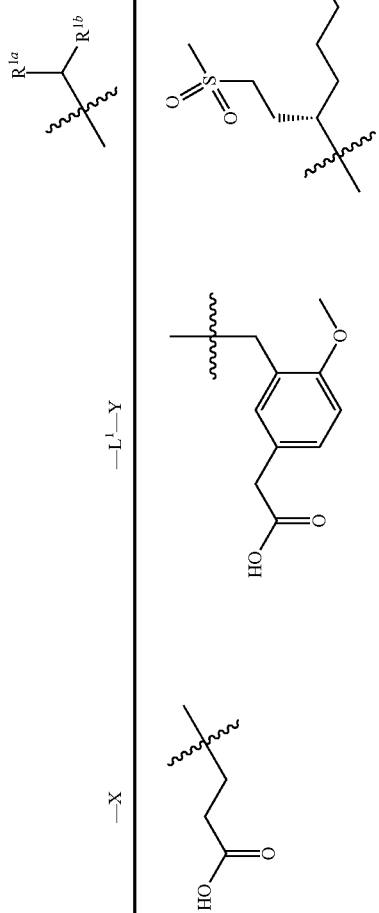 | |
| 51 | —CH₃ | | | |

Embodiment III-46

A pharmaceutical composition comprising a compound of any one of Embodiments III-1 to III-45, or a pharmaceutically acceptable salt thereof, and a pharmaceutically acceptable carrier.

Embodiment III-47

A method of treating a condition associated with TLR7 modulation in a subject in need thereof, comprising administering to the subject an effective amount of a compound of any one of Embodiments III-1 to III-45, or a pharmaceutically acceptable salt thereof.

Embodiment III-48

The method of Embodiment III-47, wherein the condition is viral infection or cancer.

Embodiment III-49

The method of Embodiment III-47 or III-48, wherein the administration is oral, intravenous, subcutaneous, intramuscular, intratumoral, intradermal, intranasal, inhaled, intravesicle, topical, sublingual, bucchal, intrarectal, intrathecal, intracranial, or other forms of local delivery.

Embodiment III-50

A compound of any one of Embodiments III-1 to III-45, or a pharmaceutically acceptable salt thereof, for use as a medicament.

Embodiment III-51

A compound of any one of Embodiments III-1 to III-45, or a pharmaceutically acceptable salt thereof, for use in treating a condition associated with TLR7 modulation.

Embodiment III-52

The compound of Embodiment III-51, wherein the condition is viral infection or cancer.

Embodiment III-53

Use of a compound of any one of Embodiments III-1 to III-45, or a pharmaceutically acceptable salt thereof, in the manufacture of a medicament for treating a condition associated with TLR7 modulation.

Embodiment III-54

The use of Embodiment III-53, wherein the condition is viral infection or cancer.

Embodiment III-55

A pharmaceutical composition of Embodiment III-46, further comprising at least one or more additional therapeutic agents.

Embodiment III-56

The pharmaceutical composition of Embodiment III-55, wherein the at least one or more additional therapeutic agent is antiviral nucleoside.

Embodiment III-57

The pharmaceutical composition of Embodiment III-55, wherein the at least one or more additional therapeutic agent is PD-1 antibody or PD-L1 antibody.

Embodiment III-58

A method of treating HBV in a subject in need thereof, comprising administering a compound of any one of Embodiments III-1 to III-45, or a pharmaceutically acceptable salt thereof, in combination with an antiviral nucleoside.

Embodiment III-59

A method of treating cancer in a subject in need thereof, comprising administering a compound of any one of Embodiments III-1 to III-45, or a pharmaceutically acceptable salt thereof, in combination with a PD-1 antibody or PD-L1 antibody.

EXAMPLES

The following examples are provided to illustrate the present disclosure, and should not be construed as limiting thereof. In these examples, all parts and percentages are by weight, unless otherwise noted. Abbreviations in the examples are noted below.

Abbreviations

| | |
|---|---|
| AIBN | azobisisobutyronitrile |
| aq. | aqueous |
| DCM | dichloromethane |
| DMAP | 4-dimethylaminopyridine |
| EA | ethyl acetate |
| eq | equivalent |
| h | hour |
| HATU | (1-[Bis(dimethylamino)methylene]-1H-1,2,3-triazolo[4,5-b]pyridinium 3-oxid hexafluorophosphate) |
| HPLC | high performance liquid chromatography |
| LC-MS | liquid chromatography mass spectrometry |
| min | minutes |
| NBS | N-bromosuccinimide |
| NMP | N-methylpyrrolidine |
| NMR | nuclear magnetic resonance |
| PE | petroleum ether |
| rt or r.t. | room temperature |
| sat. | saturated |
| TBAF | tetrabutylammonium flouride |
| TBDPS | tert-butyl diphenylsilyl |
| TEA | triethylamine |
| THF | tetrahydrofuran |
| TLC | thin layer chromatography |

Example 1: 3-(4-((2-amino-4-(butylamino)-6-methylpyrimidin-5-yl)methyl)-3-methoxyphenyl)propanoic acid (Compound 1)

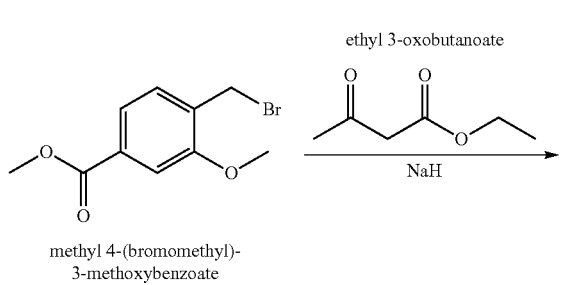

methyl 4-(bromomethyl)-3-methoxybenzoate

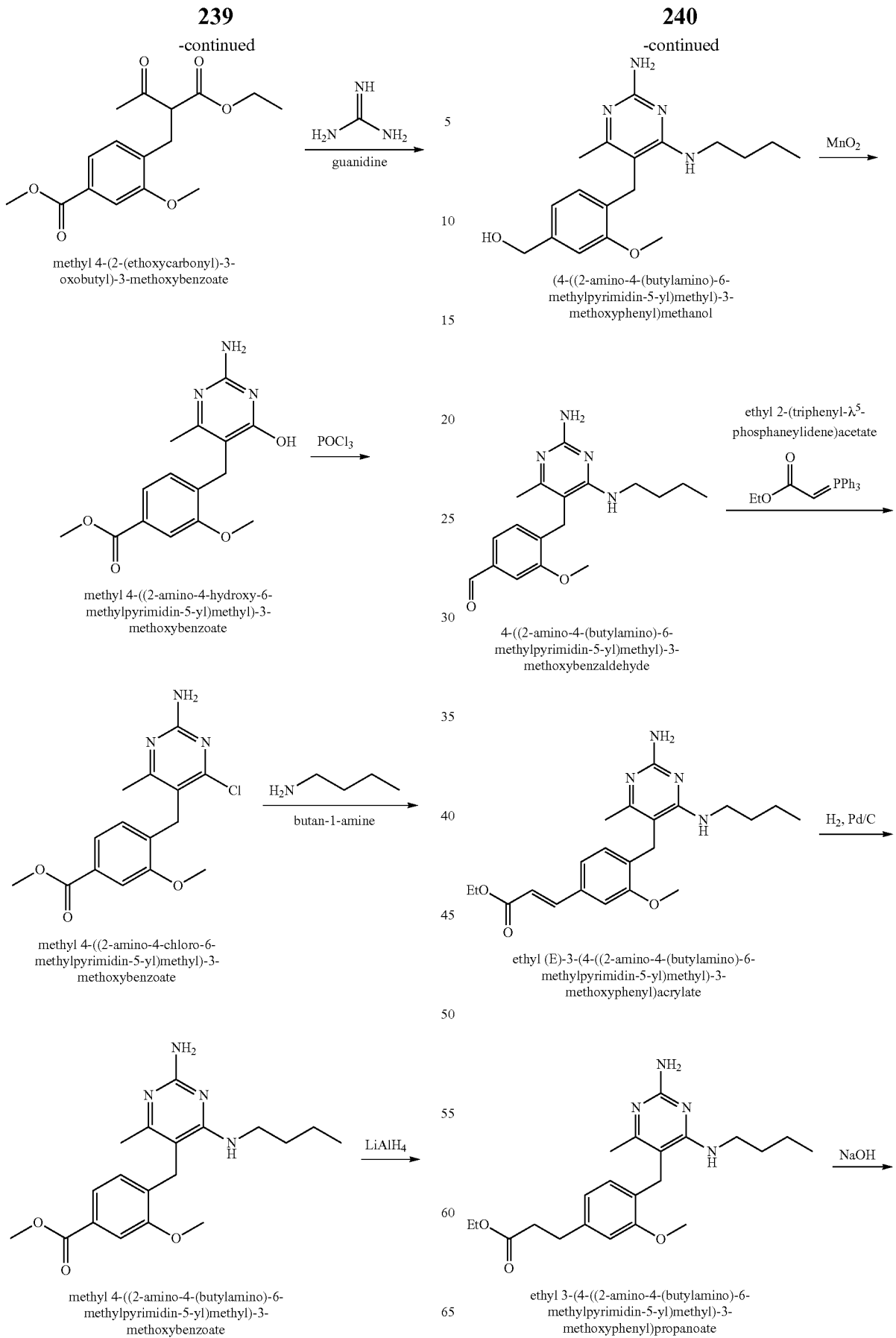

-continued

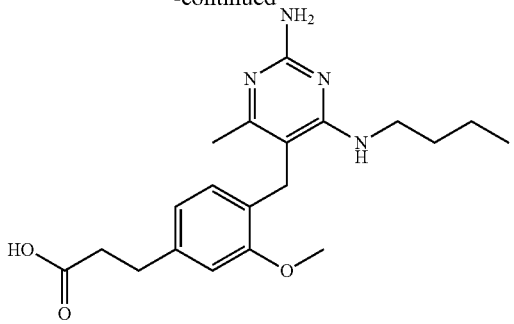

3-(4-((2-amino-4-(butylamino)-6-methylpyrimidin-5-yl)methyl)-3-methoxyphenyl)propanoic acid
Chemical Formula: $C_{20}H_{28}N_4O_3$
Exact Mass: 372.22

Step 1: methyl 4-(2-(ethoxycarbonyl)-3-oxobutyl)-3-methoxybenzoate

Sodium hydride (60% in mineral oil, 1.25 eq) was added in portions over 10 min to a solution of ethyl 3-oxobutanoate (1.2 eq) in THF (0.8M) at 0° C. The resulting suspension was stirred at 0° C. for 10 min and a solution of methyl 4-(bromomethyl)-3-methoxybenzoate (1.0 eq) in THF (0.5M) was added dropwise over 10 min. The mixture was warmed to 70° C. and stirred for 3 h. The mixture was allowed to cool and then poured into ice water and stirred for 30 min. The mixture was partitioned between EA/water. The organic layer dried over $Na_2SO_4$, filtered, concentrated and purified by flash chromatography on silica (eluent PE/EA=100/1 to 5/1) to give the title compound.

Step 2: methyl 4-((2-amino-4-hydroxy-6-methylpyrimidin-5-yl)methyl)-3-methoxybenzoate A mixture of methyl 4-(2-(ethoxycarbonyl)-3-oxobutyl)-3-methoxybenzoate (1.0 eq) and guanidine carbonate (1.0 eq) in MeOH (0.2M) was stirred overnight at 65° C. and then allowed to cool to rt. The precipitate was collected by filtration and suspended in water. The solid was collected by filtration and washed with MeOH and EA to give the title compound as a white solid.

Step 3: methyl 4-((2-amino-4-chloro-6-methylpyrimidin-5-yl)methyl)-3-methoxybenzoate Methyl 4-((2-amino-4-hydroxy-6-methylpyrimidin-5-yl)methyl)-3-methoxybenzoate (1.0 eq) in $POCl_3$ (0.5M) was stirred overnight at 100° C. under $N_2$. The mixture was cooled to rt and the solvent was removed. To the residue was added water and the pH of the mixture was adjusted to 7 with solid $NaHCO_3$. The resulting mixture was heated at 50° C. for 1 h and then allowed to cool to rt. The solid was collected, washed with water, EA and dried under vacuum to give the title compound.

Step 4: methyl 4-((2-amino-4-(butylamino)-6-methylpyrimidin-5-yl)methyl)-3-methoxybenzoate To a suspension of methyl 4-((2-amino-4-chloro-6-methylpyrimidin-5-yl)methyl)-3-methoxybenzoate (1.0 eq) in NMP (0.3M) was added butan-1-amine (4.5 eq). The resulting mixture was stirred overnight at 125° C. and the mixture was cooled to rt. The mixture was partitioned between EA/water. The organic layer was dried over $Na_2SO_4$, concentrated and purified by flash chromatography on silica (eluent PE/EA=20:1 to 1:5) to give the title compound.

Step 5: (4-((2-amino-4-(butylamino)-6-methylpyrimidin-5-yl)methyl)-3-methoxyphenyl)methanol To a stirred solution of methyl 4-((2-amino-4-(butylamino)-6-methylpyrimidin-5-yl)methyl)-3-methoxybenzoate (1.0 eq) in THF (0.1M) was added $LiAlH_4$ (1M in THF, 2.0 eq) dropwise. The resulting mixture was stirred at 0° C. for 10 min and at rt for 1 h. The mixture was diluted with EA and quenched with 2N NaOH. The mixture was partitioned between EA/water. The organic layer was dried over $Na_2SO_4$, filtered and concentrated to give the title compound as white solid.

Step 6: 4-((2-amino-4-(butylamino)-6-methylpyrimidin-5-yl)methyl)-3-methoxybenzaldehyde To a stirred solution of (4-((2-amino-4-(butylamino)-6-methylpyrimidin-5-yl)methyl)-3-methoxyphenyl)methanol (1.0 eq) in THF (0.06M) was added $MnO_2$ (5.0 eq). The resulting mixture was stirred overnight at 50° C. The mixture was filtered. The filtrate was concentrated to give the title compound.

Step 7: ethyl (E)-3-(4-((2-amino-4-(butylamino)-6-methylpyrimidin-5-yl)methyl)-3-methoxyphenyl) acrylate A mixture of 4-((2-amino-4-(butylamino)-6-methylpyrimidin-5-yl)methyl)-3-methoxybenzaldehyde (1.0 eq) and ethyl 2-(triphenyl-$\lambda^5$-phosphanylidene)acetate (1.2 eq) in THF (0.1M) was stirred at 70° C. for 5 h. The mixture was concentrated and purified by flash chromatography on silica (eluent 0-5% MeOH in DCM) to give the title compound as a white solid.

Step 8: ethyl 3-(4-((2-amino-4-(butylamino)-6-methylpyrimidin-5-yl)methyl)-3-methoxyphenyl) propanoate To a stirred solution of ethyl (E)-3-(4-((2-amino-4-(butylamino)-6-methylpyrimidin-5-yl)methyl)-3-methoxyphenyl)acrylate (1.0 eq) in EA (0.02M) was added Pd/C (20% weight). The resulting mixture was stirred overnight at 50° C. under $H_2$. The mixture was filtered. The filtrate was concentrated and purified by flash chromatography on silica (eluent 0-5% MeOH in DCM) to give the title compound.

Step 9: 3-(4-((2-amino-4-(butylamino)-6-methylpyrimidin-5-yl)methyl)-3-methoxyphenyl)propanoic acid To a stirred solution of ethyl 3-(4-((2-amino-4-(butylamino)-6-methylpyrimidin-5-yl)methyl)-3-methoxyphenyl)propanoate (1.0 eq) in MeOH (0.03M) was added 1 N NaOH (5.0 eq). The resulting mixture was stirred overnight at 45° C. Solvent was removed. The residue was neutralized with 2 N HCl to pH 7. The suspension was filtered. The solid was collected and dissolved in HCl/dioxane. The solution was concentrated to give the title compound as a white solid (HCl salt).
LC-MS: [M+H]=373.4

$^1$H NMR (400 MHz, DMSO-d$_6$) δ 12.32 (br s, 1H), 12.11 (br s, 1H), 7.83 (br s, 1H), 7.41 (br s, 2H), 6.90 (s, 1H), 6.70 (s, 2H), 3.83 (s, 3H), 3.64 (s, 2H), 3.36-3.30 (m, 2H), 2.82-2.77 (m, 2H), 2.54-2.50 (m, 2H), 2.11 (s, 3H), 1.50-1.43 (m, 2H), 1.23-1.15 (m, 2H), 0.85 (t, J=7.2 Hz, 3H).

Example 2: 5-(4-((2H-tetrazol-5-yl)methyl)-2-methoxybenzyl)-N4-butyl-6-methylpyrimidine-2,4-diamine (Compound 2)

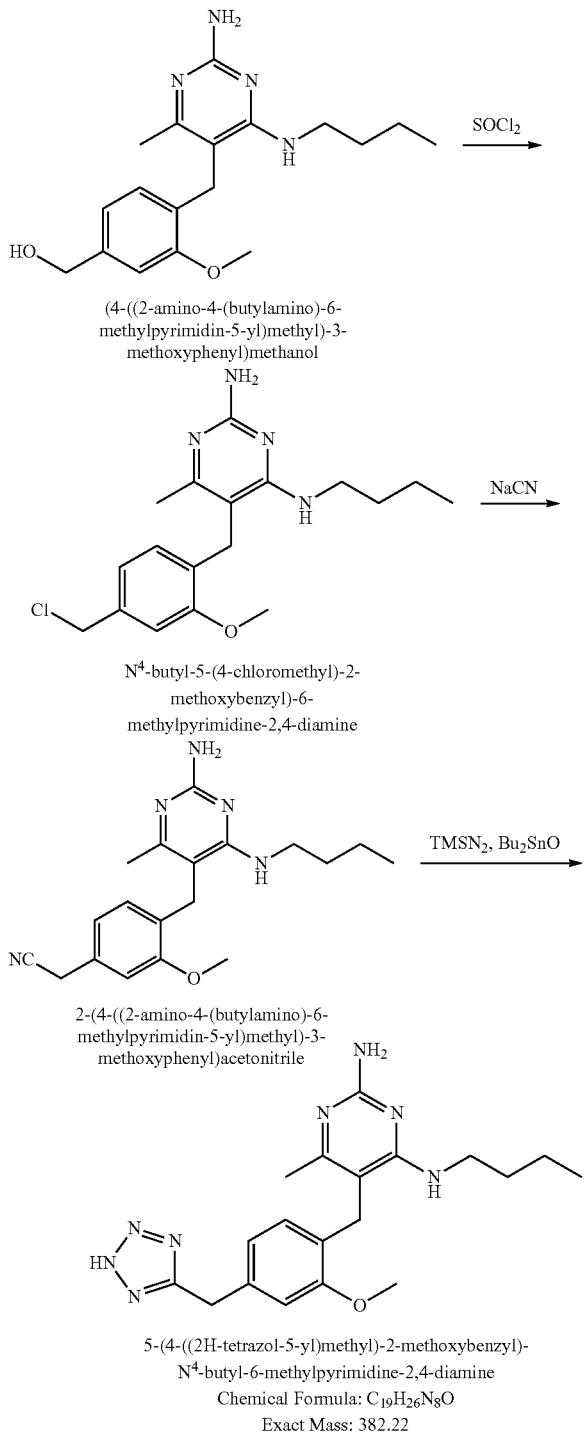

Step 1: N4-butyl-5-(4-(chloromethyl)-2-methoxybenzyl)-6-methylpyrimidine-2,4-diamine To a stirred solution of (4-((2-amino-4-(butylamino)-6-methylpyrimidin-5-yl)methyl)-3-methoxyphenyl)methanol (1.0 eq, Example 1—Step 5) in DCM (0.14M) was added SOCl$_2$ (1.8 eq) at rt under N$_2$. The mixture was stirred at rt for 1 h. The mixture was partitioned between DCM/sat. aq. NaHCO$_3$. The organic layer was dried over Na$_2$SO$_4$, filtered and concentrated to give the title compound.

Step 2: 2-(4-((2-amino-4-(butylamino)-6-methylpyrimidin-5-yl)methyl)-3-methoxyphenyl)acetonitrile A mixture of N$^4$-butyl-5-(4-(chloromethyl)-2-methoxybenzyl)-6-methylpyrimidine-2,4-diamine (1.0 eq) in 1:1 DMSO/DMF (0.14M) and NaCN (2.8 eq) was stirred overnight at rt. The mixture was partitioned between EA/water. The organic layer was dried over Na$_2$SO$_4$, filtered, concentrated and purified by flash chromatography on silica (eluent 0-5% MeOH in DCM) to give the title compound.

Step 3: 5-(4-((2H-tetrazol-5-yl)methyl)-2-methoxybenzyl)-N4-butyl-6-methylpyrimidine-2,4-diamine To a stirred mixture of 2-(4-((2-amino-4-(butylamino)-6-methylpyrimidin-5-yl)methyl)-3-methoxyphenyl)acetonitrile (1.0 eq), Bu$_2$SnO (2.0 eq) in NMP (0.06M) was added TMSN$_3$ (10.0 eq). The resulting mixture was stirred overnight at 125° C. under N$_2$. The mixture was cooled to rt. The mixture was filtered to give the title compound as a white powder.

LC-MS: [M+H]=383.5

$^1$H NMR (400 MHz, DMSO-d$_6$) δ 12.19 (s, 1H), 7.85 (br s, 1H), 7.34 (br s, 2H), 7.01 (s, 1H), 6.74 (s, 2H), 4.24 (s, 2H), 3.84 (s, 3H), 3.65 (s, 2H), 3.37-3.34 (m, 2H), 2.09 (s, 3H), 1.48-1.41 (m, 2H), 1.23-1.16 (m, 2H), 0.83 (t, J=7.2 Hz, 3H).

Example 3A: 5-(5-((2H-tetrazol-5-yl)methyl)-2-methoxybenzyl)-N4-butyl-6-methylpyrimidine-2,4-diamine (Compound 3)

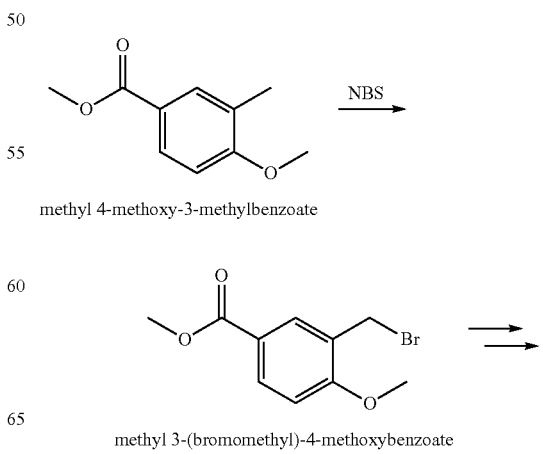

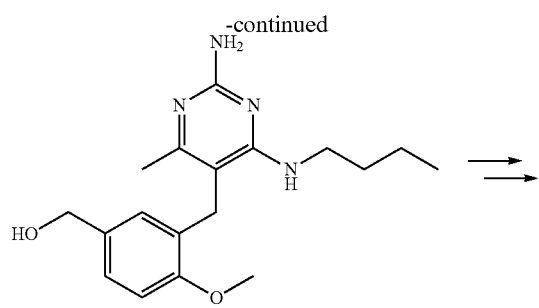

(3-((2-amino-4-(butylamino)-6-methylpyrimidin-5-yl)methyl)-4-methoxyphenyl)methanol

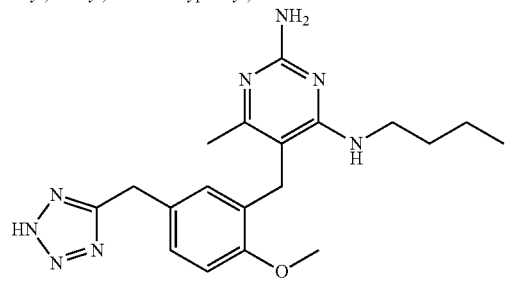

5-(5-((2H-tetrazol-5-yl)methyl)-2-methoxybenzyl)-
N⁴-butyl-6-methylpyrimidine-2,4-diamine
Chemical Formula: $C_{19}H_{26}N_8O$
Exact Mass: 382.22

Step A: methyl 3-(bromomethyl)-4-methoxybenzoate

To a mixture of methyl 4-methoxy-3-methylbenzoate (1.0 eq) in $CCl_4$ (0.37M), NBS (1.1 eq) and AIBN (0.2 eq) was stirred overnight at 95° C. under nitrogen atmosphere. The resulting mixture was concentrated and partitioned between DCM and water, the organic layer was dried over $Na_2SO_4$, concentrated and purified by flash chromatography on silica (eluent PE/EA=100:1 to 20:1) to give the title compound as a white solid.

Preparation of (3-((2-amino-4-(butylamino)-6-methylpyrimidin-5-yl)methyl)-4-methoxyphenyl)methanol Preparation of (3-((2-amino-4-(butylamino)-6-methylpyrimidin-5-yl)methyl)-4-methoxyphenyl)methanol followed Example 1—Step 1 to 5, but using methyl 3-(bromomethyl)-4-methoxybenzoate instead of methyl 4-(bromomethyl)-3-methoxybenzoate in Step 1.

Preparation of 5-(5-((2H-tetrazol-5-yl)methyl)-2-methoxybenzyl)-N4-butyl-6-methylpyrimidine-2,4-diamine Preparation of 5-(5-((2H-tetrazol-5-yl)methyl)-2-methoxybenzyl)-N⁴-butyl-6-methylpyrimidine-2,4-diamine followed Example 2—Steps 1 to 3, but using (3-((2-amino-4-(butylamino)-6-methylpyrimidin-5-yl)methyl)-4-methoxyphenyl)methanol instead of 4-((2-amino-4-(butylamino)-6-methylpyrimidin-5-yl)methyl)-3-methoxyphenyl)methanol in Step 1. The title compound was purified by prep-HPLC using acetonitrile/water as the eluent to give a white solid.
LC-MS: [M+H]=383.3

¹H NMR (400 MHz, DMSO-d₆) δ 7.03 (d, J=7.6 Hz, 1H), 6.90 (d, J=8.4 Hz, 1H), 6.73 (s, 1H), 6.60 (br s, 1H), 6.31 (s, 2H), 3.97 (s, 2H), 3.80 (s, 3H), 3.60 (s, 2H), 3.29-3.24 (m, 2H), 2.02 (s, 3H), 1.43-1.37 (m, 2H), 1.22-1.17 (m, 2H), 0.84 (t, J=7.2 Hz, 3H).

Example 3B: 5-(5-((2H-tetrazol-5-yl)methyl)-2-methoxybenzyl)-N4-butyl-6-methylpyrimidine-2,4-diamine (Compound 3)

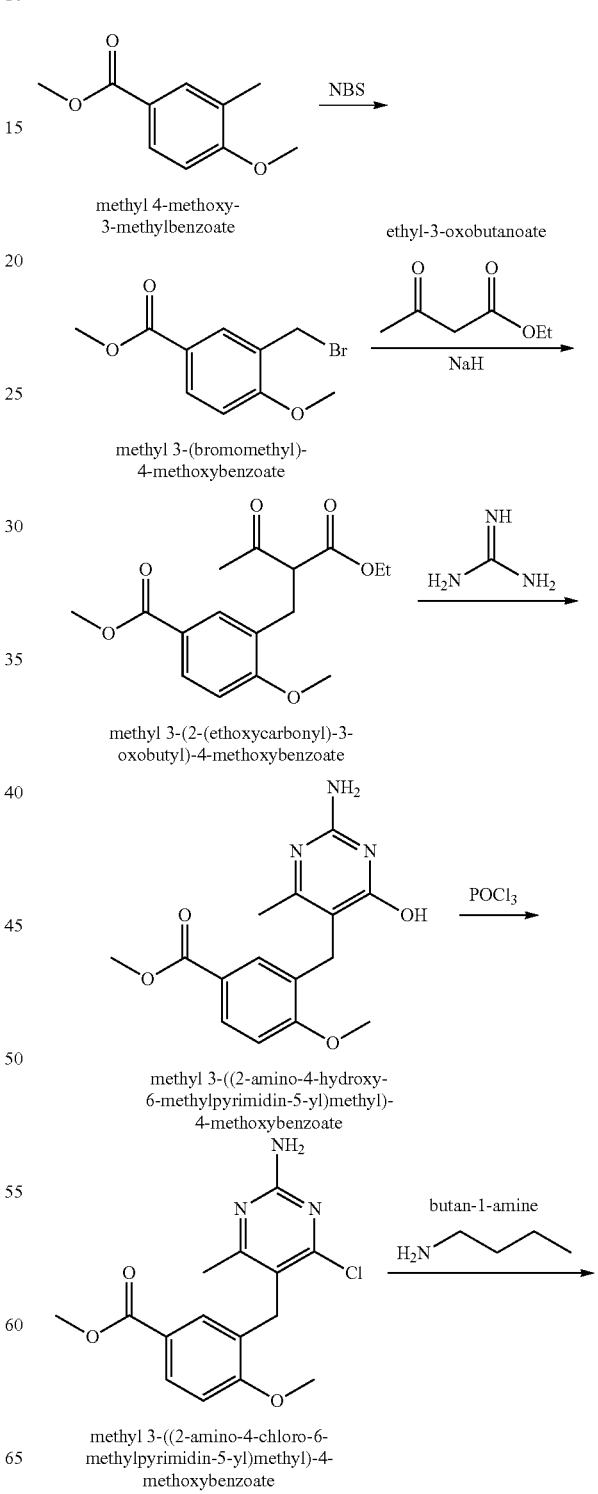

247

-continued

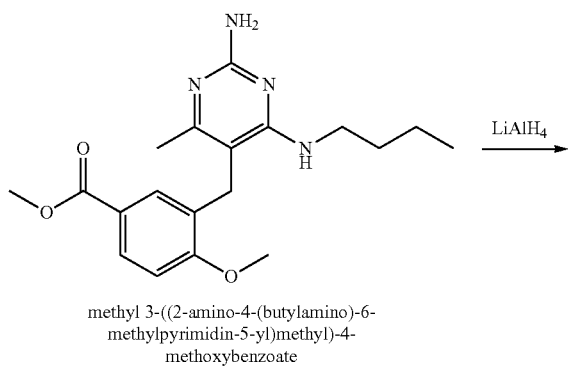

methyl 3-((2-amino-4-(butylamino)-6-methylpyrimidin-5-yl)methyl)-4-methoxybenzoate

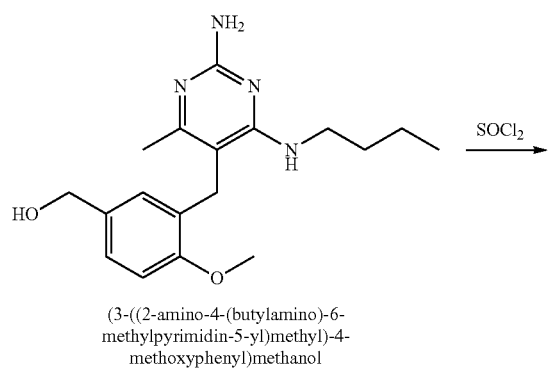

(3-((2-amino-4-(butylamino)-6-methylpyrimidin-5-yl)methyl)-4-methoxyphenyl)methanol

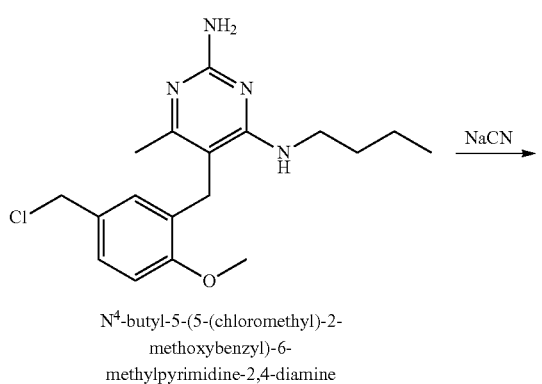

$N^4$-butyl-5-(5-(chloromethyl)-2-methoxybenzyl)-6-methylpyrimidine-2,4-diamine

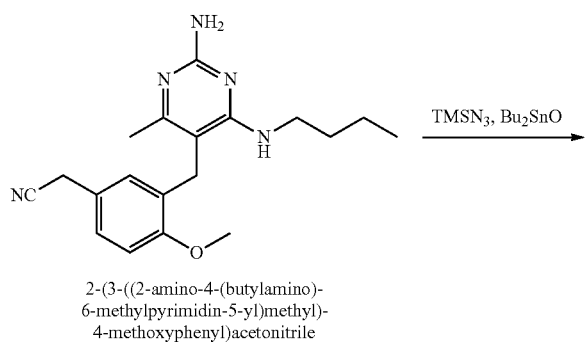

2-(3-((2-amino-4-(butylamino)-6-methylpyrimidin-5-yl)methyl)-4-methoxyphenyl)acetonitrile

248

-continued

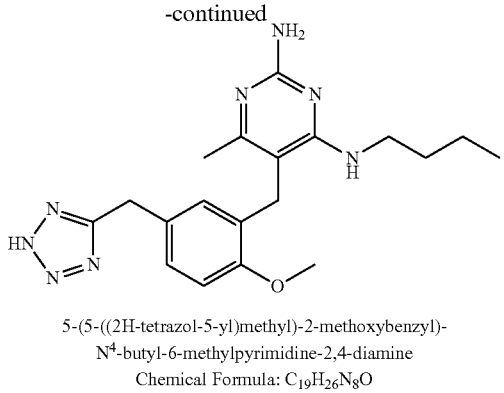

5-(5-((2H-tetrazol-5-yl)methyl)-2-methoxybenzyl)-
$N^4$-butyl-6-methylpyrimidine-2,4-diamine
Chemical Formula: $C_{19}H_{26}N_8O$
Exact Mass: 382.22

Step 1: methyl 3-(bromomethyl)-4-methoxybenzoate

To a mixture of methyl 4-methoxy-3-methylbenzoate (1.0 eq) in $CCl_4$ (0.37M), NBS (1.1 eq) and AIBN (0.2 eq) was stirred overnight at 95° C. under nitrogen atmosphere. The resulting mixture was concentrated and partitioned between DCM and water, the organic layer was dried over $Na_2SO_4$, concentrated and purified by flash chromatography on silica (eluent PE/EA=100:1 to 20:1) to give the title compound as a white solid.

Step 2: methyl 3-(2-(ethoxycarbonyl)-3-oxobutyl)-4-methoxybenzoate

To a solution of ethyl 3-oxobutanoate (1.2 eq) in THF (0.35M) at 0° C. was added in portions 60% NaH (1.25 eq) under $N_2$. The resulting suspension was stirred at 0° C. for 10 min, then a solution of methyl 3-(bromomethyl)-4-methoxybenzoate (1.0 eq) in THF (2M) was added dropwise over 10 min. The resulting mixture was stirred overnight at 70° C. The mixture was cooled down to rt and ice water was added. The mixture was extracted with ethyl acetate. The organic layer was separated and dried over $Na_2SO_4$, concentrated and purified by flash chromatography on silica (eluent PE/EA=50:1-5:1) to give the title compound as a yellow oil.

Step 3: methyl 3-((2-amino-4-hydroxy-6-methylpyrimidin-5-yl)methyl)-4-methoxybenzoate To a solution of methyl 3-(2-(ethoxycarbonyl)-3-oxobutyl)-4-methoxybenzoate (1.0 eq) in MeOH (0.2M) was added guanidine carbonate (1.0 eq). The resulting mixture was stirred at 65° C. for 16 h and then cooled down to r.t. The precipitate was collected by filtration, and the solid was triturated with water and filtered. The filter cake was washed with MeOH and EtOAc, dried under vacuum to give the title compound as a white solid.

Step 4: methyl 3-((2-amino-4-chloro-6-methylpyrimidin-5-yl)methyl)-4-methoxybenzoate To a suspension of methyl 3-((2-amino-4-hydroxy-6-methylpyrimidin-5-yl)methyl)-4-methoxybenzoate (1.0 eq) in $POCl_3$ (0.55M) was stirred at 100° C. for 15 h. The reaction mixture was allowed to cool to rt, and $POCl_3$ was evaporated to dryness under reduced pressure. The residue was diluted with water and adjusted pH to 7 with saturated NaHCO$_3$. Then the mixture was heated at 50° C. for 1 h, cooled down to rt. The precipitate was collected by filtration, and the filter cake was washed with water and EtOAc, dried over vacuum to give the title compound.

Step 5: methyl 3-((2-amino-4-(butylamino)-6-methylpyrimidin-5-yl)methyl)-4-methoxybenzoate A mixture of butan-1-amine (4.5 eq) and methyl 3-((2-amino-4-chloro-6-methylpyrimidin-5-yl)methyl)-4-methoxybenzoate (1.0 eq) in NMP (0.3M) was stirred overnight at 150° C. The reaction was allowed to cool, diluted with EtOAc, washed with water and brine. The organic phase was dried and evaporated under reduced pressure. The residue was suspended in diethyl ether, and the solid was collected by filtration to give the title compound as a solid.

Step 6: (3-((2-amino-4-(butylamino)-6-methylpyrimidin-5-yl)methyl)-4-methoxyphenyl)-methanol To a stirred solution of methyl 3-((2-amino-4-(butylamino)-6-methylpyrimidin-5-yl)methyl)-4-methoxybenzoate (1.0 eq) in THF (0.3M) was added 2.5M LiAlH$_4$ (2.0 eq) in THF at 0° C. under N$_2$ atmosphere. The resulting mixture was stirred at 0° C. for 30 min and then at r.t. for 2 h. The mixture was diluted with EtOAc and quenched with 2N NaOH. The suspension was filtered, and the filtrate was partitioned between EA/water. The organic layer was dried over Na$_2$SO$_4$, filtered and concentrated to give the title compound as a white solid.

Step 7: N$^4$-butyl-5-(5-(chloromethyl)-2-methoxybenzyl)-6-methylpyrimidine-2,4-diamine To a stirred solution of (3-((2-amino-4-(butylamino)-6-methylpyrimidin-5-yl)methyl)-4-methoxyphenyl)methanol (1.0 eq) in DCM (0.34M) was added SOCl$_2$ (1.3 eq) at rt under N$_2$. The mixture was stirred at rt for 1 h. The mixture was partitioned between DCM and saturated aqueous NaHCO$_3$. The organic layer was dried over Na$_2$SO$_4$, filtered and concentrated to give the title compound.

Step 8: 2-(3-((2-amino-4-(butylamino)-6-methylpyrimidin-5-yl)methyl)-4-methoxyphenyl)-acetonitrile A mixture of N$^4$-butyl-5-(5-(chloromethyl)-2-methoxybenzyl)-6-methylpyrimidine-2,4-diamine (1.0 eq) in 1:1 DMSO/DMF (0.34M) and NaCN (2.8 eq) was stirred overnight at rt. The mixture was partitioned between EA/water. The organic layer was dried over Na$_2$SO$_4$, filtered, concentrated and purified by flash chromatography on silica (eluent 0-5% MeOH in DCM) to give the title compound.

Step 9: 5-(5-((2H-tetrazol-5-yl)methyl)-2-methoxybenzyl)-M-butyl-6-methylpyrimidine-2,4-diamine To a stirred mixture of 2-(3-((2-amino-4-(butylamino)-6-methylpyrimidin-5-yl)methyl)-4-methoxyphenyl)acetonitrile (1.0 eq) in NMP (0.06M) and Bu$_2$SnO (2.0 eq) was added TMSN$_3$ (10.0 eq). The resulting mixture was stirred overnight at 125° C. under N$_2$. The mixture was cooled down to rt, and the mixture was concentrated and purified by prep-HPLC to give the title compound as a solid.

LC-MS: [M+H]$^+$=383.3

$^1$H NMR (400 MHz, DMSO-d$_6$) δ 7.03 (d, J=7.6 Hz, 1H), 6.90 (d, J=8.4 Hz, 1H), 6.73 (s, 1H), 6.60 (br s, 1H), 6.31 (s, 2H), 3.97 (s, 2H), 3.80 (s, 3H), 3.60 (s, 2H), 3.29-3.24 (m, 2H), 2.02 (s, 3H), 1.43-1.37 (m, 2H), 1.22-1.17 (m, 2H), 0.84 (t, J=7.2 Hz, 3H).

Example 4: 3-(3-((2-amino-4-(butylamino)-6-methylpyrimidin-5-yl)methyl)-4-methoxyphenyl)propanoic acid (Compound 4)

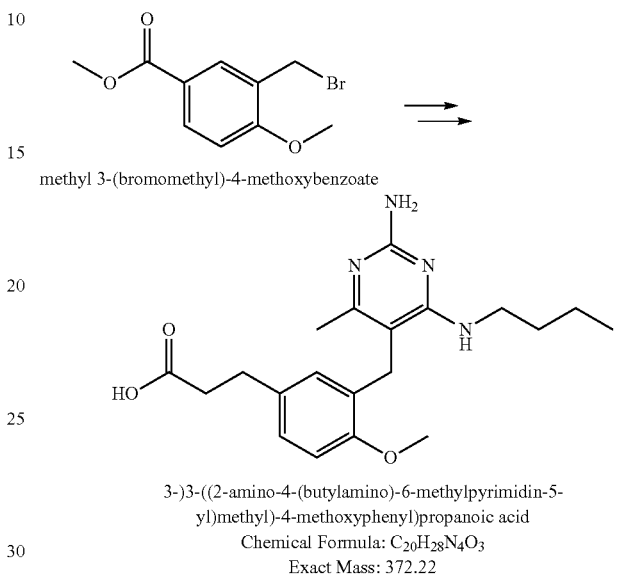

methyl 3-(bromomethyl)-4-methoxybenzoate

3-)3-((2-amino-4-(butylamino)-6-methylpyrimidin-5-yl)methyl)-4-methoxyphenyl)propanoic acid
Chemical Formula: C$_{20}$H$_{28}$N$_4$O$_3$
Exact Mass: 372.22

The title compound was prepared according to the protocols described for Example 1—Steps 1 to 9, but using methyl 3-(bromomethyl)-4-methoxybenzoate instead of methyl 4-(bromomethyl)-3-methoxybenzoate in Step 1.

LC-MS: [M+H]=373.2

$^1$H NMR (400 MHz, DMSO-d$_6$) δ 12.47 (s, 1H), 7.81 (t, J=4.8 Hz, 1H), 7.46 (br s, 2H), 7.06 (d, J=8.4 Hz, 1H), 6.91 (d, J=8.4 Hz, 1H), 6.72 (s, 1H), 3.81 (s, 3H), 3.76 (s, 2H), 3.40-3.36 (m, 2H), 2.68 (t, J=7.2 Hz, 2H), 2.41 (t, J=7.2 Hz, 2H), 2.13 (s, 3H), 1.50-1.44 (m, 2H), 1.24-1.18 (m, 2H), 0.85 (t, J=7.2 Hz, 3H).

Example 5: 2-(5-(3-((2-amino-4-(butylamino)-6-methylpyrimidin-5-yl)methyl)-4-methoxybenzyl)-2H-tetrazol-2-yl)acetic acid (Compound 5)

Example 6: 2-(5-(3-((2-amino-4-(butylamino)-6-methylpyrimidin-5-yl)methyl)-4-methoxybenzyl)-1H-tetrazol-1-yl)acetic acid (Compound 6)

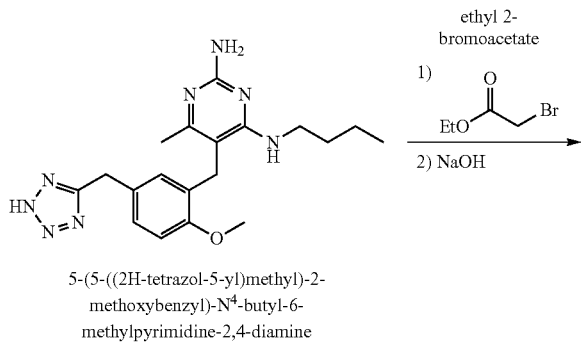

5-(5-((2H-tetrazol-5-yl)methyl)-2-methoxybenzyl)-N$^4$-butyl-6-methylpyrimidine-2,4-diamine

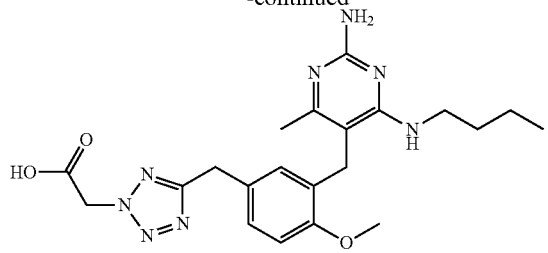

2-(5-(3-((2-amino-4-(butylamino)-6-methylpyrimidin-5-yl)methyl)-4-methoxybenzyl)-2H-tetrazol-2-yl)acetic acid
Chemical Formula: $C_{21}H_{28}N_8O_3$
Exact Mass: 440.23

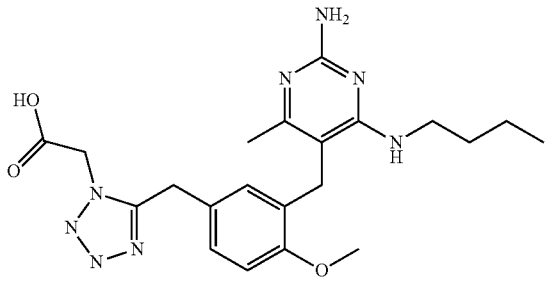 [SMILES: CCCCNc1nc(N)nc(C)c1Cc1cc(Cc2nnnn2CC(=O)O)ccc1OC]

2-(5-(3-((2-amino-4-(butylamino)-6-methylpyrimidin-5-yl)methyl)-4-methoxybenzyl)-1H-tetrazol-1-yl)acetic acid
Chemical Formula: $C_{21}H_{28}N_8O_3$
Exact Mass: 440.23

To a stirred solution of 5-(5-((2H-tetrazol-5-yl)methyl)-2-methoxybenzyl)-$N^4$-butyl-6-methylpyrimidine-2,4-diamine (1.0 eq, Example 3) in acetone (0.05M) was added $K_2CO_3$ (1.5 eq) at 0° C. under $N_2$. The resulting mixture was stirred at 0° C. for 30 min and ethyl 2-bromoacetate (1.5 eq) was added dropwise. The mixture was slowly warmed to rt and stirred for 5 h. The mixture was quenched with sat. $NH_4C_1$. The mixture was partitioned between DCM/water. The organic phase was dried over $Na_2SO_4$, concentrated and purified by prep-HPLC to give two regioisomers in 3:2 ratio as white powders. To a stirred solution of each isomer (1.0 eq) in MeOH (0.02M) was added 1N NaOH (5.0 eq). The resulting mixture was stirred at rt for 16 h. The reaction was monitored by TLC and LC-MS. The mixture was neutralized with 1N HCl and purified to give the title compounds.

Isomer 1: 2-(5-(3-((2-amino-4-(butylamino)-6-methylpyrimidin-5-yl)methyl)-4-methoxybenzyl)-2H-tetrazol-2-yl)acetic acid LC-MS: [M+H]=441.5
$^1$H NMR (400 MHz, DMSO-$d_6$) δ 12.62 (br s, 1H), 7.82 (br s, 1H), 7.50 (br s, 2H), 7.11 (d, J=7.6 Hz, 1H), 6.95 (d, J=8.8 Hz, 1H), 6.79 (s, 1H), 5.31 (s, 2H), 4.16 (s, 2H), 3.82 (s, 3H), 3.66 (s, 2H), 3.39-3.30 (m, 2H), 2.10 (s, 3H), 1.45-1.38 (m, 2H), 1.3-1.2 (m, 2H), 0.85 (t, J=7.2 Hz, 3H).

Isomer 2: 2-(5-(3-((2-amino-4-(butylamino)-6-methylpyrimidin-5-yl)methyl)-4-methoxybenzyl)-1H-tetrazol-1-yl)acetic acid LC-MS: [M+H]=441.5
$^1$H NMR (400 MHz, DMSO-$d_6$) δ 12.69 (s, 1H), 7.85 (br s, 1H), 7.51 (br s, 2H), 7.10 (d, J=8.0 Hz, 1H), 6.95 (d, J=8.4 Hz, 1H), 6.82 (s, 1H), 5.58 (s, 2H), 4.11 (s, 2H), 3.81 (s, 3H), 3.67 (s, 2H), 3.38-3.35 (m, 2H), 2.11 (s, 3H), 1.49-1.42 (m, 2H), 1.24-1.18 (m, 2H), 0.85 (t, J=7.2 Hz, 3H).

Example 7: (3-((2-amino-4-(butylamino)-6-methylpyrimidin-5-yl)methyl)-4-methoxybenzyl)phosphonic acid (Compound 7)

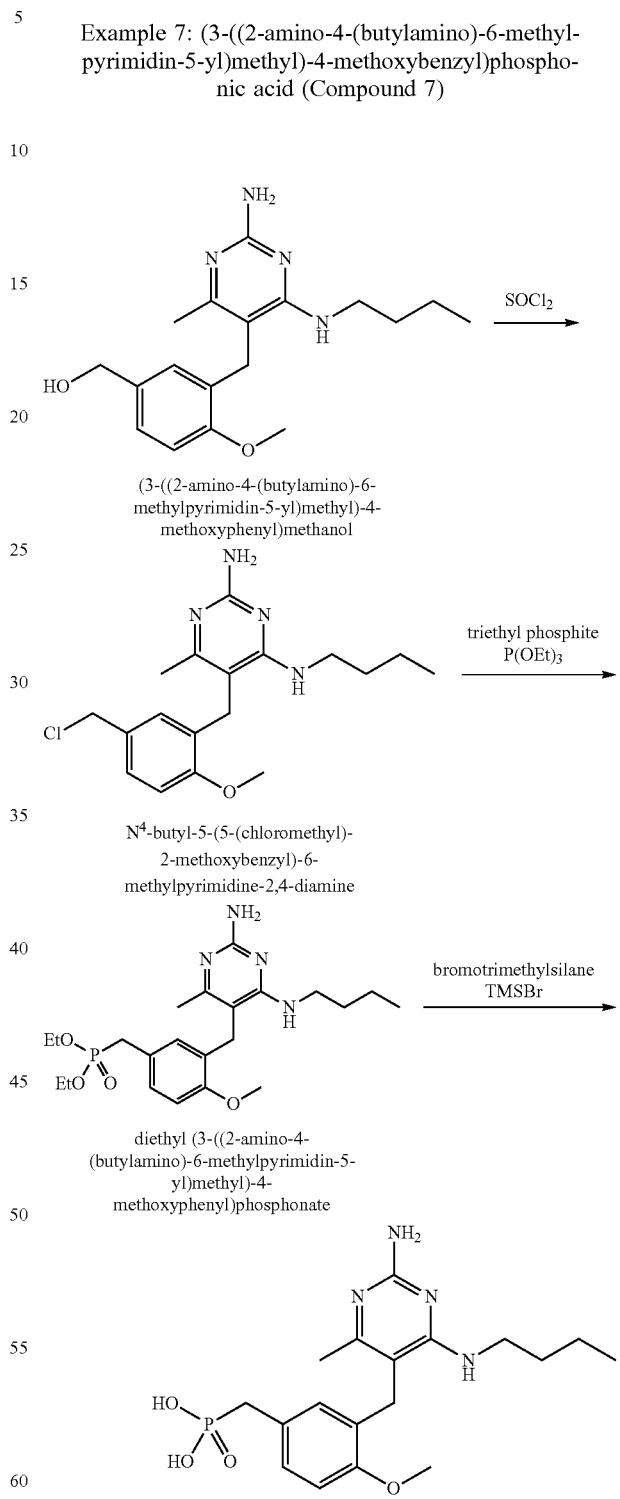

Step 1: N4-butyl-5-(5-(chloromethyl)-2-methoxy-benzyl)-6-methylpyrimidine-2,4-diamine The title compound was prepared according to the protocols described in Example 2—Step 1, but using (3-((2-amino-4-(butylamino)-6-methylpyrimidin-5-yl)methyl)-4-methoxyphenyl)methanol instead of (4-((2-amino-4-(butylamino)-6-methylpyrimidin-5-yl)methyl)-3-methoxyphenyl)methanol.

Step 2: diethyl (3-((2-amino-4-(butylamino)-6-methylpyrimidin-5-yl)methyl)-4-methoxybenzyl) phosphonate $N^4$-butyl-5-(5-(chloromethyl)-2-methoxybenzyl)-6-methylpyrimidine-2,4-diamine (1.0 eq) in neat triethyl phosphite (0.1M) was stirred at 140° C. for 2 h. The mixture was concentrated to give the title compound.

Step 3: (3-((2-amino-4-(butylamino)-6-methylpyrimidin-5-yl)methyl)-4-methoxybenzyl)phosphonic acid To a stirred solution of diethyl (3-((2-amino-4-(butylamino)-6-methylpyrimidin-5-yl)methyl)-4-methoxybenzyl)phosphonate (1.0 eq) in DCM (0.04M) was added bromotrimethylsilane (4.0 eq). The resulting mixture was stirred for 2 h at rt and then partitioned between DCM/water. The organic layer was dried over $Na_2SO_4$, concentrated. The crude product was purified by prep-HPLC (mobile phase $CH_3CN/H_2O/NH_3$) and freeze-dried to give a white powder, which was re-dissolved in $MeCN/H_2O$/1N HCl (4:2:1) and freeze-dried to give the title compound as a white solid (HCl salt).

LC-MS: [M+H]=395.1

$^1$H NMR (400 MHz, DMSO-$d_6$) δ 12.64 (br s, 2H), 7.82 (t, J=5.6 Hz, 1H), 7.48 (br s, 2H), 7.08 (d, J=8.0 Hz, 1H), 6.91 (d, J=8.4 Hz, 1H), 6.74 (s, 1H), 3.81 (s, 3H), 3.66 (s, 2H), 3.37-3.34 (m, 2H), 2.80 (d, J=20.9 Hz, 2H), 2.12 (s, 3H), 1.50-1.45 (m, 2H), 1.27-1.22 (m, 2H), 0.86 (t, J=7.2 Hz, 3H).

Example 8: (S)-2-((5-(5-((2H-tetrazol-5-yl)methyl)-2-methoxybenzyl)-2-amino-6-methylpyrimidin-4-yl)amino)pentan-1-ol (Compound 8)

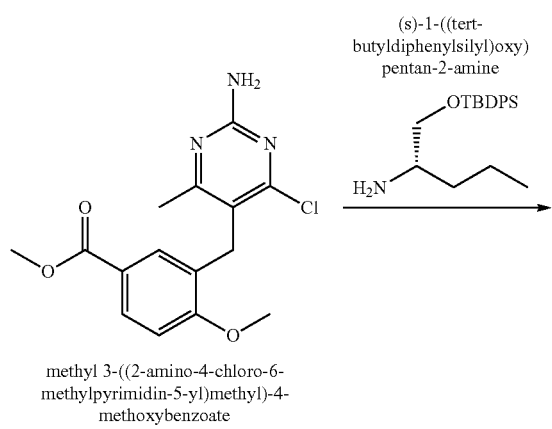

methyl 3-((2-amino-4-chloro-6-methylpyrimidin-5-yl)methyl)-4-methoxybenzoate

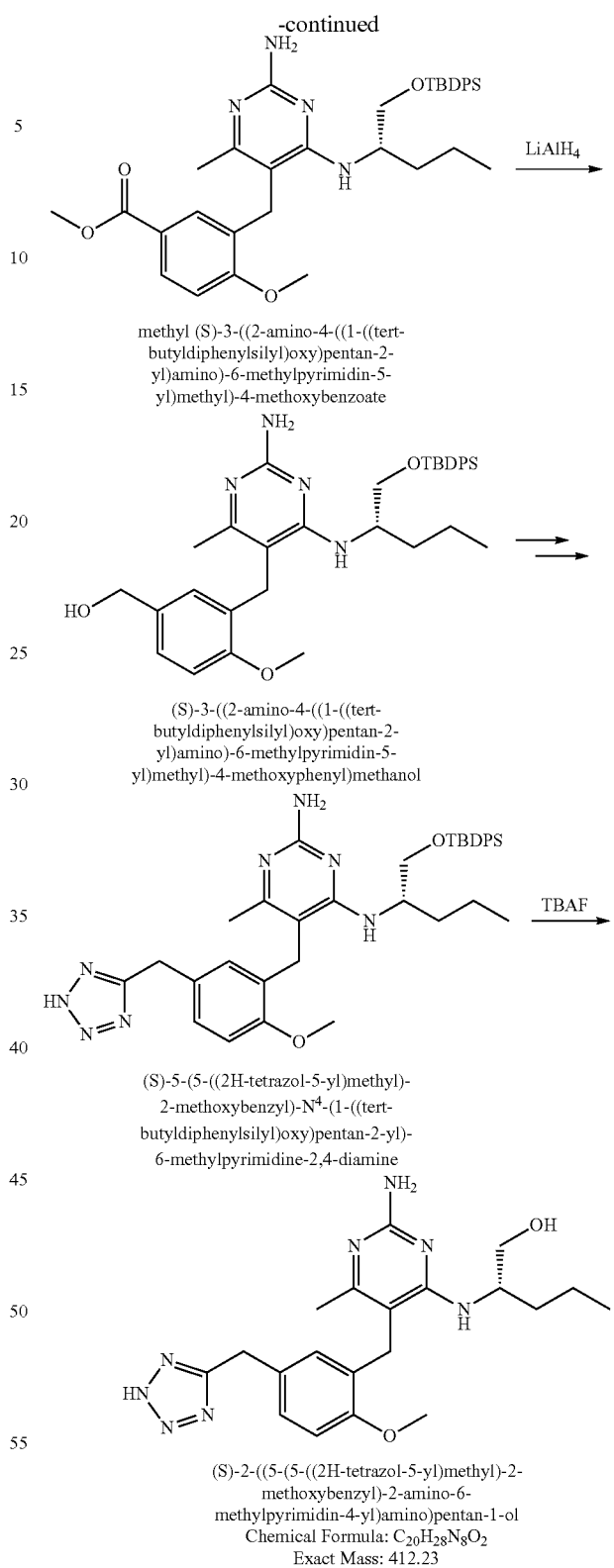

methyl (S)-3-((2-amino-4-((1-((tert-butyldiphenylsilyl)oxy)pentan-2-yl)amino)-6-methylpyrimidin-5-yl)methyl)-4-methoxybenzoate (S)-3-((2-amino-4-((1-((tert-butyldiphenylsilyl)oxy)pentan-2-yl)amino)-6-methylpyrimidin-5-yl)methyl)-4-methoxyphenyl)methanol (S)-5-(5-((2H-tetrazol-5-yl)methyl)-2-methoxybenzyl)-$N^4$-(1-((tert-butyldiphenylsilyl)oxy)pentan-2-yl)-6-methylpyrimidine-2,4-diamine (S)-2-((5-(5-((2H-tetrazol-5-yl)methyl)-2-methoxybenzyl)-2-amino-6-methylpyrimidin-4-yl)amino)pentan-1-ol
Chemical Formula: $C_{20}H_{28}N_8O_2$
Exact Mass: 412.23

Step A: (S)-1-((tert-butyldiphenylsilyl)oxy)pentan-2-amine

A mixture of (S)-2-aminopentan-1-ol (1.0 eq) in DCM (0.2M), TEA (5.0 eq), and DMAP (0.3 eq) at 0° C. was added TBDPSCl (1.5 eq). The resulting mixture was stirred at rt for 3 h. The mixture was diluted with water and DCM, separated, and the aqueous layer was back-extracted with DCM twice. The combined organic layers were dried over Na$_2$SO$_4$, concentrated under reduced pressure. The residue was purified by flash column chromatography (eluent: DCM/MeOH=200:1 to 80:1) to give the title compound as a brown oil.

Preparation of methyl (S)-3-((2-amino-4-((1-((tert-butyldiphenylsilyl)oxy)pentan-2-yl)amino)-6-methylpyrimidin-5-yl)methyl)-4-methoxybenzoate Preparation of methyl (S)-3-((2-amino-4-((1-((tert-butyldiphenylsilyl)oxy)pentan-2-yl)amino)-6-methylpyrimidin-5-yl)methyl)-4-methoxybenzoate followed Example 1—Step 4, but using methyl 3-((2-amino-4-chloro-6-methylpyrimidin-5-yl)methyl)-4-methoxybenzoate instead of methyl 4-((2-amino-4-chloro-6-methylpyrimidin-5-yl)methyl)-3-methoxybenzoate, and (S)-1-((tert-butyldiphenylsilyl)oxy)pentan-2-amine instead of butan-1-amine.

Preparation of (S)-(3-((2-amino-4-((1-((tert-butyldiphenylsilyl)oxy)pentan-2-yl)amino)-6-methylpyrimidin-5-yl)methyl)-4-methoxyphenyl)methanol Preparation of (S)-(3-((2-amino-4-((1-((tert-butyldiphenylsilyl)oxy)pentan-2-yl)amino)-6-methylpyrimidin-5-yl)methyl)-4-methoxyphenyl)methanol followed Example 1—Step 5, but using methyl (S)-3-((2-amino-4-((1-((tert-butyldiphenylsilyl)oxy)pentan-2-yl)amino)-6-methylpyrimidin-5-yl)methyl)-4-methoxybenzoate instead of methyl 4-((2-amino-4-(butylamino)-6-methylpyrimidin-5-yl)methyl)-3-methoxybenzoate.

Preparation of (S)-5-(5-((2H-tetrazol-5-yl)methyl)-2-methoxybenzyl)-N4-(1-((tert-butyldiphenylsilyl)oxy)pentan-2-yl)-6-methylpyrimidine-2,4-diamine Preparation of (S)-5-(5-((2H-tetrazol-5-yl)methyl)-2-methoxybenzyl)-N$^4$-(1-((tert-butyldiphenylsilyl)oxy)pentan-2-yl)-6-methylpyrimidine-2,4-diamine followed Example 2—Steps 1 to 3, but using (S)-(3-((2-amino-4-((1-((tert-butyldiphenylsilyl)oxy)pentan-2-yl)amino)-6-methylpyrimidin-5-yl)methyl)-4-methoxyphenyl)methanol instead of (4-((2-amino-4-(butylamino)-6-methylpyrimidin-5-yl)methyl)-3-methoxyphenyl)methanol.

Preparation of (S)-2-((5-(5-((2H-tetrazol-5-yl)methyl)-2-methoxybenzyl)-2-amino-6-methylpyrimidin-4-yl)amino)pentan-1-ol To a solution of (S)-5-(5-(2H-tetrazol-5-yl)methyl)-2-methoxybenzyl)-N$^4$-(1-((tert-butyldiphenylsilyl)oxy)pentan-2-yl)-6-methylpyrimidine-2,4-diamine (1.0 eq) in anhydrous THF (0.05M) at 0° C. was added TBAF (10 eq). The resulting mixture was stirred at rt for 16 h. LCMS showed the reaction was completed. Then the mixture was concentrated under reduced pressure. The residue was purified by prep-HPLC (mobile phase CH$_3$CN/H$_2$O/HCOOH), freeze-dried to give the title compound as a white solid (formic acid salt)

LC-MS: [M+H]=413.2

$^1$H NMR (400 MHz, DMSO) δ 8.19 (s, 1H), 7.05 (d, J=8.4 Hz, 1H), 6.91 (d, J=8.4 Hz, 1H), 6.85 (s, 1H), 6.68-6.60 (m, 2H), 6.39-6.34 (m, 1H), 4.23-4.20 (m, 1H), 3.99 (s, 2H), 3.81 (s, 3H), 3.69-3.60 (s, 2H), 3.41-3.33 (m, 2H), 2.11 (s, 3H), 1.48-1.45 (m, 1H), 1.35-1.28 (m, 1H), 1.13-1.09 (m, 2H), 0.79 (t, J=7.2 Hz, 3H).

Example 9: 2-(3-((2-amino-4-(butylamino)-6-methylpyrimidin-5-yl)methyl)-4-methoxyphenyl)-2-methylpropanoic acid (Compound 9)

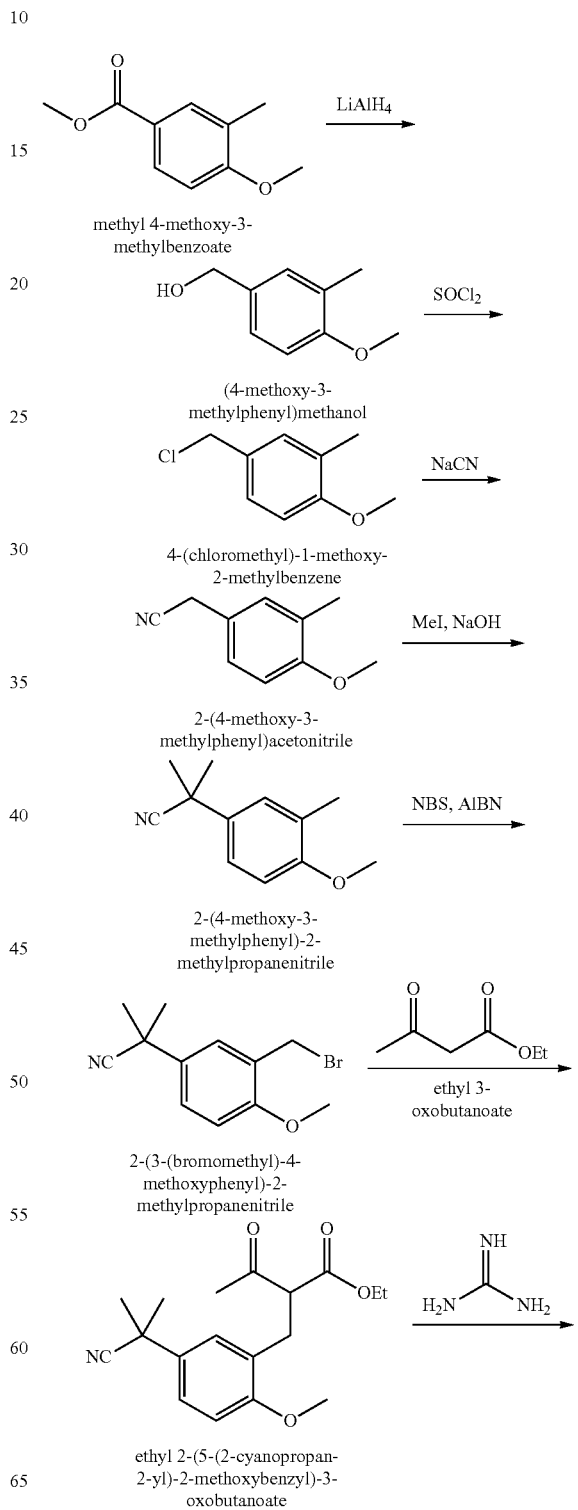

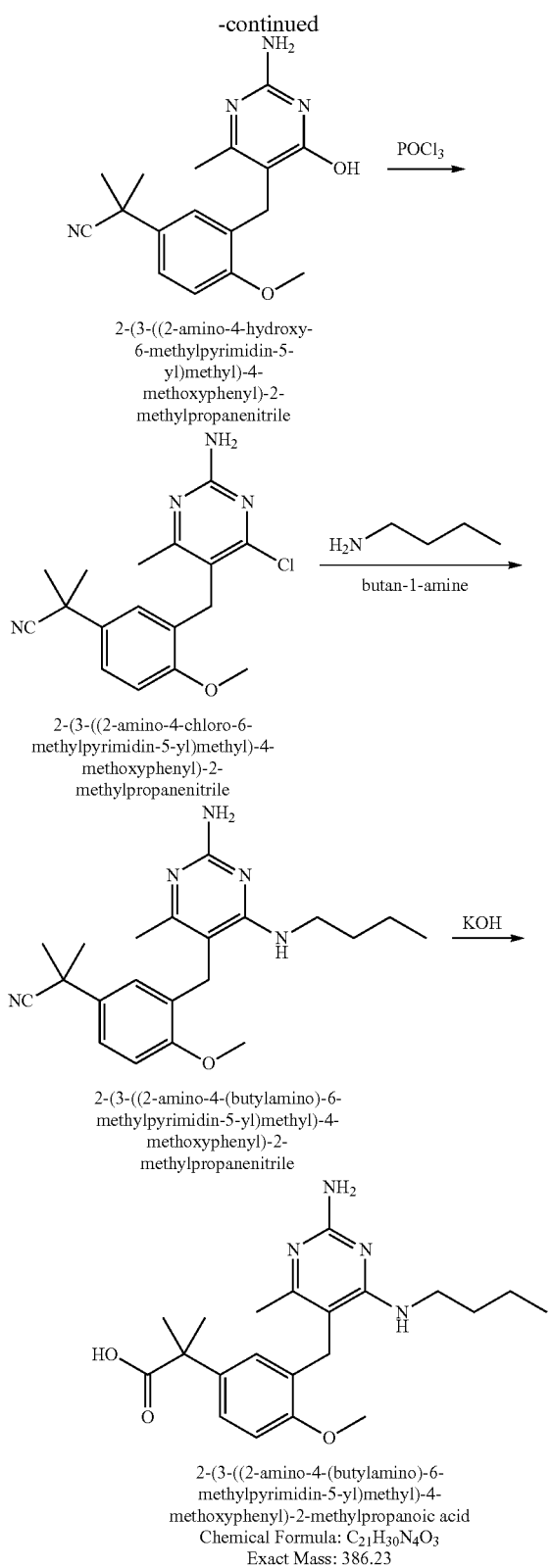

LiAlH$_4$ (2.5 M, 2.5 eq) under N$_2$. The resulting mixture was stirred at r.t. for 2 h, then the mixture was quenched with 1.25 M NaOH solution at 0° C. and extracted with EtOAc for three times. The organic layer was dried over Na$_2$SO$_4$, concentrated under reduced pressure to give the title compound, which was used directly to next step without further purification.

Step 2: 4-(chloromethyl)-1-methoxy-2-methylbenzene

To a solution of (4-methoxy-3-methylphenyl)methanol (1.0 eq) in DCM (0.3M) at 0° C. was added SOCl$_2$ (2.0 eq). The resulting mixture was stirred at r.t. for 2 h. Then the mixture was quenched with NaHCO$_3$ solution and extracted with DCM. The organic layer was dried over Na$_2$SO$_4$, concentrated under reduced pressure to give the title compound as a yellow oil.

Step 3: 2-(4-methoxy-3-methylphenyl)acetonitrile

To a solution of 4-(chloromethyl)-1-methoxy-2-methylbenzene (1.0 eq) in 1:1 DMSO/DMF (0.5M) was added NaCN (3.0 eq). The resulting mixture was stirred at r.t. for 16 h, then water was added and the mixture was extracted with EtOAc. The organic layer was washed with brine twice, dried over Na$_2$SO$_4$, concentrated under reduced pressure. The residue was purified by flash column chromatography (eluent: PE/EA=100:1 to 30:1) to give the title compound as a yellowish oil.

Step 4: 2-(4-methoxy-3-methylphenyl)-2-methylpropanenitrile

A mixture of 2-(4-methoxy-3-methylphenyl)acetonitrile (1.0 eq) in DMSO (0.4M) at 0° C. was added iodomethane (10 eq) and 50% NaOH solution (6.0 eq). The resulting mixture was stirred at r.t. for 3 h. Then the mixture was diluted with water and EtOAc, the aqueous layer was back-extracted with EtOAc twice. The organic layer was combined, dried over Na$_2$SO$_4$, concentrated under reduced pressure. The residue was purified by flash column chromatography (eluent: PE/EA=100:1 to 30:1) to give the title compound as a slightly yellow oil.

Step 5: 2-(3-(bromomethyl)-4-methoxyphenyl)-2-methylpropanenitrile

To a solution of 2-(4-methoxy-3-methylphenyl)-2-methylpropanenitrile (1.0 eq) in CCl$_4$ (0.2M) were added NBS (1.1 eq) and AIBN (0.2 eq). The resulting mixture was stirred at 95° C. for 16 h. Then the mixture was filtered and the filtration was concentrated under reduced pressure to give the crude product, which was purified by column chromatography on silica (eluent: PE/EA=100:1 to 30:1) to give the title compound as a yellow oil.

Step 6: ethyl 2-(5-(2-cyanopropan-2-yl)-2-methoxybenzyl)-3-oxobutanoate

To a solution of ethyl 3-oxobutanoate (1.2 eq) in anhydrous THF (0.17M) at 0° C. was added portion-wise NaH (60% in mineral oil, 1.3 eq). After stirring for 10 min, a solution of 2-(3-(bromomethyl)-4-methoxyphenyl)-2-methylpropanenitrile (1.0 eq) in THF (0.3M) was added dropwise into the above mixture over 10 min. The resulting mixture was stirred at 70° C. for 16 h, quenched with water and the mixture was extracted with EtOAc, dried over Na₂SO₄, concentrated under reduced pressure. The residue was purified by column chromatography on silica (eluent: PE/EA=50:1 to 10:1) to give the title compound as a yellow oil.

Step 7: 2-(3-((2-amino-4-hydroxy-6-methylpyrimidin-5-yl)methyl)-4-methoxyphenyl)-2-methylpropanenitrile A mixture of ethyl 2-(5-(2-cyanopropan-2-yl)-2-methoxybenzyl)-3-oxobutanoate (1.0 eq) and guanidine carbonate (1.0 eq) in MeOH (0.3M) was stirred at 65° C. for 16 h. The precipitated solid was collected by filtration. The solid was washed with water and dried in vacuum to give the title compound as a white solid.

Step 8: 2-(3-((2-amino-4-chloro-6-methylpyrimidin-5-yl)methyl)-4-methoxyphenyl)-2-methylpropanenitrile To a solution of 2-(3-((2-amino-4-hydroxy-6-methylpyrimidin-5-yl)methyl)-4-methoxyphenyl)-2-methylpropanenitrile (1.0 eq) in POCl₃ (0.3M) was stirred at 100° C. for 2 h. The reaction mixture was allowed to cool to r.t. and POCl₃ was evaporated to dryness under reduced pressure. The residue was diluted with water and adjusted pH to 8 with solid NaHCO₃. Then the mixture was stirred at 50° C. for 1 h, cooled to r.t. and the precipitated solid was collected by filtration. The filter cake was washed with water, dried in vacuum to give the title compound as a white solid.

Step 9: 2-(3-((2-amino-4-(butylamino)-6-methylpyrimidin-5-yl)methyl)-4-methoxyphenyl)-2-methylpropanenitrile A mixture of 2-(3 no-4-chloro-6-methylpyrimidin-5-yl)methyl)-4-methoxyphenyl)-2-methylpropanenitrile (1.0 eq) in NMP (0.2M) was added butan-1-amine (4.5 eq) and stirred at 110° C. for 16 h. Then water and EtOAc were added into the above mixture, the organic layer was dried over Na₂SO₄, concentrated under reduced pressure. The residue was purified by flash column chromatography (eluent: DCM/MeOH=100:1 to 10:1) to give the title compound as a white solid.

Step 10: 2-(3-((2-amino-4-(butylamino)-6-methylpyrimidin-5-yl)methyl)-4-methoxyphenyl)-2-methylpropanoic acid A mixture of 2-(3-((2-amino-4-(butylamino)-6-methylpyrimidin-5-yl)methyl)-4-methoxyphenyl)-2-methylpropanenitrile (1.0 eq) in 1:1 ethane-1,2-diol/H₂O (0.075M) was added KOH (10 eq) and stirred at 150° C. for 2 h. Then the mixture was allowed to cool to r.t. and adjusted pH to 8 with 1 M HCl solution. The precipitated solid was filtered and washed with water for three times. The filter cake was dissolved in MeCN, H₂O and 4M HCl in dioxane solution, then the solution was freeze-dried to give the title compound as a white solid (HCl salt).

LC-MS: [M+H]=387.2

¹H NMR (400 MHz, DMSO) δ 12.34 (s, 1H), 7.92 (s, 1H), 7.45 (br s, 2H), 7.20 (d, J=8.4 Hz, 1H), 6.96 (d, J=8.4 Hz, 1H), 6.85 (s, 1H), 3.82 (s, 3H), 3.70 (s, 2H), 3.5-3.4 (m, 2H), 2.13 (s, 3H), 1.51-1.45 (m, 2H), 1.36 (s, 6H), 1.27-1.18 (m, 2H), 0.86 (t, J=7.2 Hz, 3H).

Example 10: 5-(5-(2-(2H-tetrazol-5-yl)propan-2-yl)-2-methoxybenzyl)-N4-butyl-6-methylpyrimidine-2,4-diamine (Compound 10)

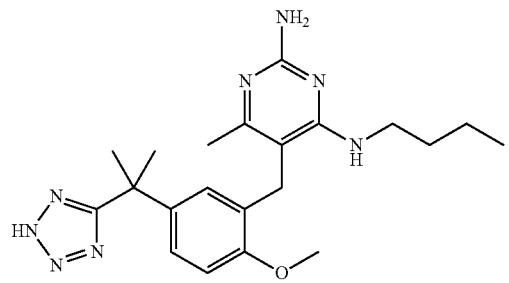

5-(5-(2-(2H-tetrazol-5-yl)propan-2-yl)-2-methoxybenzyl)-
N⁴-butyl-6-methylpyrimidine-2,4-diamine
Chemical Formula: C₂₁H₃₀N₈O
Exact Mass: 410.25

A mixture of 2-(3-((2-amino-4-(butylamino)-6-methylpyrimidin-5-yl)methyl)-4-methoxyphenyl)-2-methylpropanenitrile (1.0 eq, Example 9—Step 9) in dioxane (0.06M), TMSN₃ (10 eq) and Bu₂SnO (2.0 eq) was sealed into a tube reactor. The mixture was stirred at 125° C. for 16 h. LCMS showed the reaction was completed. Then the mixture was concentrated under reduced pressure. The residue was purified by prep-HPLC (mobile phase CH₃CN/H₂O/HCOOH), freeze-dried to give the title compound as a white solid (formic acid salt)

LC-MS: [M+H]⁺=411.2

¹H NMR (400 MHz, DMSO) δ 6.97 (d, J=6.4 Hz, 1H), 6.88 (d, J=8.4 Hz, 1H), 6.72 (s, 1H), 6.44 (br s, 1H), 6.16 (br s, 2H), 3.79 (s, 3H), 3.58 (s, 2H), 3.27-3.25 (m, 2H), 1.98 (s, 3H), 1.61 (s, 6H), 1.44-1.40 (m, 2H), 1.24-1.18 (m, 2H), 0.85 (t, J=7.2 Hz, 3H).

Example 11: N4-butyl-5-(2-methoxy-5-(2H-tetrazol-5-yl)benzyl)-6-methylpyrimidine-2,4-diamine (Compound 11)

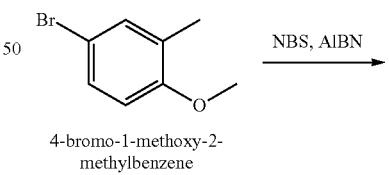

4-bromo-1-methoxy-2-methylbenzene

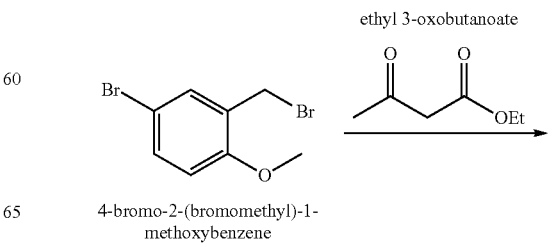

4-bromo-2-(bromomethyl)-1-methoxybenzene

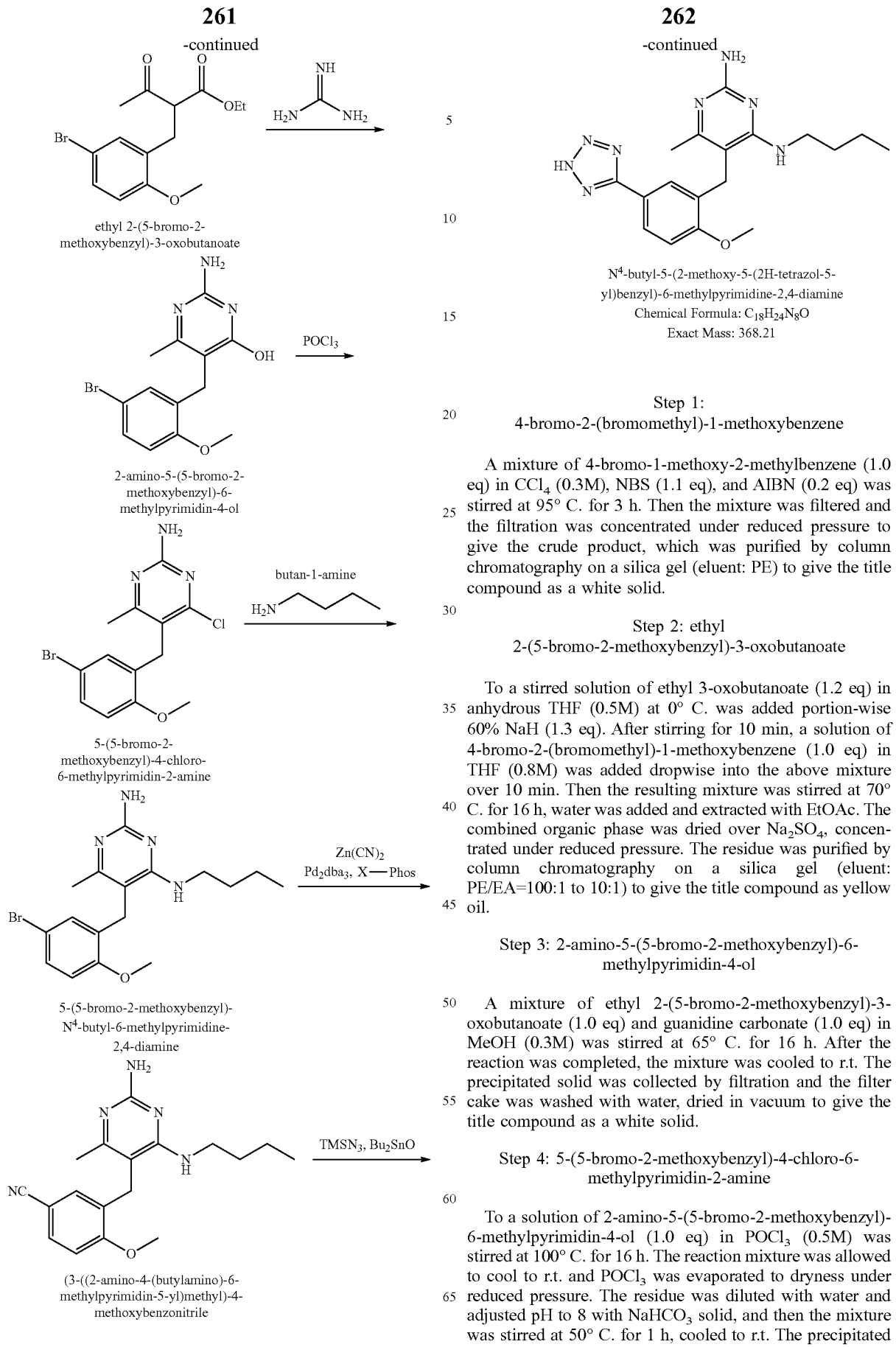

Step 1: 4-bromo-2-(bromomethyl)-1-methoxybenzene

A mixture of 4-bromo-1-methoxy-2-methylbenzene (1.0 eq) in $CCl_4$ (0.3M), NBS (1.1 eq), and AIBN (0.2 eq) was stirred at 95° C. for 3 h. Then the mixture was filtered and the filtration was concentrated under reduced pressure to give the crude product, which was purified by column chromatography on a silica gel (eluent: PE) to give the title compound as a white solid.

Step 2: ethyl 2-(5-bromo-2-methoxybenzyl)-3-oxobutanoate

To a stirred solution of ethyl 3-oxobutanoate (1.2 eq) in anhydrous THF (0.5M) at 0° C. was added portion-wise 60% NaH (1.3 eq). After stirring for 10 min, a solution of 4-bromo-2-(bromomethyl)-1-methoxybenzene (1.0 eq) in THF (0.8M) was added dropwise into the above mixture over 10 min. Then the resulting mixture was stirred at 70° C. for 16 h, water was added and extracted with EtOAc. The combined organic phase was dried over $Na_2SO_4$, concentrated under reduced pressure. The residue was purified by column chromatography on a silica gel (eluent: PE/EA=100:1 to 10:1) to give the title compound as yellow oil.

Step 3: 2-amino-5-(5-bromo-2-methoxybenzyl)-6-methylpyrimidin-4-ol

A mixture of ethyl 2-(5-bromo-2-methoxybenzyl)-3-oxobutanoate (1.0 eq) and guanidine carbonate (1.0 eq) in MeOH (0.3M) was stirred at 65° C. for 16 h. After the reaction was completed, the mixture was cooled to r.t. The precipitated solid was collected by filtration and the filter cake was washed with water, dried in vacuum to give the title compound as a white solid.

Step 4: 5-(5-bromo-2-methoxybenzyl)-4-chloro-6-methylpyrimidin-2-amine

To a solution of 2-amino-5-(5-bromo-2-methoxybenzyl)-6-methylpyrimidin-4-ol (1.0 eq) in $POCl_3$ (0.5M) was stirred at 100° C. for 16 h. The reaction mixture was allowed to cool to r.t. and $POCl_3$ was evaporated to dryness under reduced pressure. The residue was diluted with water and adjusted pH to 8 with $NaHCO_3$ solid, and then the mixture was stirred at 50° C. for 1 h, cooled to r.t. The precipitated solid was collected by filtration. The filter cake was washed with water and MeOH, dried in vacuum to give the title compound as a white solid.

Step 5: 5-(5-bromo-2-methoxybenzyl)-N4-butyl-6-methylpyrimidine-2,4-diamine

A mixture of 5-(5-bromo-2-methoxybenzyl)-4-chloro-6-methylpyrimidin-2-amine (1.0 eq) in NMP (0.4M) and butan-1-amine (4.5 eq) was stirred at 130° C. for 16 h. The mixture was diluted with water and EtOAc, the organic layer was washed with brine and dried over $Na_2SO_4$, concentrated under reduced pressure. The residue was purified by flash column chromatography (eluent: DCM/MeOH=500:1 to 50:1) to give the title compound as a white solid.

Step 6: 3-((2-amino-4-(butylamino)-6-methylpyrimidin-5-yl)methyl)-4-methoxybenzonitrile A mixture of 5-(5-bromo-2-methoxybenzyl)-$N^4$-butyl-6-methylpyrimidine-2,4-diamine (1.0 eq) in DMF (0.1M), $Zn(CN)_2$ (1.5 eq), $Pd_2(dba)_3$ (0.08 eq), and X-Phos (0.2 eq) was stirred at 110° C. for 1 h under Argon atmosphere. The resulting mixture was allowed to cool to r.t. and diluted with water and EtOAc. The organic layer was separated, dried over $Na_2SO_4$, concentrated under reduced pressure. The residue was purified by flash column chromatography (eluent: DCM/MeOH=100:1 to 10:1) to give the title compound as a white solid.

Step 7: N4-butyl-5-(2-methoxy-5-(2H-tetrazol-5-yl)benzyl)-6-methylpyrimidine-2,4-diamine A mixture of 3-((2-amino-4-(butylamino)-6-methylpyrimidin-5-yl)methyl)-4-methoxybenzonitrile (1.0 eq) in dioxane (0.07M), $TMSN_3$ (10 eq) and $Bu_2SnO$ (2.0 eq) was stirred at 120° C. for 4 h. LCMS showed the reaction was completed. Then the mixture was concentrated under reduced pressure. The residue was purified by prep-HPLC (mobile phase $CH_3CN/H_2O$/HCOOH), freeze-dried to give the title compound as a white solid (formic acid salt).

LC-MS: [M+H]=369.1

$^1$H NMR (400 MHz, DMSO) δ 7.84 (d, J=8.4 Hz, 1H), 7.56 (br s, 1H), 7.44 (s, 1H), 7.09 (d, J=8.4 Hz, 1H), 7.05 (br s, 2H), 3.90 (s, 3H), 3.73 (s, 2H), 3.4-3.3 (m, 2H), 2.13 (s, 3H), 1.49-1.41 (m, 2H), 1.19-1.12 (m, 2H), 0.76 (t, J=7.6 Hz, 3H).

Example 12: (3-((2-amino-4-(butylamino)-6-methylpyrimidin-5-yl)methyl)-4-methoxyphenyl)phosphonic acid (Compound 12)

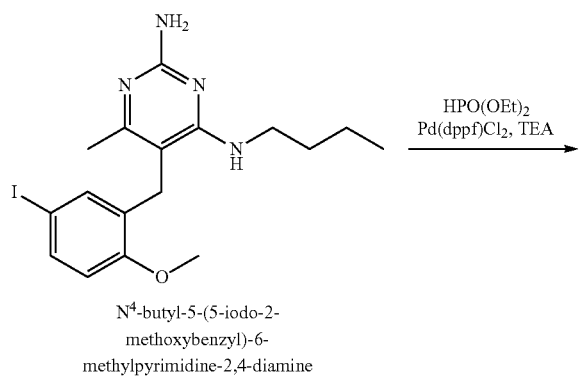

$N^4$-butyl-5-(5-iodo-2-methoxybenzyl)-6-methylpyrimidine-2,4-diamine

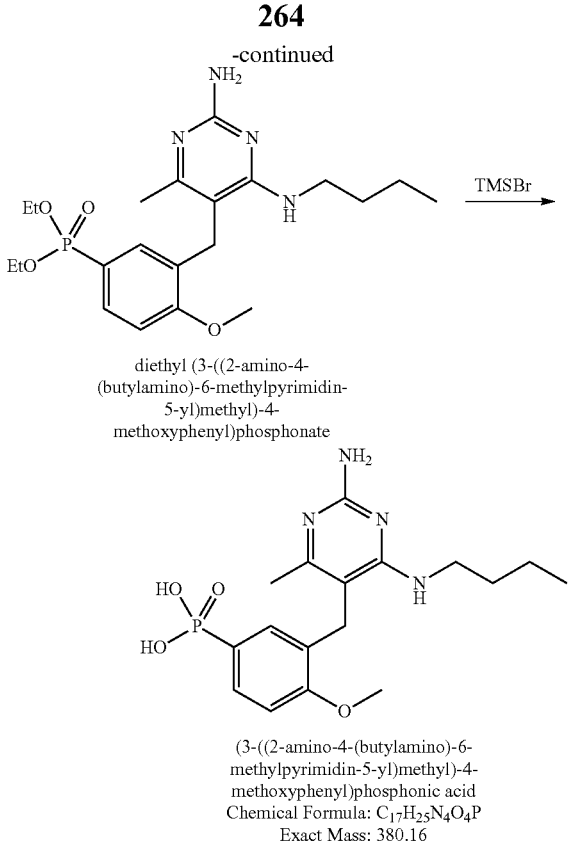

diethyl (3-((2-amino-4-(butylamino)-6-methylpyrimidin-5-yl)methyl)-4-methoxyphenyl)phosphonate (3-((2-amino-4-(butylamino)-6-methylpyrimidin-5-yl)methyl)-4-methoxyphenyl)phosphonic acid
Chemical Formula: $C_{17}H_{25}N_4O_4P$
Exact Mass: 380.16

Preparation of N4-butyl-5-(5-iodo-2-methoxybenzyl)-6-methylpyrimidine-2,4-diamine Preparation of $N^4$-butyl-5-(5-iodo-2-methoxybenzyl)-6-methylpyrimidine-2,4-diamine followed the protocols described for Example 11—Step 1 to 5, but using 4-iodo-1-methoxy-2-methylbenzene instead of 4-bromo-1-methoxy-2-methylbenzene in Step 1.

Step 1: diethyl (3-((2-amino-4-(butylamino)-6-methylpyrimidin-5-yl)methyl)-4-methoxyphenyl)phosphonate To a solution of $N^4$-butyl-5-(5-iodo-2-methoxybenzyl)-6-methylpyrimidine-2,4-diamine (1.0 eq) in toluene (0.06M), diethylphosphite (3.5 eq) and triethylamine (6.0 eq) was added $Pd(dppf)Cl_2$ (0.05 eq). The mixture was stirred at 110° C. for 16 h. The reaction mixture was allowed to cool to r.t. and was evaporated to dryness under reduced pressure to afford the crude product which was purified by flash column chromatography (eluent: DCM/MeOH=50:1 to 10:1) to give the title compound.

Step 2: (3-((2-amino-4-(butylamino)-6-methylpyrimidin-5-yl)methyl)-4-methoxyphenyl)-phosphonic acid To a solution of diethyl (3-((2-amino-4-(butylamino)-6-methylpyrimidin-5-yl)methyl)-4-methoxyphenyl)phosphonate (1.0 eq) in DCM (0.08M) was added dropwise TMSBr (20 eq). The mixture was stirred at rt for 2 h. The reaction mixture was diluted with water and DCM, the organic layer was washed with brine and dried over $Na_2SO_4$, concentrated under reduced pressure. The residue was purified by prep- HPLC (mobile phase CH$_3$CN/H$_2$O/HCOOH), freeze-dried to give the title compound as a white solid (formic acid salt).

LC-MS: [M+H]=381.3

$^1$H NMR (400 MHz, DMSO-d$_6$) δ 12.00 (s, 1H), 7.99 (t, J=4.8 Hz, 1H), 7.59-7.53 (m, 1H), 7.47 (br s, 2H), 7.10-7.06 (m, 2H), 3.89 (s, 3H), 3.72 (s, 2H), 3.40-3.35 (m, 2H), 2.10 (s, 3H), 1.53-1.45 (m, 2H), 1.25-1.19 (m, 2H), 0.87 (t, J=7.2 Hz, 3H).

Example 13: 5-(5-(1-(2H-tetrazol-5-yl)cyclopropyl)-2-methoxybenzyl)-N4-butyl-6-methylpyrimidine-2,4-diamine (Compound 13)

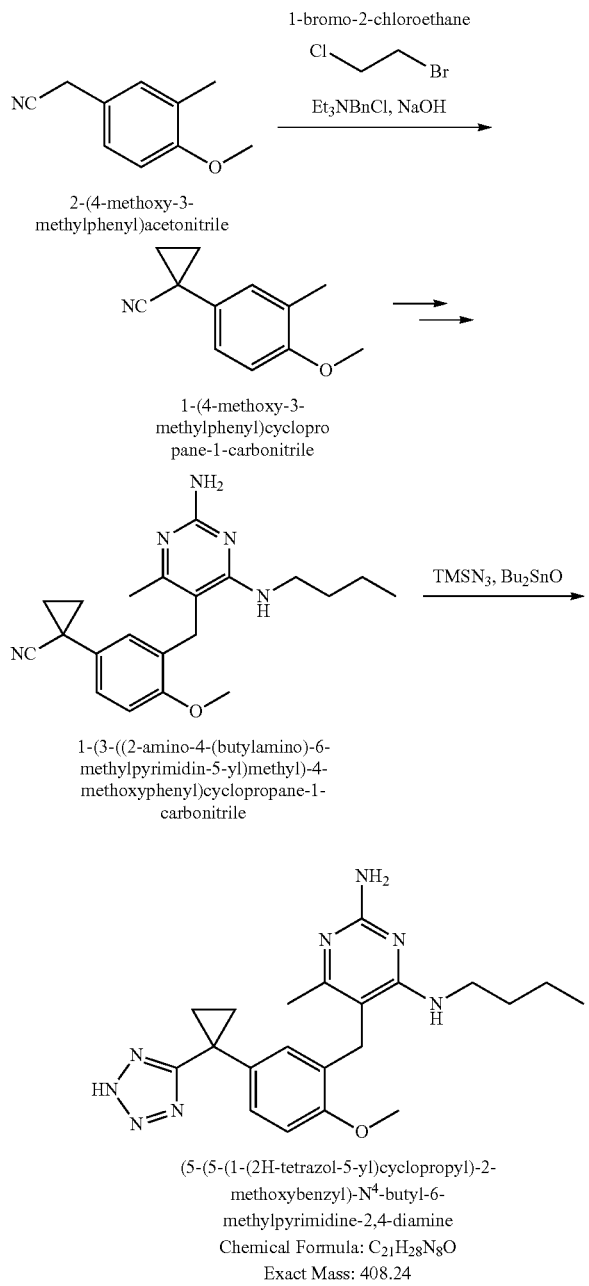

Step 1: 1-(4-methoxy-3-methylphenyl)cyclopropane-1-carbonitrile

To a flask containing 2-(4-methoxy-3-methylphenyl)acetonitrile (1.0 eq, Example 9—Step 3), 1-bromo-2-chloroethane (1.5 eq), Et3NBnCl (0.02 eq) was added 0.77 g/mL NaOH solution (6.0 eq). The resulting mixture was stirred overnight at 50° C. The mixture was partitioned between EA/water. The organic layer was dried over Na$_2$SO$_4$, concentrated and purified by flash chromatography on silica (eluent PE/EA=100:1~20:1) to give the title compound.

Preparation of 1-(3-((2-amino-4-(butylamino)-6-methylpyrimidin-5-yl)methyl)-4-methoxyphenyl)cyclopropane-1-carbonitrile Preparation of 1-(3-((2-amino-4-(butylamino)-6-methylpyrimidin-5-yl)methyl)-4-methoxyphenyl)cyclopropane-1-carbonitrile following protocols described in Example 9: Step 5 to 9, but using 1-(4-methoxy-3-methylphenyl)cyclopropane-1-carbonitrile instead of 2-(4-methoxy-3-methylphenyl)-2-methylpropanenitrile in Step 5.

Preparation of 5-(5-(1-(2H-tetrazol-5-yl)cyclopropyl)-2-methoxybenzyl)-N4-butyl-6-methylpyrimidine-2,4-diamine A mixture of 1-(3-((2-amino-4-(butylamino)-6-methylpyrimidin-5-yl)methyl)-4-methoxyphenyl)cyclopropane-1-carbonitrile (1.0 eq) in dioxane (0.1M), TMSN$_3$ (10.0 eq), Bu$_2$SnO (2.0 eq) was stirred overnight at 120° C. The reaction was monitored by LC-MS. The mixture was concentrated and purified by prep-HPLC (mobile phase CH$_3$CN/H$_2$O/HCOOH), freeze-dried to give the title compound as a white powder (formic acid salt).

LC-MS: [M+H]=409.2

$^1$H NMR (400 MHz, DMSO-d$_6$) δ 8.19 (s, 1H), 7.16 (d, J=8.8 Hz, 1H), 6.92 (d, J=8.4 Hz, 1H), 6.77 (s, 1H), 6.69 (br s, 1H), 6.42 (br s, 2H), 3.82 (s, 3H), 3.61 (s, 2H), 3.30-3.25 (m, 2H), 2.03 (s, 3H), 1.43-1.35 (m, 4H), 1.21-1.11 (m, 4H), 0.83 (t, J=7.2 Hz, 3H).

Example 14: 1-(3-((2-amino-4-(butylamino)-6-methylpyrimidin-5-yl)methyl)-4-methoxyphenyl)cyclopropane-1-carboxylic acid (Compound 14)

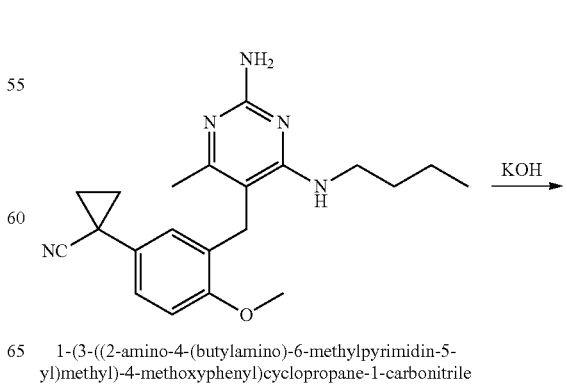

1-(3-((2-amino-4-(butylamino)-6-methylpyrimidin-5-yl)methyl)-4-methoxyphenyl)cyclopropane-1-carbonitrile

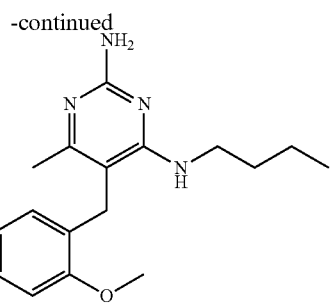

1-(3-((2-amino-4-(butylamino)-6-methylpyrimidin-5-yl)methyl)-4-methoxyphenyl)cyclopropane-1-carboxylic acid
Chemical Formula: C$_{21}$H$_{28}$N$_4$O$_3$
Exact Mass: 384.22

A mixture of 1-(3-((2-amino-4-(butylamino)-6-methylpyrimidin-5-yl)methyl)-4-methoxyphenyl)cyclopropane-1-carbonitrile (1.0 eq) in 1:1 ethylene glycol/H$_2$O (0.1M) and KOH (10 eq) was stirred for 3 h at 150° C. The reaction was monitored by LC-MS until completion. The mixture was neutralized with 1 N HCl to pH=7. The resulting suspension was filtered. The filter cake was washed with water. To the solid was added MeCN, H$_2$O and 4N HCl/dioxane. The solution was freeze-dried to give the title compound as a white solid (HCl salt).

LC-MS: [M+H]=385.2

$^1$H NMR (400 MHz, DMSO-d$_6$) δ 12.21 (s, 1H), 12.16 (s, 1H), 7.90 (t, J=5.2 Hz, 1H), 7.41 (br s, 2H), 7.16 (d, J=6.0 Hz, 1H), 6.92 (d, J=8.4 Hz, 1H), 6.81 (s, 1H), 3.81 (s, 3H), 3.68 (s, 2H), 3.4-3.3 (m, 2H), 2.12 (s, 3H), 1.51-1.43 (m, 2H), 1.38 (s, 2H), 1.26-1.17 (m, 2H), 0.99 (s, 2H), 0.86 (t, J=7.2 Hz, 3H).

Example 15: 3-(2-amino-6-(butylamino)-5-(2-methoxybenzyl)pyrimidin-4-yl)propanoic acid (Compound 15)

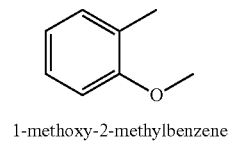

1-methoxy-2-methylbenzene

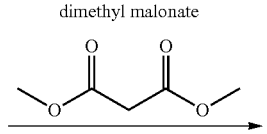

1-(bromomethyl)-2-methoxybenzene

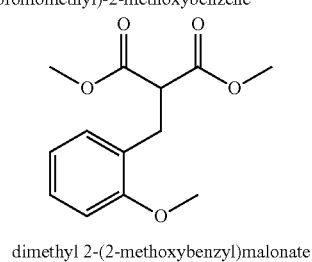

dimethyl 2-(2-methoxybenzyl)malonate

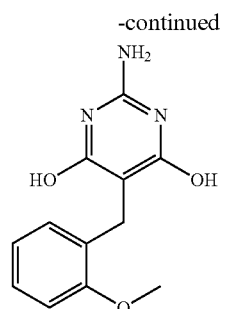

2-amino-5-(2-methoxybenzyl)pyrimidine-4,6-diol

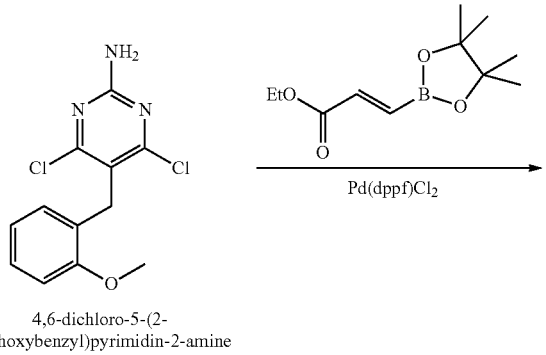

4,6-dichloro-5-(2-methoxybenzyl)pyrimidin-2-amine

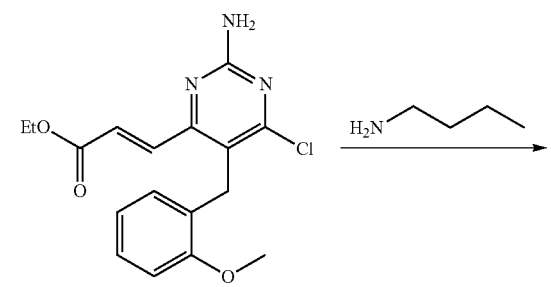

ethyl (E)-3-(2-amino-6-chloro-5-(2-methoxybenzyl)pyrimidin-4-yl)acrylate

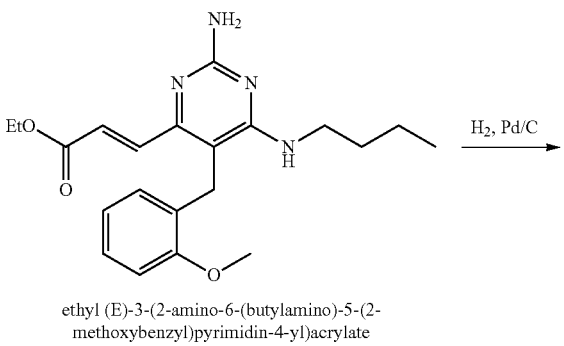

ethyl (E)-3-(2-amino-6-(butylamino)-5-(2-methoxybenzyl)pyrimidin-4-yl)acrylate

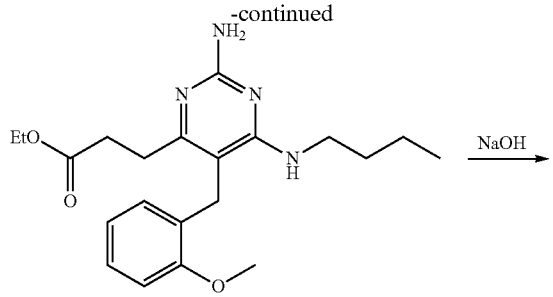

ethyl 3-(2-amino-6-(butylamino)-5-(2-methoxybenzyl)pyrimidin-4-yl)propanoate

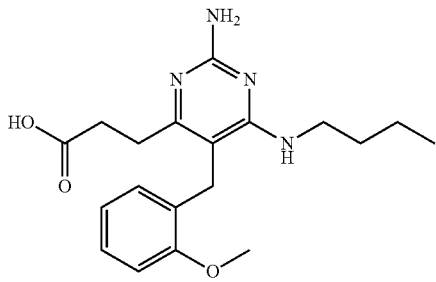 [SMILES: CCCCNc1nc(N)nc(CCC(=O)O)c1Cc1ccccc1OC]

3-(2-amino-6-(butylamino)-5-(2-methoxybenzyl)pyrimidin-4-yl)propanoic acid
Chemical Formula: $C_{19}H_{26}N_4O_3$
Exact Mass: 358.20

Step 1: 1-(bromomethyl)-2-methoxybenzene

To a solution of 1-methoxy-2-methylbenzene (1 eq) in $CCl_4$ (0.9M) was added AIBN (0.2 eq) and NBS (1.1 eq). The reaction was heated at reflux for 2 h. After the reaction was completed, the reaction was concentrated and diluted with water. The aqueous phase was extracted with DCM. Combined organic layers were washed with water then brine, dried over $Na_2SO_4$, and concentrated to give the title compound as a light yellow oil.

Step 2: dimethyl 2-(2-methoxybenzyl)malonate

To a solution of dimethyl malonate (1.2 eq) in THF (0.4M) was added NaH (1.25 eq) at 0° C. in portions under nitrogen. The solution was stirred at 0° C. for 15 min, and 1-(bromomethyl)-2-methoxybenzene (1.0 eq) was added. The reaction was stirred for 2 h at room temperature. After the reaction was completed, the reaction was quenched by addition of water. The aqueous phase was extracted with EA. Combined organic layers were washed with water, then brine, dried over $Na_2SO_4$, and concentrated. The crude product was purified by column chromatography (PE/EA=40:1) to give the title compound as light yellow oil.

Step 3: 2-amino-5-(2-methoxybenzyl)pyrimidine-4,6-diol

To a solution of dimethyl 2-(2-methoxybenzyl)malonate (1.0 eq) in MeOH (0.4M) was added guanidine carbonate (1.0 eq). The reaction was heated at 75° C. for 16 h under nitrogen. After cooling, the solid particles were filtered and collected from the solution to give the title compound as a white solid.

Step 4: 4,6-dichloro-5-(2-methoxybenzyl)pyrimidin-2-amine

To a suspension of 2-amino-5-(2-methoxybenzyl)pyrimidine-4,6-diol (1.0 eq) in $POCl_3$ (0.4M) was added 2 drops of DMF. The reaction was heated at 100° C. for 15 h under nitrogen. After cooling, the solution was poured into ice-water. The solid particles were filtered and collected from the solution to give the title compound as a white solid.

Step 5: ethyl (E)-3-(2-amino-6-chloro-5-(2-methoxybenzyl)pyrimidin-4-yl)acrylate To a solution of 4,6-dichloro-5-(2-methoxybenzyl)pyrimidin-2-amine (1.0 eq) in 3:1 dioxane/$H_2O$ (0.14M) was added ethyl (E)-3-(4,4,5,5-tetramethyl-1,3,2-dioxaborolan-2-yl)acrylate (1.2 eq), $K_2CO_3$ (2.0 eq), and Pd(dppf)$Cl_2$ (0.1 eq). The mixture was stirred at 100° C. for 3 h under nitrogen. The reaction was diluted with water, and the aqueous phase was extracted with EA. Combined organic layers were washed with water, then brine, dried over $Na_2SO_4$, and concentrated. The crude product was purified by column chromatography (PE/EA=40:3) to give the title compound as light yellow solid.

Step 6: ethyl (E)-3-(2-amino-6-(butylamino)-5-(2-methoxybenzyl)pyrimidin-4-yl)acrylate To a solution of ethyl (E)-3-(2-amino-6-chloro-5-(2-methoxybenzyl)pyrimidin-4-yl)acrylate (1.0 eq) in NMP (0.2M) was added butan-1-amine (3.0 eq) and DIEA (3.0 eq), and the mixture was stirred at 150° C. for 2 h. After the reaction was completed, the reaction was diluted with water. The aqueous phase was extracted with EA. Combined organic layers were washed with water, then brine, dried over $Na_2SO_4$, and concentrated. The crude product was purified by column chromatography (DCM/MeOH=10:1) to give the title compound as a yellow oil.

Step 7: ethyl 3-(2-amino-6-(butylamino)-5-(2-methoxybenzyl)pyrimidin-4-yl)propanoate To a solution of ethyl (E)-3-(2-amino-6-(butylamino)-5-(2-methoxybenzyl)pyrimidin-4-yl)acrylate (1.0 eq) in MeOH (0.04M) was added Pd/C (⅓ weight eq). The mixture was stirred at room temperature for 1 h under hydrogen. After the reaction was completed, the solid particles were filtered off and the filtrate was concentrated to give the title compound as a yellow oil.

Step 8: 3-(2-amino-6-(butylamino)-5-(2-methoxybenzyl)pyrimidin-4-yl)propanoic acid To a solution of ethyl 3-(2-amino-6-(butylamino)-5-(2-methoxybenzyl)pyrimidin-4-yl)propanoate (1 eq) in 1:1 MeOH/$H_2O$ (0.04M) was added NaOH (5.0 eq). The solution was stirred at room temperature for 1 h. After the reaction was completed, the pH was adjusted to 7 using acetic acid, and the solution was concentrated and purified by prep-HPLC (mobile phase: $NH_3.H_2O$/MeCN/$H_2O$) to give the title compound as a white solid (ammonium salt).

LC-MS: [M+H]=359.4

$^1$H NMR (400 MHz, MeOD) δ 7.23 (t, J=6.8 Hz, 1H), 6.99 (d, J=8.0 Hz, 1H), 6.91-6.88 (m, 2H), 3.90 (s, 3H), 3.80 (s, 2H), 3.44 (t, J=6.8 Hz, 2H), 2.85 (t, J=6.0 Hz, 2H), 2.42 (t, J=6.0 Hz 2H), 1.51-1.46 (m, 2H), 1.25-1.19 (m, 2H), 0.88 (t, J=6.8 Hz, 3H).

Example 16: 2-(3-((2-amino-4-(butylamino)-6-methylpyrimidin-5-yl)methyl)-4-methoxybenzamido)ethane-1-sulfonic acid (Compound 16)

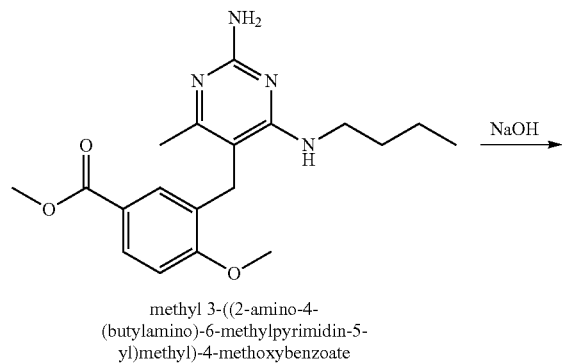

methyl 3-((2-amino-4-(butylamino)-6-methylpyrimidin-5-yl)methyl)-4-methoxybenzoate

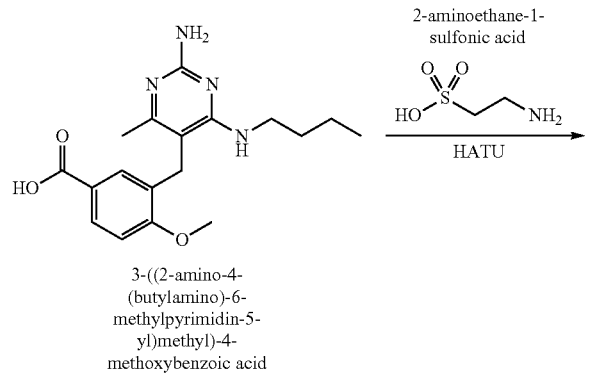

3-((2-amino-4-(butylamino)-6-methylpyrimidin-5-yl)methyl)-4-methoxybenzoic acid

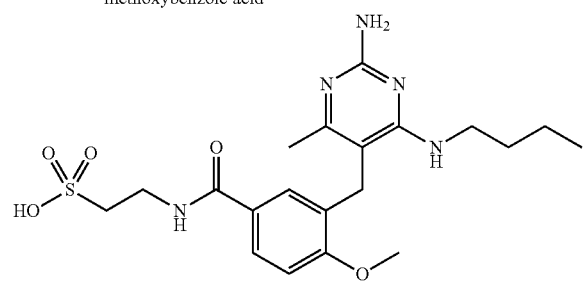

2-(3-((2-amino-4-(butylamino)-6-methylpyrimidin-5-yl)methyl)-4-methoxybenzamido)ethane-1-sulfonic acid
Chemical Formula: $C_{20}H_{29}N_5O_5S$
Exact Mass: 451.19

Preparation of methyl 3-((2-amino-4-(butylamino)-6-methylpyrimidin-5-yl)methyl)-4-methoxybenzoate followed Example 1—Steps 1 to 4, but using methyl 3-(bromomethyl)-4-methoxybenzoate as the starting material in Step 1.

Step 1: 3-((2-amino-4-(butylamino)-6-methylpyrimidin-5-yl)methyl)-4-methoxybenzoic acid To a suspension of methyl 3-((2-amino-4-(butylamino)-6-methylpyrimidin-5-yl)methyl)-4-methoxybenzoate (1.0 eq) in MeOH (0.3M) was added 1N NaOH (5.0 eq). The resulting mixture was stirred at 60° C. for 2 h. The reaction was monitored by TLC. The mixture was cooled to rt. The mixture was neutralized with 2N HCl and purified to give the title compound.

Step 2: 2-(3-((2-amino-4-(butylamino)-6-methylpyrimidin-5-yl)methyl)-4-methoxybenz-amido)ethane-1-sulfonic acid To a solution of 3-((2-amino-4-(butylamino)-6-methylpyrimidin-5-yl)methyl)-4-methoxy-benzoic acid (1.0 eq) in DMF (0.6M) was added HATU (1.0 eq), 2-aminoethane-1-sulfonic acid (1.1 eq) and DIEA (3.0 eq). The resulting mixture was stirred at rt for 3 h. The mixture was filtered and the filtrate was purified by prep-HPLC (mobile phase $CH_3CN/H_2O/HCOOH$), then freeze-dried to give the title compound as a white solid.

LC-MS: $[M+H]^+$=452.2

$^1$H NMR (400 MHz, DMSO) δ 11.89 (s, 1H), 8.35 (t, J=3.2 Hz, 1H), 7.90 (s, 1H), 7.68 (d, J=8.4 Hz, 1H), 7.40 (br s, 2H), 7.26 (s, 1H), 7.09 (d, J=8.4 Hz, 1H), 3.90 (s, 3H), 3.71 (s, 2H), 3.48-3.42 (m, 2H), 3.39-3.33 (m, 2H), 2.62 (t, J=6.8 Hz, 2H), 2.12 (s, 3H), 1.49-1.41 (m, 2H), 1.23-1.15 (m, 2H), 0.82 (t, J=7.2 Hz, 3H).

Example 17: 3-((2-amino-4-(butylamino)-6-methylpyrimidin-5-yl)methyl)-4-methoxybenzenesulfonic acid (Compound 17)

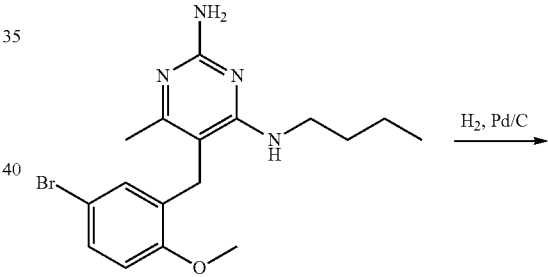

5-(5-bromo-2-methoxybenzyl)-$N^4$-butyl-6-methylpyrimidine-2,4-diamine

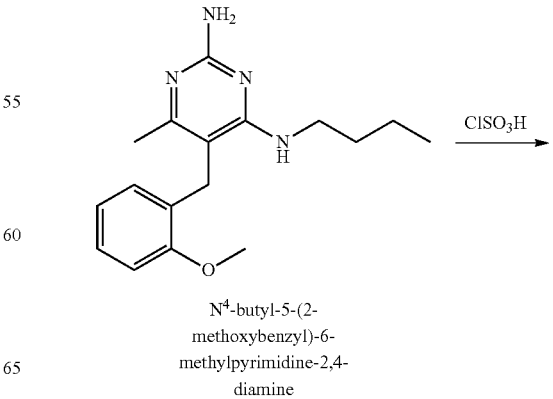

$N^4$-butyl-5-(2-methoxybenzyl)-6-methylpyrimidine-2,4-diamine

-continued

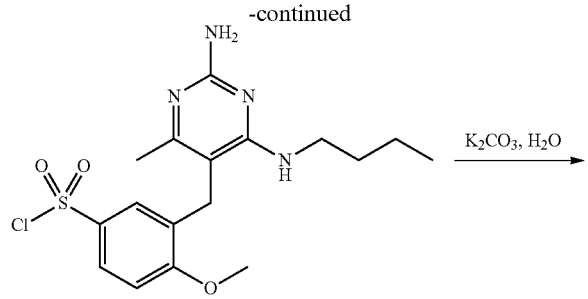

(3-((2-amino-4-(butylamino)-6-methylpyrimidin-5-yl)methyl)-4-methoxybenzenesulfonyl chloride

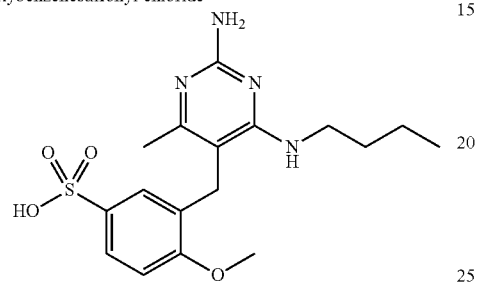

(3-((2-amino-4-(butylamino)-6-methylpyrimidin-5-yl)methyl)-4-methoxybenzenesulfonic acid
Chemical Formula: $C_{17}H_{24}N_4O_4S$
Exact Mass: 380.15

Preparation of 5-(5-bromo-2-methoxybenzyl)-$N^4$-butyl-6-methylpyrimidine-2,4-diamine followed Example 1—Steps 1 to 4, but 4-bromo-2-(bromomethyl)-1-methoxybenzene as the starting material in Step 1.

Step 1: N4-butyl-5-(2-methoxybenzyl)-6-methylpyrimidine-2,4-diamine

To a stirred solution of 5-(5-bromo-2-methoxybenzyl)-$N^4$-butyl-6-methylpyrimidine-2,4-diamine (1.0 eq) in MeOH (0.1M) was added Pd/C (10% wt eq). The resulting mixture was stirred at rt for 1 h under $H_2$ atmosphere, and then filtered. The filtrate was concentrated to give the title compound.

Step 2: 3-((2-amino-4-(butylamino)-6-methylpyrimidin-5-yl)methyl)-4-methoxybenzene-sulfonyl chloride $N^4$-butyl-5-(2-methoxybenzyl)-6-methylpyrimidine-2,4-diamine (1.0 eq) in $ClSO_3H$ (0.7M) was stirred at rt for 2 h, and then poured into ice water. The mixture was partitioned between DCM/water. The organic layer was dried over $Na_2SO_4$, filtered, concentrated to give the title compound.

Step 3: 3-((2-amino-4-(butylamino)-6-methylpyrimidin-5-yl)methyl)-4-methoxybenzenesulfonic acid To a stirred solution of 3-((2-amino-4-(butylamino)-6-methylpyrimidin-5-yl)methyl)-4-methoxybenzene-sulfonyl chloride (1.0 eq) in 1:1 MeCN/$H_2O$ (0.025M) was added $K_2CO_3$ (2.0 eq). The resulting mixture was stirred overnight at rt and then concentrated. The residue was purified by prep-HPLC (mobile phase $CH_3CN/H_2O$/HCOOH), freeze-dried to give the title compound.

LC-MS: [M−H]⁻=379.2

¹H NMR (400 MHz, DMSO-$d_6$) δ 11.92 (br s, 1H), 7.79 (br s, 1H), 7.46 (d, J=6.8 Hz, 1H), 7.22 (br s, 2H), 7.04 (s, 1H), 6.95 (d, J=8.4 Hz, 1H), 3.85 (s, 3H), 3.68 (s, 2H), 3.37-3.34 (m, 2H), 2.08 (s, 3H), 1.54-1.44 (m, 2H), 1.26-1.23 (m, 2H), 0.86 (t, J=7.2 Hz, 3H).

Example 18: (S)-3-((5-(5-((2H-tetrazol-5-yl)methyl)-2-methoxybenzyl)-2-amino-6-methylpyrimidin-4-yl)amino)heptan-1-ol (Compound 18)

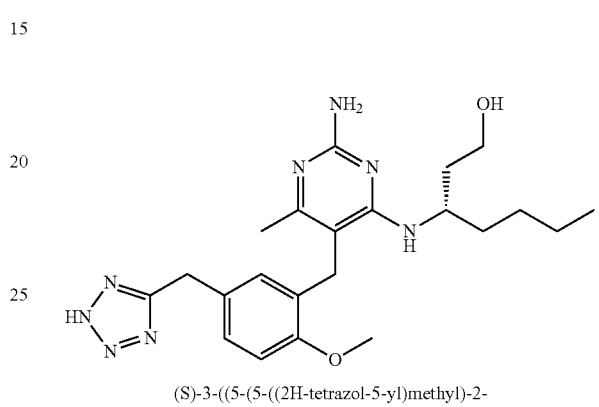

(S)-3-((5-(5-((2H-tetrazol-5-yl)methyl)-2-methoxybenzyl)-2-amino-6-methylpyrimidin-4-yl)amino)heptan-1-ol
Chemical Formula: $C_{22}H_{32}N_8O_2$
Exact Mass: 440.26

The title compound is prepared following the protocols described in Example 8, but using (S)-3-aminoheptan-1-ol (from J. Med. Chem. 2016, 59, 7936-7949) instead of (S)-2-aminopentan-1-ol in Step A. In the final step, the crude product was purified by prep-HPLC (mobile phase $CH_3CN/H_2O$/HCOOH), then freeze-dried to give the title compound as a white solid (formic acid salt).

LC-MS: [M+H]⁺=441.3

¹H NMR (400 MHz, DMSO) δ 8.22 (s, 1H), 7.03 (d, J=8.8 Hz, 1H), 6.90 (d, J=8.4 Hz, 1H), 6.78 (s, 1H), 6.52 (s, 2H), 6.35 (d, J=8.0 Hz, 1H), 4.27-4.21 (m, 1H), 3.99-3.91 (m, 2H), 3.80 (s, 3H), 3.62 (s, 2H), 3.39-3.26 (m, 3H), 2.07 (s, 3H), 1.64-1.50 (m, 2H), 1.48-1.37 (m, 2H), 1.24-1.14 (m, 2H), 1.12-1.04 (m, 2H), 0.76 (t, J=7.2 Hz, 3H).

Example 19: 3-(2-amino-6-(butylamino)-5-(4-methoxyphenethyl)pyrimidin-4-yl)pro-panoic acid (Compound 19)

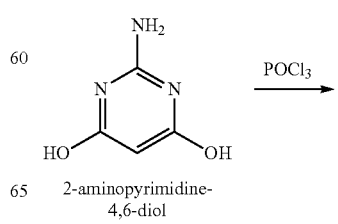

2-aminopyrimidine-4,6-diol

-continued
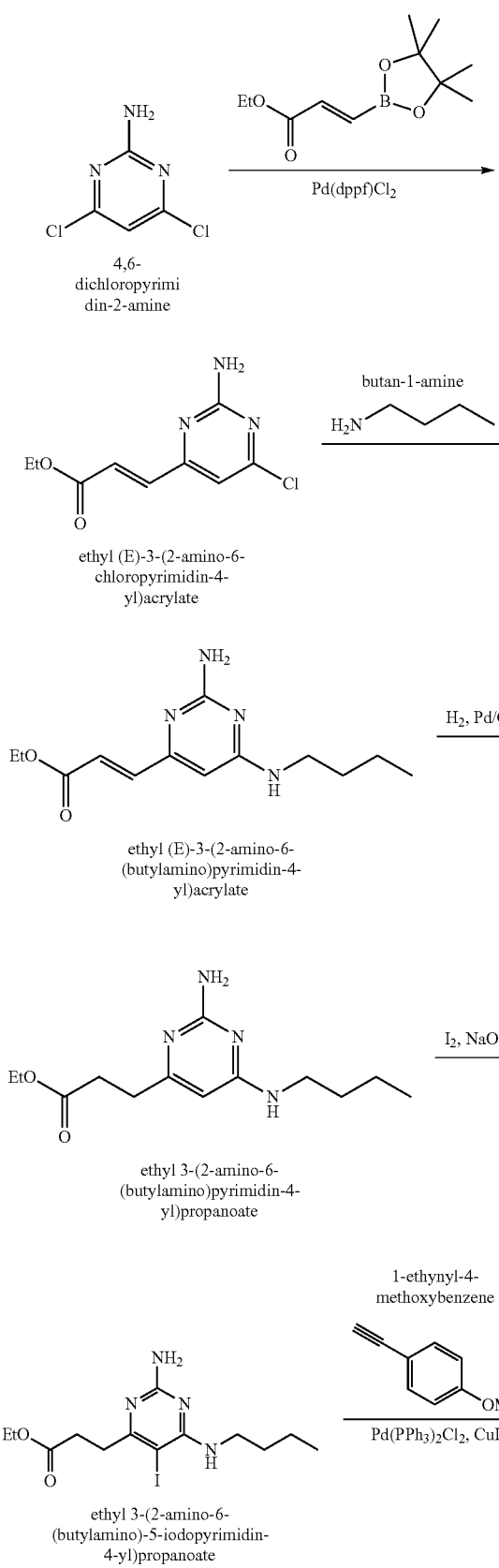
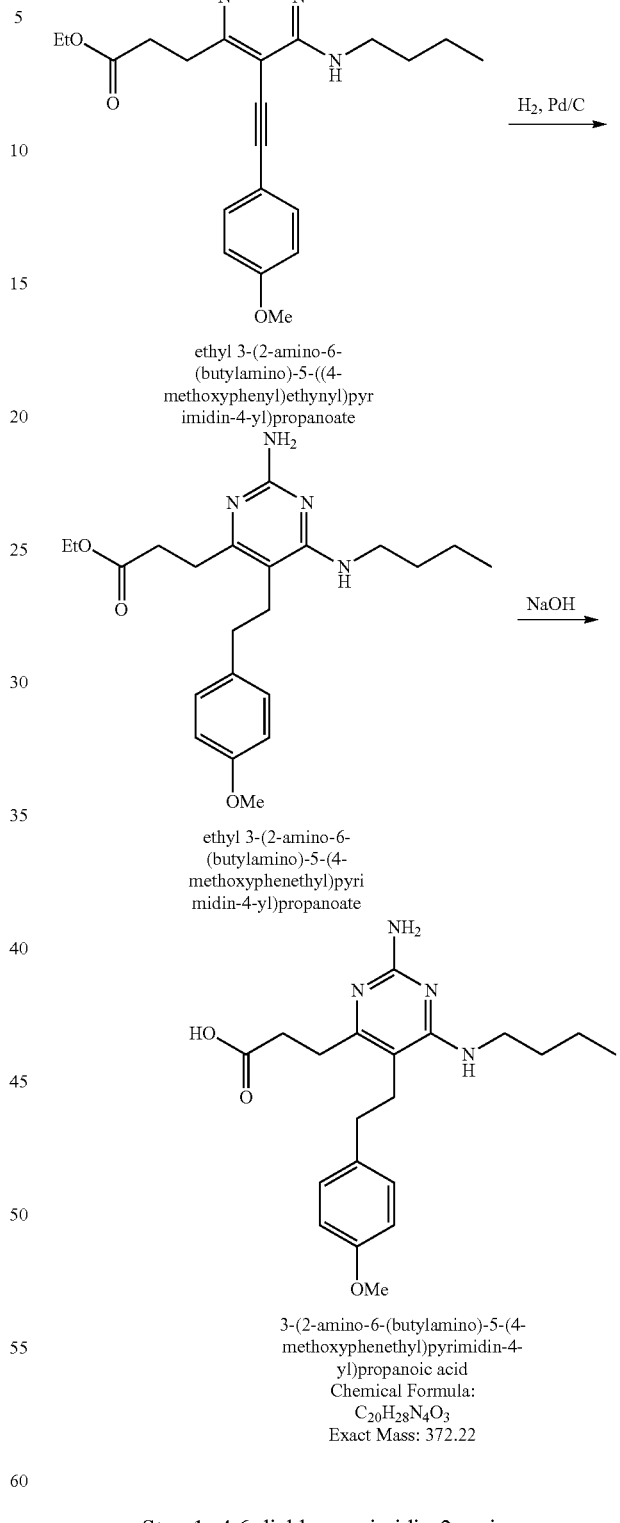
Step 1: 4,6-dichloropyrimidin-2-amine
To a solution of 2-aminopyrimidine-4,6-diol (1.0 eq) in $POCl_3$ (1M) was stirred at 100° C. for 4 h. The reaction mixture was allowed to cool to rt and the mixture was poured into ice-water. The precipitated solid was collected by filtration. The solid was washed with water and dried in vacuum to give the title compound as a yellow solid.

Step 2: ethyl (E)-3-(2-amino-6-chloropyrimidin-4-yl)acrylate

To a solution of 4,6-dichloropyrimidin-2-amine (1.0 eq) in 3:1 dioxane/H$_2$O (0.3M) was added ethyl (E)-3-(4,4,5,5-tetramethyl-1,3,2-dioxaborolan-2-yl)acrylate (1.1 eq), K$_2$CO$_3$ (2.0 eq), and Pd(dppf)Cl$_2$ (0.1 eq). The mixture was stirred at 100° C. for 2 h under nitrogen. The reaction was diluted with water, and the aqueous layer was extracted with EA. The combined organic layers were washed with water, brine, dried over Na$_2$SO$_4$, and concentrated. The crude product was purified by column chromatography (PE/EA=10:1) to give the title compound as a yellow solid.

Step 3: ethyl (E)-3-(2-amino-6-(butylamino)pyrimidin-4-yl)acrylate

To a solution of ethyl (E)-3-(2-amino-6-chloropyrimidin-4-yl)acrylate (1.0 eq) in NMP (0.4M) was added butan-1-amine (3.0 eq) and DIEA (3.0 eq). The mixture was stirred at 150° C. for 3 h. The reaction was diluted with water, and the aqueous phase was extracted with EA. The combined organic layers were washed with water, brine, dried over Na$_2$SO$_4$, and concentrated. The crude product was purified by column chromatography (PE/EA=1:1) to give the title compound as a yellow solid.

Step 4: ethyl 3-(2-amino-6-(butylamino)pyrimidin-4-yl)propanoate

To a solution of ethyl (E)-3-(2-amino-6-(butylamino)pyrimidin-4-yl)acrylate (1.0 eq) in MeOH (0.2M) was added Pd/C (20% wt eq). The mixture was stirred at 25° C. for 2 h under H$_2$ and then filtered. The filtrate was concentrated to give the title compound as a colored solid.

Step 5: ethyl 3-(2-amino-6-(butylamino)-5-iodopyrimidin-4-yl)propanoate

To a solution of ethyl 3-(2-amino-6-(butylamino)pyrimidin-4-yl)propanoate (1.0 eq) in 2:1 DCM/H$_2$O (0.05M) was added NaOH (2.0 eq), followed by I$_2$ (1.0 eq). The mixture was stirred at 25° C. for 16 h. The reaction was diluted with water, and the aqueous phase was extracted with EA. The combined organic layers were washed with water, brine, dried over Na$_2$SO$_4$, and concentrated. The crude product was purified by column chromatography (PE/EA=4:3) to give the title compound as a yellow solid.

Step 6: ethyl 3-(2-amino-6-(butylamino)-5-((4-methoxyphenyl)ethynyl)pyrimidin-4-yl)propanoate To a solution of ethyl 3-(2-amino-6-(butylamino)-5-iodopyrimidin-4-yl)propanoate (1.0 eq) in DMF (0.1M) was added 1-ethynyl-4-methoxybenzene (1.2 eq), TEA (⅕$^{th}$ reaction volume), CuI (0.2 eq), and Pd(PPh$_3$)$_2$Cl$_2$ (0.1 eq). The mixture was stirred at 50° C. for 16 h under nitrogen. The reaction was diluted with water, and the aqueous phase was extracted with EA. The combined organic layers were washed with water, brine, dried over Na$_2$SO$_4$, and concentrated. The crude product was purified by column chromatography (PE/EA=1:1) to give the title compound as a brown oil.

Step 7: ethyl 3-(2-amino-6-(butylamino)-5-(4-methoxyphenethyl)pyrimidin-4-yl)propanoate To a solution of ethyl 3-(2-amino-6-(butylamino)-5-((4-methoxyphenyl)ethynyl)pyrimidin-4-yl)propanoate (1.0 eq) in MeOH (0.08M) was added Pd/C (30% wt eq). The mixture was stirred at 50° C. for 2 h under H$_2$ and then filtered. The filtrate was concentrated to give the title compound as a yellow oil.

Step 8: 3-(2-amino-6-(butylamino)-5-(4-methoxyphenethyl)pyrimidin-4-yl)propanoic acid To a solution of ethyl 3-(2-amino-6-(butylamino)-5-(4-methoxyphenethyl)pyrimidin-4-yl)propanoate (1.0 eq) in 1:1 MeOH/H$_2$O (0.2M) was added NaOH (5.0 eq). The resulting mixture was stirred at 25° C. for 1 h. The pH was adjusted to 7 using acetic acid, and the solution was concentrated and purified by prep-HPLC (mobile phase: NH$_4$OH/MeCN/H$_2$O) to give the title compound as a white solid (ammonium salt).

LC-MS: [M+H]$^+$=373.4

$^1$H NMR (400 MHz, CD$_3$OD) δ 7.00 (d, J=8.4 Hz, 2H), 6.81 (d, J=8.8 Hz, 2H), 3.75 (s, 3H), 3.48 (t, J=7.6 Hz, 2H), 2.75-2.71 (m, 4H), 2.43 (t, J=6.0 Hz, 2H), 2.18 (t, J=6.4 Hz, 2H), 1.60-1.54 (m, 2H), 1.40-1.35 (m, 2H), 0.97 (t, J=6.8 Hz, 3H)

Example 20A: (S)-3-((5-(5-((2H-tetrazol-5-yl)methyl)-2-methoxybenzyl)-2-amino-6-methylpyrimidin-4-yl)amino)heptanoic acid (Compound 20)

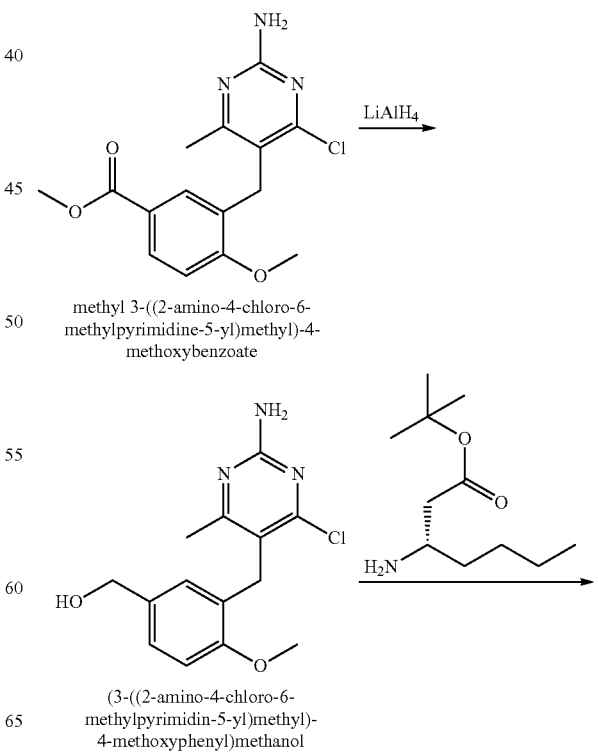

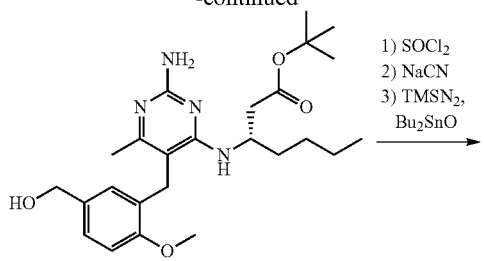

tert-butyl (S)-3-((2-amino-5-(5-(hydroxymethyl)-2-methoxybenzyl)-6-methylpyrimidin-4-yl)amino)heptanoate

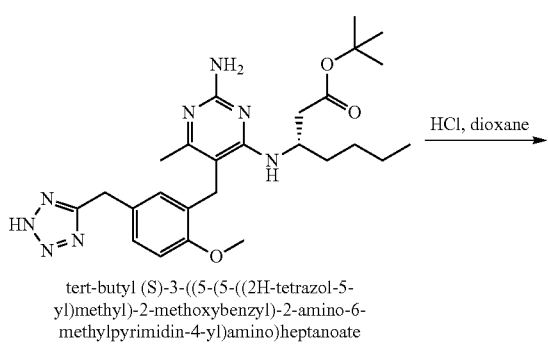

tert-butyl (S)-3-((5-(5-((2H-tetrazol-5-yl)methyl)-2-methoxybenzyl)-2-amino-6-methylpyrimidin-4-yl)amino)heptanoate

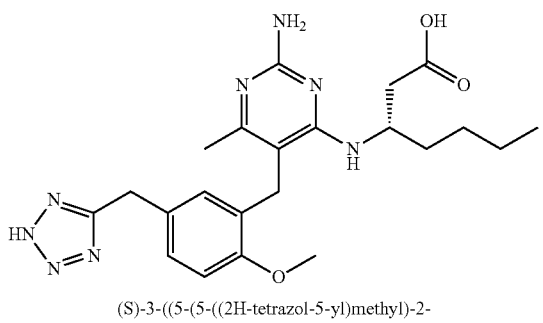

(S)-3-((5-(5-((2H-tetrazol-5-yl)methyl)-2-methoxybenzyl)-2-amino-6-methylpyrimidin-4-yl)amino)heptanoic acid
Chemical Formula: $C_{22}H_{30}N_8O_3$
Exact Mass: 454.24

Methyl 3-((2-amino-4-chloro-6-methylpyrimidin-5-yl)methyl)-4-methoxybenzoate was prepared following Example 1—Steps 1 to 3, but using methyl 3-(bromomethyl)-4-methoxybenzoate as the staring material instead of methyl 4-(bromomethyl)-3-methoxybenzoate.

Step 1: (3-((2-amino-4-chloro-6-methylpyrimidin-5-yl)methyl)-4-methoxyphenyl)-methanol To a stirred solution of methyl 3-((2-amino-4-chloro-6-methylpyrimidin-5-yl)methyl)-4-methoxybenzoate (1.0 eq) in THF (0.2M) at 0° C. was added dropwise 2.5M LiAlH$_4$ (2.5 eq). The resulting mixture was stirred at rt for 1 h. Then the mixture was quenched with 1 M NaOH solution and filtered. The filtration was extracted with EtOAc. The organic layer was dried over Na$_2$SO$_4$, filtered, concentrated under reduced pressure. The residue was purified by flash column chromatography (eluent DCM/MeOH=100:1 to 10:1) to give the title compound as a yellow solid.

Step 2: tert-butyl (S)-3-((2-amino-5-(5-(hydroxymethyl)-2-methoxybenzyl)-6-methyl-pyrimidin-4-yl)amino)heptanoate A mixture of tert-butyl (S)-3-aminoheptanoate (4.0 eq; prepared following procedures reported in J. Med. Chem. 2016, 59, 7936-7949) and (3-((2-amino-4-chloro-6-methylpyrimidin-5-yl)methyl)-4-methoxyphenyl)-methanol (1.0 eq) in NMP (0.8M) was stirred at 120° C. for 16 h. Then water and EtOAc were added into the reaction mixture. The organic layer was separated, dried over Na$_2$SO$_4$, concentrated under reduced pressure. The residue was purified by flash column chromatography (eluent: DCM/MeOH=100:1 to 20:1) to give the title compound as a yellow oil.

Step 3 to 5: tert-butyl (S)-3-((5-(5-((2H-tetrazol-5-yl)methyl)-2-methoxybenzyl)-2-amino-6-methylpyrimidin-4-yl)amino)heptanoate The title compound was prepared following Example 2—Steps 1 to 3, but using tert-butyl (S)-3-((2-amino-5-(5-(hydroxymethyl)-2-methoxybenzyl)-6-methyl-pyrimidin-4-yl)amino)heptanoate as the starting material. The crude product was purified by prep-HPLC (mobile phase CH$_3$CN/H$_2$O/HCOOH), and freeze-dried to give the title compound as a white solid (formic acid salt).
LC-MS: [M+H]$^+$=511.4
$^1$H NMR (400 MHz, DMSO) δ 8.20 (s, 1H), 7.04 (dd, J=8.4, 2.0 Hz, 1H), 6.93 (d, J=8.0 Hz, 1H), 6.77 (s, 1H), 6.60 (br s, 2H), 6.39 (br s, 1H), 4.55-4.52 (m, 1H), 4.02 (s, 2H), 3.83 (s, 3H), 3.67-3.57 (m, 2H), 2.37 (d, J=6.8 Hz, 2H), 2.07 (s, 3H), 1.46-1.38 (m, 2H), 1.32 (s, 9H), 1.26-1.13 (m, 2H), 1.09-1.01 (m, 2H), 0.77 (t, J=7.2 Hz, 3H).

Step 6: (S)-3-((5-(5-((2H-tetrazol-5-yl)methyl)-2-methoxybenzyl)-2-amino-6-methylpyrimidin-4-yl)amino)heptanoic acid Tert-butyl (S)-3-((5-(5-((2H-tetrazol-5-yl)methyl)-2-methoxybenzyl)-2-amino-6-methylpyrimidin-4-yl)amino)heptanoate (1 eq) was added 3.0 M HCl/dioxane (20 eq) at 0° C., and warmed to rt. After stirring at 1 h, the mixture was concentrated under reduced pressure. The residue was purified by prep-HPLC (mobile phase CH$_3$CN/H$_2$O/HCOOH), freeze-dried to give the title compound as a white solid.
LC-MS: [M+H]$^+$=455.2
$^1$H NMR (400 MHz, DMSO) δ 7.35 (br s, 1H), 7.07 (br s, 2H), 6.96 (d, J=7.6 Hz, 1H), 6.88 (d, J=8.4 Hz, 1H), 6.76 (s, 1H), 4.56-4.54 (m, 1H), 4.07-3.97 (m, 2H), 3.79 (s, 3H), 3.68-3.66 (m, 2H), 2.46-2.38 (m, 2H), 2.05 (s, 3H), 1.53-1.50 (m, 2H), 1.27-1.16 (m, 4H), 0.82 (t, J=6.8 Hz, 3H).

Example 20B: (S)-3-((5-(5-((2H-tetrazol-5-yl)methyl)-2-methoxybenzyl)-2-amino-6-methylpyrimidin-4-yl)amino)heptanoic acid (Compound 20)

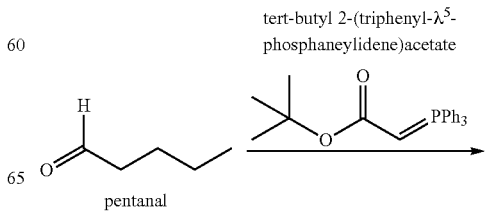

pentanal
tert-butyl 2-(triphenyl-λ$^5$-phosphaneylidene)acetate

-continued

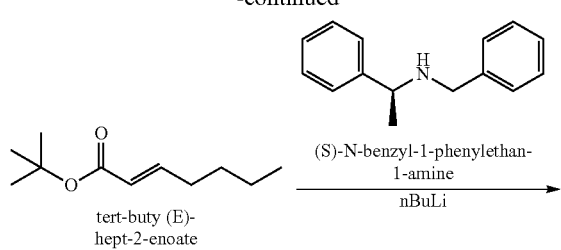
tert-buty (E)-hept-2-enoate
(S)-N-benzyl-1-phenylethan-1-amine
nBuLi

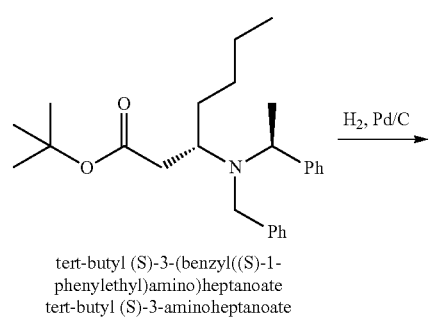
tert-butyl (S)-3-(benzyl((S)-1-phenylethyl)amino)heptanoate
tert-butyl (S)-3-aminoheptanoate H₂, Pd/C

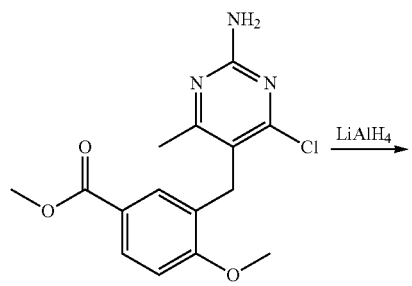
tert-butyl (S)-3-aminoheptanoate

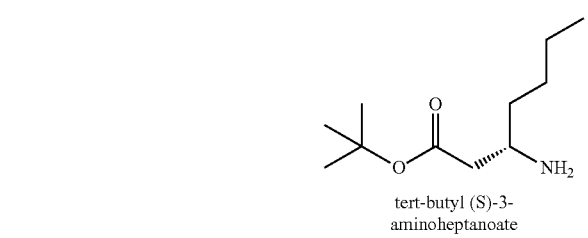
methyl 3-((2-amino-4-chloro-6-methylpyrimidin-5-yl)methyl)-4-methoxybenzoate LiAlH₄

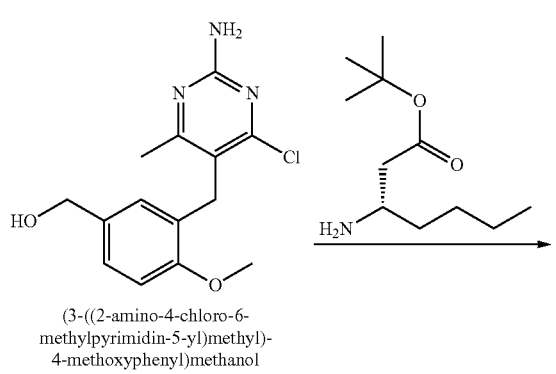
(3-((2-amino-4-chloro-6-methylpyrimidin-5-yl)methyl)-4-methoxyphenyl)methanol -continued

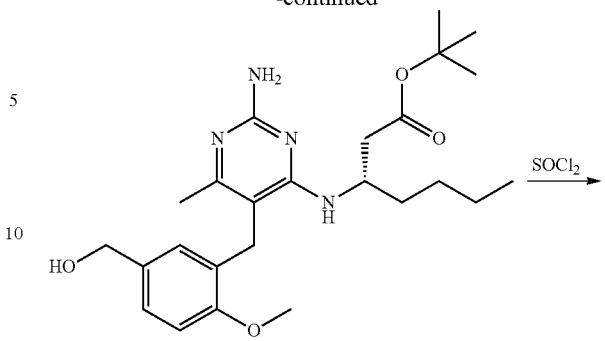
tert-butyl (S)-3-((2-amino-5-(5-(hydroxymethyl)-2-methoxybenzyl)-6-methylpyrimidin-4-yl)amino)heptanoate SOCl₂

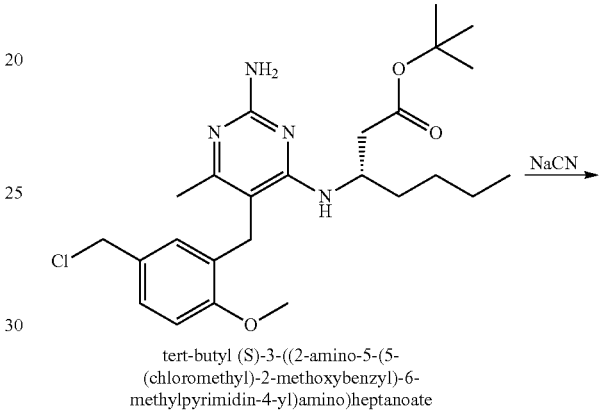
tert-butyl (S)-3-((2-amino-5-(5-(chloromethyl)-2-methoxybenzyl)-6-methylpyrimidin-4-yl)amino)heptanoate NaCN

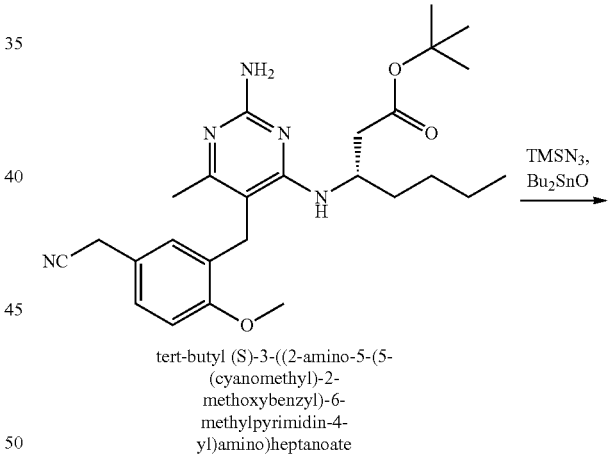
tert-butyl (S)-3-((2-amino-5-(5-(cyanomethyl)-2-methoxybenzyl)-6-methylpyrimidin-4-yl)amino)heptanoate TMSN₃, Bu₂SnO

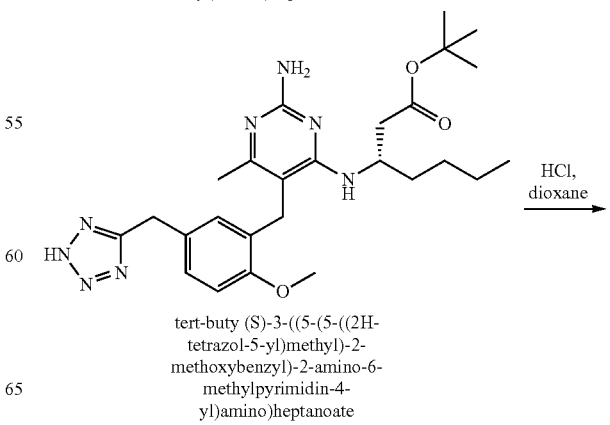
tert-buty (S)-3-((5-(5-((2H-tetrazol-5-yl)methyl)-2-methoxybenzyl)-2-amino-6-methylpyrimidin-4-yl)amino)heptanoate HCl, dioxane

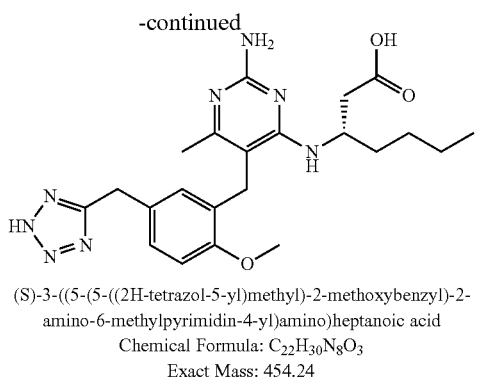

(S)-3-((5-(5-((2H-tetrazol-5-yl)methyl)-2-methoxybenzyl)-2-amino-6-methylpyrimidin-4-yl)amino)heptanoic acid
Chemical Formula: C$_{22}$H$_{30}$N$_{8}$O$_{3}$
Exact Mass: 454.24

Step 1: tert-butyl (E)-hept-2-enoate

A mixture of pentanal (1.0 eq) and tert-butyl 2-(triphenyl-λ$^5$-phosphanylidene)acetate (1.05 eq) was stirred at 50° C. for 16 h. Then the mixture was concentrated under reduced pressure, and petroleum ether (PE) was added. The solids were filtered off, and the filtrate was evaporated to dryness, which was purified by flash column chromatography (eluent: 0-1% EA in PE) to give the title compound as a yellow oil.

Step 2: tert-butyl (S)-3-(benzyl((S)-1-phenylethyl)amino)heptanoate

To a solution of (S)—N-benzyl-1-phenylethan-1-amine (1.3 eq) in THF (0.9M) at −78° C. was added dropwise 2.5M n-BuLi (1.2 eq) over 20 min. The mixture was stirred at −78° C. for 10 min, then tert-butyl (E)-hept-2-enoate (1.0 eq) in THF (0.7M) was added dropwise into the above mixture. The resulting mixture was stirred at −78° C. for 30 min. Then the mixture was quenched with aq. NH$_4$Cl and extracted with EtOAc. The organic layer was dried over Na$_2$SO$_4$, filtered, concentrated under reduced pressure. The residue was purified by flash column chromatography (eluent: 0-1% EA in PE) to give the title compound as a yellow oil.

Step 3: tert-butyl (S)-3-aminoheptanoate

To a solution of tert-butyl (S)-3-(benzyl((S)-1-phenylethyl)amino)heptanoate (1.0 eq) in MeOH (0.5M) was added 10% wt Pd/C (1/10$^{th}$ weight equivalent). The resulting mixture was stirred at 50° C. for 16 h under H$_2$. The solid was filtered off and the filtrate was concentrated under reduced pressure to give the title compound as a brown oil, which was used directly to next step without further purification.

Step 4: (3-((2-amino-4-chloro-6-methylpyrimidin-5-yl)methyl)-4-methoxyphenyl)-methanol To a stirred solution of methyl 3-((2-amino-4-chloro-6-methylpyrimidin-5-yl)methyl)-4-methoxybenzoate (1.0 eq; from Example 3B—Step 4) in THF (0.2M) at 0° C. was added dropwise 2.5M LiAlH$_4$ (2.5 eq). The resulting mixture was stirred at rt for 1 h. Then the mixture was quenched with 1 M NaOH solution and filtered. The filtration was extracted with EtOAc. The organic layer was dried over Na$_2$SO$_4$, filtered, concentrated under reduced pressure. The residue was purified by flash column chromatography (eluent DCM/MeOH=100:1 to 10:1) to give the title compound as a yellow solid.

Step 5: tert-butyl (S)-3-((2-amino-5-(5-(hydroxymethyl)-2-methoxybenzyl)-6-methyl-pyrimidin-4-yl)amino)heptanoate A mixture of tert-butyl (S)-3-aminoheptanoate (4.0 eq) and (3-((2-amino-4-chloro-6-methylpyrimidin-5-yl)methyl)-4-methoxyphenyl)-methanol (1.0 eq) in NMP (0.8M) was stirred at 120° C. for 16 h. Then water and EtOAc were added into the reaction mixture. The organic layer was separated, dried over Na$_2$SO$_4$, concentrated under reduced pressure. The residue was purified by flash column chromatography (eluent: DCM/MeOH=100:1 to 20:1) to give the title compound as a yellow oil.

Step 6: tert-butyl (S)-3-((2-amino-5-(5-(chloromethyl)-2-methoxybenzyl)-6-methylpyrimidin-4-yl)amino)heptanoate To a stirred solution of tert-butyl (S)-3-((2-amino-5-(5-(hydroxymethyl)-2-methoxybenzyl)-6-methyl-pyrimidin-4-yl)amino)heptanoate (1.0 eq) in DCM (0.05M) at 0° C. was added SOCl$_2$ (2.0 eq). The resulting mixture was stirred at 0° C. for 1 h. Then the mixture was quenched with NaHCO$_3$ solution and extracted with DCM. The organic layer was dried over Na$_2$SO$_4$, concentrated under reduced pressure to give the title compound as a yellow oil.

Step 7: tert-butyl (S)-3-((2-amino-5-(5-(cyanomethyl)-2-methoxybenzyl)-6-methylpyrimidin-4-yl)amino)heptanoate A mixture of tert-butyl (S)-3-((2-amino-5-(5-(chloromethyl)-2-methoxybenzyl)-6-methylpyrimidin-4-yl)amino)heptanoate (1.0 eq) in 1:1 DMSO/DMF (0.12M) and NaCN (3.0 eq) was stirred at rt for 16 h. The resulting mixture was partitioned between EtOAc and water. The organic layer was washed with brine, dried over Na$_2$SO$_4$, concentrated under reduced pressure. The residue was purified by flash column chromatography (eluent: DCM/MeOH=100:1 to 20:1) to give the title compound as a yellow oil.

Step 8: tert-butyl (S)-3-((5-(5-((2H-tetrazol-5-yl)methyl)-2-methoxybenzyl)-2-amino-6-methylpyrimidin-4-yl)amino)heptanoate A mixture of tert-butyl (S)-3-((2-amino-5-(5-(cyanomethyl)-2-methoxybenzyl)-6-methyl-pyrimidin-4-yl)amino)heptanoate (1.0 eq) in dioxane (1.2M), TMSN$_3$ (10 eq) and Bu$_2$SnO (2.0 eq) was stirred at 120° C. for 2 h. Then the mixture was concentrated under reduced pressure to give crude product as brown oil, which was used directly to next step without further purification.

Step 9: (S)-3-((5-(5-((2H-tetrazol-5-yl)methyl)-2-methoxybenzyl)-2-amino-6-methylpyrimidin-4-yl)amino)heptanoic acid Tert-butyl (S)-3-((5-(5-((2H-tetrazol-5-yl)methyl)-2-methoxybenzyl)-2-amino-6-methylpyrimidin-4-yl)amino)heptanoate (1 eq) was added 3.0 M HCl/dioxane (20 eq) at 0° C., and warmed to rt. After stirring at 1 h, the mixture was concentrated under reduced pressure. The residue was purified by prep-HPLC (mobile phase CH₃CN/H₂O/HCOOH), freeze-dried to give the title compound as a white solid (formic acid salt).

LC-MS: [M+H]⁺=455.2

$^1$H NMR (400 MHz, DMSO) δ 7.35 (br s, 1H), 7.07 (br s, 2H), 6.96 (d, J=7.6 Hz, 1H), 6.88 (d, J=8.4 Hz, 1H), 6.76 (s, 1H), 4.56-4.54 (m, 1H), 4.07-3.97 (m, 2H), 3.79 (s, 3H), 3.68-3.66 (m, 2H), 2.46-2.38 (m, 2H), 2.05 (s, 3H), 1.53-1.50 (m, 2H), 1.27-1.16 (m, 4H), 0.82 (t, J=6.8 Hz, 3H).

Example 20C: (R)-3-((5-(5-((2H-tetrazol-5-yl)methyl)-2-methoxybenzyl)-2-amino-6-methylpyrimidin-4-yl)amino)heptanoic acid (Compound 20C)

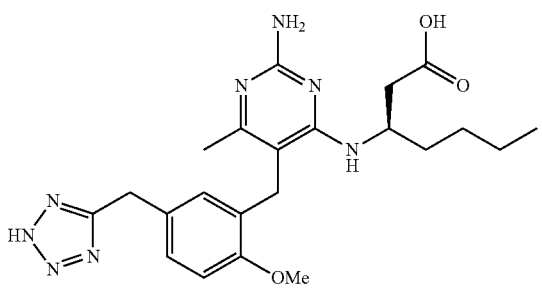

The title compound was prepared by following the procedure described in Example 20B, but using (R)—N-benzyl-1-phenylethan-1-amine instead of (S)—N-benzyl-1-phenylethan-1-amine in Step 2. The title compound showed identical H NMR and LCMS data as Example 20A/20B.

To demonstrate the chirality, samples of Example 20A/20B (e.g., (S)-enantiomer) and Example 20C (e.g., (R)-enantiomer) were injected on a Superchiral S-OZ column (0.46 cm I.D.×25 cm L) and eluted with Hexane/EtOH/MeOH/diethylamine (v/v/v/v=80/6.6/13.4/0.05) at 0.8 mL/min. The (R)-enantiomer showed a retention time of 12.2 min, whereas Example 20A/20B (e.g., (S)-enantiomer) showed a retention time of 13.2 min.

Example 21: (S)-3-(2-amino-6-((1-hydroxyheptan-3-yl)amino)-5-methoxypyrimidin-4-yl)propanoic acid (Compound 21)

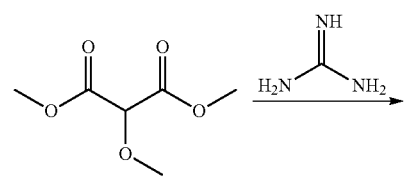

dimethyl 2-methyoxymalonate

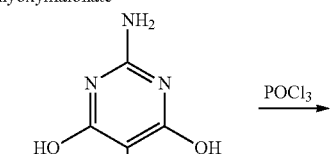

2-amino-5-methoxypyrimidine-4,6-diol

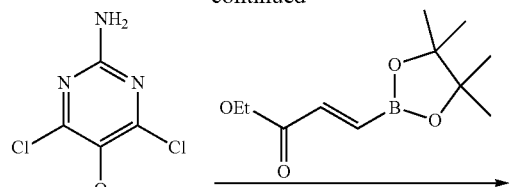

4,6-dichloro-5-methoxyprimidine-2-amine

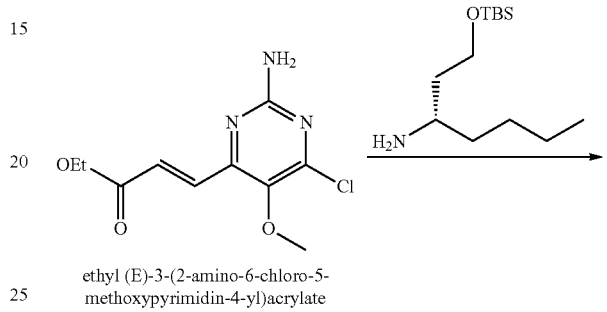

ethyl (E)-3-(2-amino-6-chloro-5-methoxypyrimidin-4-yl)acrylate

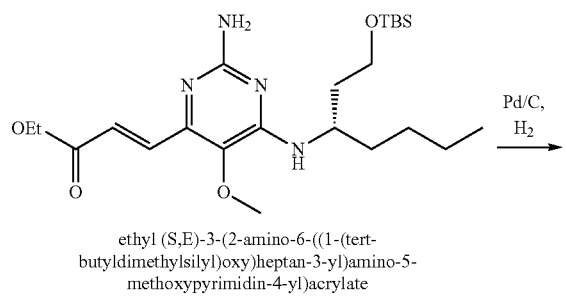

ethyl (S,E)-3-(2-amino-6-((1-(tert-butyldimethylsilyl)oxy)heptan-3-yl)amino)-5-methoxypyrimidin-4-yl)acrylate

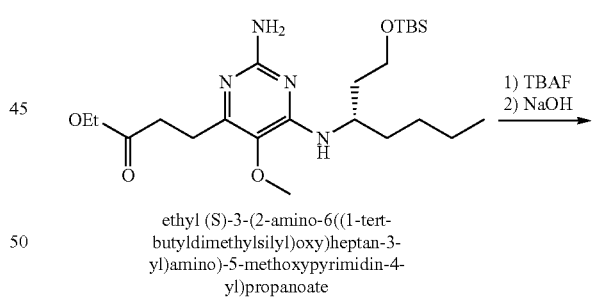

ethyl (S)-3-(2-amino-6-((1-tert-butyldimethylsilyl)oxy)heptan-3-yl)amino)-5-methoxypyrimidin-4-yl)propanoate

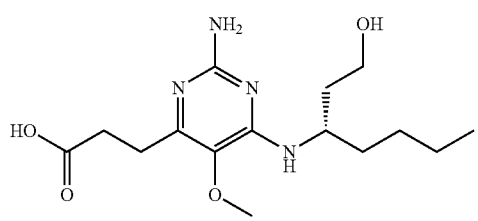 [SMILES: CCCC[C@@H](CCO)Nc1nc(N)nc(CCC(=O)O)c1OC]

(S)-3-(2-amino-6-((1-hydroxyheptan-3-yl)amino)-5-methoxypyrimidin-4-yl)propanoic acid The title compound can be prepared according to the steps of Example 15.

Example 22: (S)-5-(5-((2H-tetrazol-5-yl)methyl)-2-methoxybenzyl)-6-methyl-N⁴-(1-(methylthio)heptan-3-yl)pyrimidine-2,4-diamine (Compound 22)

(S)-1-(methylthio)heptan-3-amine

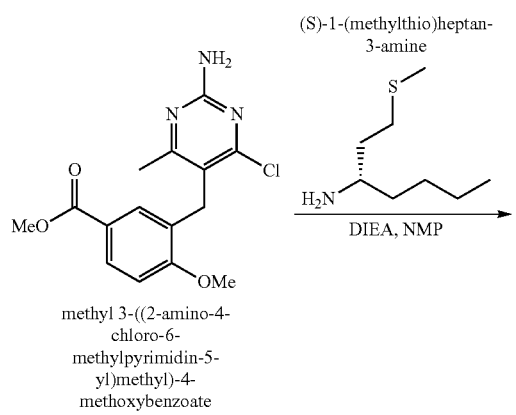

methyl 3-((2-amino-4-chloro-6-methylpyrimidin-5-yl)methyl)-4-methoxybenzoate

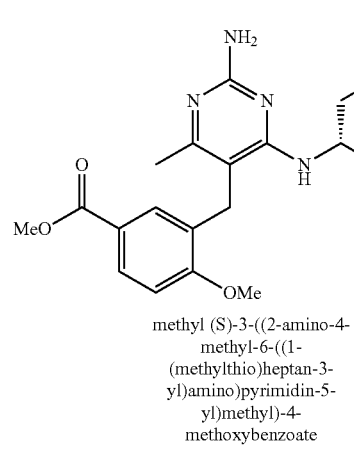

methyl (S)-3-((2-amino-4-methyl-6-((1-(methylthio)heptan-3-yl)amino)pyrimidin-5-yl)methyl)-4-methoxybenzoate

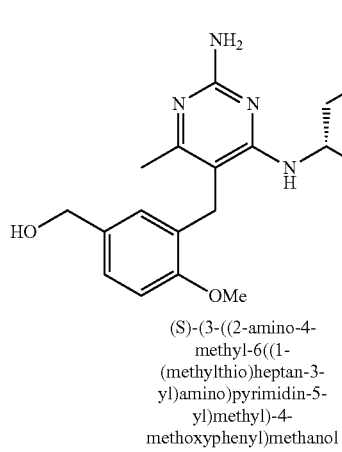

(S)-(3-((2-amino-4-methyl-6-((1-(methylthio)heptan-3-yl)amino)pyrimidin-5-yl)methyl)-4-methoxyphenyl)methanol

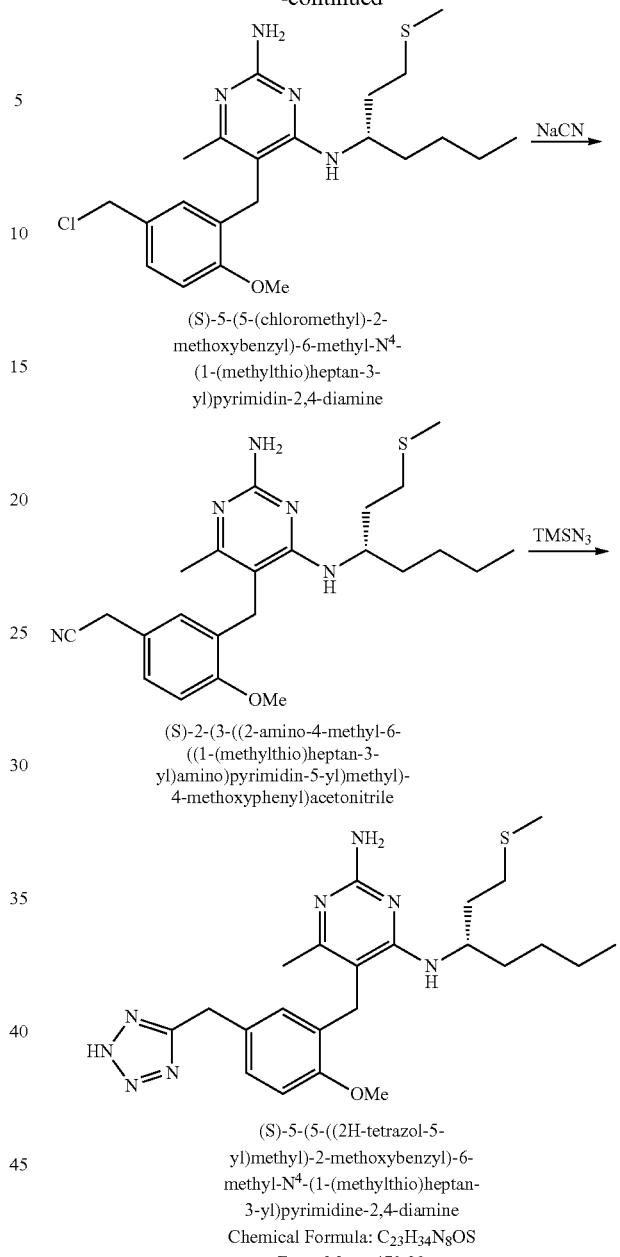

(S)-5-(5-(chloromethyl)-2-methoxybenzyl)-6-methyl-N⁴-(1-(methylthio)heptan-3-yl)pyrimidin-2,4-diamine (S)-2-(3-((2-amino-4-methyl-6-((1-(methylthio)heptan-3-yl)amino)pyrimidin-5-yl)methyl)-4-methoxyphenyl)acetonitrile (S)-5-(5-((2H-tetrazol-5-yl)methyl)-2-methoxybenzyl)-6-methyl-N⁴-(1-(methylthio)heptan-3-yl)pyrimidine-2,4-diamine
Chemical Formula: $C_{23}H_{34}N_8OS$
Exact Mass: 470.28

Step 1: methyl (S)-3-((2-amino-4-methyl-6-((1-(methylthio)heptan-3-yl)amino)pyrimidin-5-yl)methyl)-4-methoxybenzoate A mixture of methyl 3-((2-amino-4-chloro-6-methylpyrimidin-5-yl)methyl)-4-methoxybenzoate (1.0 eq, from Example 3B—Step 4) in NMP (0.8M), (S)-1-(methylthio)heptan-3-amine (1.0 eq; prepared by following procedures reported in WO2014/128189, pg 8, compound D) and DIEA (3.0 eq) was stirred for 48 h at 120° C. under N₂ atmosphere. The reaction was allowed to cool, diluted with EtOAc, washed with water and brine. The organic layer was dried over Na₂SO₄, concentrated and purified by column chromatography on silica gel (eluent 0-5% MeOH in DCM) to give the title compound.

Step 2: (S)-(3-((2-amino-4-methyl-6-((1-(methyl-thio)heptan-3-yl)amino)pyrimidin-5-yl)methyl)-4-methoxyphenyl)methanol To a stirred solution of methyl (S)-3-((2-amino-4-methyl-6-((1-(methylthio)heptan-3-yl)amino)-pyrimidin-5-yl)methyl)-4-methoxybenzoate (1.0 eq) in THF (0.18M) was added dropwise of 2.5M LiAlH₄ (2.0 eq) at 0° C. The reaction was stirred at r.t. for 1 h before it was quenched with EA and 1N NaOH. The mixture was filtered, and the filtrate was partitioned between EA/water. The organic layer was dried over Na₂SO₄, concentrated and purified by column chromatography on silica gel (eluent 0-5% MeOH in DCM) to give the title compound.

Step 3: (S)-5-(5-(chloromethyl)-2-methoxybenzyl)-6-methyl-N⁴-(1-(methylthio)heptan-3-yl)pyrimidine-2,4-diamine To a stirred solution of (S)-(3-((2-amino-4-methyl-6-((1-(methylthio)heptan-3-yl)amino)-pyrimidin-5-yl)methyl)-4-methoxyphenyl)methanol (1.0 eq) in DCM (0.1M) was added SOCl₂ (5.0 eq) at rt. The resulting mixture was stirred at rt for 2 h before it was quenched with sat. NaHCO₃. The mixture was partitioned between DCM/water. The organic layer was dried over Na₂SO₄ and concentrated to give the title compound.

Step 4: (S)-2-(3-((2-amino-4-methyl-6-((1-(methyl-thio)heptan-3-yl)amino)pyrimidin-5-yl)methyl)-4-methoxyphenyl)acetonitrile To a stirred solution of (S)-5-(5-(chloromethyl)-2-methoxybenzyl)-6-methyl-N⁴-(1-(methylthio)-heptan-3-yl)pyrimidine-2,4-diamine (1.0 eq) in 1:1 DMSO/DMF (0.1M) was added NaCN (3.0 eq). The mixture was stirred at rt for 16 h before it was quenched with sat. NaHCO₃. The mixture was partitioned between EA/water. The organic layer was dried over Na₂SO₄, concentrated and purified to give the title compound.

Step 5: (S)-5-(5-((2H-tetrazol-5-yl)methyl)-2-methoxybenzyl)-6-methyl-N⁴-(1-(methylthio)-heptan-3-yl)pyrimidine-2,4-diamine A mixture of (S)-2-(3-((2-amino-4-methyl-6-((1-(methylthio)heptan-3-yl)amino)pyrimidin-5-yl)methyl)-4-methoxyphenyl)acetonitrile (1.0 eq) in dioxane (0.15M) was added TMSN₃ (10.0 eq), Bu₂SnO (2.0 eq), and stirred overnight at 120° C. The mixture was concentrated and purified by prep-HPLC (mobile phase CH₃CN/H₂O/HCOOH), freeze-dried to give the title compound as a white powder (formic acid salt).

LCMS: [M+H]⁺=471.3

¹H NMR (400 MHz, DMSO) δ 7.03 (d, J=8.4 Hz, 1H), 6.92 (d, J=8.4 Hz, 1H), 6.79 (s, 1H), 6.44 (s, 2H), 6.24 (d, J=8.8 Hz, 1H), 4.25-4.22 (m, 1H), 4.00 (s, 2H), 3.82 (s, 3H), 3.64 (s, 2H), 2.29-2.27 (m, 2H), 2.08 (s, 3H), 1.95 (s, 3H), 1.68-1.64 (m, 2H), 1.44-1.34 (m, 2H), 1.19-1.16 (m, 2H), 1.12-1.02 (m, 2H), 0.78 (t, J=7.2 Hz, 3H).

Example 23: (S)-5-(5-((2H-tetrazol-5-yl)methyl)-2-methoxybenzyl)-6-methyl-N⁴-(1-(methylsulfonyl)heptan-3-yl)pyrimidine-2,4-diamine (Compound 23)

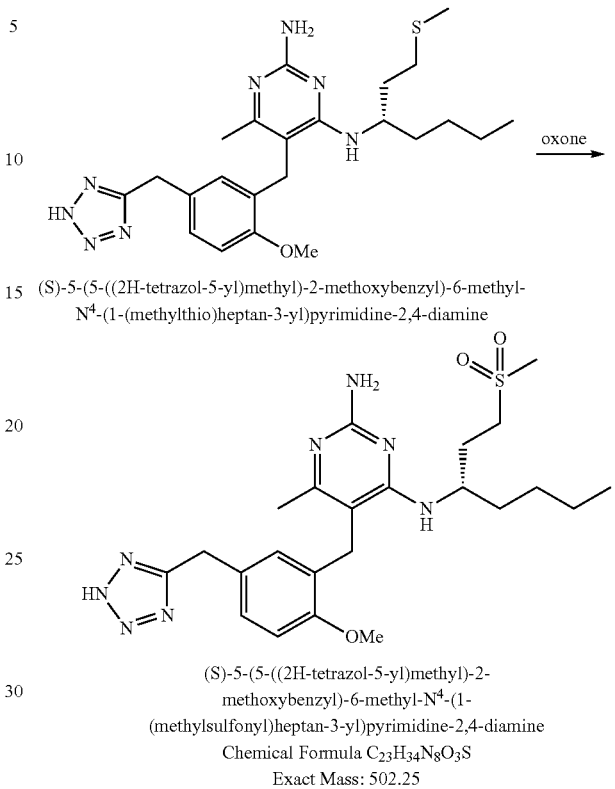

(S)-5-(5-((2H-tetrazol-5-yl)methyl)-2-methoxybenzyl)-6-methyl-N⁴-(1-(methylthio)heptan-3-yl)pyrimidine-2,4-diamine (S)-5-(5-((2H-tetrazol-5-yl)methyl)-2-methoxybenzyl)-6-methyl-N⁴-(1-(methylsulfonyl)heptan-3-yl)pyrimidine-2,4-diamine
Chemical Formula C₂₃H₃₄N₈O₃S
Exact Mass: 502.25

To a stirred solution of (S)-5-(5-((2H-tetrazol-5-yl)methyl)-2-methoxybenzyl)-6-methyl-N⁴-(1-(methylthio)heptan-3-yl)pyrimidine-2,4-diamine (1.0 eq, Example 22) in acetone (0.02M) was added oxone (2.0 eq) at r.t. The resulting mixture was stirred at r.t. for 3 h before it was filtered and purified by prep-HPLC (mobile phase CH₃CN/H₂O/HCOOH), freeze-dried to give the title compound as a white powder (formic acid salt).

LCMS: [M+H]⁺=503.3

¹H NMR (400 MHz, DMSO) δ 7.05 (d, J=8.4 Hz, 1H), 6.93 (d, J=8.4 Hz, 1H), 6.76 (s, 1H), 6.47 (s, 2H), 6.38 (d, J=6.4 Hz, 1H), 4.25-4.23 (m, 1H), 4.04 (s, 2H), 3.82 (s, 3H), 3.66 (s, 2H), 3.01-2.85 (m, 5H), 2.05 (s, 3H), 1.92-1.90 (m, 1H), 1.81-1.80 (m, 1H), 1.49-1.34 (m, 2H), 1.18-1.15 (m, 2H), 1.11-0.99 (m, 2H), 0.77 (t, J=7.2 Hz, 3H).

Example 24: (3-((2-amino-4-(butylamino)-6-methyl-pyrimidin-5-yl)methyl)-4-methoxyphenyl)boronic acid (Compound 24)

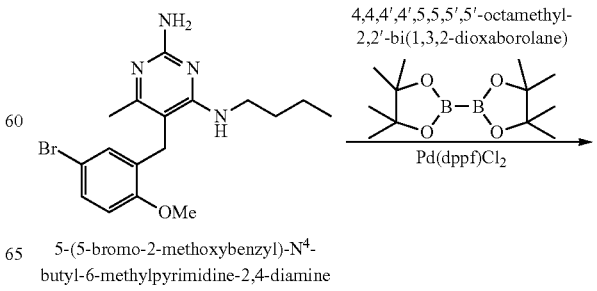

5-(5-bromo-2-methoxybenzyl)-N⁴-butyl-6-methylpyrimidine-2,4-diamine

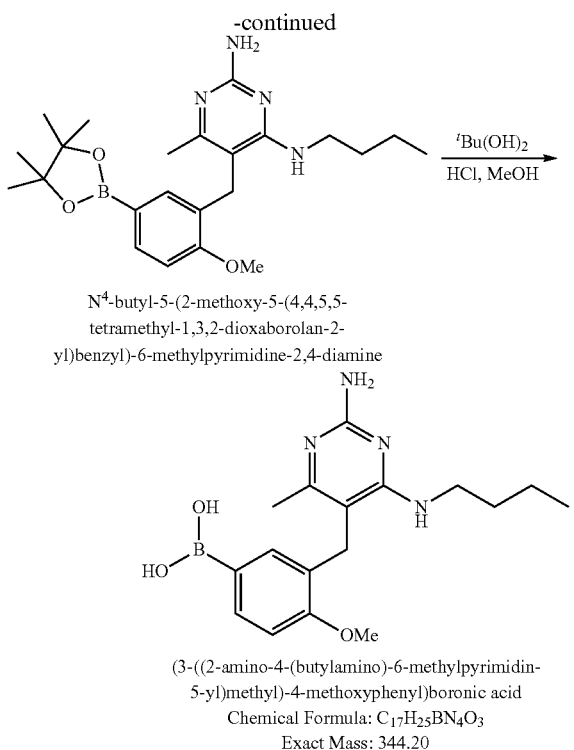

N⁴-butyl-5-(2-methoxy-5-(4,4,5,5-tetramethyl-1,3,2-dioxaborolan-2-yl)benzyl)-6-methylpyrimidine-2,4-diamine (3-((2-amino-4-(butylamino)-6-methylpyrimidin-5-yl)methyl)-4-methoxyphenyl)boronic acid
Chemical Formula: C₁₇H₂₅BN₄O₃
Exact Mass: 344.20

Step 1: N⁴-butyl-5-(2-methoxy-5-(4,4,5,5-tetramethyl-1,3,2-dioxaborolan-2-yl)benzyl)-6-methylpyrimidine-2,4-diamine A mixture of 5-(5-bromo-2-methoxybenzyl)-N⁴-butyl-6-methylpyrimidine-2,4-diamine (1.0 eq, from Example 11—Step 5) in dioxane (0.03M), 4,4,4',4',5,5,5',5'-octamethyl-2,2'-bi(1,3,2-dioxaborolane) (1.2 eq), KOAc (3.0 eq), and Pd(dppf)Cl₂ (0.1 eq) was stirred at 90° C. for 4 h. Then the mixture was filtered and the filtrate was concentrated under reduced pressure to give the crude product, which was purified by column chromatography on silica gel (eluent: 0-5% MeOH in DCM) to give the title compound as a white solid.

Step 2: (3-((2-amino-4-(butylamino)-6-methylpyrimidin-5-yl)methyl)-4-methoxyphenyl)-boronic acid To a mixture of N⁴-butyl-5-(2-methoxy-5-(4,4,5,5-tetramethyl-1,3,2-dioxaborolan-2-yl)benzyl)-6-methylpyrimidine-2,4-diamine (1.0 eq) in MeOH (0.05M) was added ᵗBuB(OH)₂ (2.0 eq) and 6N HCl (¹⁄₁₀ᵗʰ of total reaction volume). The mixture was stirred at rt for 16 h under nitrogen atmosphere. The mixture was concentrated under reduced pressure and purified by prep-HPLC (mobile phase: FA/H₂O/CH₃CN) to give the title compound as a solid (formic acid salt).

LCMS: [M+H]⁺=345.3

¹H NMR (400 MHz, DMSO-d₆) δ 7.76 (s, 2H), 7.66 (d, J=7.6 Hz, 1H), 7.25 (s, 1H), 6.96 (d, J=8.0 Hz, 1H), 6.76 (br s, 1H), 6.56 (br s, 2H), 3.86 (s, 3H), 3.63 (s, 2H), 3.30-3.28 (m, 2H), 2.06 (s, 3H), 1.44-1.41 (m, 2H), 1.18-1.15 (m, 2H), 0.82 (t, J=7.2 Hz, 3H).

Example 25: 4-(3-((2-amino-4-(butylamino)-6-methylpyrimidin-5-yl)methyl)-4-methoxybenzamido)butanoic acid (Compound 25)

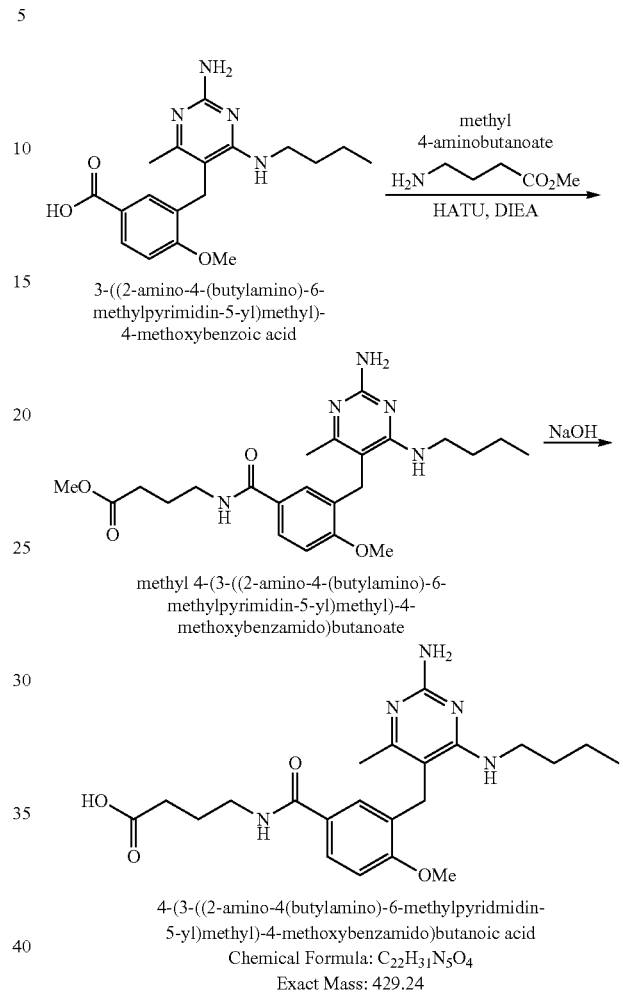

3-((2-amino-4-(butylamino)-6-methylpyrimidin-5-yl)methyl)-4-methoxybenzoic acid methyl 4-(3-((2-amino-4-(butylamino)-6-methylpyrimidin-5-yl)methyl)-4-methoxybenzamido)butanoate 4-(3-((2-amino-4(butylamino)-6-methylpyridmidin-5-yl)methyl)-4-methoxybenzamido)butanoic acid
Chemical Formula: C₂₂H₃₁N₅O₄
Exact Mass: 429.24

Step 1: methyl 4-(3-((2-amino-4-(butylamino)-6-methylpyrimidin-5-yl)methyl)-4-methoxy-benzamido)butanoate A mixture of 3-((2-amino-4-(butylamino)-6-methylpyrimidin-5-yl)methyl)-4-methoxybenzoic acid (1.0 eq, from Example 16—Step 1) in DMF (0.06M), methyl 4-aminobutanoate (1.0 eq), HATU (1.5 eq) and DIEA (4.0 eq) was stirred at 50° C. for 5 h. The mixture was cooled to rt and water was added. The aqueous layer was extracted with DCM. The combined organic layers were dried over Na₂SO₄ and concentrated under reduced pressure. The residue was purified by column chromatography on silica gel (eluent: DCM/MeOH=100:1 to 10:1) to give the title compound as a brown solid.

Step 2: 4-(3-((2-amino-4-(butylamino)-6-methylpyrimidin-5-yl)methyl)-4-methoxy-benzamido)butanoic acid To a stirred solution of methyl 4-(3-((2-amino-4-(butylamino)-6-methylpyrimidin-5-yl)methyl)-4-methoxybenzamido)butanoate (1.0 eq) in MeOH (0.025M) was added 1N NaOH (6 eq). The resulting mixture was stirred at 50° C. for 2 h. The mixture was cooled to rt and adjusted to pH 7 using 1N HCl. The precipitated solids were collected by filtration and triturated with water, dried under vacuum to give the title compound as a white solid.

LCMS: [M+H]⁺=430.3

¹H NMR (400 MHz, DMSO) δ 8.28 (br s, 1H), 7.70 (d, J=9.2 Hz, 1H), 7.29 (s, 1H), 7.02 (d, J=8.8 Hz, 1H), 5.99 (br s, 1H), 5.81-5.79 (m, 2H), 3.89 (s, 3H), 3.62 (s, 2H), 2.36-3.16 (m, 4H), 2.21 (t, J=7.2 Hz, 2H), 1.98 (s, 3H), 1.72-1.67 (m, 2H), 1.42-1.38 (m, 2H), 1.20-1.14 (m, 2H), 0.81 (t, J=7.6 Hz, 3H).

Example 26: 5-(5-((2H-tetrazol-5-yl)methyl)-2-methoxybenzyl)-6-methyl-M-pentylpyrimidine-2,4-diamine (Compound 26)

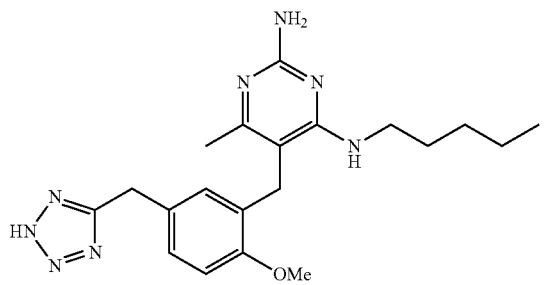

5-(5-((2H-tetrazol-5-yl)methyl)-2-methoxybenzyl)-6-methyl-N⁴-pentylpyrimidine-2,4-diamine
Chemical Formula: C₂₀H₂₈N₈O
Exact Mass: 396.24

The title compound was prepared according to the procedures described in Example 3, but using pentan-1-amine instead of butan-1-amine in Step 5. The final product was purified by prep-HPLC (mobile phase CH₃CN/H₂O/HCOOH), freeze-dried to give the title compound as a white solid (formic acid salt).

LC-MS: [M+H]⁺=397.2

¹H NMR (400 MHz, DMSO) δ 7.03 (d, J=8.8 Hz, 1H), 6.91 (d, J=8.0 Hz, 1H), 6.74 (s, 1H), 6.64 (br s, 1H), 6.48 (br s, 2H), 3.97 (s, 2H), 3.81 (s, 3H), 3.61 (s, 2H), 3.30-3.24 (m, 2H), 2.04 (s, 3H), 1.46-1.40 (m, 2H), 1.29-1.21 (m, 2H), 1.20-1.39 (m, 2H), 0.83 (t, J=6.8 Hz, 3H).

Example 27: (S)-3-(2-amino-6-((1-hydroxyheptan-3-yl)amino)-5-(2-methoxybenzyl)-pyrimidin-4-yl)propanoic acid (Compound 27)

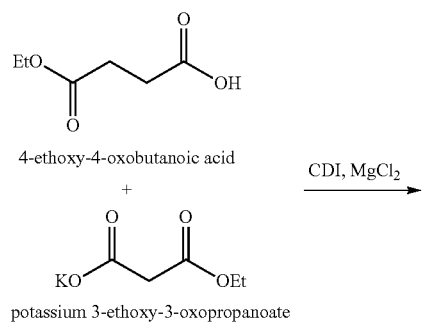

4-ethoxy-4-oxobutanoic acid
+
potassium 3-ethoxy-3-oxopropanoate

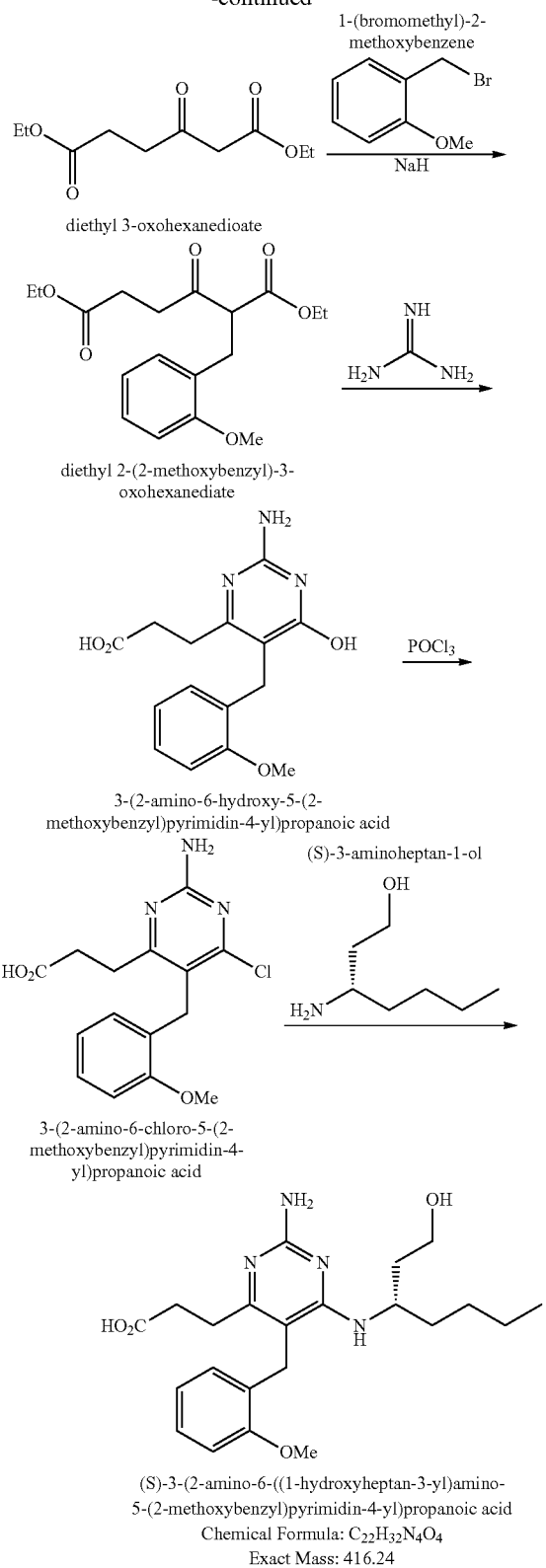

diethyl 3-oxohexanedioate diethyl 2-(2-methoxybenzyl)-3-oxohexanediate 3-(2-amino-6-hydroxy-5-(2-methoxybenzyl)pyrimidin-4-yl)propanoic acid 3-(2-amino-6-chloro-5-(2-methoxybenzyl)pyrimidin-4-yl)propanoic acid (S)-3-(2-amino-6-((1-hydroxyheptan-3-yl)amino-5-(2-methoxybenzyl)pyrimidin-4-yl)propanoic acid
Chemical Formula: C₂₂H₃₂N₄O₄
Exact Mass: 416.24

Step 1: diethyl 3-oxohexanedioate

To a solution of 4-ethoxy-4-oxobutanoic acid (1.0 eq) in anhydrous THF (0.5M) at r.t. was added carbonyl di-imidazole (1.2 eq) under $N_2$. The resulting mixture was stirred at r.t. for 1 h, then $MgCl_2$ (1.0 eq) and potassium 3-ethoxy-3-oxopropanoate (1.0 eq) were added into the above solution at r.t. and heated at 60° C. for 2 h. The mixture was filtered and the filtration was concentrated under reduced pressure to give the crude product, which was purified by column chromatography on silica (eluent: PE/EA=100:1 to 3:1) to give the title compound as a yellow oil.

Step 2: diethyl 2-(2-methoxybenzyl)-3-oxohexanedioate

To a solution of diethyl 3-oxohexanedioate (1.2 eq) in anhydrous THF (1.2M) was added 60% NaH (1.3 eq) in portions at 0° C. After stirring for 10 min, a solution of 1-(bromomethyl)-2-methoxybenzene (1.0 eq; from Example 15—Step 1) in THF (1M) was added dropwise into above mixture. The resulting mixture was stirred at 60° C. for 16 h and quenched with water. The mixture was extracted with EA, and the combined organic layers were dried over $Na_2SO_4$, concentrated under reduced pressure. The residue was purified by flash chromatography on silica (eluent: PE/EA=50:1 to 10:1) to give the title compound as a yellow oil.

Step 3: 3-(2-amino-6-hydroxy-5-(2-methoxybenzyl)pyrimidin-4-yl)propanoic acid A mixture of diethyl 2-(2-methoxybenzyl)-3-oxohexanedioate (1.0 eq) and guanidine carbonate (1.0 eq) in MeOH (0.3M) was stirred at 90° C. for 16 h. The precipitate was collected by filtration, washed with water, and dried in vacuum to give the title compound as a white solid.

Step 4: 3-(2-amino-6-chloro-5-(2-methoxybenzyl)pyrimidin-4-yl)propanoic acid A solution of 3-(2-amino-6-hydroxy-5-(2-methoxybenzyl)pyrimidin-4-yl)propanoic acid (1.0 eq) in $POCl_3$ (0.26M) was stirred at 100° C. for 2 h under nitrogen. The reaction was cooled to rt and $POCl_3$ was evaporated under reduced pressure. The residue was diluted with water and the pH was adjusted to 7 by adding solid $NaHCO_3$. The mixture was stirred at 50° C. for 1 h, then cooled to rt, and the precipitate was collected by filtration. The filter cake was washed with water, dried in vacuum to give the title compound as a white solid.

Step 5: (S)-3-(2-amino-6-((1-hydroxyheptan-3-yl)amino)-5-(2-methoxybenzyl)pyrimidin-4-yl)propanoic acid A solution of 3-(2-amino-6-chloro-5-(2-methoxybenzyl)pyrimidin-4-yl)propanoic acid (1.0 eq) in neat (S)-3-aminoheptan-1-ol (1.6M; prepared from *J. Med. Chem.* 2016, 59, 7936-7949) was stirred at 120° C. for 2 h. The mixture was diluted with water, and the aqueous phase was extracted with EA. The combined organic layers were washed with 1N HCl, brine, dried over $Na_2SO_4$, and concentrated. The crude was purified by prep-HPLC (mobile phase: $NH_4OH$/MeCN/$H_2O$) to give the title compound white solid.

LCMS: $[M+H]^+=417.3$ $^1H$ NMR (400 MHz, $CD_3OD$) δ 7.24 (t, J=8.0 Hz, 1H), 7.02-6.96 (m, 2H), 6.89 (t, J=7.2 Hz, 1H), 4.42-4.40 (m, 1H), 3.92 (s, 3H), 3.82 (s, 2H), 3.46-3.38 (m, 2H), 2.95-2.90 (m, 2H), 2.48 (t, J=7.2 Hz, 2H), 1.8-1.0 (m, 8H), 0.80 (t, J=7.2 Hz, 3H).

Example 28: N-(3-(2H-tetrazol-5-yl)propyl)-3-((2-amino-4-(butylamino)-6-methyl-pyrimidin-5-yl)methyl)-4-methoxybenzamide (Compound 28)

1,3-dioxoisoindolin-2-ide

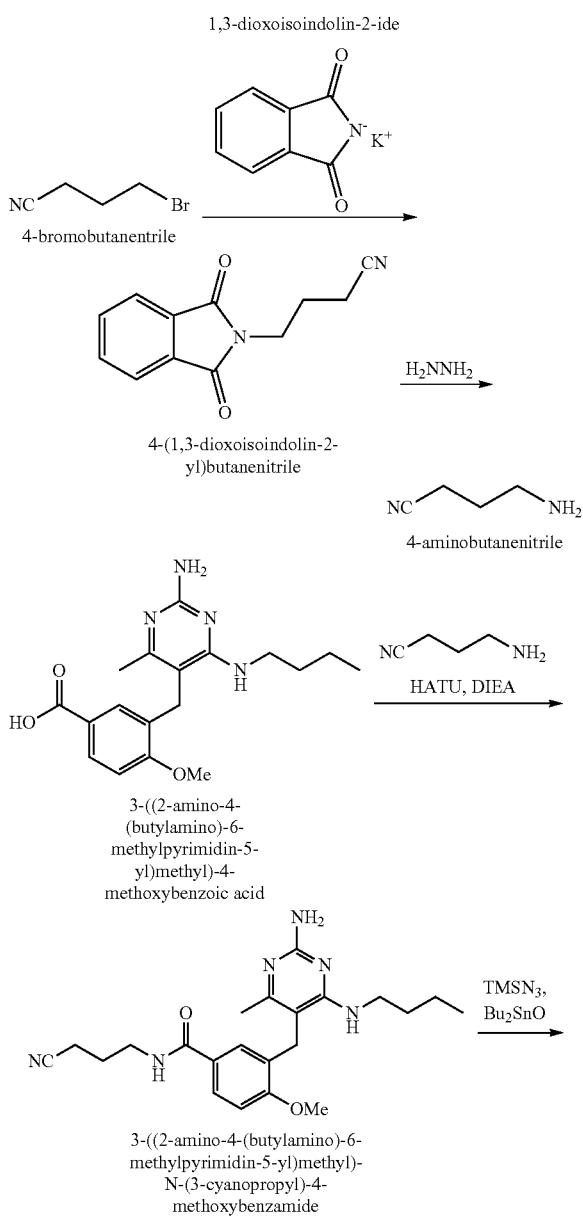

-continued

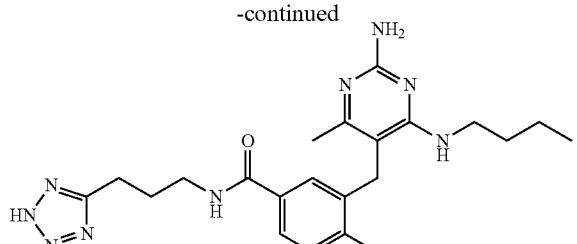

N-(3-(2H-tetrazol-5-yl)propyl)-3-((2-amino-4-(butylamino)-6-methylpyrimidin-5-yl)methyl)-4-methoxybenzamide
Chemical Formula: C₂₂H₃₁N₉O₂
Exact Mass: 453.26

Step 1: 4-(1,3-dioxoisoindolin-2-yl)butanenitrile

A mixture of 4-bromobutanenitrile (1.5 eq) and 1,3-dioxoisoindolin-2-ide (1.0 eq) in DMF (0.3M) was stirred at 100° C. for 8 h. The mixture was filtered and the filtrate was concentrated under reduced pressure. The residue was purified by flash chromatography on silica (eluent: PE/EA=100:1 to 1:1) to give the title compound as a white solid.

Step 2: 4-aminobutanenitrile

A solution of 4-(1,3-dioxoisoindolin-2-yl)butanenitrile (1.0 eq) in EtOH (0.26M) was added NH₂NH₂—H₂O (2.0 eq) and stirred at rt for 16 h. The mixture was concentrated, then diluted with water. The aqueous phase was extracted with DCM. The combined organic phase was dried over Na₂SO₄, concentrated under reduced pressure to give the title compound as a brown oil.

Step 3: 3-((2-amino-4-(butylamino)-6-methylpyrimidin-5-yl)methyl)-N-(3-cyanopropyl)-4-methoxybenzamide A mixture of 3-((2-amino-4-(butylamino)-6-methylpyrimidin-5-yl)methyl)-4-methoxybenzoic acid (1.0 eq; from Example 16—Step 1) in DMF (0.09M), 4-aminobutanenitrile (2.0 eq), HATU (2.0 eq) DIEA (3.0 eq) was stirred at 50° C. for 5 h. The mixture was cooled to rt, then water was added and the aqueous phase was extracted with DCM. The combined organic phase was dried over Na₂SO₄, concentrated under reduced pressure. The residue was purified by flash chromatography on silica (PE/EA=50:1 to 1:2) to give the title compound as a brown solid.

Step 4: N-(3-(2H-tetrazol-5-yl)propyl)-3-((2-amino-4-(butylamino)-6-methylpyrimidin-5-yl)methyl)-4-methoxybenzamide To a stirred solution of 3-((2-amino-4-(butylamino)-6-methylpyrimidin-5-yl)methyl)-N-(3-cyanopropyl)-4-methoxybenzamide (1.0 eq) in NMP (0.08M) was added Bu₂SnO (2.0 eq) and TMSN₃ (10.0 eq). The resulting mixture was stirred overnight at 125° C. under N₂. The mixture was cooled to rt, concentrated and purified by prep-HPLC (mobile phase: CH₃CN/H₂O/0.1% NH₄OH) to give the title compound as a solid.

LC-MS: [M+H]⁺=454.5

¹H NMR (400 MHz, DMSO) δ 8.45 (s, 1H), 7.74 (d, J=8.0 Hz, 1H), 7.32 (s, 1H), 7.04 (d, J=8.8 Hz, 1H), 6.57 (br s, 1H), 6.30-6.20 (m, 2H), 3.90 (s, 3H), 3.65 (s, 2H), 3.30-3.26 (m, 4H), 2.82 (t, J=7.2 Hz, 2H), 2.03 (s, 3H), 1.90 (t, J=6.8 Hz, 2H), 1.46-1.38 (m, 2H), 1.23-1.12 (m, 2H), 0.80 (t, J=7.2 Hz, 3H).

Example 29: (S)-3-((2-amino-6-(2-carboxyethyl)-5-(2-methoxybenzyl)pyrimidin-4-yl)amino)heptanoic acid (Compound 29)

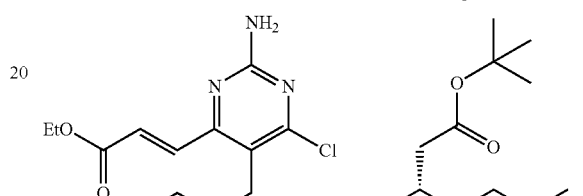

ethyl (E)-3-(2-amino-6-chloro-5-(2-methoxybenzyl)pyrimidin-4-yl)acrylate tert-butyl (S)-3-aminoheptanoate

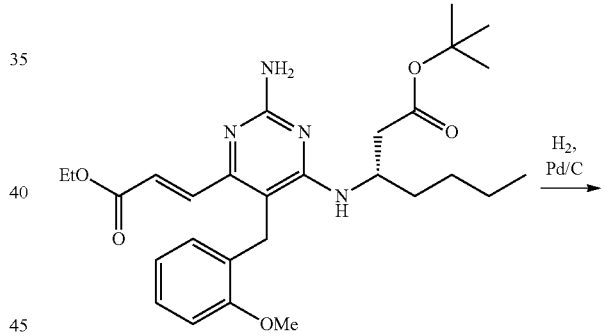

tert-butyl (S,E)-3-((2-amino-6-(3-ethoxy-3-oxoprop-1-en-1-yl)-5-(2-methoxybenzyl)pyrimidin-4-yl)amino)heptanoate

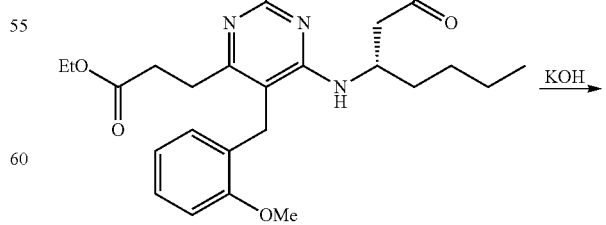

tert-butyl (S)-3-((2-amino-6-(3-ethoxy-3-oxopropyl)-5-(2-methoxybenzyl)pyrimidin-4-yl)amino)heptanoate -continued

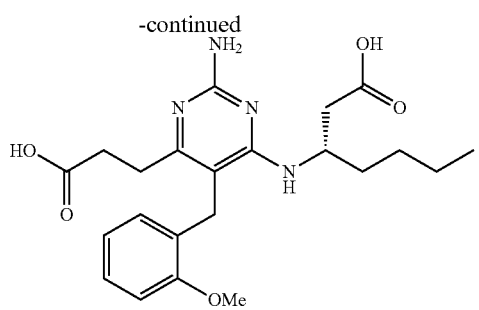

(S)-3-((2-amino-6-(2-carboxyethyl)-5-
(2-methoxybenzyl)pyrimidin-4-
yl)amino)heptanoic acid
Chemical Formula: $C_{22}H_{30}N_4O_5$
Exact Mass: 430.22

Step 1: tert-butyl (S,E)-3-((2-amino-6-(3-ethoxy-3-oxoprop-1-en-1-yl)-S-(2-methoxybenzyl)-pyrimidin-4-yl)amino)heptanoate A solution of ethyl (E)-3-(2-amino-6-chloro-5-(2-methoxybenzyl)pyrimidin-4-yl)acrylate (1.0 eq, from Example 15—Step 5) in neat tert-butyl (S)-3-aminoheptanoate (0.6M, from Example 20B—Step 3) was stirred at 120° C. for 2 h. The reaction solution was diluted with water, and the aqueous layer was extracted with EA. Combined organic layers were washed with water, brine, dried over $Na_2SO_4$, and concentrated. The crude was purified by column chromatography (DCM/MeOH=10:1) to give the title compound as a yellow solid.

Step 2: tert-butyl (S)-3-((2-amino-6-(3-ethoxy-3-oxopropyl)-S-(2-methoxybenzyl)pyrimidin-4-yl)amino)heptanoate To a solution of tert-butyl (S,E)-3-((2-amino-6-(3-ethoxy-3-oxoprop-1-en-1-yl)-S-(2-methoxy-benzyl)-pyrimidin-4-yl)amino)heptanoate (1.0 eq) in MeOH (0.04M) was added Pd/C (⅓ weight equivalent). The mixture was stirred under $H_2$ atmosphere at room temperature for 2 h. The Pd/C was filtered off, and the filtrate was concentrated to give the title compound as a yellow solid.

Step 3: (S)-3-((2-amino-6-(2-carboxyethyl)-5-(2-methoxybenzyl)pyrimidin-4-yl)amino)-heptanoic acid To a solution of tert-butyl (S)-3-((2-amino-6-(3-ethoxy-3-oxopropyl)-S-(2-methoxybenzyl)-pyrimidin-4-yl)amino) heptanoate (1.0 eq) in 4:1 EtOH/$H_2O$ (0.06M) was added KOH (5.0 eq). The solution was stirred at 100° C. for 3 h. pH was adjusted to 7 using acetic acid, and the solution was concentrated and then purified by prep-HPLC (mobile phase: $NH_4OH/MeCN/H_2O$) to give the title compound as a white solid.

LC-MS: $[M+H]^+$=431.4

$^1$H NMR (400 MHz, $CD_3OD$) δ 7.23 (t, J=7.2 Hz, 1H), 7.01-6.97 (m, 2H), 6.89 (t, J=7.2 Hz, 1H), 4.61 (m, 1H), 3.91 (s, 3H), 3.82 (s, 2H), 2.94-2.92 (m, 2H), 2.47-2.41 (m, 2H), 1.6-0.9 (m, 8H), 0.80 (t, J=7.2 Hz, 3H).

Example 30: (3-(3-((2-amino-4-(butylamino)-6-methylpyrimidin-5-yl)methyl)-4-methoxybenzamido)propyl)phosphonic acid (Compound 30)

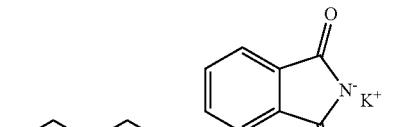

diethyl (3-bromopropyl)phosphonate 1,3-dioxoisoindolin-2-ide

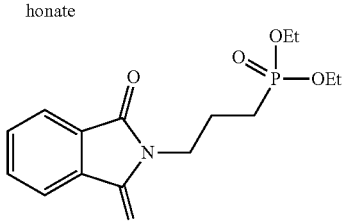

diethyl (3-(1,3-dioxoisoindolin-2-yl)propyl)phosphonate

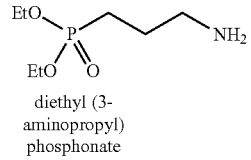

diethyl (3-aminopropyl)phosphonate

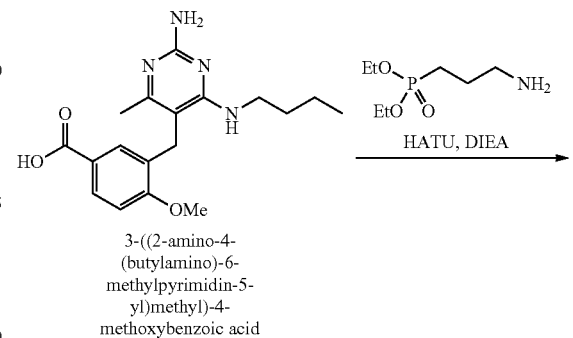

3-((2-amino-4-(butylamino)-6-methylpyrimidin-5-yl)methyl)-4-methoxybenzoic acid

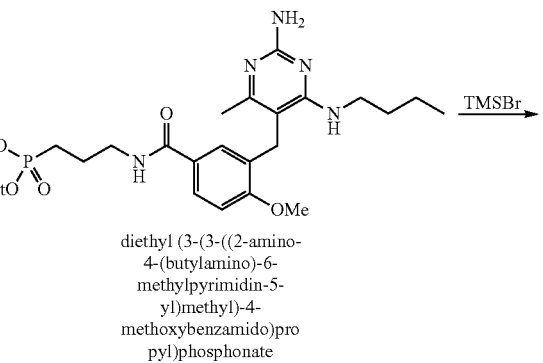

diethyl (3-(3-((2-amino-4-(butylamino)-6-methylpyrimidin-5-yl)methyl)-4-methoxybenzamido)propyl)phosphonate

301

-continued

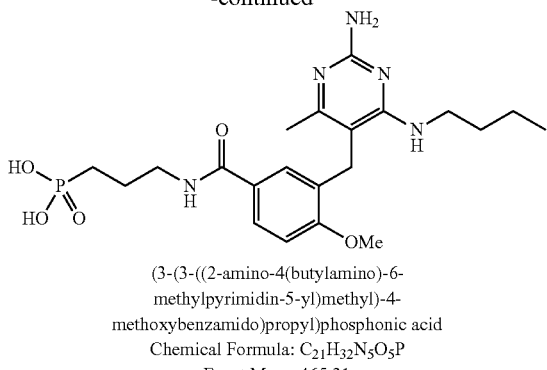

(3-(3-((2-amino-4(butylamino)-6-methylpyrimidin-5-yl)methyl)-4-methoxybenzamido)propyl)phosphonic acid
Chemical Formula: $C_{21}H_{32}N_5O_5P$
Exact Mass: 465.21

Step 1: diethyl (3-(1,3-dioxoisoindolin-2-yl)propyl)phosphonate

A mixture of diethyl (3-bromopropyl)phosphonate (1.2 eq) and 1,3-dioxoisoindolin-2-ide (1.0 eq) in DMF (0.2M) was stirred at 100° C. for 8 h. The reaction was filtered, and the filtrate was concentrated under reduced pressure to give the title compound as a white solid.

Step 2: diethyl (3-aminopropyl)phosphonate

A mixture of diethyl (3-(1,3-dioxoisoindolin-2-yl)propyl) phosphonate (1.0 eq) in EtOH (0.25M) and $NH_2NH_2.H_2O$ (2.0 eq) was stirred at rt for 16 h. The reaction was filtered, the filtrate was poured in water, and the aqueous phase was extracted with DCM. The organic phase was dried over $Na_2SO_4$, concentrated under reduced pressure to give the title compound as a brown oil.

Step 3: diethyl (3-(3-((2-amino-4-(butylamino)-6-methylpyrimidin-5-yl)methyl)-4-methoxy-benzamido)propyl)phosphonate A mixture of 3-((2-amino-4-(butylamino)-6-methylpyrimidin-5-yl)methyl)-4-methoxybenzoic acid (1.0 eq; from Example 16—Step 1) in DMF (0.1M), diethyl (3-aminopropyl)phosphonate (2.0 eq), HATU (2.0 eq) and DIEA (3.0 eq) was stirred at 50° C. for 5 h under nitrogen. The mixture was cooled to rt, diluted with water, and the aqueous phase was extracted with DCM. The organic phase was dried over $Na_2SO_4$, concentrated under reduced pressure to give the title compound as a brown solid.

Step 4: (3-(3-((2-amino-4-(butylamino)-6-methylpyrimidin-5-yl)methyl)-4-methoxy-benzamido)propyl)phosphonic acid A solution of diethyl (3-(3-((2-amino-4-(butylamino)-6-methylpyrimidin-5-yl)methyl)-4-methoxybenzamido)propyl)phosphonate (1.0 eq) in DCM (0.08M) and TMSBr (10.0 eq) was stirred overnight at rt under nitrogen. The mixture was concentrated, purified by prep-HPLC (mobile phase $CH_3CN/H_2O/0.1\%$ $NH_4OH$) to give the title compound as a solid.

302

LC-MS: $[M+H]^+=466.4$ $^1H$ NMR (400 MHz, DMSO) δ 8.59 (s, 1H), 7.76 (d, J=8.0 Hz, 1H), 7.27 (s, 1H), 7.20 (br s, 1H), 7.03 (d, J=8.4 Hz, 1H), 3.88 (s, 3H), 3.64 (s, 2H), 3.35-3.28 (m, 2H), 3.25-3.16 (m, 2H), 2.07 (s, 3H), 1.74-1.62 (m, 2H), 1.48-1.33 (m, 4H), 1.22-1.11 (m, 2H), 0.81 (t, J=7.2 Hz, 3H).

Example 31: 5-((5-((2H-tetrazol-5-yl)methyl)-2-methoxyphenyl)thio)-$N^4$-butyl-6-methylpyrimidine-2,4-diamine (Compound 31)

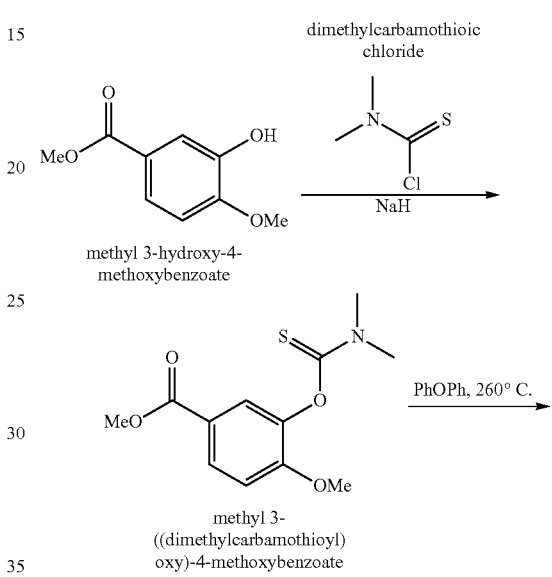

methyl 3-hydroxy-4-methoxybenzoate methyl 3-((dimethylcarbamothioyl)oxy)-4-methoxybenzoate methyl 3-((dimethylcarbarmoyl)thio)-4-methoxybenzoate

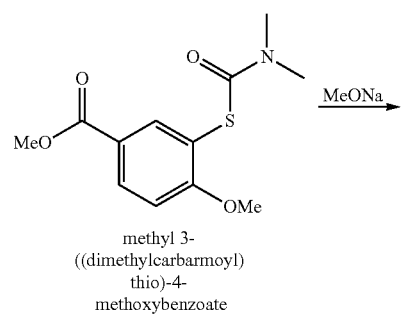

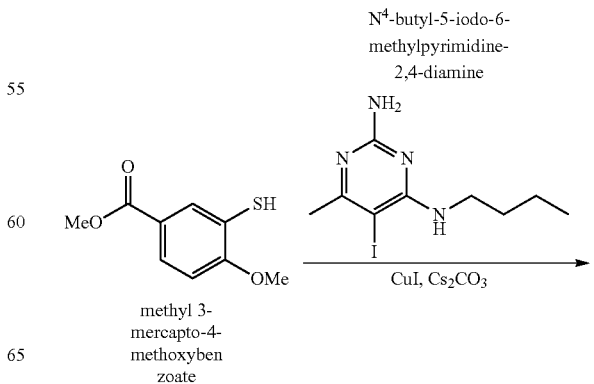

methyl 3-mercapto-4-methoxybenzoate $N^4$-butyl-5-iodo-6-methylpyrimidine-2,4-diamine

303
-continued

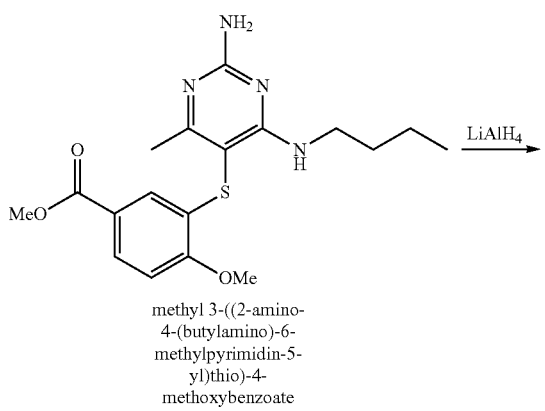

methyl 3-((2-amino-
4-(butylamino)-6-
methylpyrimidin-5-
yl)thio)-4-
methoxybenzoate

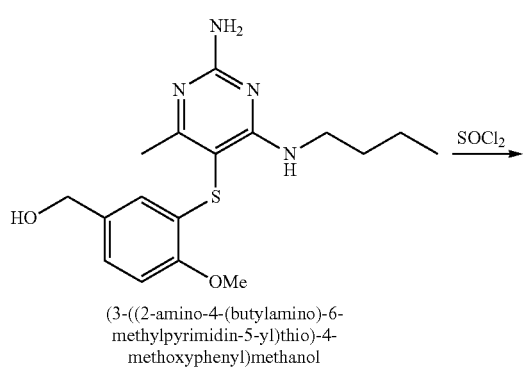

(3-((2-amino-4-(butylamino)-6-
methylpyrimidin-5-yl)thio)-4-
methoxyphenyl)methanol

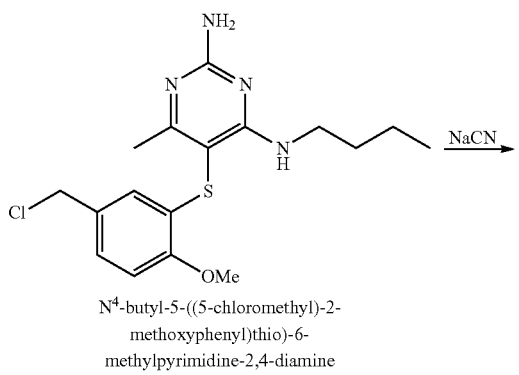

$N^4$-butyl-5-((5-chloromethyl)-2-
methoxyphenyl)thio)-6-
methylpyrimidine-2,4-diamine

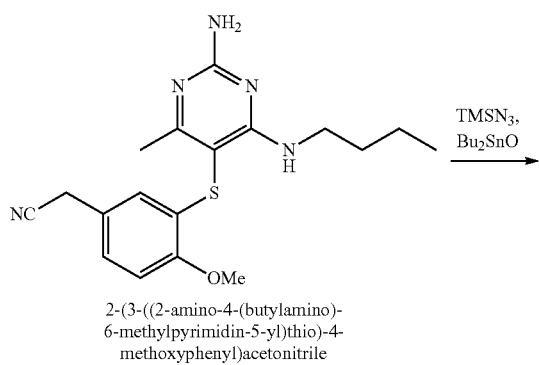

2-(3-((2-amino-4-(butylamino)-
6-methylpyrimidin-5-yl)thio)-4-
methoxyphenyl)acetonitrile

304
-continued

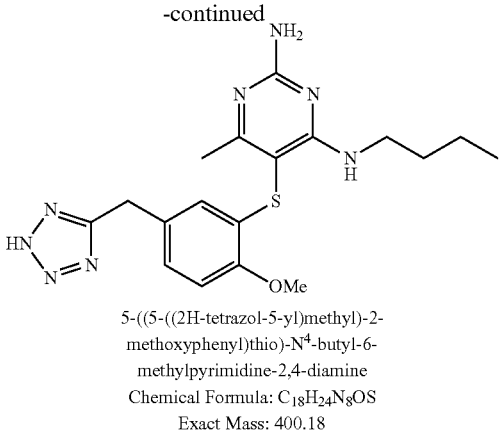

5-((5-((2H-tetrazol-5-yl)methyl)-2-
methoxyphenyl)thio)-$N^4$-butyl-6-
methylpyrimidine-2,4-diamine
Chemical Formula: $C_{18}H_{24}N_8OS$
Exact Mass: 400.18

Step 1: methyl
3-((dimethylcarbamothioyl)oxy)-4-methoxybenzoate

To a stirred solution of methyl 3-hydroxy-4-methoxybenzoate (1.0 eq) in DMF (0.55M) was added NaH (1.1 eq) at 0° C. The mixture was warmed to rt and stirred for 30 min before treated with dimethylcarbamothioic chloride (1.1 eq). The mixture was stirred overnight and partitioned between ether/water. The resulting suspension was filtered. The solid was collected and dried under vacuum to give the title compound as a white solid.

Step 2: methyl
3-((dimethylcarbamoyl)thio)-4-methoxybenzoate

Methyl 3-((dimethylcarbamothioyl)oxy)-4-methoxybenzoate (1.0 eq) in PhOPh (1M) was stirred for 16 h at 260° C. The mixture was cooled to rt and the mixture was purified by flash chromatography on silica (eluent PE/EA=100:1-2:1) to give the title compound.

Step 3: methyl 3-mercapto-4-methoxybenzoate

To a stirred solution of methyl 3-((dimethylcarbamoyl)thio)-4-methoxybenzoate (1.0 eq) in THF (0.3M) was added MeONa (2.0 eq) at rt. The resulting mixture was stirred at 60° C. for 2 h. The mixture was cooled down to rt and quenched with 1N HCl. The mixture was partitioned between EA/water. The organic phase was dried over $Na_2SO_4$ and concentrated and purified by flash chromatography on silica (eluent PE/EA=100:1~5:1) to give the title compound.

Step 4: methyl 3-((2-amino-4-(butylamino)-6-methylpyrimidin-5-yl)thio)-4-methoxybenzoate A mixture of methyl 3-mercapto-4-methoxybenzoate (1.0 eq) in dioxane (0.3M), $N^4$-butyl-5-iodo-6-methylpyrimidine-2,4-diamine (1.5 eq), $Cs_2CO_3$ (2.0 eq), CuI (2.0 eq) was stirred overnight at 100° C. The mixture was partitioned between EA/$NH_4OH$. The organic layer was washed with brine, dried over $Na_2SO_4$, concentrated and purified by flash chromatography on silica (eluent PE/EA=100:1-1:1) to give the title compound.

Step 5: (3-((2-amino-4-(butylamino)-6-methylpyrimidin-5-yl)thio)-4-methoxyphenyl)-methanol To a stirred solution of methyl 3-((2-amino-4-(butylamino)-6-methylpyrimidin-5-yl)thio)-4-methoxybenzoate (1.0 eq) in THF (0.2M) was added 1M LiAlH$_4$ (2.0 eq) dropwise at 0° C. The resulting mixture was stirred at 0° C. for 10 min and at rt for 1 h. The mixture was diluted with EA and quenched with 2N NaOH. The mixture was partitioned between EA/water. The organic layer was dried over Na$_2$SO$_4$, filtered and concentrated to give the title compound.

Step 6: N$^4$-butyl-5-((5-(chloromethyl)-2-methoxyphenyl)thio)-6-methylpyrimidine-2,4-diamine To a stirred solution of (3-((2-amino-4-(butylamino)-6-methylpyrimidin-5-yl)thio)-4-methoxyphenyl)methanol (1.0 eq) in DCM (0.2M) was added SOCl$_2$ (2.0 eq) at rt under N$_2$. The mixture was stirred at rt for 1 h. The mixture was partitioned between DCM and saturated aqueous NaHCO$_3$. The organic layer was dried over Na$_2$SO$_4$, filtered and concentrated to give the title compound.

Step 7: 2-(3-((2-amino-4-(butylamino)-6-methylpyrimidin-5-yl)thio)-4-methoxyphenyl)acetonitrile A mixture of N$^4$-butyl-5-((5-(chloromethyl)-2-methoxyphenyl)thio)-6-methylpyrimidine-2,4-diamine (1.0 eq) in 1:1 DMSO/DMF (0.1M) and NaCN (3.0 eq) was stirred overnight at rt. The mixture was partitioned between EA/water. The organic layer was dried over Na$_2$SO$_4$, filtered, concentrated and purified by flash chromatography on silica (eluent 0-5% MeOH in DCM) to give the title compound.

Step 8: 5-((5-((2H-tetrazol-5-yl)methyl)-2-methoxyphenyl)thio)-M-butyl-6-methylpyrimidine-2,4-diamine A mixture of 2-(3-((2-amino-4-(butylamino)-6-methylpyrimidin-5-yl)thio)-4-methoxyphenyl)acetonitrile (1.0 eq) in NMP (0.1M), Bu$_2$SnO (2.0 eq), and TMSN$_3$ (10.0 eq) was stirred for 3 h at 120° C. under N$_2$. The mixture was cooled down to rt and the mixture was concentrated and purified by prep-HPLC (mobile phase CH$_3$CN/H$_2$O/NH$_4$OH), freeze-dried to give the title compound as a white powder.
LCMS: [M+H]$^+$=401.4
$^1$H NMR (400 MHz, DMSO) δ 7.03-6.92 (m, 2H), 6.46-6.42 (m, 2H), 6.39 (s, 2H), 4.06 (s, 2H), 3.83 (s, 3H), 3.26-3.21 (m, 2H), 2.14 (s, 3H), 1.39-1.32 (m, 2H), 1.17-1.1.10 (m, 2H), 0.81 (t, J=7.2 Hz, 3H).

Example 32: (S)-5-(5-((2H-tetrazol-5-yl)methyl)-2-methoxybenzyl)-N$^4$-(1-methoxyheptan-3-yl)-6-methylpyrimidine-2,4-diamine (Compound 32)

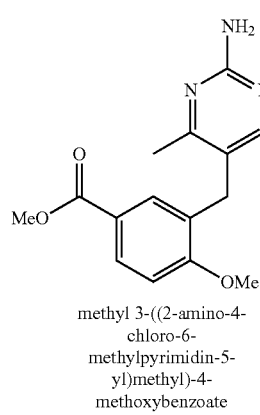

methyl 3-((2-amino-4-chloro-6-methylpyrimidin-5-yl)methyl)-4-methoxybenzoate

LiAlH$_4$ →

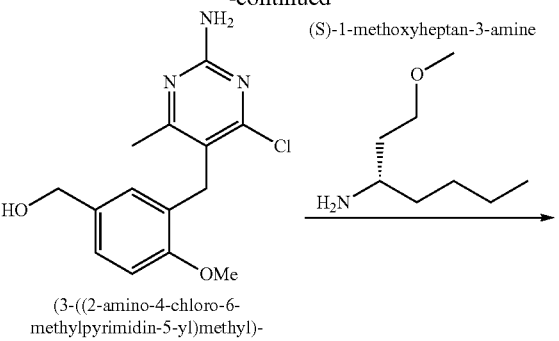

(3-((2-amino-4-chloro-6-methylpyrimidin-5-yl)methyl)-4-methoxyphenyl)methanol (S)-1-methoxyheptan-3-amine

H$_2$N →

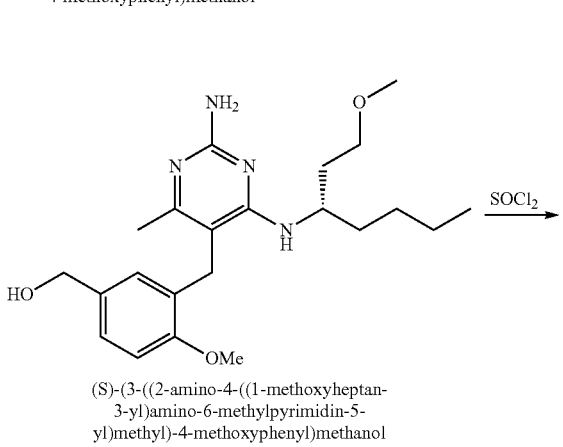

(S)-(3-((2-amino-4-((1-methoxyheptan-3-yl)amino)-6-methylpyrimidin-5-yl)methyl)-4-methoxyphenyl)methanol SOCl$_2$ →

(S)-5-(5-(chloromethyl)-2-methoxybenzyl)-N$^4$-(1-methoxyheptan-3-yl)-6-methylpyrimidine-2,4-diamine NaCN →

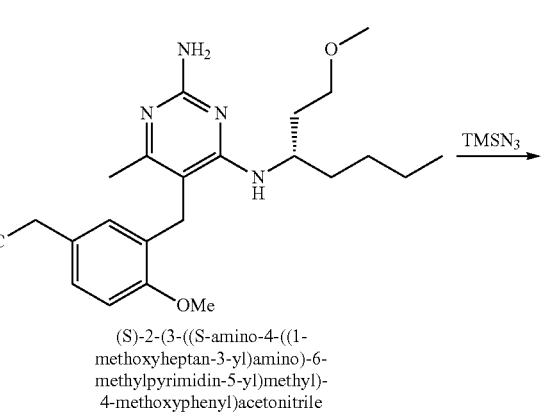

(S)-2-(3-((S-amino-4-((1-methoxyheptan-3-yl)amino)-6-methylpyrimidin-5-yl)methyl)-4-methoxyphenyl)acetonitrile

TMSN$_3$ →

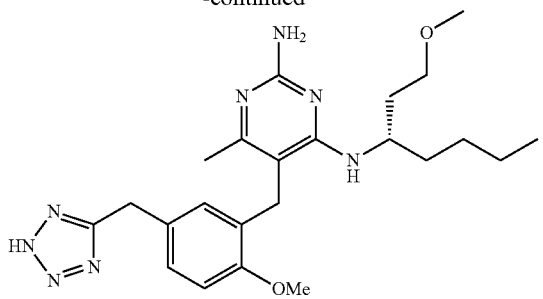

(S)-5-(5-((2H-tetrazol-5-yl)methyl)-2-
methoxybenzyl)-N⁴-(1-methoxyheptan-3-
yl)-6-methylpyrimidine-2,4-diamine
Chemical Formula: $C_{23}H_{34}N_8O_2$
Exact Mass: 454.28

Step 1: (3-((2-amino-4-chloro-6-methylpyrimidin-5-yl)methyl)-4-methoxyphenyl)methanol To a solution of methyl 3-((2-amino-4-chloro-6-methyl-pyrimidin-5-yl)methyl)-4-methoxybenzoate (1.0 eq, from Example 3B—Step 4) in THF (1.6M) was added LiAlH₄ (3.0 eq) at r.t. The reaction was stirred at r.t. for 2 h. The reaction solution was diluted with water. The aqueous layer was extracted with DCM. The organic layer was washed with water, brine, separated, dried over Na₂SO₄, and concentrated to give the title compound as a pale solid.

Step 2: (S)-(3-((2-amino-4-((1-methoxyheptan-3-yl)amino)-6-methylpyrimidin-5-yl)methyl)-4-methoxyphenyl)methanol A mixture of (3-((2-amino-4-chloro-6-methylpyrimidin-5-yl)methyl)-4-methoxyphenyl)methanol (1.0 eq) in NMP (0.4M) and (S)-1-methoxyheptan-3-amine (2.0 eq) was stirred at 120° C. for 16 h under nitrogen. The reaction solution was diluted with water. The aqueous phase was extracted with EA. The organic layer was washed with water, brine, dried over Na₂SO₄, and concentrated. The crude was purified by column chromatography (DCM/MeOH=50:1) to give the title compound as a yellow solid.

Step 3: (S)-5-(5-(chloromethyl)-2-methoxybenzyl)-N⁴-(1-methoxyheptan-3-yl)-6-methylpyrimidine-2,4-diamine To a stirred solution of (S)-(3-((2-amino-4-((1-methoxy-heptan-3-yl)amino)-6-methylpyrimidin-5-yl)methyl)-4-methoxy-phenyl)methanol (1.0 eq) in DCM (0.3M) was added SOCl₂ (2.0 eq) dropwise. The resulting mixture was stirred at 20° C. for 1 h, then quenched with H₂O. The mixture was partitioned between DCM/water. The organic layer was separated, dried over Na₂SO₄, filtered, and concentrated to give the title compound as a brown oil.

Step 4: (S)-2-(3-((2-amino-4-((1-methoxyheptan-3-yl)amino)-6-methylpyrimidin-5-yl)methyl)-4-methoxyphenyl)acetonitrile A mixture of (S)-5-(5-(chloromethyl)-2-methoxybenzyl)-N⁴-(1-methoxyheptan-3-yl)-6-methylpyrimidine-2,4-diamine (1.0 eq) in DMSO (0.4M) and KCN (3.0 eq) was stirred at 80° C. for 4 h, then cooled to r.t. Water was added, and the solution was extracted with DCM. The organic phase was dried over Na₂SO₄, concentrated, and purified by column chromatography (DCM/MeOH=40:1) to give the title compound as a white solid.

Step 5: (S)-5-(5-((2H-tetrazol-5-yl)methyl)-2-methoxybenzyl)-N⁴-(1-methoxyheptan-3-yl)-6-methylpyrimidine-2,4-diamine To a stirred mixture of (S)-2-(3-((2-amino-4-((1-methoxyheptan-3-yl)amino)-6-methylpyrimidin-5-yl)methyl)-4-methoxyphenyl)acetonitrile (1.0 eq) in dioxane (0.2M) and Bu₂SnO (2.0 eq) was added TMSN₃ (10.0 eq). The resulting mixture was stirred at 110° C. for 4 h under N₂, then cooled down to r.t. The mixture was concentrated and purified by prep-HPLC (mobile phase 0.1% NH₃.H₂O/CH₃CN) to give the title compound as a solid.

LC-MS: [M+H]⁺=455.4

¹H NMR (400 MHz, CDCl₃) δ 6.86 (s, 1H), 6.84 (d, J=8.4 Hz, 1H), 6.50 (d, J=8.4 Hz, 1H), 4.28-4.23 (m, 3H), 3.90 (s, 3H), 3.58 (s, 2H), 3.19-3.16 (m, 2H), 3.14 (s, 3H), 2.50 (s, 3H), 1.83-1.81 (m, 1H), 1.59-1.06 (m, 7H), 0.83 (t, J=7.2 Hz, 3H).

Example 33: (S)-2-(3-((2-amino-4-methyl-6-((1-(methylthio)heptan-3-yl)amino)pyrimidin-5-yl)methyl)-4-methoxyphenyl)-2-methylpropanoic acid (Compound 33)

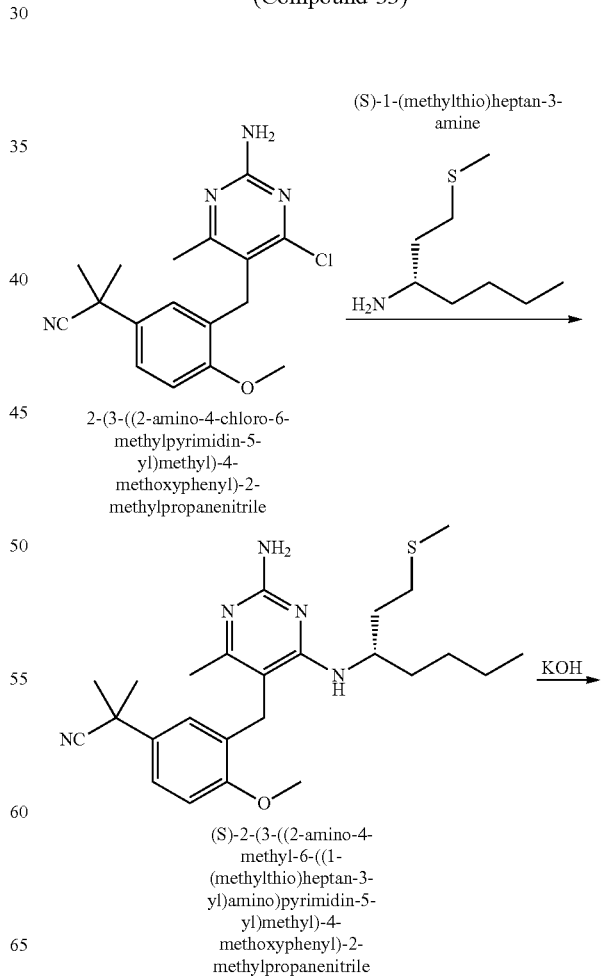

309
-continued

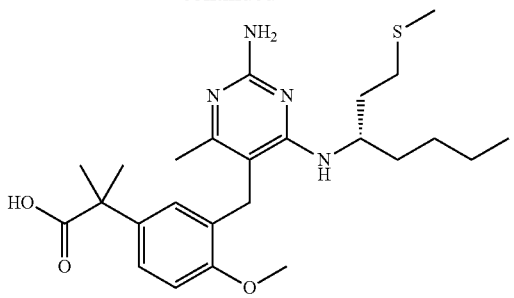

(S)-2-(3-((2-amino-4-methyl-6-
((1-(methylthio)heptan-3-
yl)amino)pyrimidin-5-
yl)methyl)-4-methoxyphenyl)-2-
methylpropanoic acid
$C_{25}H_{38}N_4O_3S$
Exact Mass: 474.27

Step 1: (S)-2-(3-((2-amino-4-methyl-6-((1-(methyl-thio)heptan-3-yl)amino)pyrimidin-5-yl)methyl)-4-methoxyphenyl)-2-methylpropanenitrile A mixture of 2-(3-((2-amino-4-chloro-6-methylpyrimidin-5-yl)methyl)-4-methoxyphenyl)-2-methylpropanenitrile (1.0 eq, from Example 9—Step 8) in NMP (0.6M), (S)-1-(methylthio)heptan-3-amine (1.5 eq; prepared by following procedures reported in WO2014/128189, pg 8, compound D) and DIEA (3.0 eq) was stirred at 120° C. for 48 h. Water was added to the mixture, and it was extracted with EtOAc. The organic layer was dried over $Na_2SO_4$ and concentrated under reduced pressure. The residue was purified by flash chromatography on silica (eluent: DCM/MeOH=100:1-20:1) to give the title compound as a brown oil.

Step 2: (S)-2-(3-((2-amino-4-methyl-6-((1-(methyl-thio)heptan-3-yl)amino)pyrimidin-5-yl)methyl)-4-methoxyphenyl)-2-methylpropanoic acid To a stirred solution of (S)-2-(3-((2-amino-4-methyl-6-((1-(methylthio)heptan-3-yl)amino)pyrimidin-5-yl)methyl)-4-methoxyphenyl)-2-methylpropanenitrile (1.0 eq) in 1:1 ethane-1,2-diol/$H_2O$ (0.1M) was added KOH (10 eq) and heated in a sealed tube at 150° C. for 16 h. The mixture was acidified by 1N HCl solution to pH=2-3 and filtered. The filtrate was purified by prep-HPLC (mobile phase $CH_3CN$/$H_2O$/$NH_3.H_2O$), then freeze-dried to give the title compound as a white solid.

LC-MS: $[M+H]^+$=475.3

$^1$H NMR (400 MHz, DMSO-$d_6$) δ 7.14 (dd, J=8.4, 2.0 Hz, 1H), 6.91 (d, J=8.8 Hz, 1H), 6.86 (s, 1H), 5.91 (br s, 2H), 5.72 (d, J=9.2 Hz, 1H), 4.25-4.15 (m, 1H), 3.82 (s, 3H), 3.62 (s, 2H), 2.31-2.25 (m, 2H), 2.02 (s, 3H), 1.95 (s, 3H), 1.70-1.52 (m, 2H), 1.44-1.34 (m, 2H), 1.31 (s, 6H), 1.25-1.05 (m, 4H), 0.78 (t, J=6.8 Hz, 3H).

310

Example 34: (S)-5-(2-methoxy-5-(2H-tetrazol-5-yl)benzyl)-6-methyl-$N^4$-(1-(methylthio)heptan-3-yl)pyrimidine-2,4-diamine (Compound 34)

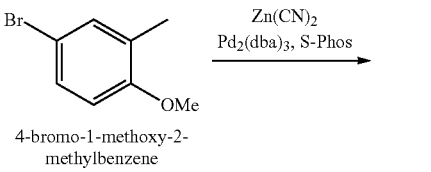

4-bromo-1-methoxy-2-methylbenzene

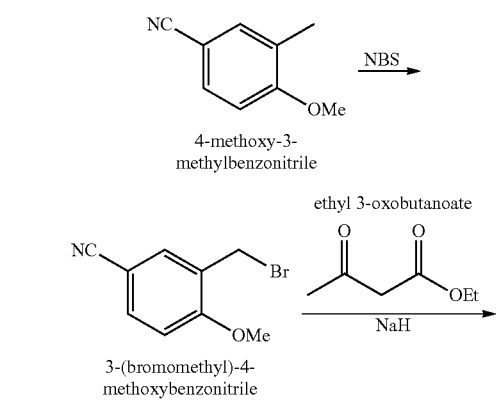

4-methoxy-3-methylbenzonitrile 3-(bromomethyl)-4-methoxybenzonitrile ethyl 3-oxobutanoate

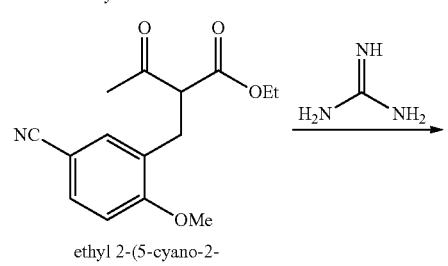

ethyl 2-(5-cyano-2-methoxybenzyl)-3-oxobutanoate

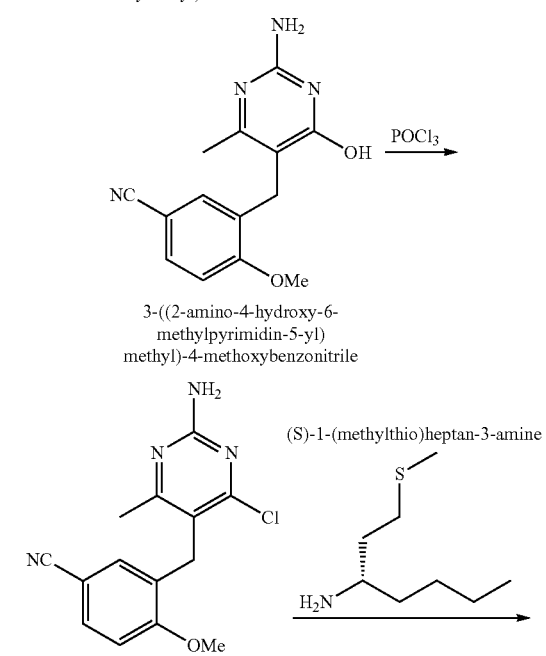

3-((2-amino-4-hydroxy-6-methylpyrimidin-5-yl)methyl)-4-methoxybenzonitrile 3-((2-amino-4-chloro-6-methylpyrimidin-5-yl)methyl)-4-methoxybenzonitrile (S)-1-(methylthio)heptan-3-amine

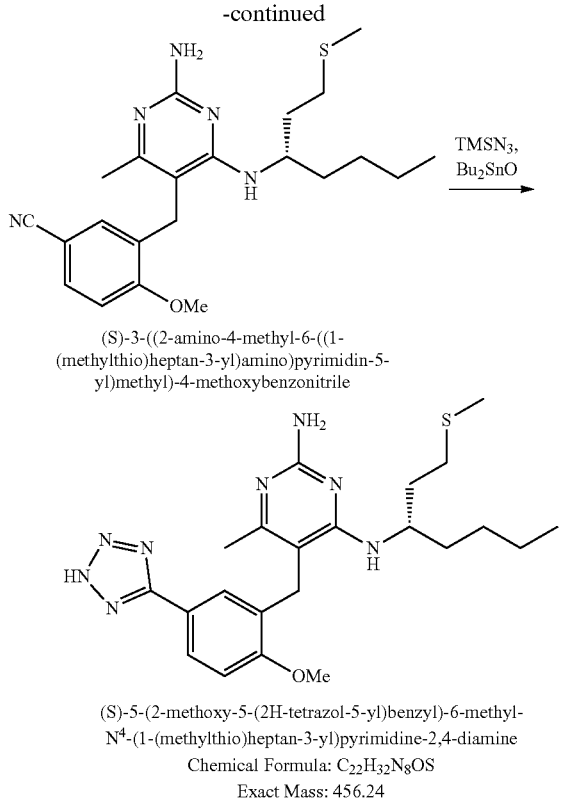

(S)-3-((2-amino-4-methyl-6-((1-(methylthio)heptan-3-yl)amino)pyrimidin-5-yl)methyl)-4-methoxybenzonitrile (S)-5-(2-methoxy-5-(2H-tetrazol-5-yl)benzyl)-6-methyl-N⁴-(1-(methylthio)heptan-3-yl)pyrimidine-2,4-diamine
Chemical Formula: $C_{22}H_{32}N_8OS$
Exact Mass: 456.24

Step 1: 4-methoxy-3-methylbenzonitrile

A mixture of 4-bromo-1-methoxy-2-methylbenzene (1.0 eq) in DMF (1M), Zn(CN)$_2$ (1.5 eq), Pd$_2$(dba)$_3$ (0.02 eq) and S-phos (0.05 eq) was stirred at 80° C. for 16 h. The resulting mixture was concentrated and purified by column chromatography on silica gel (eluent PE/EA=100:1~20:1) to give the title compound.

Step 2: 3-(bromomethyl)-4-methoxybenzonitrile

A mixture of 4-methoxy-3-methylbenzonitrile (1.0 eq) in CCl$_4$ (0.7M), NBS (1.1 eq) and AIBN (0.1 eq) was stirred at 95° C. for 16 h under nitrogen. The resulting mixture was concentrated and partitioned between DCM and water. The organic layer was dried over Na$_2$SO$_4$, concentrated, and purified by column chromatography on a silica gel (eluent PE/EA=100:1~20:1) to give the title compound as a white solid.

Step 3: ethyl 2-(5-cyano-2-methoxybenzyl)-3-oxobutanoate

To a solution of 3-(bromomethyl)-4-methoxybenzonitrile (1.5 eq) in THF (0.6M) at 0° C. was added portion-wise 60% NaH (1.5 eq) under N$_2$. The resulting suspension was stirred at 0° C. for 10 min, then a solution of ethyl 3-oxobutanoate (1.0 eq) in THF (1M) was added drop-wise over 10 min at 0° C. The resulting mixture was stirred at 70° C. for 15 h. The reaction was cooled to r.t., and ice water was added. The mixture was extracted with ethyl acetate. The organic layer was dried over Na$_2$SO$_4$, concentrated and purified by column chromatography on silica gel (eluent PE/EA=50:1~5:1) to give the title compound as yellow oil.

Step 4: 3-((2-amino-4-hydroxy-6-methylpyrimidin-5-yl)methyl)-4-methoxybenzonitrile To a solution of ethyl 2-(5-cyano-2-methoxybenzyl)-3-oxobutanoate (1.0 eq) in MeOH (0.7M) was added guanidine carbonate (1.0 eq). The resulting mixture was stirred at 70° C. for 16 h. The mixture was concentrated, and the residue was suspended in EtOAc and then filtered. The filter cake was washed with water and EtOAc. The resulting solid was collected and dried under vacuum to give the title compound as a white solid.

Step 5: 3-((2-amino-4-chloro-6-methylpyrimidin-5-yl)methyl)-4-methoxybenzonitrile The suspension of 3-((2-amino-4-hydroxy-6-methylpyrimidin-5-yl)methyl)-4-methoxybenzonitrile (1.0 eq) in POCl$_3$ (0.3M) was stirred at 100° C. for 16 h. The reaction mixture was cooled to r.t., and solvent was evaporated under reduced pressure. The residue was diluted with water, and pH was adjusted to 7 using solid NaHCO$_3$. The precipitate was collected by filtration, and the filter cake was washed with water and EtOAc, dried under vacuum to give the title compound.

Step 6: (S)-3-((2-amino-4-methyl-6-((1-(methylthio)heptan-3-yl)amino)pyrimidin-5-yl)methyl)-4-methoxybenzonitrile A mixture of 3-((2-amino-4-chloro-6-methylpyrimidin-5-yl)methyl)-4-methoxybenzonitrile (1.0 eq) in NMP (0.3M) and (S)-1-(methylthio)heptan-3-amine (1.5 eq, prepared by following procedures reported in WO2014/128189, pg 8, compound D) was stirred at 150° C. for 4 h under nitrogen. The reaction solution was diluted with water, and the aqueous phase was extracted with EA. The organic layer was washed with water, brine, dried over Na$_2$SO$_4$, and concentrated. The crude was purified by column chromatography (DCM/MeOH=50:1) to give the title compound as a yellow solid.

Step 7: (S)-5-(2-methoxy-5-(2H-tetrazol-5-yl)benzyl)-6-methyl-N⁴-(1-(methylthio)heptan-3-yl)pyrimidine-2,4-diamine To a stirred mixture of (S)-3-((2-amino-4-methyl-6-((1-(methylthio)heptan-3-yl)amino)pyrimidin-5-yl)methyl)-4-methoxybenzonitrile (1.0 eq) in dioxane (0.4M), Bu$_2$SnO (2.0 eq) was added TMSN$_3$ (10.0 eq). The resulting mixture was stirred at 110° C. for 4 h under N$_2$. The mixture was cooled to r.t., and the mixture was concentrated and purified by prep-HPLC (mobile phase 0.1% NH$_3$.H$_2$O/CH$_3$CN) to give the title compound.

LC-MS: [M+H]$^+$=457.3

$^1$H NMR (400 MHz, DMSO-d$_6$) δ 7.82 (d, J=8.8 Hz, 1H), 7.50 (s, 1H), 7.07 (d, J=8.4 Hz, 1H), 6.55 (br, 3H), 4.28-4.26 (m, 1H), 3.89 (s, 3H), 3.73 (s, 2H), 2.27 (t, J=7.6 Hz, 2H), 2.14 (s, 3H), 1.88 (s, 3H), 1.67-1.65 (m, 2H), 1.41-1.39 (m, 2H), 1.12-1.04 (m, 4H), 0.69 (t, J=6.8 Hz, 3H).

Example 35: (S)-(3-(3-((2-amino-4-methyl-6-((1-(methylthio)heptan-3-yl)amino)pyrimidin-5-yl)methyl)-4-methoxybenzamido)propyl)phosphonic acid (Compound 35)
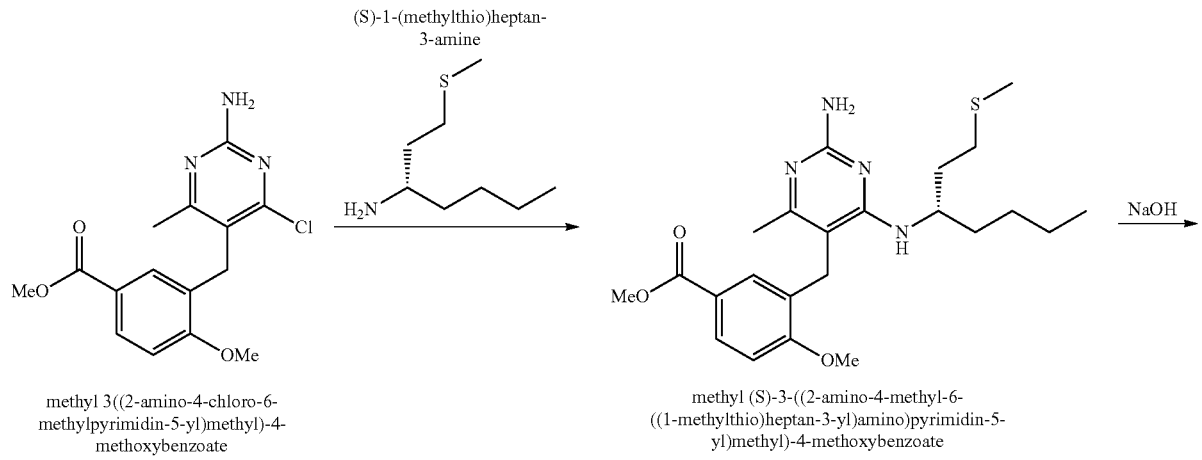
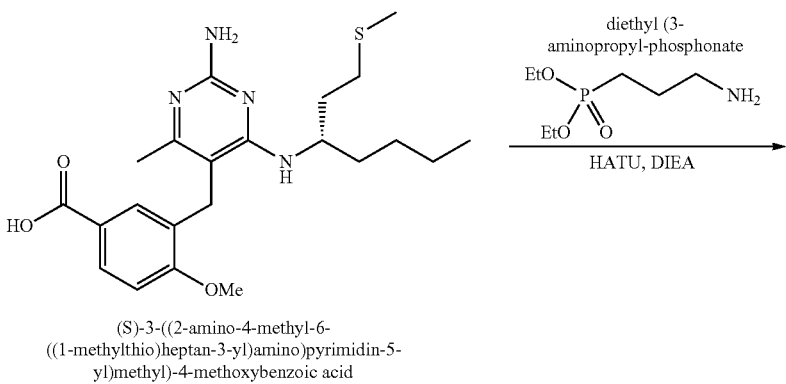
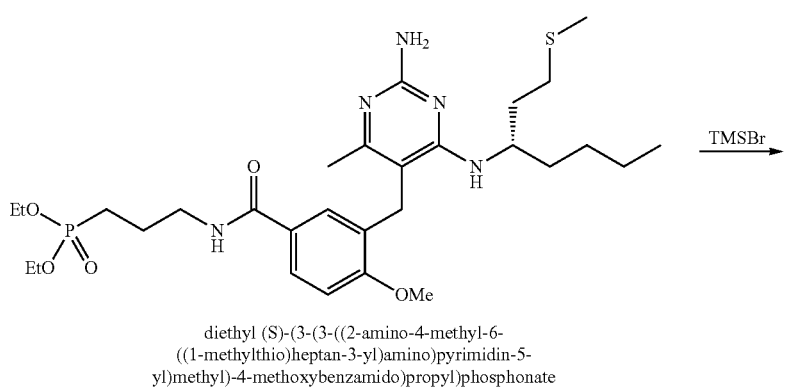

-continued

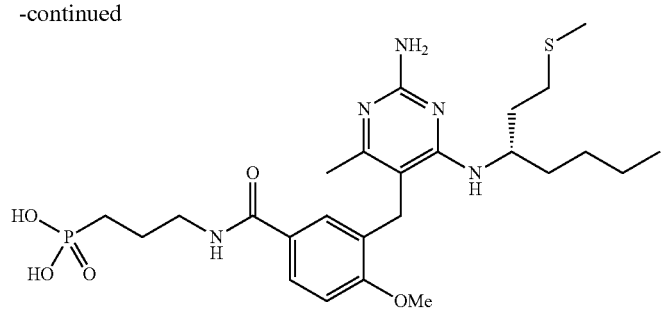

(S)-(3-(3-((2-amino-4-methyl-6-
((1-methylthio)heptan-3-yl)amino)pyrimidin-5-
yl)methyl)-4-methoxybenzamido)propyl)phosphonic acid
Chemical Formula: $C_{25}H_{40}N_5O_5PS$
Exact Mass: 553.25

Step 1: methyl (S)-3-((2-amino-4-methyl-6-((1-(methylthio)heptan-3-yl)amino)pyrimidin-5-yl)methyl)-4-methoxybenzoate A mixture of methyl 3-((2-amino-4-chloro-6-methylpyrimidin-5-yl)methyl)-4-methoxybenzoate (1.0 eq, from Example 3B—Step 4) in NMP (0.16M) and (S)-1-(methylthio)heptan-3-amine (1.5 eq, prepared by following procedures reported in WO2014/128189, pg 8, compound D) was stirred at 150° C. for 4 h under nitrogen. The mixture was diluted with water. The aqueous phase was extracted with EA. The organic layer was washed with water, brine, dried over $Na_2SO_4$, and concentrated. The residue was purified by column chromatography (DCM/MeOH=50:1) to give the title compound as a yellow solid.

Step 2: (S)-3-((2-amino-4-methyl-6-((1-(methylthio)heptan-3-yl)amino)pyrimidin-5-yl)methyl)-4-methoxybenzoic acid A mixture of methyl (S)-3-((2-amino-4-methyl-6-((1-(methylthio)heptan-3-yl)amino)pyrimidin-5-yl)methyl)-4-methoxybenzoate (1.0 eq) in 1:1 EtOH/$H_2O$ (0.02M) and NaOH (10.0 eq) was stirred at 70° C. for 16 h. The mixture was neutralized using 1N HCl, and the resulting suspension was filtered. The filter cake was washed with water to give a solid which was dissolved in MeCN/$H_2O$. 4N HCl/dioxane was added, and the resulting solution was freeze-dried to give the title compound as a white solid.

Step 3: diethyl (S)-(3-(3-((2-amino-4-methyl-6-((1-(methylthio)heptan-3-yl)amino)pyrimidin-5-yl)methyl)-4-methoxybenzamido)propyl)phosphonate A mixture of (S)-3-((2-amino-4-methyl-6-((1-(methylthio)heptan-3-yl)amino)pyrimidin-5-yl)methyl)-4-methoxybenzoic acid (1.0 eq) in DMF (0.1M), diethyl (3-aminopropyl)phosphonate (1.1 eq, from Example 30—Step 2), HATU (1.5 eq) and DIEA (2.0 eq) was stirred at 30° C. for 16 h. The mixture was cooled to r.t., and water was added. The mixture was extracted with DCM. The organic phase was dried over $Na_2SO_4$, concentrated under reduced pressure to give the title compound as a colorless oil.

Step 4: (S)-(3-(3-((2-amino-4-methyl-6-((1-(methylthio)heptan-3-yl)amino)pyrimidin-5-yl)methyl)-4-methoxybenzamido)propyl)phosphonic acid A mixture of diethyl (S)-(3-(3-((2-amino-4-methyl-6-((1-(methylthio)heptan-3-yl)amino)pyrimidin-5-yl)methyl)-4-methoxybenzamido)propyl)phosphonate (1.0 eq) in DCM (0.05M) and TSMBr (10.0 eq) was stirred at 35° C. for 5 h under $N_2$. The mixture was cooled and concentrated. The residue was purified by prep-HPLC (mobile phase $CH_3CN$/$H_2O$/$NH_3.H_2O$) to give the title compound.

LC-MS: $[M+H]^+$=554.3

$^1$H NMR (400 MHz, $CDCl_3$) δ 13.93 (s, 1H), 10.36 (s, 1H), 10.12 (s, 1H), 7.94 (d, J=8.0 Hz, 1H), 7.80 (s, 1H), 6.96 (d, J=8.8 Hz, 1H), 5.94 (d, J=8.4 Hz, 1H), 4.23-4.21 (m, 1H), 3.98 (s, 3H), 3.73-3.30 (m, 4H), 2.76 (s, 3H), 2.43-2.41 (m, 1H), 2.05-1.80 (m, 7H), 1.70 (s, 3H), 1.55-1.20 (m, 6H), 0.86 (t, J=4.0 Hz, 3H).

Example 36: (S)—$N^4$-(1-(2H-tetrazol-5-yl)heptan-3-yl)-5-(2-methoxybenzyl)-6-methylpyrimidine-2,4-diamine (Compound 36)

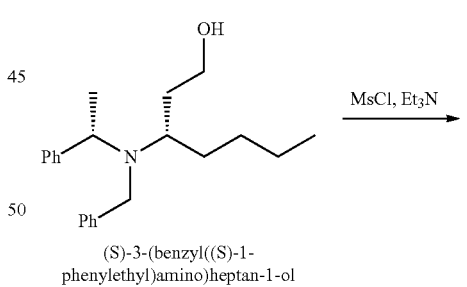

(S)-3-(benzyl((S)-1-phenylethyl)amino)heptan-1-ol

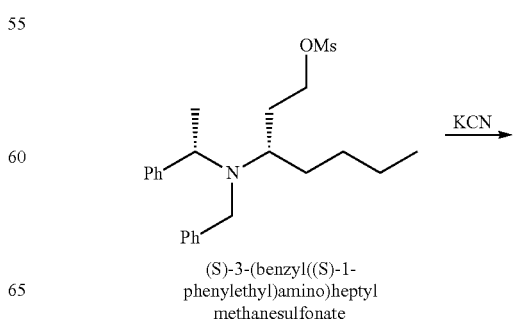

(S)-3-(benzyl((S)-1-phenylethyl)amino)heptyl methanesulfonate

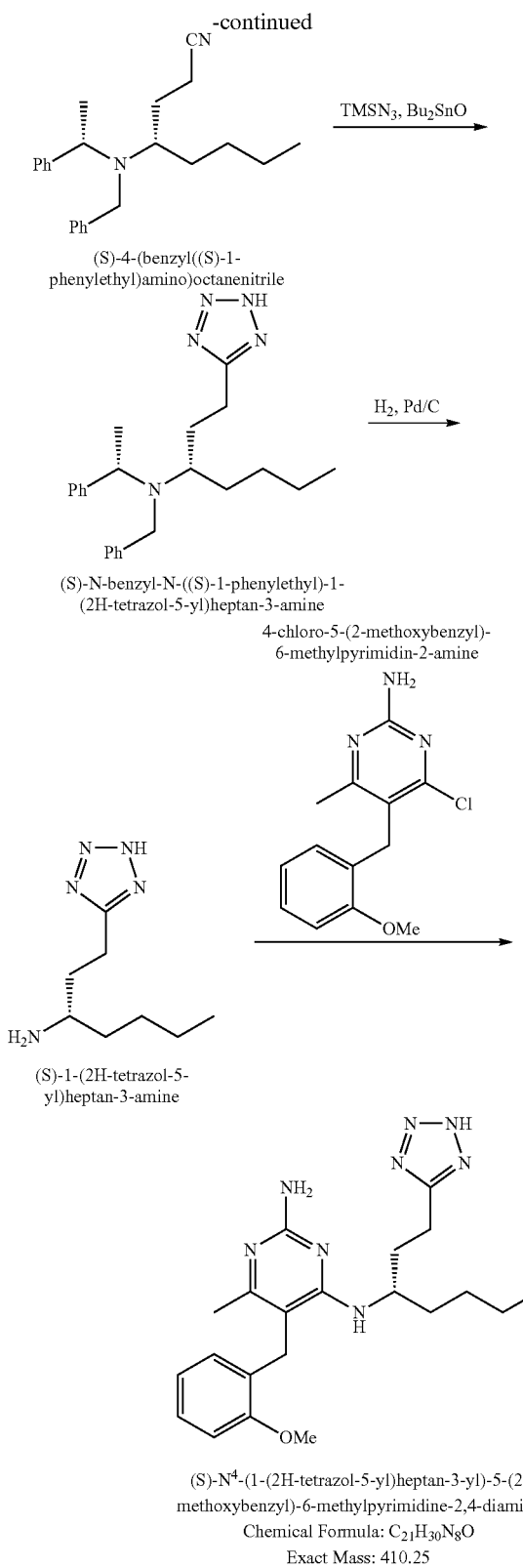

Step 1: (S)-3-(benzyl((S)-1-phenylethyl)amino)heptyl methanesulfonate

To a stirred solution of (S)-3-(benzyl((S)-1-phenylethyl)amino)heptan-1-ol (1.0 eq, prepared from *J. Med. Chem.* 2016, 59, 7936-7949) and DIEA (1.1 eq) in DCM (0.5M) was added MsCl (1.1 eq) at 0° C. The resulting mixture was warmed to r.t. over 3 h. Solvent was removed, and the residue was diluted with EA. The organic layer was washed with 1N HCl, 1N NaOH, brine, dried and concentrated to give the title compound.

Step 2: (S)-4-(benzyl((S)-1-phenylethyl)amino)octanenitrile

A mixture of (S)-3-(benzyl((S)-1-phenylethyl)amino)heptyl methanesulfonate (1.0 eq) in DMSO (0.3M) and KCN (7.5 eq) was stirred at 30° C. for 16 h. The reaction was diluted with water. The aqueous layer was extracted with EA. The organic layer was separated, dried and concentrated to give the title compound as a light yellow oil.

Step 3: (S)—N-benzyl-N—((S)-1-phenylethyl)-1-(2H-tetrazol-5-yl)heptan-3-amine

A mixture of (S)-4-(benzyl((S)-1-phenylethyl)amino)octanenitrile (1.0 eq) in dioxane (0.2M), TMSN$_3$ (2.5 eq) and Bu$_2$SnO (2.0 eq) was stirred at 120° C. in a seal tube for 18 h. The mixture was diluted with EA and then washed with water. The organic layer was dried and concentrated. The crude was purified by column chromatography (eluent PE:EA=10:1) to give the title compound as a light brown oil.

Step 4: (S)-1-(2H-tetrazol-5-yl)heptan-3-amine

To a solution of (S)—N-benzyl-N—((S)-1-phenylethyl)-1-(2H-tetrazol-5-yl)heptan-3-amine (1.0 eq) in MeOH (0.2M) was added 50% Pd/C (0.3 wt eq) under nitrogen. The reaction was stirred at 40° C. under H$_2$ atmosphere for 16 h. Pd/C was filtered off, and the filtrate was concentrated to give the title compound as a light yellow solid.

Step 5: (S)—N$^4$-(1-(2H-tetrazol-5-yl)heptan-3-yl)-5-(2-methoxybenzyl)-6-methylpyrimidine-2,4-diamine A solution of 4-chloro-5-(2-methoxybenzyl)-6-methylpyrimidin-2-amine (1.0 eq, from Example 41—Step 3) in NMP (0.4M) and (S)-1-(2H-tetrazol-5-yl)heptan-3-amine (2.0 eq) was stirred at 150° C. for 3 h under nitrogen. The reaction was diluted with water, and the aqueous was extracted with EA. The organic layers were combined and washed with water, brine, dried, and concentrated. The crude was purified by prep-HPLC (mobile phase 0.1% NH$_3$H$_2$O/CH$_3$CN) to give the title compound.

LC-MS: [M+H]$^+$=411.4

$^1$H NMR (400 MHz, MeOD) δ 7.17 (t, J=7.2 Hz, 1H), 6.96 (d, J=8.8 Hz, 2H), 6.85 (t, J=7.2 Hz, 1H), 4.24-4.20 (m, 1H), 3.91 (s, 3H), 3.78-3.63 (m, 2H), 3.19-3.16 (m, 1H), 2.72 (t, J=8.0 Hz, 2H), 2.28 (s, 3H), 2.28-0.80 (m, 8H), 0.77 (t, J=7.2 Hz, 3H).

Example 37: 6-(2-(2H-tetrazol-5-yl)ethyl)-N⁴-butyl-5-(2-methoxybenzyl)pyrimidine-2,4-diamine (Compound 37)

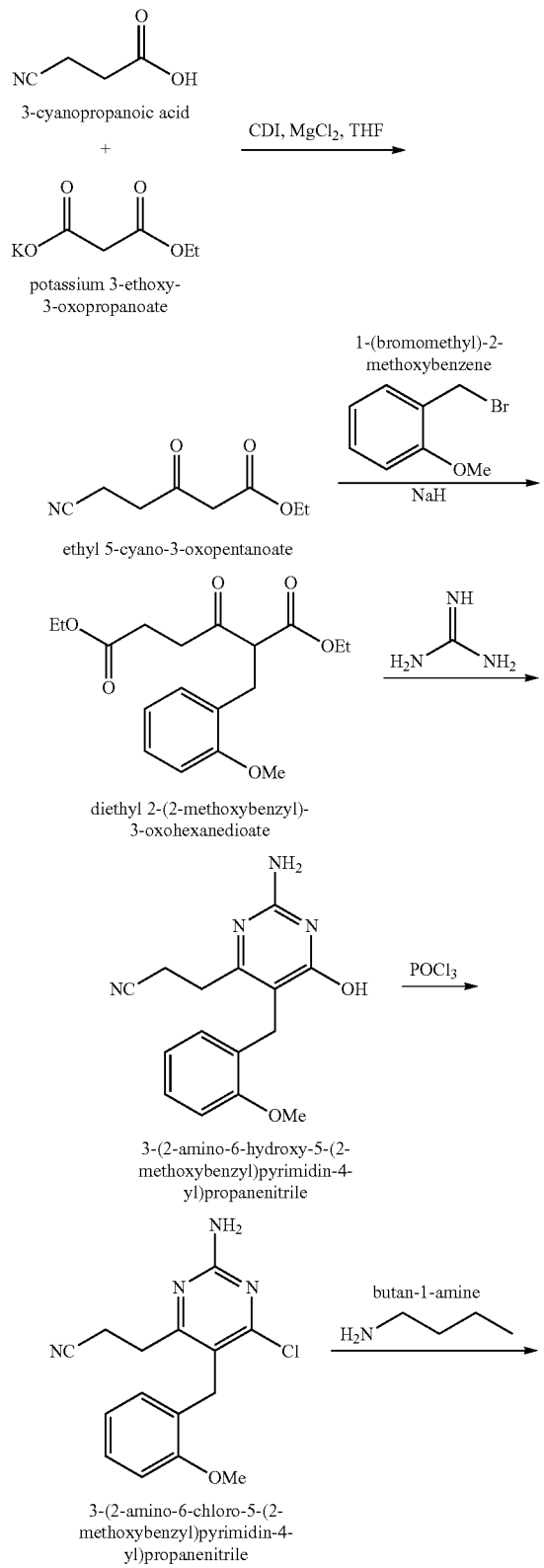

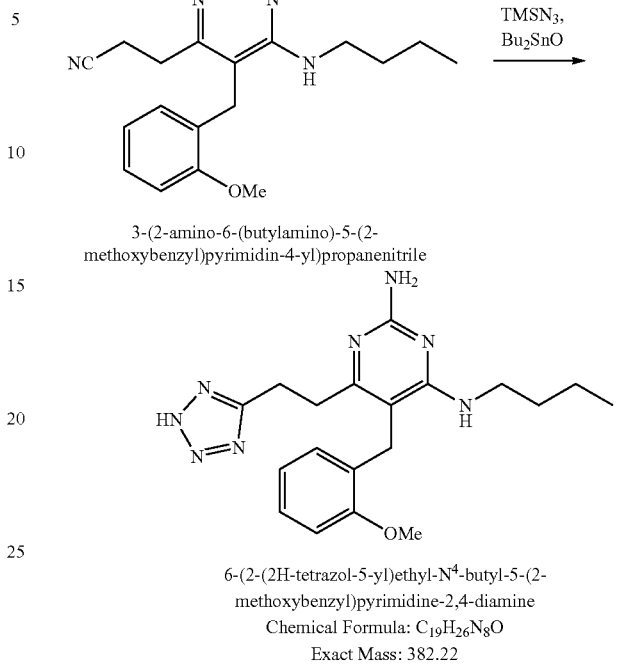

6-(2-(2H-tetrazol-5-yl)ethyl)-N⁴-butyl-5-(2-methoxybenzyl)pyrimidine-2,4-diamine
Chemical Formula: $C_{19}H_{26}N_8O$
Exact Mass: 382.22

Step 1: ethyl 5-cyano-3-oxopentanoate

To a solution of 3-cyanopropanoic acid (1.0 eq) in THF (0.5M) was added CDI (1.2 eq). The reaction solution was stirred at 25° C. for 1 h. MgCl₂ (1.0 eq) and potassium 3-ethoxy-3-oxopropanoate (1.0 eq) were added to the above solution and stirred at 60° C. for 2 h. The solution was cooled to room temperature and quenched by H₂O. The aqueous phase was extracted with EA. The combined organic layer was washed with water then brine. The organic layer was separated and dried over Na₂SO₄, concentrated and purified by column chromatography (PE/EA=3:1) to give the title compound as a yellow oil.

Step 2: diethyl 2-(2-methoxybenzyl)-3-oxohexanedioate

To a solution of ethyl 5-cyano-3-oxopentanoate (1.2 eq) in THF (0.3M) was added NaH (1.3 eq) at 0° C. in portions under nitrogen. The solution was stirred at 0° C. for 15 min, then 1-(bromomethyl)-2-methoxybenzene (1.0 eq) was added. The reaction was stirred at 40° C. for 16 h. The reaction mixture was quenched by water. The aqueous layer was extracted with EA. The combined organic layer was washed with water, brine, dried over Na₂SO₄, and concentrated. The crude was purified by column chromatography (PE/EA=5:1) to give the title compound as a light yellow oil.

Step 3: 3-(2-amino-6-hydroxy-5-(2-methoxybenzyl)pyrimidin-4-yl)propanenitrile To a solution of diethyl 2-(2-methoxybenzyl)-3-oxohexanedioate (1.0 eq) in MeOH (0.6M) was added guanidine carbonate (1.0 eq). The reaction was heated at 70° C. for 16 h under nitrogen. After cooling, the reaction solution was concentrated under reduce pressure and added 1:1 MO/EA. The precipitates were filtered and collected to give the title compound as an off-white solid.

Step 4: 3-(2-amino-6-chloro-5-(2-methoxybenzyl)pyrimidin-4-yl)propanenitrile

A mixture of 3-(2-amino-6-hydroxy-5-(2-methoxybenzyl)pyrimidin-4-yl)propanenitrile (1.0 eq) and $POCl_3$ (0.3M) was stirred at 100° C. for 2 h under nitrogen. The reaction was cooled to room temperature and poured onto ice-water. The pH was adjusted to 7 using $NaHCO_3$ solution. The aqueous solution was extracted with EA. The organic layer was washed with water, brine, dried over $Na_2SO_4$, and concentrated to give the title compound as a grey solid.

Step 5: 3-(2-amino-6-(butylamino)-5-(2-methoxybenzyl)pyrimidin-4-yl)propanenitrile To a solution of 3-(2-amino-6-chloro-5-(2-methoxybenzyl)pyrimidin-4-yl)propanenitrile (1.0 eq) in NMP (0.16M) was added butan-1-amine (3.0 eq) and DIEA (3.0 eq). The mixture was stirred at 100° C. for 16 h under nitrogen. The reaction solution was diluted with water and extracted with EA. The organic layer was washed with water, brine, dried over $Na_2SO_4$, and concentrated. The crude product was purified by column chromatography (DCM/MeOH=50:1) to give the title compound as a yellow solid.

Step 6: 6-(2-(2H-tetrazol-5-yl)ethyl)-$N^4$-butyl-5-(2-methoxybenzyl)pyrimidine-2,4-diamine To a solution of 3-(2-amino-6-(butylamino)-5-(2-methoxybenzyl)pyrimidin-4-yl)propanenitrile (1.0 eq) in dioxane (0.06M) was added $TMSN_3$ (2.0 eq) and $Bu_2SnO$ (2.0 eq). The mixture was stirred at 120° C. for 3 h. The solution was concentrated and purified by prep-HPLC (mobile phase: $NH_4HCO_3$/MeCN/$H_2O$) to give the title compound as a white solid.

LC-MS: $[M+H]^+$=383.4

$^1H$ NMR (400 MHz, DMSO-$d_6$) δ 7.18 (t, J=8.4 Hz, 1H), 6.98 (d, J=8.0 Hz, 1H), 6.81 (t, J=7.2 Hz, 1H), 6.73 (d, J=7.6 Hz, 1H), 6.59 (t, J=5.6 Hz, 1H), 6.27 (br s, 2H), 3.84 (s, 3H), 3.65 (s, 2H), 3.30-3.25 (m, 2H), 3.02 (t, J=7.6 Hz, 2H), 2.76 (t, J=7.6 Hz, 2H), 1.49-1.37 (m, 2H), 1.23-1.16 (m, 2H), 0.83 (t, J=7.6 Hz, 3H).

Example 38: (S)-3-(2-amino-5-(2-methoxybenzyl)-6-((1-(methylthio)heptan-3-yl)amino)pyrimidin-4-yl)propanoic acid (Compound 38)

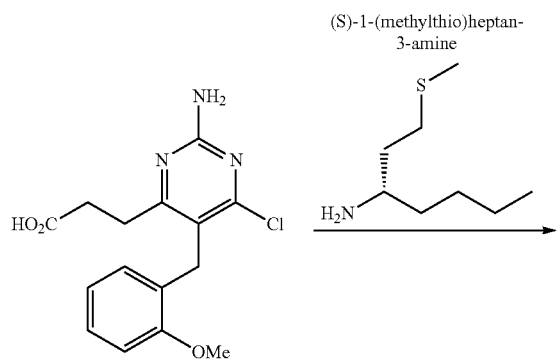

3-(2-amino-6-chloro-5-(2-methoxybenzyl)pyrimidin-4-yl)propanoic acid (S)-1-(methylthio)heptan-3-amine

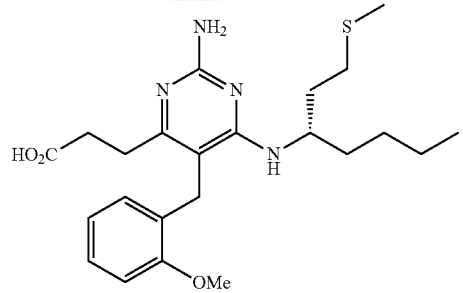

(S)-3-(2-amino-5-(2-methoxybenzyl)-6-((1-(methylthio)heptan-3-yl)amino)pyrimidin-4-yl)propanoic acid
Chemical Formula: $C_{23}H_{34}N_4O_3S$
Exact Mass: 446.24

Step 1: (S)-3-(2-amino-5-(2-methoxybenzyl)-6-((1-(methylthio)heptan-3-yl)amino)pyrimidin-4-yl)propanoic acid A mixture of 3-(2-amino-6-chloro-5-(2-methoxybenzyl)pyrimidin-4-yl)propanoic acid (1.0 eq, from Example 27—Step 4) and neat (S)-1-(methylthio)heptan-3-amine (4.0 eq, prepared by following procedures reported in WO2014/128189, pg 8, compound D) was stirred at 120° C. for 24 h. The reaction was diluted with water, and the aqueous solution was extracted with EA. The organic layers were combined and washed with 1N HCl, brine, dried over $Na_2SO_4$, concentrated and purified by prep-HPLC (mobile phase: 0.1% $NH_3.H_2O$/MeCN/$H_2O$) to give the title compound as a white solid.

LC-MS: $[M+H]^+$=447.3

$^1H$ NMR (400 MHz, MeOD) δ 7.23 (t, J=8.0 Hz, 1H), 7.02 (d, J=8.0 Hz, 1H), 6.97 (d, J=8.0 Hz, 1H), 6.92 (t, J=8.0 Hz, 1H), 4.41-4.34 (m, 1H), 3.92 (s, 3H), 3.83 (s, 2H), 2.93 (t, J=7.2 Hz, 2H), 2.49 (t, J=6.8 Hz, 2H), 2.25 (t, J=7.2 Hz, 2H), 1.96 (s, 3H), 1.76-0.90 (m, 8H), 0.81 (t, J=7.6 Hz, 3H).

Example 39: 5-(5-((2H-tetrazol-5-yl)methyl)-2-methoxybenzyl)-6-methyl-$N^4$-(pentan-2-yl)pyrimidine-2,4-diamine (Compound 39)

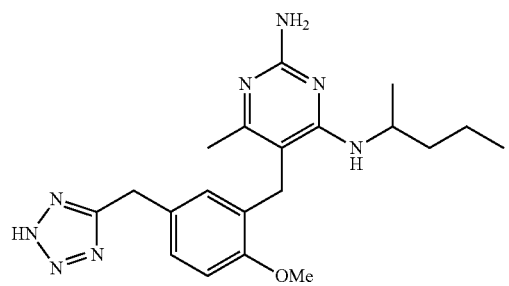 [SMILES: CCCC(C)Nc1nc(N)nc(C)c1Cc1cc(Cc2nn[nH]n2)ccc1OC]

5-(5-((2H-tetrazol-5-yl)methyl)-2-methoxybenzyl)-6-methyl-$N^4$-(pentan-2-yl)pyrimidine-2,4-diamine
Chemical Formula: $C_{20}H_{28}N_8O$
Exact Mass: 396.24

The title compound was prepared following the procedures described for Example 3, but using pentan-2-amine instead of butan-1-amine in Step 5.

LC-MS: [M+H]⁺=397.4

$^1$H NMR (400 MHz, CDCl$_3$) δ 7.26 (d, J=8.4 Hz, 1H), 6.92 (s, 1H), 6.85 (d, J=8.4 Hz, 1H), 6.49 (d, J=6.8 Hz, 1H), 4.26 (s, 2H), 4.20-4.18 (m, 1H), 3.92 (s, 3H), 3.58 (s, 2H), 2.59 (s, 3H), 1.48-1.46 (m, 2H), 1.40-1.38 (m, 2H), 1.08 (d, J=6.4 Hz, 3H), 0.85 (t, J=7.2 Hz, 3H).

Example 40: 3-(5-(5-((2H-tetrazol-5-yl)methyl)-2-methoxybenzyl)-2-amino-6-(butylamino)pyrimidin-4-yl)propanoic acid (Compound 40)

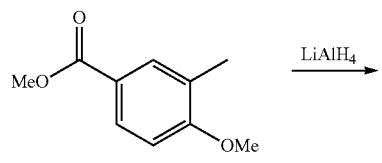

methyl 4-methoxy-3-methylbenzoate

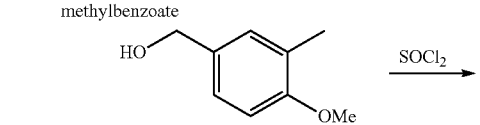

(4-methoxy-3-methylphenyl)methanol

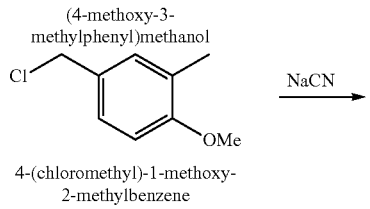

4-(chloromethyl)-1-methoxy-2-methylbenzene

2-(4-methoxy-3-methylphenyl)acetonitrile

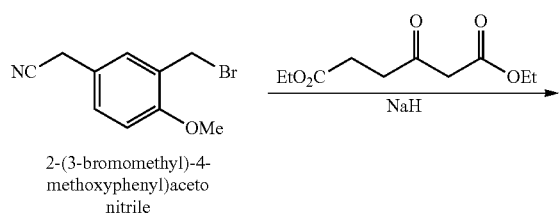

2-(3-bromomethyl)-4-methoxyphenyl)acetonitrile

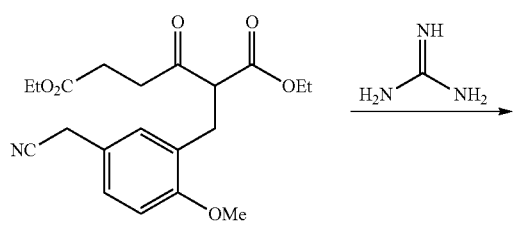

diethyl 2-(5-(cyanomethyl)-2-methoxybenzyl)-3-oxohexanedioate

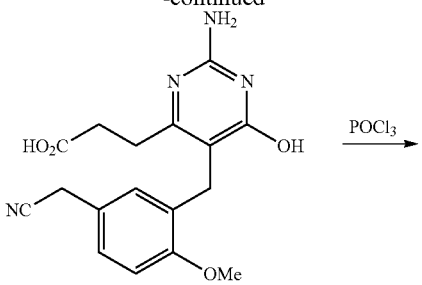

3-(2-amino-5-(5-(cyanomethyl)-2-methoxybenzyl)-6-hydroxypyrimidin-4-yl)propanoic acid

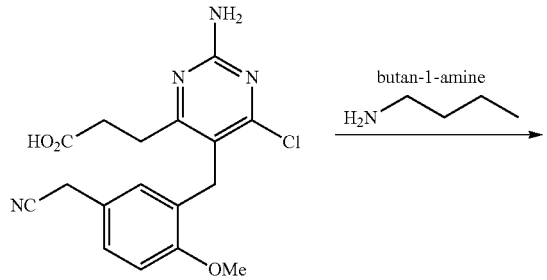

3-(2-amino-6-chloro-5-(5-(cyanomethyl)-2-methoxybenzyl)-pyrimidin-4-yl)propanoic acid

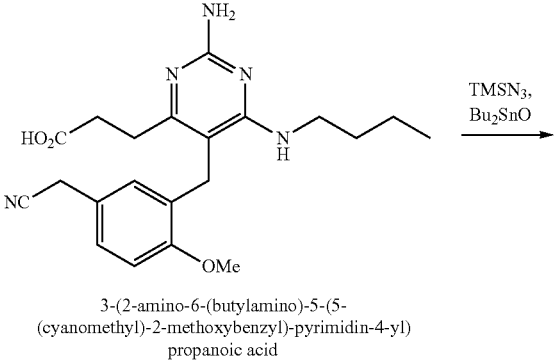

3-(2-amino-6-(butylamino)-5-(5-(cyanomethyl)-2-methoxybenzyl)-pyrimidin-4-yl)propanoic acid

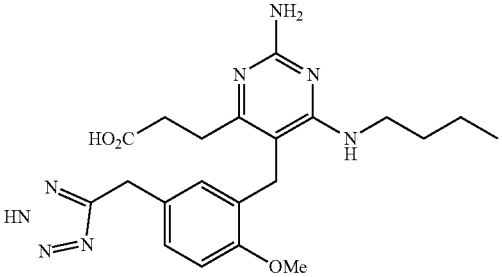 [SMILES: CCCCNc1nc(N)nc(CCC(=O)O)c1Cc1cc(Cc2nn[nH]n2)ccc1OC]

3-(5-(5-((2H-tetrazol-5-yl)methyl)-2-methoxybenzyl)-2-amino-6-(butylamino)pyrimidin-4-yl)propanoic acid
Chemical Formula: C$_{21}$H$_{28}$N$_8$O$_3$
Exact Mass: 440.23

Step 1: (4-methoxy-3-methylphenyl)methanol

To a stirred solution of methyl 4-methoxy-3-methylbenzoate (1.0 eq) in THF (0.6M) was added LiAlH$_4$ (1.2 eq) in portions at 4° C. under nitrogen. The resulting mixture was warmed to r.t over 2 h. The mixture was quenched with aqueous Na₂SO₄ solution. The solution was filtered, and the filtrate was concentrated to give the title compound as a colorless oil.

Step 2: 4-(chloromethyl)-1-methoxy-2-methylbenzene

To a stirred solution of (4-methoxy-3-methylphenyl)methanol (1.0 eq) in DCM (1.4M) was added SOCl₂ (1.5 eq) at r.t. under N₂. The mixture was stirred at r.t. for 1 h and then concentrated. The residue was partitioned between DCM and saturated aqueous NaHCO₃ solution. The organic layer was dried over Na₂SO₄, filtered and concentrated to give the title compound.

Step 3: 2-(4-methoxy-3-methylphenyl)acetonitrile

A mixture of 4-(chloromethyl)-1-methoxy-2-methylbenzene (1.0 eq) in 1:1 DMSO/DMF (0.9M) and NaCN (2.0 eq) was stirred for 16 h at r.t. The mixture was partitioned between EA and water. The organic layer was dried over Na₂SO₄, filtered, concentrated and purified by flash chromatography on silica (eluent PE/EA=100:1-20:1) to give the title compound.

Step 4: 2-(3-(bromomethyl)-4-methoxyphenyl)acetonitrile

To a solution of 2-(4-methoxy-3-methylphenyl)acetonitrile (1.0 eq) in CCl₄ (0.35M) was added NBS (1.2 eq) and AIBN (2.0 g, 13 mmol, 0.1 eq). The resulting mixture was heated at reflux for 1 h. Then the mixture was filtered, and the filtration was concentrated under reduced pressure to give the crude product, which was purified by flash chromatography on silica (eluent: PE/EA=40:1 to 4:1) to give the title compound as a yellow solid.

Step 5: diethyl 2-(5-(cyanomethyl)-2-methoxybenzyl)-3-oxohexanedioate

To a solution of 2-(3-(bromomethyl)-4-methoxyphenyl)acetonitrile (1.0 eq) in anhydrous THF (0.73 ML) at 0° C. was added portion-wise of 60% NaH (1.2 eq). After stirring for 10 min, a solution of diethyl 3-oxohexanedioate (1.1 eq, from Example 27—Step 1) in THF (2.4M) was added drop-wise into the above mixture over 10 min. The resulting mixture was warmed to r.t. and stirred for 20 h. The reaction was quenched with water. The mixture was extracted with EtOAc, dried over Na₂SO₄, concentrated under reduced pressure. The residue was purified by flash chromatography on silica (eluent: PE/EA=50:1 to 10:1) to give the title compound as a yellow oil.

Step 6: 3-(2-amino-5-(5-(cyanomethyl)-2-methoxybenzyl)-6-hydroxypyrimidin-4-yl)propanoic acid A mixture of diethyl 2-(5-(cyanomethyl)-2-methoxybenzyl)-3-oxohexanedioate (1.0 eq) in MeOH (0.3M) and guanidine carbonate (1.5 eq) was stirred at 70° C. for 16 h. Solvent was removed, and the residue was diluted with water and acidified by adding 1 N HCl to pH 5. The resulting precipitate was filtered and dried to give the title compound as a white solid.

Step 7: 3-(2-amino-6-chloro-5-(5-(cyanomethyl)-2-methoxybenzyl)pyrimidin-4-yl)propanoic acid A mixture of 3-(2-amino-5-(5-(cyanomethyl)-2-methoxybenzyl)-6-hydroxypyrimidin-4-yl)propanoic acid (1.0 eq) in POCl₃ (1.9M) was stirred at 100° C. for 3 h. The reaction mixture was cooled to r.t., and POCl₃ was evaporated under reduced pressure. The residue was diluted with water. The pH was adjusted to 7 with solid NaHCO₃. The precipitate was collected by filtration, washed with water, and dried under vacuum to give the title compound as a greenish solid.

Step 8: 3-(2-amino-6-(butylamino)-5-(5-(cyanomethyl)-2-methoxybenzyl)pyrimidin-4-yl)propanoic acid A mixture of 3-(2-amino-6-chloro-5-(5-(cyanomethyl)-2-methoxybenzyl)pyrimidin-4-yl)propanoic acid (1.0 eq) in EtOH (0.3M), butan-1-amine (4 eq), and DIEA (5 eq) was stirred at 85° C. for 48 h. Solvent was removed, and the residue was purified by flash column chromatography (eluent: DCM/MeOH=40:1) to give the title compound as a pale solid.

Step 9: 3-(5-(5-((2H-tetrazol-5-yl)methyl)-2-methoxybenzyl)-2-amino-6-(butylamino)pyrimidin-4-yl)propanoic acid A mixture of 3-(2-amino-6-(butylamino)-5-(5-(cyanomethyl)-2-methoxybenzyl)pyrimidin-4-yl)propanoic acid (1.0 eq) in dioxane (0.1M), TMSN₃ (5 eq) and Bu₂SnO (2.0 eq) was heated in a seal tube at 70° C. for 3 h. The mixture was concentrated under reduced pressure, and the crude was purified by prep-HPLC (mobile phase: 0.1% NH₃.H₂O in CH₃CN) to give the title compound as an off-with solid.

LC-MS: [M+H]⁺=441.2

¹H NMR (400 MHz, CDCl₃) δ 7.46 (s, 1H), 7.24 (d, J=8.4 Hz, 1H), 6.84 (d, J=8.4 Hz, 1H), 5.78 (br s, 1H), 4.17 (s, 2H), 3.90 (s, 3H), 3.70 (s, 2H), 3.36-3.31 (m, 2H), 3.17 (t, J=6.0 Hz, 2H), 2.77 (t, J=6.0 Hz, 2H), 1.41-1.38 (m, 2H), 1.18-1.13 (m, 2H), 0.84 (t, J=6.8 Hz, 3H).

Example 41: (S)-3-((2-amino-5-(2-methoxybenzyl)-6-methylpyrimidin-4-yl)amino)heptanoic acid (Compound 41)

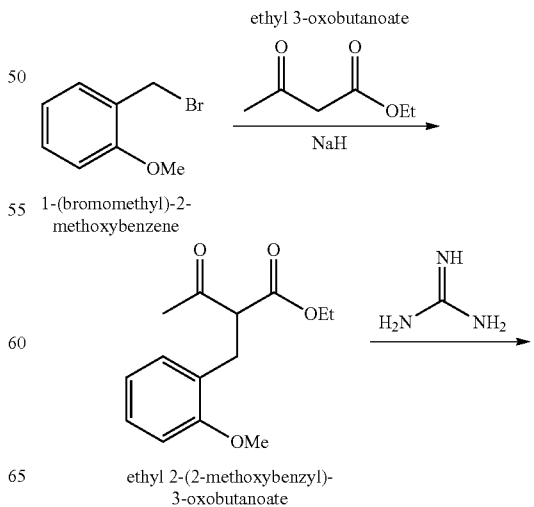

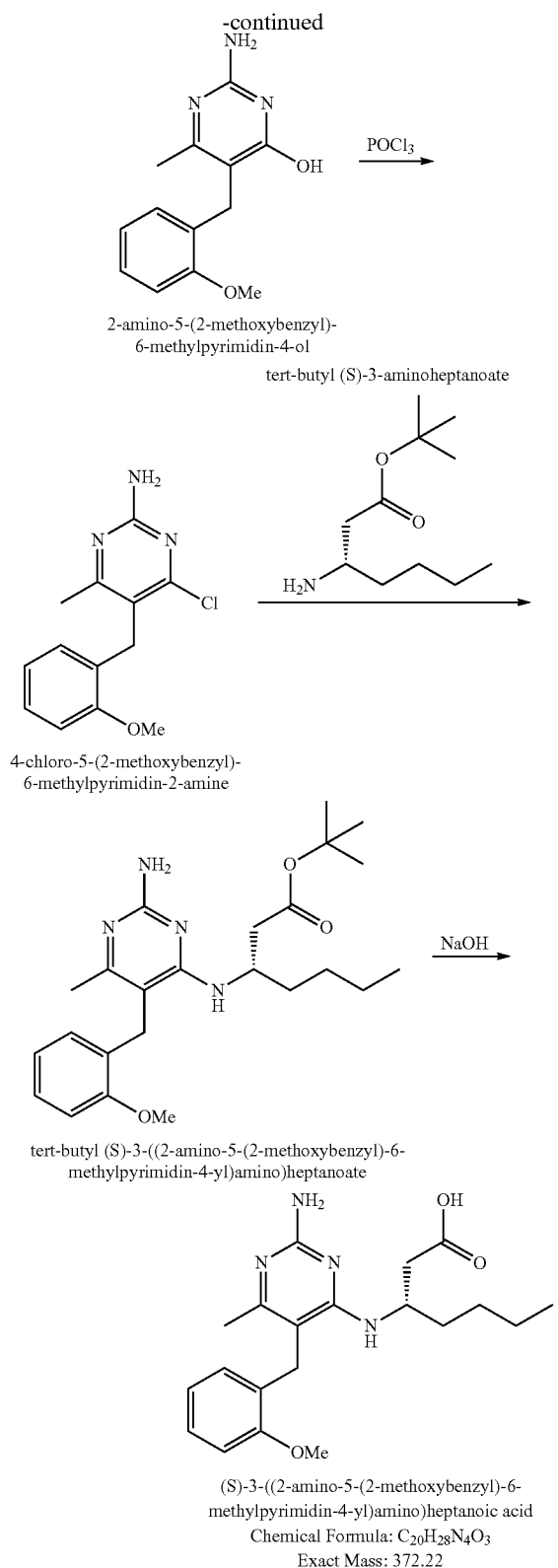

Step 1: ethyl 2-(2-methoxybenzyl)-3-oxobutanoate

To a solution of 1-(bromomethyl)-2-methoxybenzene (1.2 eq) in THF (0.6M) at 0° C. was added 60% NaH (1.25 eq) in portions under $N_2$. The resulting suspension was stirred at 0° C. for 10 min, then a solution of ethyl 3-oxobutanoate (1.0 eq) in THF (5M) was added drop-wise over 10 min. The resulting mixture was stirred for 15 h at 70° C. The mixture was cooled to r.t. and ice water was added. The mixture was extracted with ethyl acetate. The organic layer was dried over $Na_2SO_4$, concentrated, and purified by column chromatography on silica gel (eluent PE/EA=50:1~5:1) to give the title compound as a yellow oil.

Step 2: 2-amino-5-(2-methoxybenzyl)-6-methylpyrimidin-4-ol

To a solution of ethyl 2-(2-methoxybenzyl)-3-oxobutanoate (1.0 eq) in MeOH (0.9M) was added guanidine carbonate (1.0 eq). The resulting mixture was stirred overnight at 65° C. The mixture was concentrated to dryness. The residue was suspended in EtOAc and then filtered. The filter cake was washed with water and EtOAc, and then dried under vacuum to give the title compound as a white solid.

Step 3: 4-chloro-5-(2-methoxybenzyl)-6-methylpyrimidin-2-amine

A suspension of 2-amino-5-(2-methoxybenzyl)-6-methylpyrimidin-4-ol (1.0 eq) in $POCl_3$ (1M) was stirred at 100° C. for 24 h. The mixture was cooled to r.t. and $POCl_3$ was evaporated to dryness under reduced pressure. The residue was diluted with water, and pH was adjusted to 7 using solid $NaHCO_3$. The precipitate was collected by filtration, washed with water and EtOAc, and dried under vacuum to give the title compound.

Step 4: tert-butyl (S)-3-((2-amino-5-(2-methoxybenzyl)-6-methylpyrimidin-4-yl)amino)heptanoate A mixture of 4-chloro-5-(2-methoxybenzyl)-6-methylpyrimidin-2-amine (1.0 eq) in NMP (1.3M) and tert-butyl (S)-3-aminoheptanoate (4.5 eq, from Example 20B—Step 3) was stirred at 120° C. for 3 h. The mixture was partitioned between water and EtOAc. The organic layer was washed with brine, dried over $Na_2SO_4$, and concentrated under reduced pressure. The residue was purified by flash column chromatography (eluent: DCM/MeOH=100:1 to 30:1) to give the title compound as a yellow solid.

Step 5: (S)-3-((2-amino-5-(2-methoxybenzyl)-6-methylpyrimidin-4-yl)amino)heptanoic acid A mixture of tert-butyl (S)-3-((2-amino-5-(2-methoxybenzyl)-6-methylpyrimidin-4-yl)amino)heptanoate (1.0 eq) in 1:1 EtOH/$H_2O$ (0.1M) and NaOH (10.0 eq) was heated at 100° C. for 2 h. The reaction was cooled to r.t., and the solvent was removed. The residue was diluted with $H_2O$ and acidified using 1N HCl to pH 2. The resulting suspension was extracted with DCM. The combined organic layers were dried and concentrated. The crude was purified by prep-TLC ($CHCl_3$: MeOH=10:1) to give an oil, which was dissolved in 1:1 $CH_3CN$/$H_2O$ and added 4N HCl/dioxane. The solution was freeze-dried to give the title compound as a white solid.
LC-MS: [M+H]$^+$=373.2
$^1$H NMR (400 MHz, DMSO-$d_6$) δ 12.20 (br, 1H), 7.20-7.17 (m, 1H), 6.99 (d, J=8.4 Hz, 1H), 6.82-6.79 (m, 2H), 6.68 (br, 2H), 4.53-4.50 (m, 1H), 3.85 (s, 3H), 3.66 (s, 2H), 2.50-2.37 (m, 2H), 2.07 (s, 3H), 1.51-1.38 (m, 2H), 1.24-0.98 (m, 4H), 0.77 (t, J=6.8 Hz, 3H).

Example 42: (S)-3-((2-amino-5-(5-(2-carboxypropan-2-yl)-2-methoxybenzyl)-6-methylpyrimidin-4-yl)amino)heptanoic acid (Compound 42)

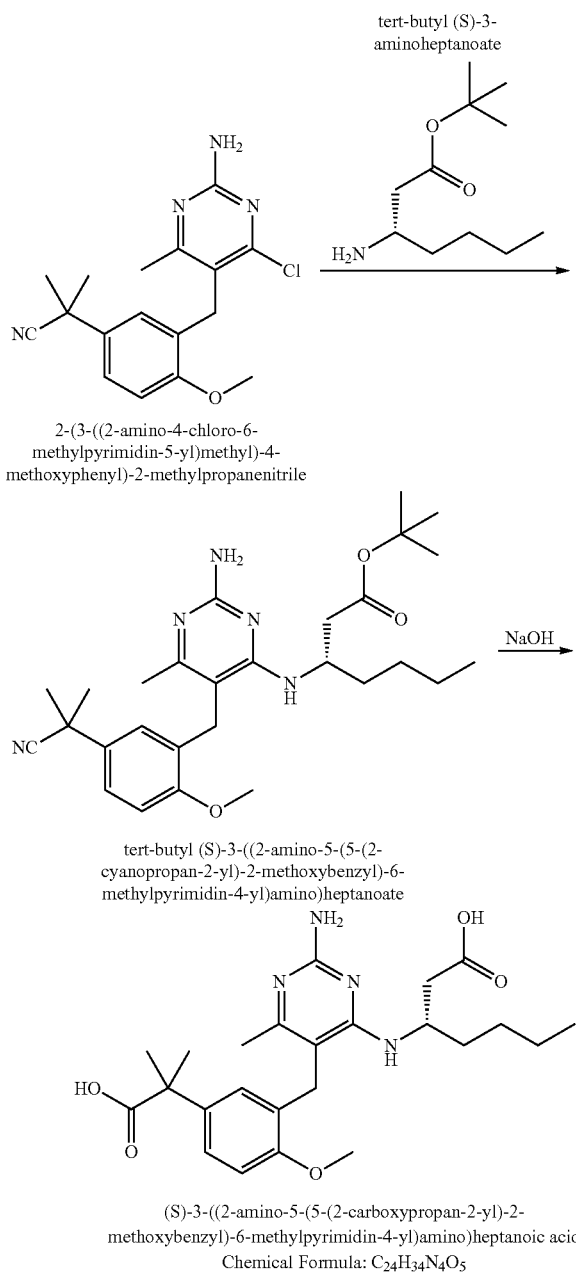

Step 1: tert-butyl (S)-3-((2-amino-5-(5-(2-cyanopropan-2-yl)-2-methoxybenzyl)-6-methylpyrimidin-4-yl)amino)heptanoate A mixture of 2-(3-((2-amino-4-chloro-6-methylpyrimidin-5-yl)methyl)-4-methoxyphenyl)-2-methyl-propanenitrile (1.0 eq, from Example 9—Step 8) in NMP (0.9M) and tert-butyl (S)-3-aminoheptanoate (1.3 eq, from Example 20B—Step 3) was stirred at 120° C. for 16 h under nitrogen. The reaction mixture was diluted with water. The aqueous phase was extracted with EA. The combined organic layer was washed with water, then brine. The organic layer was separated and dried over $Na_2SO_4$, concentrated and purified by flash chromatography on silica (eluent DCM/MeOH=50:1) to give the title compound as a yellow solid.

Step 2: (S)-3-((2-amino-5-(5-(2-carboxypropan-2-yl)-2-methoxybenzyl)-6-methylpyrimidin-4-yl)amino)heptanoic acid A mixture of tert-butyl (S)-3-((2-amino-5-(5-(2-cyanopropan-2-yl)-2-methoxybenzyl)-6-methyl-pyrimidin-4-yl)amino)heptanoate (1.0 eq) in 1:1 ethylene glycol/$H_2O$ (0.1M) was added NaOH (10.0 eq) and stirred at 150° C. for 16 h. The mixture was neutralized by adding 1 N HCl. The resulting suspension was filtered. The filter cake was washed with water and purified by prep-HPLC (mobile phase: 0.1% HCOOH/MeCN/$H_2O$) to give the title compound as a white solid.

LC-MS: $[M+H]^+$=459.3

$^1$H NMR (400 MHz, DMSO-$d_6$) δ 7.19 (br, 1H), 7.18 (dd, J=8.4, 2.4 Hz, 1H), 6.96 (d, J=8.4 Hz, 1H), 6.84 (d, J=2.0 Hz, 1H), 4.58-4.56 (m, 1H), 3.83 (s, 3H), 3.79 (s, 2H), 2.48-2.42 (m, 2H) 2.13 (s, 3H), 1.52-1.50 (m, 2H), 1.38 (s, 3H), 1.35 (s, 3H), 1.25-1.18 (m, 2H), 1.24-1.07 (m, 2H), 0.91 (t, J=7.2 Hz, 3H).

Example 43: 2-(3-((2-amino-4-(butylamino)-6-(2-carboxyethyl)pyrimidin-5-yl)methyl)-4-methoxyphenyl)-2-methylpropanoic acid (Compound 43)

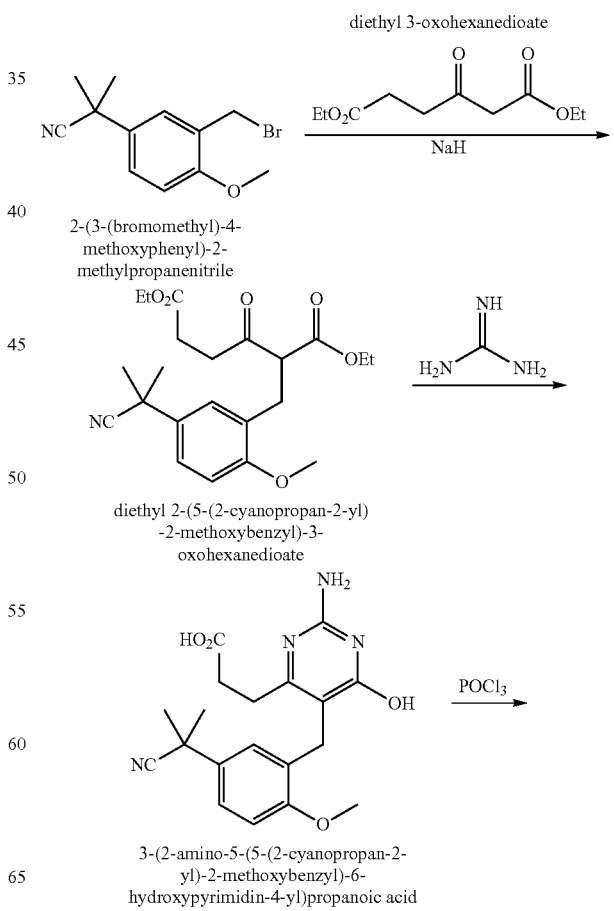

-continued

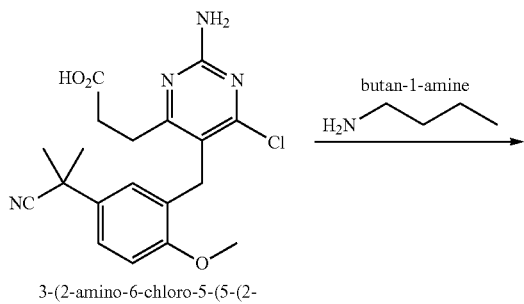

3-(2-amino-6-chloro-5-(5-(2-cyanopropan-2-yl)-2-methoxybenzyl)pyrimidin-4-yl)propanoic acid

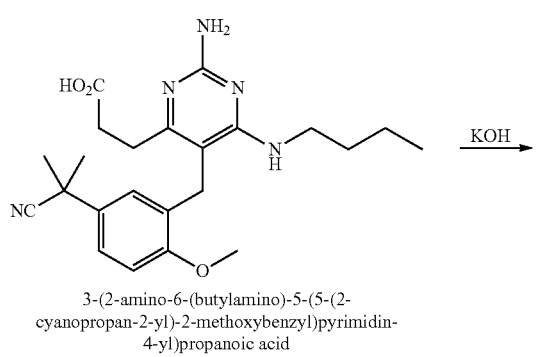

3-(2-amino-6-(butylamino)-5-(5-(2-cyanopropan-2-yl)-2-methoxybenzyl)pyrimidin-4-yl)propanoic acid

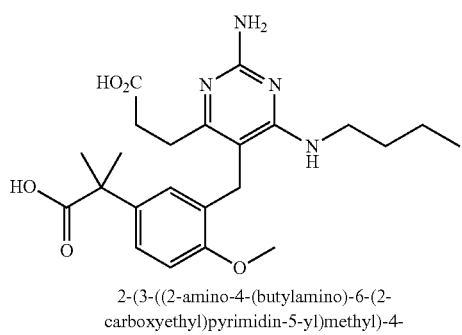

2-(3-((2-amino-4-(butylamino)-6-(2-carboxyethyl)pyrimidin-5-yl)methyl)-4-methoxyphenyl)-2-methylpropanoic acid
Chemical Formula: $C_{23}H_{32}N_4O_5$
Exact Mass: 444.24

Step 1: diethyl 2-(5-(2-cyanopropan-2-yl)-2-methoxybenzyl)-3-oxohexanedioate

To a solution of 2-(3-(bromomethyl)-4-methoxyphenyl)-2-methylpropanenitrile (1.1 eq, from Example 9—Step 5) in THF (0.3M) was added NaH (1.2 eq) at 0° C. in portions under nitrogen. The mixture was stirred at 0° C. for 10 min. A solution of diethyl 3-oxohexanedioate (1.0 eq, from Example 27—Step 1) in THF (0.75M) was added to the above solution, and the reaction was stirred at 60° C. for 16 h. The reaction was quenched by water. The aqueous solution was extracted with EA. The combined organic layers were washed with water, brine, dried over $Na_2SO_4$, and concentrated. The crude product was purified by column chromatography (PE/EA=10:1) to give the title compound as a yellow oil.

Step 2: 3-(2-amino-5-(5-(2-cyanopropan-2-yl)-2-methoxybenzyl)-6-hydroxypyrimidin-4-yl)propanoic acid To a solution of diethyl 2-(5-(2-cyanopropan-2-yl)-2-methoxybenzyl)-3-oxohexanedioate (1.0 eq) in MeOH (0.7M) was added guanidine carbonate (1.0 eq). The reaction was heated at 65° C. for 16 h under nitrogen. After cooling, the reaction solution was concentrated under reduced pressure. The residue was purified by column chromatography (DCM/MeOH=5:1) to give the title compound as a white solid.

Step 3: 3-(2-amino-6-chloro-5-(5-(2-cyanopropan-2-yl)-2-methoxybenzyl)pyrimidin-4-yl)propanoic acid A solution of 3-(2-amino-5-(5-(2-cyanopropan-2-yl)-2-methoxybenzyl)-6-hydroxypyrimidin-4-yl)propanoic acid (1.0 eq) in $POCl_3$ (0.3M) was stirred at 100° C. for 16 h under nitrogen. After cooling, the mixture was concentrated and poured into water. The pH value was adjusted to 8 by adding $NaHCO_3$. The aqueous phase was extracted with EA. Combined organic layers were dried over $Na_2SO_4$, concentrated, and purified by column chromatography (DCM/MeOH=10:1) to give the title compound as a brown solid.

Step 4: 3-(2-amino-6-(butylamino)-5-(5-(2-cyanopropan-2-yl)-2-methoxybenzyl)pyrimidin-4-yl)propanoic acid A solution of 3-(2-amino-6-chloro-5-(5-(2-cyanopropan-2-yl)-2-methoxybenzyl)pyrimidin-4-yl)propanoic acid (1.0 eq) in neat butan-1-amine (0.15M) was stirred at 120° C. for 3 h under nitrogen. The reaction was purified by column chromatography (DCM/MeOH=10:1) to give the title compound as a brown oil.

Step 5: 2-(3-((2-amino-4-(butylamino)-6-(2-carboxyethyl)pyrimidin-5-yl)methyl)-4-methoxyphenyl)-2-methylpropanoic acid To a solution of 3-(2-amino-6-(butylamino)-5-(5-(2-cyanopropan-2-yl)-2-methoxybenzyl)pyrimidin-4-yl)propanoic acid (1.0 eq) in 1:1 ethylene glycol/$H_2O$ (0.07M) was added KOH (20 eq). The mixture was stirred at 150° C. for 16 h. After cooling, pH was adjusted to 6 by adding 4N HCl. The mixture was extracted with EA. The organic layer was washed with brine, dried over $Na_2SO_4$, concentrated. The crude product was purified by prep-HPLC (mobile phase: $NH_4HCO_3$/MeCN/$H_2O$) to give the title compound as a white solid.

LC-MS: $[M+H]^+$=445.3

$^1$H NMR (400 MHz, $CD_3OD$) δ 7.27 (dd, J=8.4, 2.4 Hz, 1H), 6.95 (d, J=8.4 Hz, 1H), 6.93 (s, 1H), 3.89 (s, 3H), 3.78 (s, 2H), 3.45 (t, J=7.0 Hz, 2H), 2.84 (t, J=6.0 Hz, 2H), 2.42 (t, J=6.4 Hz, 2H), 1.54-1.47 (m, 2H), 1.45 (s, 6H), 1.26-1.21 (m, 2H), 0.88 (t, J=7.2 Hz, 3H).

Example 44: (S)-3-((2-amino-5-(2-methoxy-5-((3-phosphonopropyl)carbamoyl)benzyl)-6-methyl-pyrimidin-4-yl)amino)heptanoic acid (Compound 44)
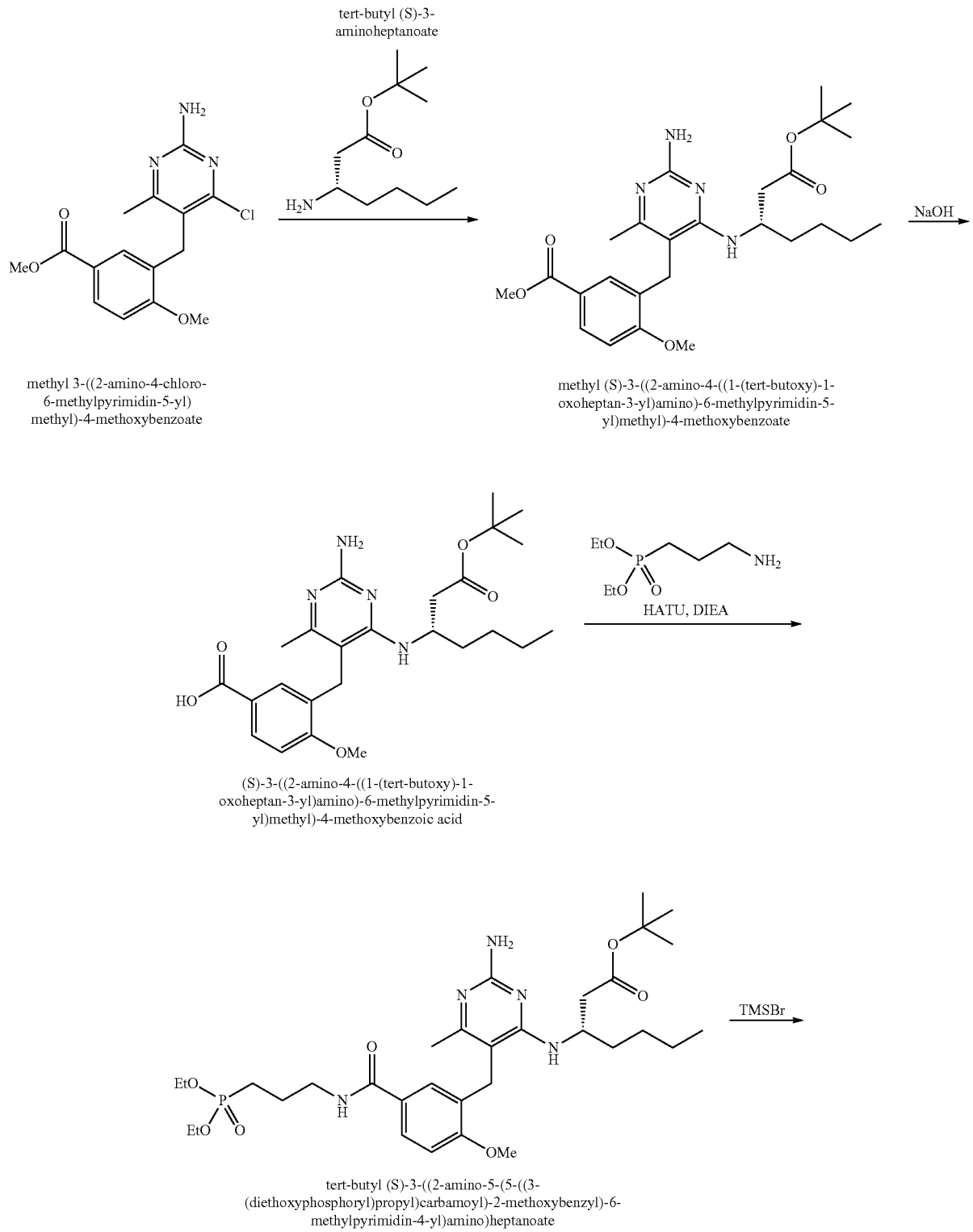

-continued

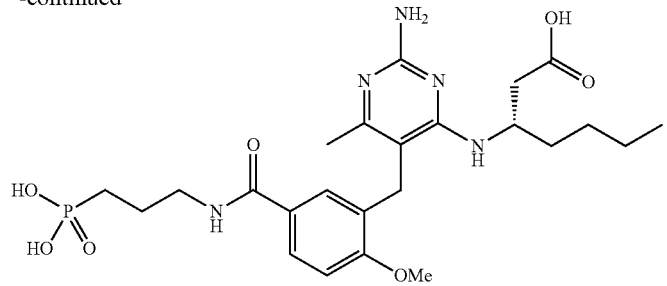

(S)-3-((2-amino-5-(2-methoxy-5-((3-phosphonopropyl)carbamoyl)
benzyl)-6-methylpyrimidin-4-yl)amino)heptanoic acid
Chemical Formula: $C_{24}H_{36}N_5O_7P$
Exact Mass: 537.24

Step 1: methyl (S)-3-((2-amino-4-((1-(tert-butoxy)-1-oxoheptan-3-yl)amino)-6-methylpyrimidin-5-yl)methyl)-4-methoxybenzoate A mixture of methyl 3-((2-amino-4-chloro-6-methylpyrimidin-5-yl)methyl)-4-methoxybenzoate (1.0 eq, from Example 3B—Step 4) in NMP (2M) and tert-butyl (S)-3-aminoheptanoate (2.0 eq, from Example 20B—Step 3) was stirred at 120° C. for 16 h under nitrogen. The reaction solution was diluted with water and extracted with EA. The organic layer was washed with water, brine, dried over $Na_2SO_4$, and concentrated. The residue was purified by column chromatography (DCM/MeOH=50:1) to give the title as a yellow solid.

Step 2: (S)-3-((2-amino-4-((1-(tert-butoxy)-1-oxoheptan-3-yl)amino)-6-methylpyrimidin-5-yl)methyl)-4-methoxybenzoic acid A mixture of methyl (S)-3-((2-amino-4-((1-(tert-butoxy)-1-oxoheptan-3-yl)amino)-6-methylpyrimidin-5-yl)methyl)-4-methoxybenzoate (1.0 eq) in 1:1 ethanol/$H_2O$ (0.1M) and NaOH (10.0 eq) was stirred at 30° C. for 4 h. The mixture was neutralized by adding 1 N HCl to pH 7. The resulting suspension was filtered. The filter cake was washed with water to give the title compound.

Step 3: tert-butyl (S)-3-((2-amino-5-(5-(3-(diethoxyphosphoryl)propyl)carbamoyl)-2-methoxybenzyl)-6-methylpyrimidin-4-yl)amino)heptanoate A mixture of (S)-3-((2-amino-4-((1-(tert-butoxy)-1-oxoheptan-3-yl)amino)-6-methylpyrimidin-5-yl)methyl)-4-methoxybenzoic acid (1.0 eq) in DMF (0.1M), diethyl (3-aminopropyl)phosphonate (2.0 eq, from Example 30—Step 2), HATU (2.0 eq) and DIEA (3.0 eq) was stirred at 50° C. for 16 h. The mixture was cooled to r.t. and added water. The mixture was extracted with DCM. The combined organic phase was dried over $Na_2SO_4$, and concentrated under reduced pressure to give the title compound as a colorless oil.

Step 4: (S)-3-((2-amino-5-(2-methoxy-S-((3-phosphonopropyl)carbamoyl)benzyl)-6-methyl-pyrimidin-4-yl)amino)heptanoic acid A solution of tert-butyl (S)-3-((2-amino-5-(5-((3-(diethoxyphosphoryl)propyl)carbamoyl)-2-methoxy-benzyl)-6-methylpyrimidin-4-yl)amino)heptanoate (1.0 eq) in DCM (0.08M) was added TSMBr (10.0 eq) and stirred at 35° C. for 16 h under $N_2$. The mixture was concentrated, and the residue was purified by trituration and prep-HPLC (mobile phase $CH_3CN/H_2O/NH_3H_2O$) to give the title compound.

LC-MS: $[M+H]^+=538.3$ $^1$H NMR (400 MHz, DMSO) δ 8.69 (br, 1H), 7.72 (d, J=8.8 Hz, 1H), 7.50 (s, 1H), 7.01 (d, J=8.4 Hz, 1H), 6.63 (br, 1H), 4.47-4.45 (m, 1H), 3.85 (s, 3H), 3.27-3.25 (m, 4H), 2.4 (d, J=6.0 Hz, 2H), 2.13 (s, 3H), 1.72-1.68 (m, 2H), 1.46-1.26 (m, 4H), 1.12-0.96 (m, 2H), 0.96-0.94 (m, 2H), 0.70 (t, J=7.2 Hz, 3H).

Example 45: (S)-3-((2-amino-6-(2-carboxyethyl)-5-(5-(2-carboxypropan-2-yl)-2-methoxy-benzyl)pyrimidin-4-yl)amino)heptanoic acid (Compound 45)

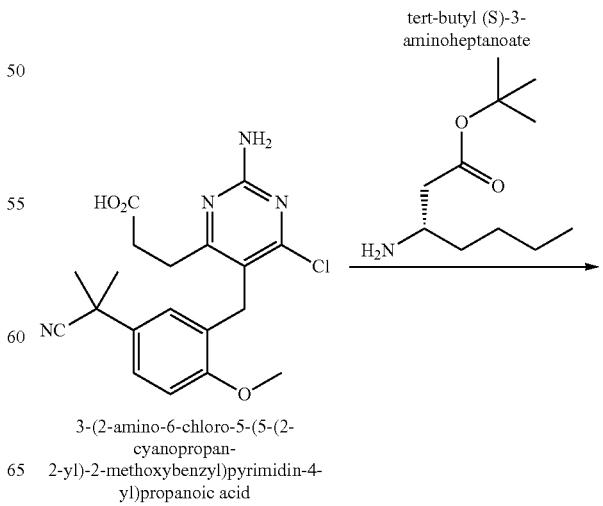

3-(2-amino-6-chloro-5-(5-(2-cyanopropan-2-yl)-2-methoxybenzyl)pyrimidin-4-yl)propanoic acid tert-butyl (S)-3-aminoheptanoate

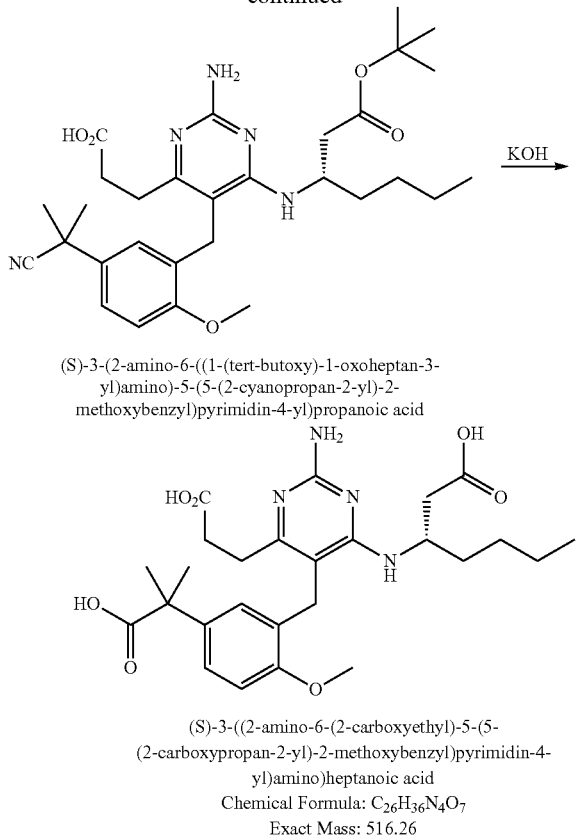

(S)-3-(2-amino-6-((1-(tert-butoxy)-1-oxoheptan-3-yl)amino)-5-(5-(2-cyanopropan-2-yl)-2-methoxybenzyl)pyrimidin-4-yl)propanoic acid (S)-3-((2-amino-6-(2-carboxyethyl)-5-(5-(2-carboxypropan-2-yl)-2-methoxybenzyl)pyrimidin-4-yl)amino)heptanoic acid
Chemical Formula: $C_{26}H_{36}N_4O_7$
Exact Mass: 516.26

Step 1: (S)-3-(2-amino-6-((1-(tert-butoxy)-1-oxoheptan-3-yl)amino)-5-(5-(2-cyanopropan-2-yl)-2-methoxybenzyl)pyrimidin-4-yl)propanoic acid To a solution of 3-(2-amino-6-chloro-5-(5-(2-cyanopropan-2-yl)-2-methoxybenzyl)pyrimidin-4-yl)propanoic acid (1.0 eq, from Example 43—Step 3) in NMP (0.15M) was added tert-butyl (S)-3-aminoheptanoate (5.0 eq, from Example 20B—Step 3) and $K_2CO_3$ (3.0 eq). The mixture was stirred at 150° C. for 16 h. The reaction solution was diluted with water/EA and concentrated to give the title compound as a crude oil.

Step 2: (S)-3-((2-amino-6-(2-carboxyethyl)-5-(5-(2-carboxypropan-2-yl)-2-methoxybenzyl)-pyrimidin-4-yl)amino)heptanoic acid To a solution of (S)-3-(2-amino-6-((1-(tert-butoxy)-1-oxoheptan-3-yl)amino)-5-(5-(2-cyanopropan-2-yl)-2-methoxybenzyl)pyrimidin-4-yl)propanoic acid (crude) in 1:1 ethylene glycol/$H_2O$ was added excess KOH and stirred at 150° C. for 16 h. After cooling, the reaction mixture was diluted with water/EA. The pH was adjusted to 6 by adding 4N HCl, then extracted with 3:1 $CHCl_3$/IPA. The combined organic layer was washed with brine, dried over $Na_2SO_4$, and concentrated. The crude product was purified by prep-HPLC (mobile phase: $NH_4OH$/MeCN/$H_2O$) to give the title compound as a white solid.
LC-MS: $[M+H]^+$=517.3
$^1$H NMR (400 MHz, $CD_3OD$) δ 7.27 (dd, J=8.0, 2.4 Hz, 1H), 7.00-6.95 (m, 2H), 4.61-4.57 (m, 1H), 3.90 (s, 3H), 3.80 (s, 2H), 2.94-2.87 (m, 2H), 2.50-2.38 (m, 4H), 1.56-1.53 (m, 1H), 1.48 (s, 3H), 1.45 (s, 3H), 1.46-1.44 (m, 1H), 1.27-1.17 (m, 2H), 1.08-1.03 (m, 2H), 0.79 (t, J=7.4 Hz, 3H).

Example 46: (S)-3-((5-(5-((2H-tetrazol-5-yl)methyl)-2-methoxybenzyl)-2-amino-6-(2-carboxyethyl)-pyrimidin-4-yl)amino)heptanoic acid (Compound 46)

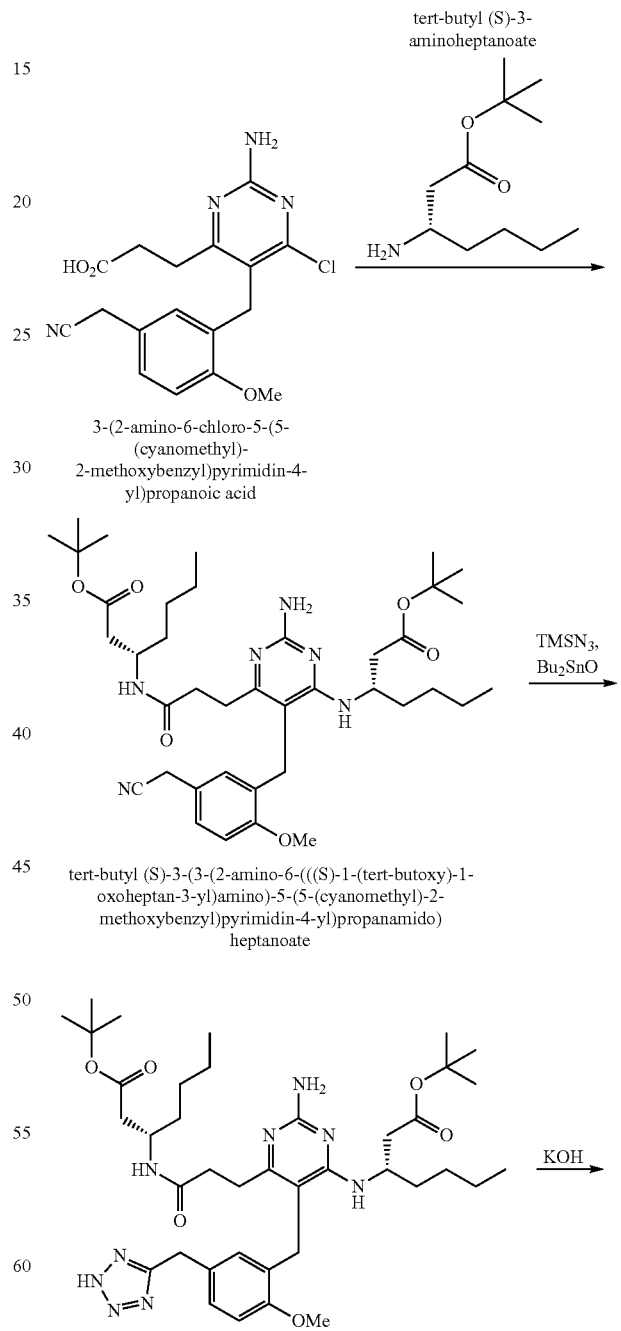

-continued

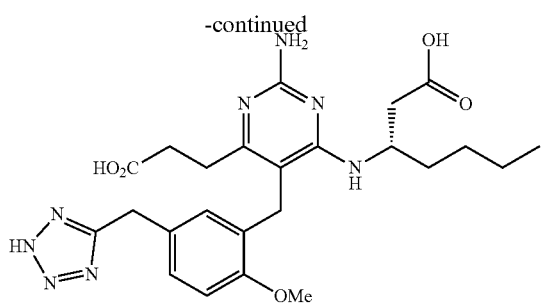

(S)-3-((5-(5-(((2H-tetrazol-5-yl)methyl)-2-
methoxybenzyl)-2-amino-6-(2-carboxyethyl)pyrimidin-4-yl)
amino)heptanoic acid
Chemical Formula: $C_{24}H_{32}N_8O_5$
Exact Mass: 512.25

Step 1: tert-butyl (S)-3-(3-(2-amino-6-(((S)-1-(tert-butoxy)-1-oxoheptan-3-yl)amino)-5-(5-(cyanomethyl)-2-methoxybenzyl)pyrimidin-4-yl)propanamido)heptanoate A mixture of 3-(2-amino-6-chloro-5-(5-(cyanomethyl)-2-methoxybenzyl)pyrimidin-4-yl)propanoic acid (1.0 eq, from Example 40—Step 7) and tert-butyl (S)-3-aminoheptanoate (3 eq., from Example 20B—Step 3) was stirred at 140° C. for 3 h. The crude product was used directly in next step.

Step 2: tert-butyl (S)-3-(3-(5-(5-((2H-tetrazol-5-yl)methyl)-2-methoxybenzyl)-2-amino-6-(((S)-1-(tert-butoxy)-1-oxoheptan-3-yl)amino)pyrimidin-4-yl)propanamido)heptanoate A mixture of tert-butyl (S)-3-(3-(2-amino-6-(((S)-1-(tert-butoxy)-1-oxoheptan-3-yl)amino)-5-(5-(cyanomethyl)-2-methoxybenzyl)pyrimidin-4-yl)propanamido)heptanoate (1.0 eq) in dioxane (0.2M), $TMSN_3$ (3 eq) and $Bu_2SnO$ (2.0 eq) was heated at 110° C. in a seal tube for 6 h. The mixture was diluted with EA and washed with water. The organic layer was dried, concentrated, and the residue was purified by column chromatography (DCM:MeOH=100:1~10:1) to give the title compound as a light brown solid.

Step 3: (S)-3-((5-(5-(((2H-tetrazol-5-yl)methyl)-2-methoxybenzyl)-2-amino-6-(2-carboxyethyl)-pyrimidin-4-yl)amino)heptanoic acid A solution of tert-butyl (S)-3-(3-(5-(5-((2H-tetrazol-5-yl)methyl)-2-methoxybenzyl)-2-amino-6-(((S)-1-(tert-butoxy)-1-oxoheptan-3-yl)amino)pyrimidin-4-yl)propanamido)heptanoate (1.0 eq) in ethane-1,2-diol (0.1M) was added 10M aqueous KOH (44 eq) and heated at 150° C. for 5 days. The solid was filtered off, and the filtrate was concentrated and purified by prep-HPLC (mobile phase: 0.1% $NH_3.H_2O$, $CH_3CN$) to give the title compound as a white solid.

LC-MS: $[M+H]^+$=513.2

$^1$H NMR (400 MHz, MeOD) δ 7.09 (dd, J=8.4, 2.0 Hz, 1H), 6.95 (s, 1H), 6.89 (d, J=8.4 Hz, 1H), 4.51-4.49 (m, 1H), 4.04 (s, 2H), 3.87 (s, 3H), 3.77 (s, 2H), 2.92-2.85 (m, 2H), 2.52-2.21 (m, 4H), 1.5-0.9 (m, 6H), 0.73 (t, J=7.6 Hz, 3H).

Example 47: 3-(2-amino-6-(butylamino)-5-(2-methoxybenzyl)pyrimidin-4-yl)propan-1-ol (Compound 47)

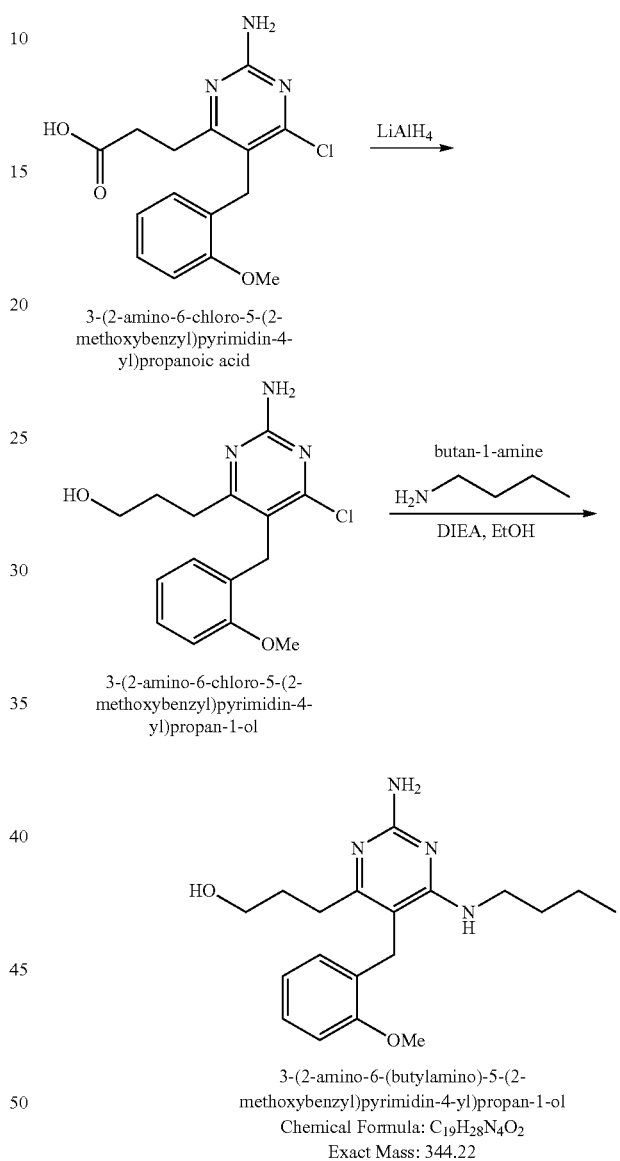

Step 1: 3-(2-amino-6-chloro-5-(2-methoxybenzyl)pyrimidin-4-yl)propan-1-ol

To a solution of 3-(2-amino-6-chloro-5-(2-methoxybenzyl)pyrimidin-4-yl)propanoic acid (1.0 eq, from Example 27—Step 4) in THF (0.16M) was added LAH (3.0 eq). The reaction solution was stirred at r.t. for 2 h, and then quenched with water. The aqueous layer was extracted with DCM. The combined organic layers were washed with water, brine, dried over $Na_2SO_4$, and concentrated to give the title compound as a pale solid.

Step 2: 3-(2-amino-6-(butylamino)-5-(2-methoxybenzyl)pyrimidin-4-yl)propan-1-ol A solution of 3-(2-amino-6-chloro-5-(2-methoxybenzyl)pyrimidin-4-yl)propan-1-ol (1.0 eq) in EtOH (0.2M), butan-1-amine (4.0 eq), and DIEA (5 eq) was stirred at 85° C. for 3 days. The reaction solution was concentrated, diluted with 1N HCl, and extracted with DCM. The combined organic layers were washed with brine, dried over $Na_2SO_4$, concentrated, and purified by flash column chromatography (eluent: DCM/MeOH=100:1~20:1) to give the title compound as a pale solid.

LC-MS: $[M+H]^+$=345.4

$^1$H NMR (400 MHz, DMSO) δ 7.80 (br, 1H), 7.40 (br, 2H), 7.22 (t, J=8.0 Hz, 1H), 7.01 (d, J=8.4 Hz, 1H), 6.84 (t, J=7.6 Hz, 1H), 6.78 (d, J=8.4 Hz, 1H), 3.85 (s, 3H), 3.72 (s, 2H), 3.38-3.34 (m, 2H), 2.50-2.44 (m, 2H), 1.61-1.54 (m, 2H), 1.50-1.42 (m, 2H), 1.34-1.15 (m, 4H), 0.84 (t, J=7.6 Hz, 3H).

Example 48: (S)-3-(5-(5-((2H-tetrazol-5-yl)methyl)-2-methoxybenzyl)-2-amino-6-((1-(methylthio)-heptan-3-yl)amino)pyrimidin-4-yl)propanoic acid (Compound 48)

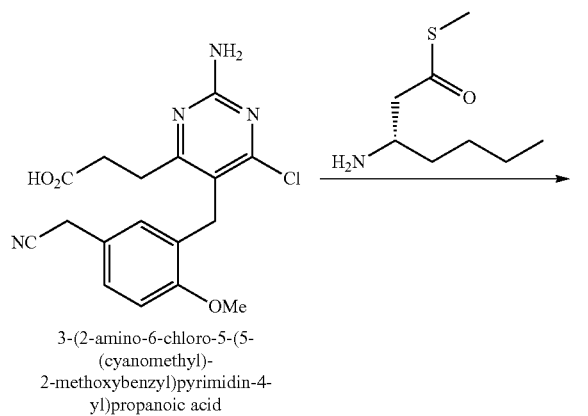

(S)-1-(methylthio)heptan-3-amine 3-(2-amino-6-chloro-5-(5-(cyanomethyl)-2-methoxybenzyl)pyrimidin-4-yl)propanoic acid

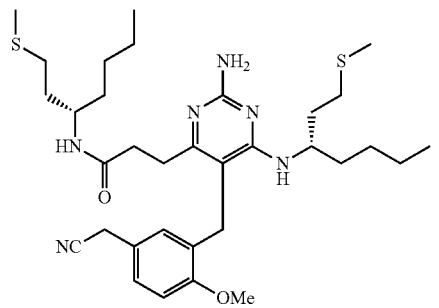

3-(2-amino-5-(5-(cyanomethyl)-2-methoxybenzyl)-6-(((S)-1-(methylthio)heptan-3-yl)amino)pyrimidin-4-yl)-N-((S)-1-(methylthio)heptan-3-yl)propanamide

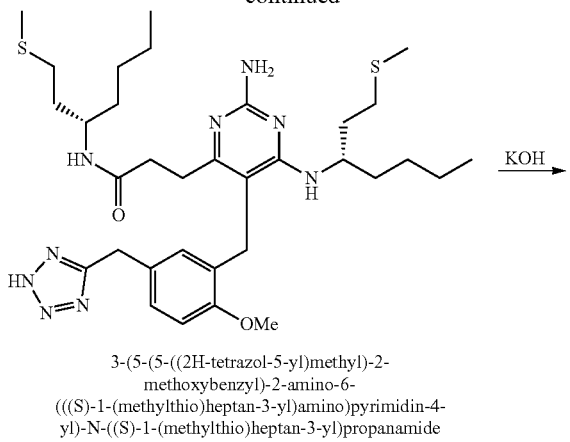

3-(5-(5-((2H-tetrazol-5-yl)methyl)-2-methoxybenzyl)-2-amino-6-(((S)-1-(methylthio)heptan-3-yl)amino)pyrimidin-4-yl)-N-((S)-1-(methylthio)heptan-3-yl)propanamide

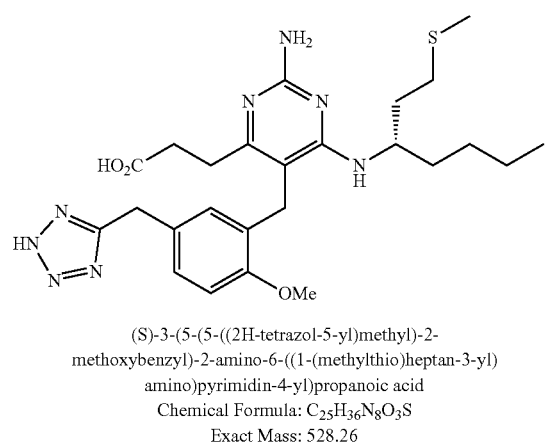

(S)-3-(5-(5-((2H-tetrazol-5-yl)methyl)-2-methoxybenzyl)-2-amino-6-((1-(methylthio)heptan-3-yl)amino)pyrimidin-4-yl)propanoic acid
Chemical Formula: $C_{25}H_{36}N_8O_3S$
Exact Mass: 528.26

Step 1: 3-(2-amino-5-(5-(cyanomethyl)-2-methoxybenzyl)-6-(((S)-1-(methylthio)heptan-3-yl)amino)-pyrimidin-4-yl)-N—((S)-1-(methylthio)heptan-3-yl)propanamide A solution of 3-(2-amino-6-chloro-5-(5-(cyanomethyl)-2-methoxybenzyl)pyrimidin-4-yl)propanoic acid (1.0 eq, from Example 40—Step 7) in EtOH (0.4M) and (S)-1-(methylthio)heptan-3-amine (2.3 eq) was stirred at 90° C. for 3 days. Solvent was removed, the residue was purified by column chromatography (eluent DCM:MeOH=20:1) to give the title compound as a light brown oil.

Step 2: 3-(5-(5-((2H-tetrazol-5-yl)methyl)-2-methoxybenzyl)-2-amino-6-(((S)-1-(methylthio)heptan-3-yl)amino)pyrimidin-4-yl)-N—(S)-1-(methylthio)heptan-3-yl)propanamide A mixture of 3-(2-amino-5-(5-(cyanomethyl)-2-methoxybenzyl)-6-(((S)-1-(methylthio)heptan-3-yl)amino)-pyrimidin-4-yl)-N—((S)-1-(methylthio)heptan-3-yl)propanamide (1.0 eq) in dioxane (0.04M), $TMSN_3$ (3.8 eq), and $Bu_2SnO$ (2.5 eq) was heated at 90° C. for 6 h in a seal tube. The reaction solution was cooled down and used directly in the next step without any purification.

Step 3: (S)-3-(5-(5-((2H-tetrazol-5-yl)methyl)-2-methoxybenzyl)-2-amino-6-((1-(methylthio)heptan-3-yl)amino)pyrimidin-4-yl)propanoic acid The crude product from the previous step was dissolved in ethane-1, 2-diol and added aqueous KOH (excess). The reaction was heated at 150° C. for 5 days. The solid was filtered, and the filtrate was concentrated and purified by prep-HPLC (mobile phase: 0.1% TFA/CH$_3$CN/H$_2$O) to give the title compound as a white solid.

LC-MS: [M+H]$^+$=529.3

$^1$H NMR (400 MHz, MeOD) δ 7.20 (d, J=7.6 Hz, 1H), 7.01 (d, J=8.8 Hz, 1H), 6.93 (s, 1H), 4.43-4.40 (m, 1H), 4.19 (s, 2H), 3.91 (s, 3H), 3.83 (s, 2H), 2.92 (t, J=6.8 Hz, 2H), 2.56 (t, J=7.6 Hz, 2H), 2.24 (t, J=7.6 Hz, 2H), 1.93 (s, 3H), 1.78-1.75 (m, 1H), 1.67-1.63 (m, 1H), 1.51-1.49 (m, 1H), 1.41-1.39 (m, 1H), 1.26-1.19 (m, 2H), 1.10-1.04 (m, 2H), 0.80 (t, J=7.6 Hz, 3H).

Example 49: (S)-3-(5-(5-((2H-tetrazol-5-yl)methyl)-2-methoxybenzyl)-2-amino-6-((1-methoxyheptan-3-yl)amino)pyrimidin-4-yl)propanoic acid (Compound 49)

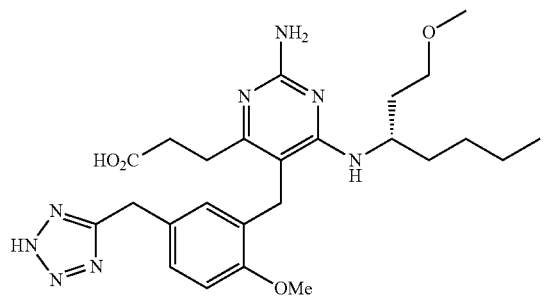

(S)-3-(5-(5-((2H-tetrazol-5-yl)methyl)-2-methoxybenzyl)-2-amino-6-((1-methoxyheptan-3-yl)amino)pyrimidin-4-yl)propanoic acid
Chemical Formula: C$_{25}$H$_{36}$N$_8$O$_4$
Exact Mass: 512.29

The title compound was prepared following the procedures described for Example 48, but using (S)-1-methoxyheptan-3-amine instead of (S)-1-(methylthio)heptan-3-amine in Step 1.

LC-MS: [M+H]$^+$=513.3

$^1$H NMR (400 MHz, CDCl$_3$) δ 7.21 (d, J=8.4 Hz, 1H), 7.17 (s, 1H), 6.82 (d, J=8.4 Hz, 1H), 6.14 (d, J=8.0 Hz, 1H), 4.26-4.05 (m, 2H), 4.03 (d, J=15.2 Hz, 1H), 3.88 (s, 3H), 3.74-3.61 (m, 2H), 3.33-3.25 (m, 2H), 3.17-3.05 (m, 2H), 3.04 (s, 3H), 2.72-2.68 (m, 1H), 2.53-2.48 (m, 1H), 1.81-1.76 (m, 1H), 1.55-1.50 (m, 1H), 1.41-1.15 (m, 4H), 1.03-0.95 (m, 2H), 0.78 (t, J=7.6 Hz, 3H).

Example 50: (S)-3-(2-amino-5-(5-(carboxymethyl)-2-methoxybenzyl)-6-((1-(methylsulfonyl)heptan-3-yl)amino)pyrimidin-4-yl)propanoic acid (Compound 50)

(S)-1-(methylthio)heptan-3-amine

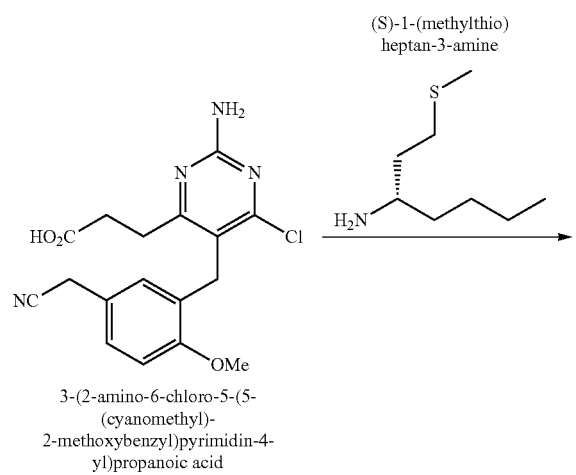

3-(2-amino-6-chloro-5-(5-(cyanomethyl)-2-methoxybenzyl)pyrimidin-4-yl)propanoic acid

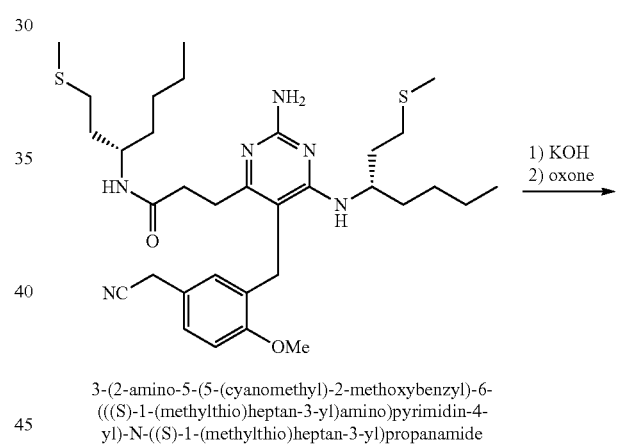

3-(2-amino-5-(5-(cyanomethyl)-2-methoxybenzyl)-6-(((S)-1-(methylthio)heptan-3-yl)amino)pyrimidin-4-yl)-N-((S)-1-(methylthio)heptan-3-yl)propanamide

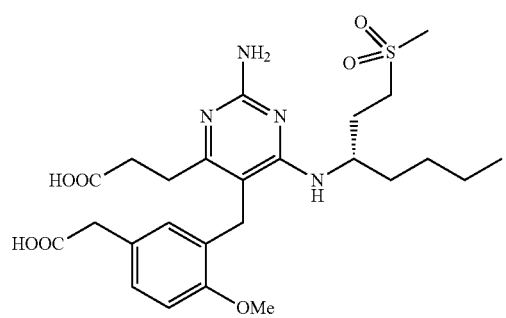

(S)-3-(2-amino-5-(5-(carboxymethyl)-2-methoxybenzyl)-6-((1-(methylsulfonyl)heptan-3-yl)amino)pyrimidin-4-yl)propanoic acid
Chemical Formula: C$_{25}$H$_{36}$N$_4$O$_7$S
Exact Mass: 536.23

Step 1: 3-(2-amino-5-(5-(cyanomethyl)-2-methoxy-benzyl)-6-(((S)-1-(methylthio)heptan-3-yl)amino)-pyrimidin-4-yl)-N—((S)-1-(methylthio)heptan-3-yl) propanamide The title compound was prepared following the procedures described for Example 48—Step 1.

Step 2: (S)-3-(2-amino-5-(5-(carboxymethyl)-2-methoxybenzyl)-6-((1-(methylsulfonyl)heptan-3-yl) amino)pyrimidin-4-yl)propanoic acid To a solution of KOH in 10% H$_2$O in nBuOH (10M) was added 3-(2-amino-5-(5-(cyanomethyl)-2-methoxybenzyl)-6-(((S)-1-(methylthio)heptan-3-yl)amino)-pyrimidin-4-yl)-N—((S)-1-(methylthio)heptan-3-yl)propanamide (1.0 eq). The resulting mixture was heated in a seal tube at 150° C. for 16 h. The mixture was cooled to r.t. and filtered. To the filtrate was added oxone (5.0 eq) and stirred at r.t. for 5 h. The reaction was concentrated under reduced pressure to ⅓ volume. The insoluble solid was filtered off and the filtrate was purified by prep-HPLC (mobile phase: 0.1% HCOOH/MeCN/H$_2$O) and freeze-dried to give the title compound as a white solid.

LC-MS: [M+H]$^+$=537.4

Example 51: (S)-2-(3-((2-amino-4-methyl-6-((1-(methylsulfonyl)heptan-3-yl)amino)pyrimidin-5-yl) methyl)-4-methoxyphenyl)acetic acid (Compound 51)

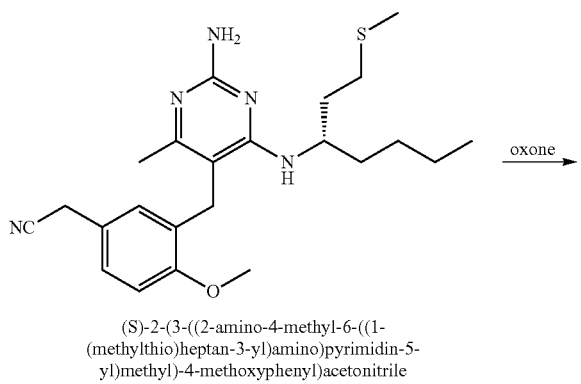

(S)-2-(3-((2-amino-4-methyl-6-((1-(methylthio)heptan-3-yl)amino)pyrimidin-5-yl)methyl)-4-methoxyphenyl)acetonitrile oxone

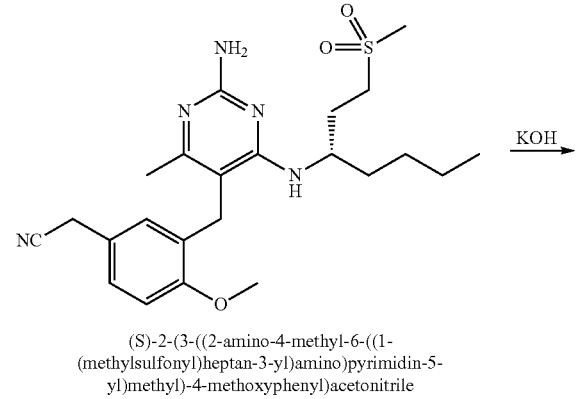

(S)-2-(3-((2-amino-4-methyl-6-((1-(methylsulfonyl)heptan-3-yl)amino)pyrimidin-5-yl)methyl)-4-methoxyphenyl)acetonitrile

KOH

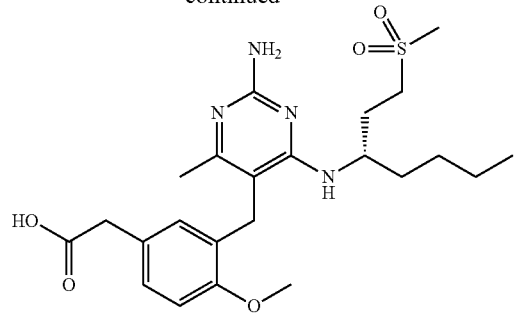

(S)-2-(3-((2-amino-4-methyl-6-((1-(methylsulfonyl)heptan-3-yl)amino)pyrimidin-5-yl)methyl)-4-methoxyphenyl)acetic acid
Chemical Formula: C$_{23}$H$_{34}$N$_4$O$_5$S
Exact Mass: 478.22

Step 1: (S)-2-(3-((2-amino-4-methyl-6-((1-(methylsulfonyl)heptan-3-yl)amino)pyrimidin-5-yl)methyl)-4-methoxyphenyl)acetonitrile To a solution of (S)-2-(3-((2-amino-4-methyl-6-((1-(methylthio)heptan-3-yl)amino)pyrimidin-5-yl)methyl)-4-methoxyphenyl)acetonitrile (1 eq, from Example 22—Step 4) in 1:1:1 THF/MeOH/H$_2$O (0.2M) was added oxone (1.2 eq) in portions at r.t. The reaction was stirred at r.t. for 2 h, and then diluted with DCM. The organic layer was washed with water and brine, dried, and concentrated to give a light yellow solid, which was used in the next step directly.

Step 2: (S)-2-(3-((2-amino-4-methyl-6-((1-(methylsulfonyl)heptan-3-yl)amino)pyrimidin-5-yl)methyl)-4-methoxyphenyl)acetic acid To a solution of (S)-2-(3-((2-amino-4-methyl-6-((1-(methylsulfonyl)heptan-3-yl)amino)pyrimidin-5-yl) methyl)-4-methoxyphenyl)acetonitrile (1.0 eq) in 1:1 MeOH/H$_2$O (0.1M) was added KOH (7.5 eq). The reaction was stirred at 120° C. for 4 h. Solvent was removed and HCl was added to achieve pH 9. The mixture was purified by prep-HPLC (0.1% NH$_3$.H$_2$O/CH$_3$CN) to give the title compound as a light yellow solid.

LCMS: [M+H]$^+$=479.3

$^1$H NMR (400 MHz, CD$_3$OD) δ 7.16 (dd, J=8.4, 2.0 Hz, 1H), 6.98 (d, J=2.0 Hz, 1H), 6.91 (d, J=8.4 Hz, 1H), 4.30-4.22 (m, 1H), 3.89 (s, 3H), 3.77-3.68 (m, 2H), 3.32 (s, 2H), 2.91-2.70 (m, 5H), 2.32 (s, 3H), 2.08-1.95 (m, 1H), 1.81-1.69 (m, 1H), 1.56-1.05 (m, 6H), 0.83 (t, J=7.2 Hz, 3H).

Biological Examples

Biological Example 1: HEK TLR7 Assay

HEK-Blue™ TLR7 cells were purchased from Invivogen (San Diego, Calif.). The following description was taken from the product information sheet.

"HEK-Blue™ hTLR7 cells are designed for studying the stimulation of human TLR7 (hTLR7) by monitoring the activation of NF-kB. HEK-Blue™ hTLR7 cells were obtained by co-transfection of the hTLR7 gene and an optimized secreted embryonic alkaline phosphatase (SEAP) reporter gene into HEK293 cells. The SEAP reporter gene is placed under the control of the IFN-b minimal promoter fused to five NF-kB and AP-1-binding sites. Stimulation with a TLR7 ligand activates NF-kB and AP-1 which induce the production of SEAP, which is detected by the HEK-Blue™ Detection cell culture medium."

A typical assay protocol involved the following steps:

1. Cells were cultured according to the product information sheet.
2. 10 mM compound stock in DMSO were first diluted to 3 mM and then 3-fold serially diluted using DMSO to afford a 10-pt dilution.
3. 3 µl of the diluted DMSO were added to 57 µl HEK-Blue™ Detection media for a further 20-fold dilution.
4. 10 µl of the diluted compound in assay media were added into 40 µl cell culture (in HEK-Blue™ Detection media) in 384-well plate. Final cell concentration=8,000 cells per well.
5. The plates were incubated at 37° C. in 5% CO2 for 16 h. SEAP was determined using a spectrophotometer at 620-655 nm.

| Example | HEK-TLR7 EC$_{50}$ |
|---|---|
| 1 | C |
| 2 | C |
| 3 | B |
| 4 | C |
| 5 | C |
| 6 | C |
| 7 | C |
| 8 | B |
| 9 | B |
| 10 | B |
| 11 | B |
| 12 | B |
| 13 | B |
| 14 | C |
| 15 | B |
| 16 | B |
| 17 | A |
| 18 | A |
| 19 | C |
| 20 (S-enantiomer) | B |
| 20C (R-enantiomer) | C |
| 21 | C |
| 22 | A |
| 23 | A |
| 24 | A |
| 25 | B |
| 26 | B |
| 27 | B |
| 28 | C |
| 29 | B |
| 30 | B |
| 31 | C |
| 32 | A |
| 33 | A |
| 34 | A |
| 35 | A |
| 36 | B |
| 37 | B |
| 38 | A |
| 39 | B |
| 40 | B |
| 41 | B |
| 42 | B |
| 43 | C |
| 44 | B |
| 45 | C |
| 46 | B |
| 47 | B |
| 48 | A |
| 49 | B |
| 50 | B |
| 51 | B |

EC$_{50}$ category:
A = <100 nM
B = 100-1000 nM
C = 1000-10000 nM

As discussed herein, $R^{1A}$ and $R^{1B}$ in formula (1) can create a chiral center. Compounds 20 and 20C differ by the stereocenter of the carbon bearing $R^{1A}$ and $R^{1B}$.

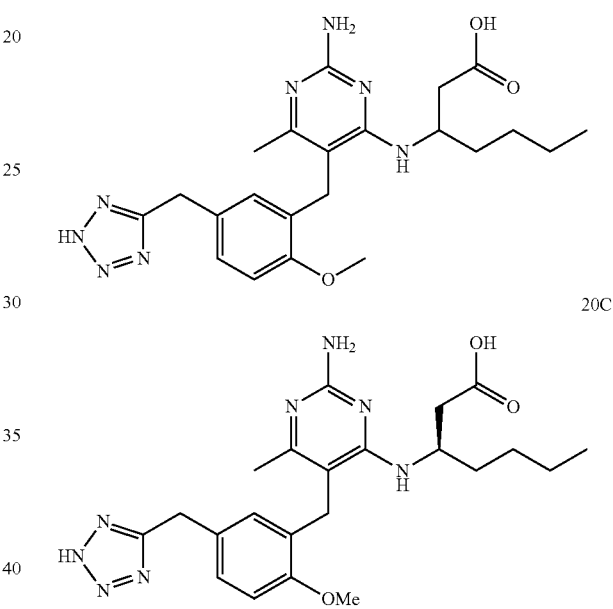

As shown above, the (S)-enantiomer (e.g. Compound 20) is >10-fold more potent than the (R)-enantiomer (e.g. Compound 20C) in the HEK-TLR7 assay. Other examples can follow the same trend.

Biological Example 2: Pharmacokinetics Experiments

BALB/c mice were dosed p.o. with 10 mg/kg compound formulated in 0.5% carboxy methylcellulose+0.5% Tween-80 suspension. Mice were bled retro-orbitally at different time points post dose. Blood was processed into serum by centrifugation followed by protein precipitation, reverse-phase gradient elution and MRM detection via ESI+mass spectrometry to determine compound concentration. Animals were sacrificed after the final blood collection (5 hour), liver removed and flash frozen in liquid nitrogen for tissue PK analyses. The liver-to-serum concentration (L:S) at 5 hour post dose is one parameter for identifying compounds with potential enrichment in liver.

Mouse liver-to-serum concentration (L:S) table below provides results.

| Example | L:S at 5 hr |
|---|---|
| 3 | A |
| 9 | A |
| 10 | B |
| 11 | A |
| 12 | B |
| 13 | B |
| 15 | B |
| 17 | B |
| 18 | A |
| 20 | A |
| 22 | A |
| 23 | A |
| 24 | B |
| 29 | A |
| 30 | A |
| 32 | A |
| 33 | A |
| 34 | A |
| 40 | A |
| 41 | B |
| 42 | A |
| 43 | A |
| 44 | B |
| 45 | A |
| 46 | B |

L:S category:
A = >100 represents high liver-enrichment
B = 10-100 represents moderate liver-enrichment
C = <10 represents low liver-enrichment

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

I claim:
1. A compound of Formula (1):

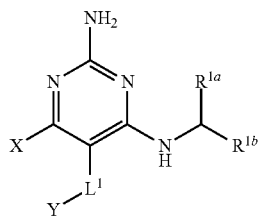

(1)

or a pharmaceutically acceptable salt thereof, wherein:
$R^{1a}$ is selected from the group consisting of $C_1$-$C_4$ alkyl and A, wherein $C_1$-$C_4$ alkyl is optionally substituted with —OH, —NH$_2$, —NHCOCH$_3$, —COOH, —SO$_2$CH$_3$, —SCH$_3$, —OCH$_3$, tetrazol-5-yl or A;
$R^{1b}$ is $C_2$-$C_5$ alkyl;
X is $C_1$-$C_4$ alkyl, optionally substituted with A, —OH or —C(CH$_3$)$_2$OH;
$L^1$ is selected from the group consisting of —CH$_2$— and —CF$_2$—;
Y is aryl, optionally substituted with 1, 2, 3, 4 or 5 substituents independently selected from the group consisting of A, $C_1$-$C_3$ alkyl and $C_1$-$C_3$ alkoxy;
A is -$L^2$-COOH;
$L^2$ is —(CH$_2$)$_n$—; and
n is 1, 2, 3 or 4;
with the proviso that the compound is substituted with at least one A; and further
with the proviso that if X is —CH$_3$, $L^1$ is —CH$_2$—, Y is aryl substituted with A and $L^2$ is —CH$_2$—, then A is not -$L^2$-COOH, except when $R^{1a}$ comprises —COOH or —SO$_2$CH$_3$.

2. The compound of claim 1, or a pharmaceutically acceptable salt thereof, wherein $R^{1a}$ is $C_1$-$C_4$ alkyl, optionally substituted with —OH, —OCH$_3$, —SCH$_3$, or —SO$_2$CH$_3$.

3. The compound of claim 1, or a pharmaceutically acceptable salt thereof, wherein $R^{1a}$ is —CH$_2$C(CH$_3$)$_2$OH.

4. The compound of claim 1, or a pharmaceutically acceptable salt thereof, wherein $R^{1a}$ is $C_1$-$C_4$ alkyl, optionally substituted with —COOH.

5. The compound of claim 1, or a pharmaceutically acceptable salt thereof, wherein $R^{1b}$ is —CH$_2$CH$_3$.

6. The compound of claim 1, or a pharmaceutically acceptable salt thereof, wherein $R^{1b}$ is —(CH$_2$)$_2$CH$_3$.

7. The compound of claim 1, or a pharmaceutically acceptable salt thereof, wherein $R^{1b}$ is —(CH$_2$)$_3$CH$_3$.

8. The compound of claim 1, or a pharmaceutically acceptable salt thereof, wherein

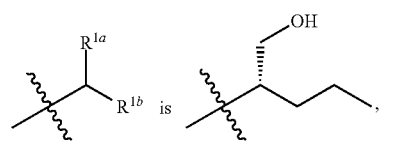

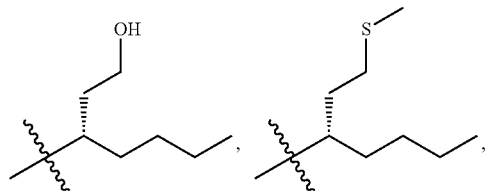

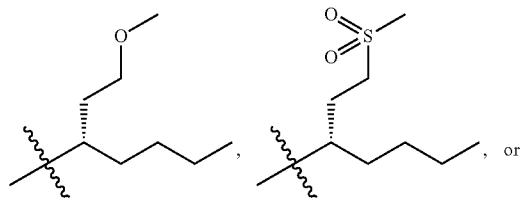

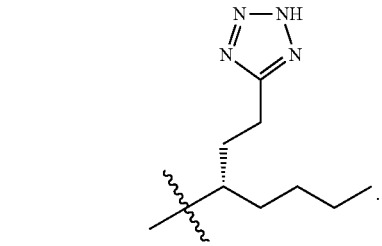

9. The compound of claim 1, or a pharmaceutically acceptable salt thereof, wherein

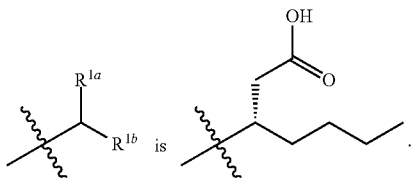

10. The compound of claim 1, or a pharmaceutically acceptable salt thereof, wherein $L^1$ is $CF_2$—.

11. The compound of claim 1, or a pharmaceutically acceptable salt thereof, wherein $L^1$ is —$CH_2$—.

12. The compound of claim 1, or a pharmaceutically acceptable salt thereof, wherein -$L^2$ is —$CH_2$—.

13. The compound of claim 1, or a pharmaceutically acceptable salt thereof, wherein $L^2$ is —$(CH_2)_2$—.

14. The compound of claim 1, or a pharmaceutically acceptable salt thereof, wherein $L^2$ is —$(CH_2)_3$—.

15. The compound of claim 1, or a pharmaceutically acceptable salt thereof, wherein X is $C_1$-$C_4$ alkyl, substituted with A.

16. The compound of claim 1, or a pharmaceutically acceptable salt thereof, wherein X is $C_1$-$C_4$ alkyl, substituted with -$L^2$-COOH.

17. The compound of claim 1, or a pharmaceutically acceptable salt thereof, wherein X is $CH_3$.

18. The compound of claim 1, or a pharmaceutically acceptable salt thereof, wherein Y is aryl, substituted with 1 or 2 $C_1$-$C_3$ alkyl.

19. The compound of claim 1, or a pharmaceutically acceptable salt thereof, wherein Y is aryl, substituted with 1 or 2 $C_1$-$C_3$ alkoxy.

20. The compound of claim 1, or a pharmaceutically acceptable salt thereof, wherein Y is aryl, substituted with 1 or 2 A.

21. The compound of claim 1, wherein the compound is a compound of Formula (1a):

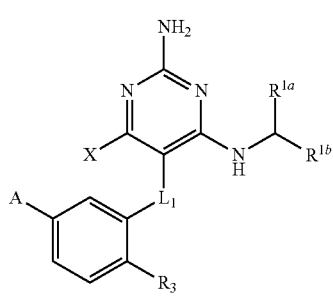

or a pharmaceutically acceptable salt thereof, wherein:
  X is $CH_3$;
  A is -$L^2$-COOH;
  $L^2$ is —$(CH_2)_n$—;
  n is 1 or 2; and
  $R^3$ is H, $C_1$-$C_3$ alkyl or $C_1$-$C_3$ alkoxy.

22. The compound of claim 1, wherein the compound is a compound of Formula (1a):

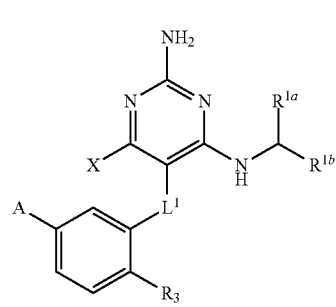

or a pharmaceutically acceptable salt thereof,
wherein:
  X is —$CH_2$-$A^{1a}$, —$(CH_2)_2$-$A^{1a}$, —$(CH_2)_3$-$A^{1a}$ or —$CH_2C(CH_3)_2$-$A^{1a}$;
  $A^{1a}$ is —COOH;
  A is -$L^2$-COOH;
  $L^2$ is —$(CH_2)_n$—;
  n is 1 or 2; and
  $R^3$ is H, $C_1$-$C_3$ alkyl or $C_1$-$C_3$ alkoxy.

23. The compound of claim 1, wherein the compound is a compound of Formula (1b):

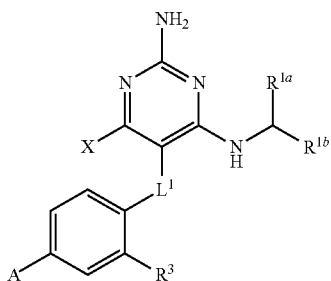

or a pharmaceutically acceptable salt thereof,
wherein:
  X is $CH_3$;
  A is -$L^2$-COOH;
  $L^2$ is —$(CH_2)_n$—;
  n is 1 or 2; and
  $R^3$ is H, $C_1$-$C_3$ alkyl or $C_1$-$C_3$ alkoxy.

24. The compound of claim 1, wherein the compound is a compound of Formula (1b):

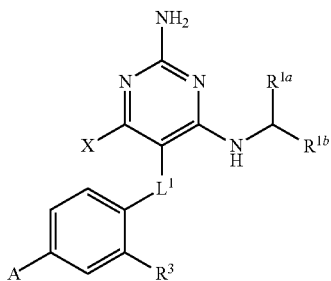

or a pharmaceutically acceptable salt thereof,
wherein:
  X is —$CH_2$-$A^{1a}$, —$(CH_2)_2$-$A^{1a}$, —$(CH_2)_3$-$A^{1a}$ or —$CH_2C(CH_3)_2$-$A^{1a}$;

$A^{1a}$ is —COOH;
A is -$L^2$-COOH;
$L^2$ is —$(CH_2)_n$—;
n is 1 or 2; and
$R^3$ is H, $C_1$-$C_3$ alkyl or $C_1$-$C_3$ alkoxy.

25. The compound of claim 1, wherein the compound is a compound of Formula (1c):

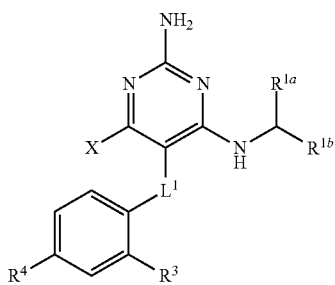

(1c)

or a pharmaceutically acceptable salt thereof,
wherein:
X is —$CH_2$-$A^{1a}$, —$(CH_2)_2$-$A^{1a}$, —$(CH_2)_3$-$A^{1a}$ or —$CH_2C(CH_3)_2$-$A^{1a}$;
$A^{1a}$ is —COOH;
$R^3$ is H, $C_1$-$C_3$ alkyl or $C_1$-$C_3$ alkoxy; and
$R^4$ is H or $C_1$-$C_3$ alkoxy.

26. The compound of claim 1, wherein the compound is a compound of Formula (1e):

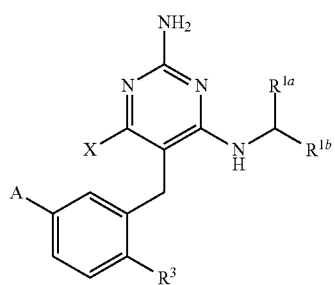

(1e)

or a pharmaceutically acceptable salt thereof,
wherein:
$R^3$ is H, $C_1$-$C_3$ alkyl or $C_1$-$C_3$ alkoxy.

27. The compound of claim 1, wherein the compound is a compound of Formula (1g):

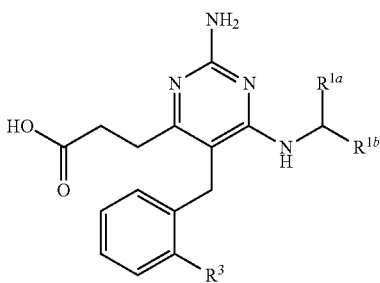

(1g)

or a pharmaceutically acceptable salt thereof,
wherein:
$R^3$ is H, $C_1$-$C_3$ alkyl or $C_1$-$C_3$ alkoxy.

28. The compound of claim 1, wherein the compound is a compound of Formula (1k):

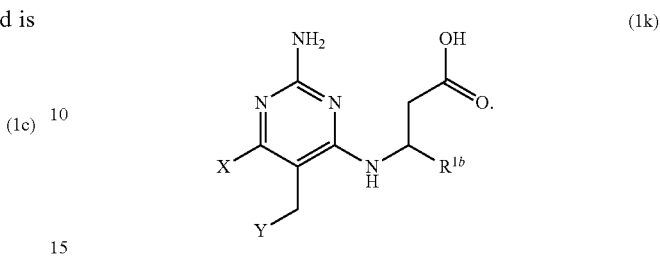

(1k)

or a pharmaceutically acceptable salt thereof.

29. A pharmaceutical composition comprising a compound of claim 1, or a pharmaceutically acceptable salt thereof, and a pharmaceutically acceptable carrier.

30. The pharmaceutical composition of claim 29, wherein the pharmaceutical composition further comprises one or more additional therapeutic agents.

31. The pharmaceutical composition of claim 30, wherein the additional therapeutic agent is an antiviral nucleoside.

32. The pharmaceutical composition of claim 30, wherein the additional therapeutic agent is programmed cell death protein-1 antibody or programmed cell death protein ligand-1 antibody.

33. A method for modulating toll-like receptor 7 activity in a subject, comprising administering to the subject in need thereof an effective amount of a compound of claim 1, or a pharmaceutically acceptable salt thereof.

34. The method of claim 33, wherein the administration to the subject is inhaled, oral, topical, bucchal, sublingual, subcutaneous, intravenous, intramuscular, intratumoral, intradermal, intranasal, intravesical, intrarectal, intrathecal or intracranial.

35. The method of claim 33, wherein the subject has a condition associated with toll-like receptor 7 modulation.

36. The method of claim 35, wherein the condition associated with toll-like receptor 7 modulation is selected from the group consisting of a viral infection and cancer.

37. A method for modulating toll-like receptor 7 activity in a subject having cancer, comprising administering to the subject in need thereof an effective amount of a compound of claim 1, or a pharmaceutically acceptable salt thereof, in combination with a programmed cell death protein-1 antibody or a programmed cell death protein-ligand 1 antibody.

38. A method for treating hepatitis B virus in a subject, comprising administering to the subject in need thereof an effective amount of a compound of claim 1, or a pharmaceutically acceptable salt thereof, in combination with an antiviral nucleoside.

39. A compound selected from the group consisting of:

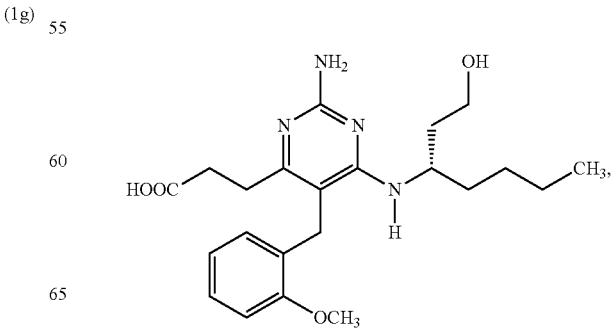

355
-continued
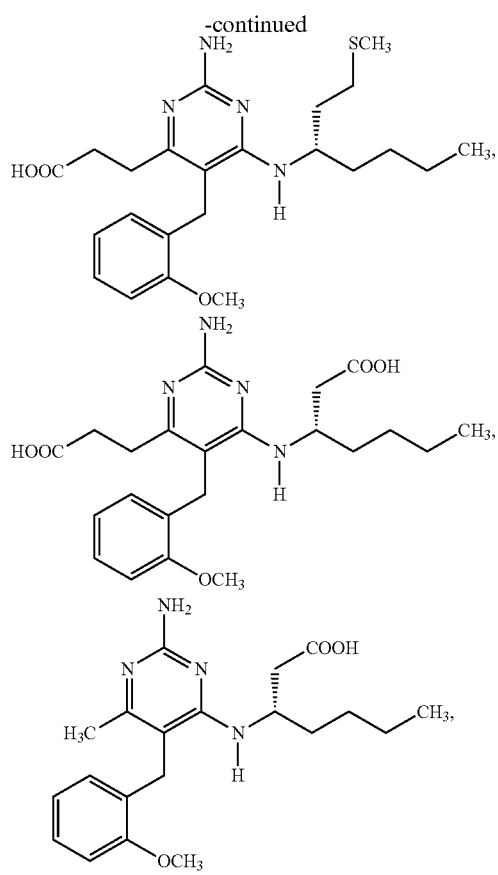
356
-continued
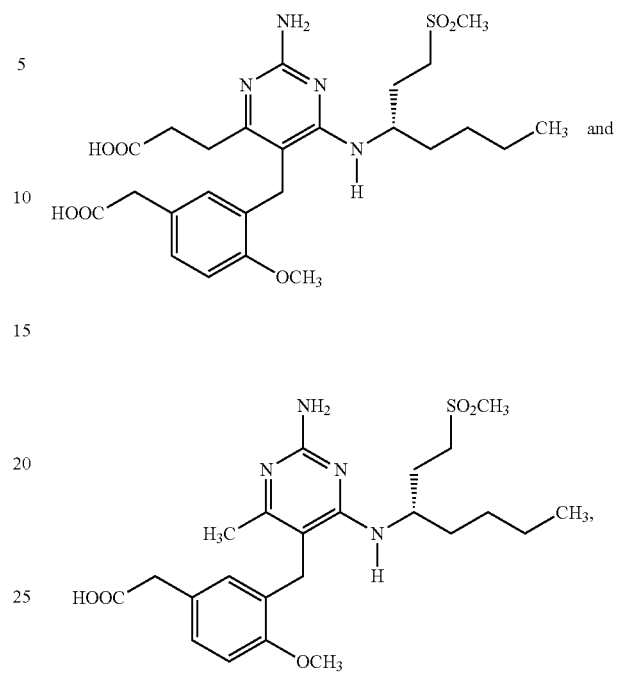
or a pharmaceutically acceptable salt thereof.
* * * * *